US008802861B2

(12) United States Patent
Quattropani et al.

(10) Patent No.: US 8,802,861 B2
(45) Date of Patent: Aug. 12, 2014

(54) THIAZOLE DERIVATIVES AND USE THEREOF

(75) Inventors: Anna Quattropani, Geneva (CH);
Thomas Rueckle, Geneva (CH);
Matthias Schwarz, Geneva (CH);
Jerome Dorbais, Annecy (FR);
Wolfgang Sauer, Plan-les-Ouates (CH);
Christophe Cleva, La Tour (FR);
Gwenaelle Desforges, Saint Julien en Genevois (FR)

(73) Assignee: Merck Serono SA, Vaud (CH)

( * ) Notice: Subject to any disclaimer, the term of this patent is extended or adjusted under 35 U.S.C. 154(b) by 1280 days.

(21) Appl. No.: 10/585,635

(22) PCT Filed: Jan. 11, 2005

(86) PCT No.: PCT/EP2005/050102
§ 371 (c)(1),
(2), (4) Date: Jul. 11, 2006

(87) PCT Pub. No.: WO2005/068444
PCT Pub. Date: Jul. 28, 2005

(65) Prior Publication Data
US 2009/0029998 A1 Jan. 29, 2009

(30) Foreign Application Priority Data

Jan. 12, 2004 (EP) .................................... 04100083

(51) Int. Cl.
*A61K 31/427* (2006.01)
*C07D 417/04* (2006.01)
*C07D 417/14* (2006.01)
(52) U.S. Cl.
USPC ........... 548/195; 544/133; 544/310; 544/331;
544/369; 546/209; 546/270.7; 548/132; 548/138;
548/144; 514/236.8; 514/326; 514/342; 514/371;
514/272; 514/274; 514/252.12; 514/363;
514/364
(58) Field of Classification Search
USPC ........................................................ 548/195
See application file for complete search history.

(56) References Cited

U.S. PATENT DOCUMENTS 4,649,146 A * 3/1987 Takaya et al. ................. 514/307

FOREIGN PATENT DOCUMENTS

| EP | 0 117 082 A2 | 8/1984 |
|---|---|---|
| EP | 1 256 578 | 11/2002 |
| JP | 11-209284 | 8/1999 |
| JP | 2002/53566 A * | 2/2002 |
| WO | WO 95/01979 | 1/1995 |
| WO | 00 26202 | 5/2000 |
| WO | 00 75120 | 12/2000 |
| WO | 01 44217 | 6/2001 |
| WO | 03 072557 | 9/2003 |
| WO | WO-2006/050351 A2 * | 5/2006 |

OTHER PUBLICATIONS

Suciu, CA 75:35865, 1971.*
CA Registry No. 421580-67-8 {entry date in the Registry file on STN May 24, 2002}.*
CA Registry No. 421580-64-5 {entry date in the Registry file on STN May 24, 2002}.*
CA Registry No. 421580-59-8 {entry date in the Registry file on STN May 24, 2002}.*
CA Registry No. 421580-54-3 {entry date in the Registry file on STN May 24, 2002}.*
CA Registry No. 421580-52-1 {entry date in the Registry file on STN May 24, 2002}.*
CA Registry No. 412919-68-7 {entry date in the Registry file on STN May 9, 2002}.*
CA Registry No. 315705-85-2 {entry date in the Registry file on STN Jan. 22, 2001}.*
CA Registry No. 315704-55-3 {entry date in the Registry file on STN Jan. 22, 2001}.*
An English translation of JP 2002/53566, 2002.*
CA Registry No. 412919-72-3 {entry date in the Registry file on STN May 9, 2002}.*
Chemical Abstracts Registry No. 472981-38-7, indexed in the Registry file on STN CAS Online Nov. 11, 2002.*
Chemical Abstracts Registry No. 472981-15-0, indexed in the Registry file on STN CAS Online Nov. 11, 2002.*
Chemical Abstracts Registry No. 472981-35-4, indexed in the Registry file on STN CAS Online Nov. 11, 2002.*
Chemical Abstracts Registry No. 472980-03-3, indexed in the Registry file on STN CAS Online Nov. 11, 2002.*
Chemical Abstracts Registry No. 472979-69-4, indexed in the Registry file on STN CAS Online Nov. 11, 2002.*
Chemical Abstracts Registry No. 472979-32-1, indexed in the Registry file on STN CAS Online Nov. 11, 2002.*
Chemical Abstracts Registry No. 472979-29-6, indexed in the Registry file on STN CAS Online Nov. 11, 2002.*
Chemical Abstracts Registry No. 472979-27-4, indexed in the Registry file on STN CAS Online Nov. 11, 2002.*
Chemical Abstracts Registry No. 472979-26-3, indexed in the Registry file on STN CAS Online Nov. 11, 2002.*
Chemical Abstracts Registry No. 471915-18-1, indexed in the Registry file on STN CAS Online Nov. 8, 2002.*

(Continued)

*Primary Examiner* — Laura L Stockton
(74) *Attorney, Agent, or Firm* — Oblon, Spivak, McClelland, Maier & Neustadt, L.L.P.

(57) ABSTRACT

The present invention is related to thiazole derivatives of Formula (I) in particular for the treatment and/or prophylaxis of autoimmune disorders and/or inflammatory diseases, cardiovascular diseases, neurodegenerative diseases, bacterial or viral infections, kidney diseases, platelet aggregation, cancer, transplantation, graft rejection or lung injuries.

15 Claims, No Drawings

(56) References Cited

OTHER PUBLICATIONS

Chemical Abstracts Registry No. 471915-13-6, indexed in the Registry file on STN CAS Online Nov. 8, 2002.*
Chemical Abstracts Registry No. 412919-82-5, indexed in the Registry file on STN CAS Online May 9, 2002.*
Chemical Abstracts Registry No. 368859-44-3, indexed in the Registry file on STN CAS Online Nov. 12, 2001.*
Chemical Abstracts Registry No. 368857-86-7, indexed in the Registry file on STN CAS Online Nov. 12, 2001.*
Chemical Abstracts Registry No. 368857-84-5, indexed in the Registry file on STN CAS Online Nov. 12, 2001.*
Chemical Abstracts Registry No. 368857-82-3, indexed in the Registry file on STN CAS Online Nov. 12, 2001.*
Chemical Abstracts Registry No. 368857-79-8, indexed in the Registry file on STN CAS Online Nov. 12, 2001.*
Chemical Abstracts Registry No. 315704-42-8, indexed in the Registry file on STN CAS Online Jan. 22, 2001.*
Chemical Abstracts Registry No. 315705-89-6, indexed in the Registry file on STN CAS Online Jan. 22, 2001.*
Chemical Abstracts Registry No. 368857-81-2, indexed in the Registry file on STN CAS Online Nov. 12, 2001.*
Ward, Stephen et al., "Therapeutic Potential of Phosphoinositide 3-Kinase Inhibitors", Chemistry & Biology, vol. 10, No. 3, pp. 207-213, 2003.
Cantley, Lewis C., "The Phosphoinositide 3-Kinase Pathway", Science, vol. 296, pp. 1655-1657, 2002.
Vanhaesebroeck, Bart et al., "Phosphoinositide 3-Kinases: a Conserved Family of Signal Transducers", TIBS, vol. 22, No. 2, pp. 267-272, 1997.
Vanhaesebroeck, Bart et al., "Synthesis and Function of 3-Phosphorylated Inositol Lipids", Annu. Rev. Biochem., vol. 70, pp. 535-602, 2001.
Katso, Roy et al., "Cellular Function of Phosphoinositide 3-Kinases: Implications for Development, Immunity, Homeostasis, and Cancer", Annu. Rev. Cell. Dev. Biol., vol. 17, pp. 615-675, 2001.
Toker, A., "Phosphoinositides and Signal Transduction", CMLS, Cell Mol. Life. Sci., vol. 59, pp. 761-779, 2002.
Stein, Robert C. et al., "PI3-Kinase Inhibition: a Target for Drug Development?", Molecular Medicine Today, vol. 6, pp. 347-357, 2000.
Wymann, Matthias P. et al., "Lipids on the Move: Phosphoisitide 3-Kinases in Leukocyte Function", Trends Immunology Today, vol. 21, No. 6, pp. 260-264, 2000.
Hirsch, Emilio et al., "Central Role for G Protein-Coupled Phosphoinositide 3-Kinase γ in Inflammation", Science, vol. 287, pp. 1049-1053, 2000.
Hirsch, Emilio et al., "Resistance to Thromboembolism in PI3Kγ-Deficient Mice", The FASEB Journal, vol. 15, pp. 2019-2021, 2001.
Gerard, Craig et al., "Chemokines and Disease", Nature Immunology, vol. 2. No. 2, pp. 108-115, 2001.
Parker, Peter J., "PI 3-Kinase Puts GTP on the Rac", Current Biology, vol. 5, No. 6, pp. 577-579, 1995.
Yao, Ryoji et al., "Requirement for Phosphatidylinositol-3 Kinase in the Prevention of Apoptosis by Nerve Growth Factor", Science, vol. 267, pp. 2003-2006, 1995.
Pages, Francoise et al., "Binding of Phosphatidylinositol-3-OH Kinase to CD28 is Required for T-cell Signalling" Letters to Nature, vol. 369, pp. 327-329. 1994.
Fraser, James D. et al., "Regulation of Interleukin-2 Gene Enhancer Activity by the T Cell Accessory Molecule CD28", Science, vol. 251, pp. 313-316, 1991.
Lopez-Ilasaca, Marco et al., "Phosphoinositide 3-Kinase γ Is a Mediator of Gβγ-Dependent Jun Kinase Activation", The Journal of Biological Chemistry, vol. 273, No. 5, pp. 2505-2508, 1998.
Laffargue, Muriel et al., "Phosphoinositide 3-Kinase γ Is an Essential Amplifier of Mast Cell Function", Immunity, vol. 16, pp. 441-451, 2002.
Lawlor, Margaret A. et al., "PKB/Akt: key Mediator of Cell Proliferation, Survival and Insulin Responses?", Journal of Cell Science, vol. 114. No. 16, pp. 2903-2910. 2001.
Stephens, Len et al., Roles of PI3Ks in Leukocyte Chemotaxis and Phagocytosis, Current Opinion in Cell Biology, vol. 14, pp. 203-213, 2002.
Fruman, David A. et al., "Phosphoinositide Kinases", Annu. Rev. Biochem., vol. 67. pp. 481-507, 1998.
Thelen, Marcus et al., "Worthmannin Binds Specifically to 1-Phosphatidylinositol 3-Kinase While Inhibiting Guanine Nucleotide-Binding Protein-Coupled Receptor Signaling in Neutrophil Leukocytes", Cell. Biology, vol. 91, pp. 4960-4964, 1994.
Grant, Steven, "Targeted Therapies in Cancer—Second International Congress", IDrugs, vol. 6, No. 10, pp. 946-948, 2003.
Wilson, Kenneth J. et al., "Synthesis of Thiophene-2-Carboxamidines Containing 2-Aminothiazoles and Their Biological Evaluation as Urokinase Inhibitors", Bioorganic & Medicinal Chemistry Letters, vol. 11, pp. 915-918, 2001.
Brandsma, L. et al., "An Efficient Synthesis of 1,3-Thiazole", Synthesis, pp. 948-949, 1985.
Alvarez-Ibarra, Carlos et al., "A New Synthetic Approximation to Thiazoles With a Versatile Persubstitution and/or Perfunctionalization", Heterocycles, vol. 32, No. 11, pp. 2127-2137, 1991.
El-Maghraby, M. A.et al., "Synthesis of New Heterocyclic Sulphonamides", Indian, J., Chem., vol. 20B, pp. 256-257, 1981.
Feldmen, Paul L., "Synthesis of the Putative L-Arginine Metabolite $L^{NG}$-Hydroxyarginine", Tetrahedron Letters, vol. 32, No. 7, pp. 875-878, 1991.
Fukatsu, Hiroshi, et al., "Synthesis and Cardiotonic Activity of 5-(2-Substituted Thiazol-4-YL)-2-Pyridones and Thiazolo[4,5-f]Quinolinones", Heterocycles, vol. 29, No. 8, pp. 1517-1528, 1989.
Hartmann, Von Horst et al., "Darstellung und Charakterisierung 1,1-Disubstituierter Thioharnstoffe", Journal F. Prakt. Chemie., Band. 315, Heft. 1. pp. 144-148, 1973.
Kodomari, Mitsuo et al., "One-Pot Synthesis of 2-Aminothiazoles Using Supported Reagents", Tetrahedron Letters, vol. 43, pp. 1717-1720, 2002.
Konno, Shoetsu, et al., "Synthesis of 4,5-Diarylthiazole Derivatives as Blood Platelet Aggregation Inhibitors", Regular Articles, vol. 110, No. 2, pp. 105-114, 1990. (With Partial English Translation).
Kropf, Heinz et al., "Synthesis and Some Reactions of 4-Bromoimidazole-5-Sulfonyl Derivatives. A Reinvestigation", J. Chem. Eng. Data, vol. 33, pp. 537-538, 1988.
Lipinski, Christopher A. et al., "An Improved Preparation and Use of 2-Bromoacetoacetaldehyde in a New Synthesis of 2-Substituted-4-Acetylimidazoles", J. Org. Chem., vol. 49, No. 3, pp. 566-570, 1984.
Nair, V. et al., "Carbon Disulfide as a 2-π Component in Its Cycloaddition with 1-Azirines", J.Org. Chem., vol. 40, No. 9, pp. 1348-1349, 1975.
Leslie, Nick R. et al., "Phosphoinositide-Regulated Kinases and Phosphoinositide Phosphatases", Chem. Rev. vol. 101, No. 8, pp. 2365-2380, 2001.
Oehler, Elisabeth et al., "(1,2-Epoxy-3-oxoalkyl)phosphonsaeureester als Synthone Fuer Heterocyclische Carbonylverbindungen: Synthese von Acylsubstituierten Thiazolen, Indolizinen, Imidazo[1,2-a]-Pyridinen und Imidazo[1,2-a]Pyrimidinen", Chem. Ber. vol. 118, pp. 4099-4130, 1985.
Chan, Ming Fai et al., "The Discovery and Structure-Activity Relationships of Nonpeptide, Low Molecular Weight Antagonists Selective for the Endothelin $ET_b$ Receptor[1]", Bioorganic & Medicinal Chemistry, vol. 6, pp. 2301-2316, 1998.
Rasmussen, C.R. et al., "Improved Procedures for the Preparation of Cycloalkyl-, Arylalkyl-, and Arylthioureas[1]", Papers Synthesis, pp. 456-459, 1988.
Michael C. Pirrung, et al., "Trityl Isothiocyanate Support for Solid-Phase Synthesis" J. Comb Chem, vol. 3, 2001, pp. 90-96.
R. Jason Herr, et al., "A Convenient Method for the Preparation of Primary and Symmetrical N,N'-Disubstituted Thioureas" Synthesis, No. 11, 2000, pp. 1569-1574.

(56) References Cited

OTHER PUBLICATIONS

G. Mazzone, et al., "Sintesi D1 1-Aroil-4H(R)-Tiosemicarbazidi, DEI Corrispondenti 5-ARIL-4H(R)-1,2,4-Triazolin-3-Tioni E DI Alcuni Derivati DI Interesse Farmaceutico" II Farmaco—Ed. Sc. vol. 36, No. 3, 1980, pp. 181-196.

Pattan S. R., et al., "Synthesis and Microbiological Evaluation of Some New Methyl-2-Alkyl/Arylthio-4-Thiazole Acetates for Their Antimicrobial Activity" Indian Drugs, vol. 39, No. 8, Aug. 2002, pp. 429-433.

Surendra P. Bhatti, et al., "Synthesis and Anticancer Activity of Some 8-Thiazolylchromones" Indian Journal of Heterocyclic Chemistry, vol. 10, Oct.-Dec. 2000, pp. 81-84.

Christopher A. Lipinski, et al., "Bioisosteric Prototype Design of Biaryl Imidazolyl and Triazolyl Competitive Histamine $H_2$-Receptor Antagonists" J. Med. Chem, vol. 29, 1986, pp. 2154-2163.

Samia M. Sayed, et al., "Synthesis and Reactivity of Cyanomethyl 2-Amino-4-Methylthiazolyl Ketone. A Facile Synthesis of Novel Pyrazolo[5,1-C]1,2,4-Triazine, 1,2,4-Triazolo[5,1-C]1,2,4-Triazine, 1,2,4-Triazino[4,3-A]Benzimidazole, Pyridazine-6-Imine and 6-Oxopyridazinone Derivatives" Heteroatom Chemistry, vol. 10, No. 5, 1999, pp. 385-390.

Rajinder Dahiya, et al., "Facile Synthesis of Aminothiazoles" Indian Journal of Chemistry, vol. 25B, Sep. 1986, p. 966.

Australian Examiner's Report dated Apr. 27, 2010 as received in the corresponding Australian Application No. 2005205201.

\* cited by examiner

THIAZOLE DERIVATIVES AND USE THEREOF

FIELD OF THE INVENTION

This present invention is related to the use of thiazole derivatives of Formula (I) for the treatment and/or prophylaxis of autoimmune disorders and/or inflammatory diseases, cardiovascular diseases, neurodegenerative diseases, bacterial or viral infections, allergy, asthma, pancreatitis, multi-organe failure, kidney diseases, platelet aggregation, cancer, sperm motility, graft rejection or lung injuries. Specifically, the present invention is related to thiazole derivatives for the modulation, notably the inhibition of the activity or function of the phospboinositide-3-kinases, PI3Ks.

BACKGROUND OF THE INVENTION

Phosphoinositide 3-kinases (PI3Ks) have a critical signalling role in cell proliferation, cell survival, vascularization, membrane trafficking, glucose transport, neurite outgrowth, membrane ruffling, superoxide production, actin reorganization and chemotaxis (Cantley, 2000, *Science*, 296, 1655-1657 and Vanhaesebroeck et al., 2001, *Annu. Rev. Biochem.*, 70, 535-602).

The term PI3K is given to a family of lipid linases which, in mammals, consists in eight identified PI3Ks that are divided into three sub-families according to their structure and their substrate specificity.

Class I group of PI3Ks consists in two sub-groups, Class IA and Class IB.

Class IA consists in a 85 kDa regulatory unit (responsible for protein-protein interactions via the interaction of Src homology 2 (SH2) domain with phosphotyrosine residues of other proteins) and a catalytic sub-unit of 110 kDa. Three catalytic forms (p100α, p110β and p100δ) and five regulatory isoforms (p85α, p85β, p55γ, p55α and p50α) exist for this class.

Class IB are stimulated by G protein βγ sub-units of heterodimeric G proteins. The only characterized member of Class IB is PI3Kγ (p110γ catalytic sub-unit complexed with a 101-kDa regulatory protein, p101).

Class II PI3Ks comprises α, β and γ isoforms, which are approximately of 170 kDa and characterized by the presence of a C-terminal C2 domain.

Class III PI3Ks includes the phosphatidylinositol specific 3-kinases.

The evolutionary conserved isoforms p110α and β are ubiquitiously expressed, while δ and γ are more specifically expressed in the haematopoetic cell system, smooth muscle cells, myocytes and endothelial cells (Vanhaesebroeck et al., 1997, *Trends Biochem Sci.*, 22(7), 267-72). Their expression might also be regulated in an inducible manner depending on the cellular-, tissue type and stimuli as well as disease context.

PI3Ks are enzymes involved in phospholipid signalling and are activated in response to a variety of extra-cellular signals such as growth factors, mitogens, integrins (cell-cell interactions) hormones, cytokines, viruses and neurotransmitters and also by intra-cellular cross regulation by other signaling molecules (cross-talk, where the original signal can activate some parallel pathways that in a second step transmitt signals to PI3Ks by intra-cellular signaling events), such as small GTPases, kinases or phosphatases for example.

Phosphatidylinositol (PtdIns) is the basic building block for the intracellular inositol lipids in eukaryotic cells, consisting of D-myo-inositol-1-phosphate (Ins1P) linked via its phosphate group to diacylglycerol. The inositol head group of PtdIns has five free hydroxy groups and three of these are found to be phosphorylated in cells in different combinations. PtdIns and its phosphorylated derivatives are collectively referred as inositol phospholipids or phosphoinositides (PIs). Eight PI species have been documented in eukaryotic cells (Vanhaesebroeck et al., 2001, above). PIs all reside in membranes and are substrates for kinases, phosphatases and lipases.

In vitro, PI3Ks phosphorylate the 3-hydroxyl group of the inositol ring in three different substrates: phosphatidylinositol (PtdIns), phosphatidylinositol-4-phosphate (PI(4)P) and phosphatidylinositol-4,5-biphosphate (PI(4,5)$P_2$), respectively generating three lipid products, namely phosphatidylinositol 3-monophosphate (PI(3)P), phosphatidylinositol 3,4-bisphosphate (PI(3,4)$P_2$) and phosphatidylinositol 3,4,5-trisphosphate (PI(3,4,5)$P_3$ (see Scheme A below).

Scheme A

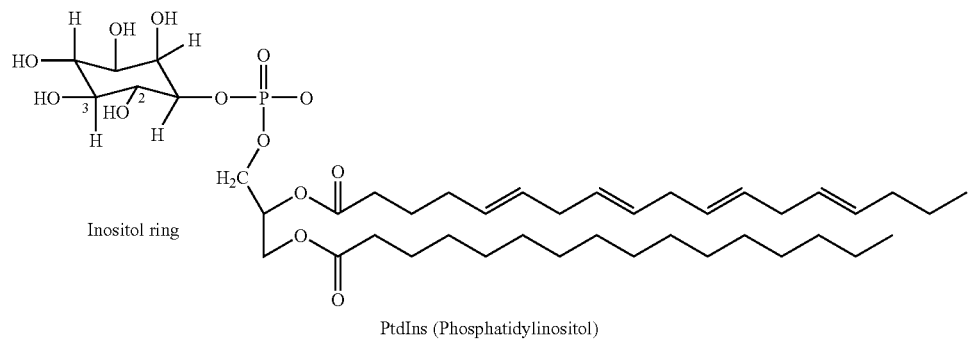

Inositol ring

PtdIns (Phosphatidylinositol)

↓ PI3K

-continued

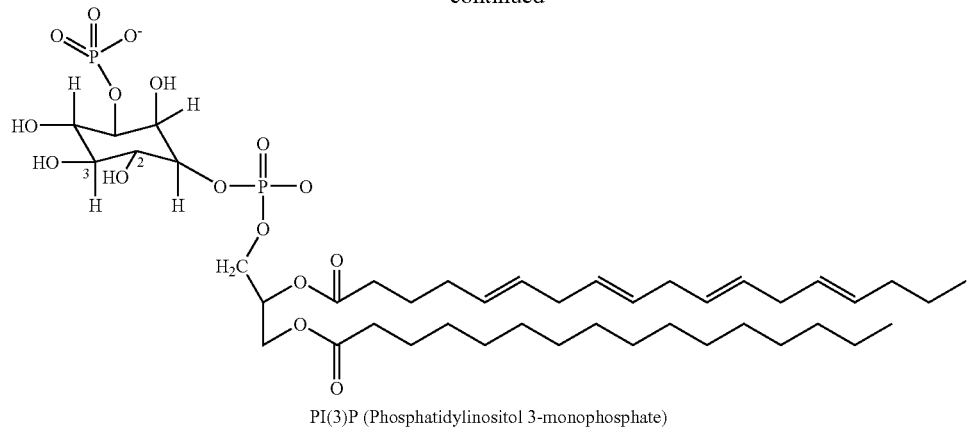

PI(3)P (Phosphatidylinositol 3-monophosphate)

The preferred substrate for Class I PI3Ks is PI(4,5)P$_2$. Class II PIKs have a strong preference for PtdIns as substrate over PI(4)P and PI(4,5)P$_2$. Class III PI3Ks can only use PtdIns as substrate in vivo and are likely to be responsible for the generation of most PI(3)P in cells (Vanhaesebroeck et al., 2001, above).

The phosphoinositides intracellular signalling pathway begins with the binding of a signalling molecule (extracellular ligands, stimuli, receptor dimerization, transactivation by heterologous receptor (e.g. receptor tyrosine kinase)) to a G-protein linked transmembrane receptor integrated into the plasma membrane resulting in the activation of PI3Ks.

Once activated, PI3Ks convert the membrane phospholipid PI(4,5)P$_2$ into PI(3,4,5)P$_3$ which in turn can be further converted into another 3' phosphorylated form of phosphoinositides by 5'-specific phosphoinositide phosphatases, thus PI3K enzymatic activity results either directly or indirectly in the generation of two 3'-phosphoinositide sub-types that function as second messengers in intra-cellular signal transduction (Leslie et al., 2001, Chem. Rev. 101(8) 2365-80; Katso et al, 2001, Annu. Rev. Cell Dev. Biol. 1, 615-75 and Toker et al, 2002, Cell Mol. Life. Sci. 59(5) 761-79).

The role as second messengers of phosphorylated products of PtdIns act is involved in a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Stein, 2000, Mol. Med. Today 6(9) 347-57). Chemotaxis—the directed movement of cells toward a concentration gradient of chemical attractants, also called chemokines is involved in many important diseases such as inflammation/auto-immunity, neurodegeneration, angiogenesis, invasion/metastasis and wound healing (Wyman et al., 2000, Immunol Today 21(6) 260-4; Hirsch et al., 2000, Science 287(5455) 1049-53; Hirsch et al, 2001, FASEB J. 15(11) 2019-21 and Gerard et al., 2001, Nat Immunol 2(2) 108-15).

PI3-kinase activation, is therefore believed to be involved in a range of cellular responses including cell growth, differentiation and apoptosis (Parker et al., 1995, Current Biology, 5, 577-99; Yao et al., 1995, Science, 267, 2003-05).

Recent biochemical studies revealed that, Class I PI3Ks (e.g. Class IB isoform PI3Kγ) are dual-specific kinase enzymes, i.e. they display both lipid kinase activity (phosphorylation of phospho-inositides) as well as protein kinase activity, as they are able to induce the phosphorylation of other protein as substrates, including auto-phosphorylation as intra-molecular regulatory mechanism.

PI3Ks appear to be involved in a number of aspects of leukocyte activation. A p85 associated PI3-kinase activity has been shown to physically associate with the cytoplasmic domain of CD28, which is an important co-stimulatory molecule for the activation of T-cells in response to antigen (Pages et al., 1994, Nature, 369, 327-29). These effects are linked to increases in the transcription of a number of genes including interleukin-2 (IL2), an important T cell growth factor (Fraser et al, 1991, Science, 251, 313-16). Mutation of CD28 such that it can longer interact with PI3-kinase leads to a failure to initiate IL2 production, suggesting a critical role for PI3-kinase in T cell activation.

Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3Kγ has been identified as a mediator of G beta-gamma-dependent regulation of JNK activity wherein G beta-gamma are subunits of heterotrimeric G proteins (Lopez-Ilasaca et al., 1998, J. Biol. Chem. 273(5) 2505-8).

Recently, it has been described that PI3Kγ relays inflammatory signals through various G(i)-coupled receptors (Laffargue et al, 2002, Immunity 16(3) 441-51) and its central to mast cell function, stimuli in context of leukocytes, immunology includes cytokines, chemokines, adenosines, antibodies, integrins, aggregation factors, growth factors, viruses or hormones for example (Lawlor et al., 2001, J. Cell. Sci., 114 (Pt 16) 2903-1 and Stephens et al., 2002, Curr. Opinion Cell Biol. 14(2), 203-13).

Specific inhibitors against individual members of a family of enzymes provide valuable tools for deciphering functions of each enzyme.

Two compounds, LY294002 and wortmannin (cf. hereinafter), have been widely used as PI3-kinase inhibitors. These compounds are non-specific PI3K inhibitors, as they do not distinguish among the four members of Class I PI3-kinases.

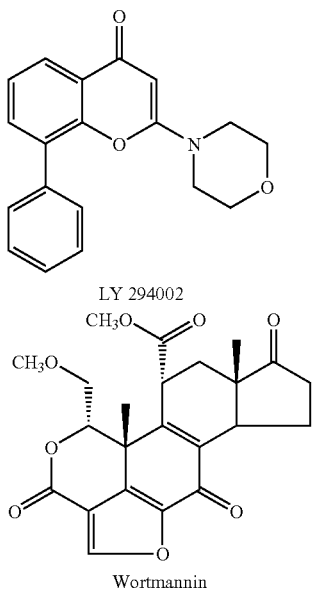

LY 294002

Wortmannin

IC$_{50}$ values of wortmannin against each of the various Class I PI3-kinases are in the range of 1-10 nM and IC$_{50}$ values for LY294002 against each of these PI3-kinases are about 15-20 µM (Fruman et al., 1998, *Ann. Rev. Biochem.*, 67, 481-507), also 5-10 mM on CK2 protein kinase and some inhibitory activity on phospholipases.

Wortmannin is a fungal metabolite which irreversibly inhibits PI3K activity by binding covalently to the catalytic domain of this enzyme. Inhibition of PI3K activity by wortmannin eliminates the subsequent cellular response to the extracellular factor (Thelen et al., 1994, *Proc. Natl. Acad. Sci. USA*, 91, 4960-64). Experiments with wortmannin, show that PI3K activity in cells of hematopoietic lineage, particularly neutrophils, monocytes, and other types of leukocytes, is involved in many of the non-memory immune response associated with acute and chronic inflammation.

Based on studies using wortmannin, there is evidence that PI3-kinase function is also required for some aspects of leukocyte signaling through G-protein coupled receptors (Thelen et al., 1994). Moreover, it has been shown that wortmannin and LY294002 block neutrophil migration and superoxide release. However, in as much as these compounds do not distinguish among the various isoforms of PI3K, it remains unclear which particular PI3K isoform or isoforms are involved in these phenomena.

Some results have indicated that PI3K inhibitors, for example, LY294002, can increase the in vivo antitumor activity of certain cytotoxic agents (e.g. paclitaxel) (Grant, 2003, *Current Drugs*, 6(10), 946-948).

Recently, 5-phenylthiazole derivatives have been recently developed as PI3K inhibitors (WO 03/072557).

The high relevance of the PI3K pathway in some widely spread diseases stresses the need to develop inhibitors, including selective inhibitors, of PIKs.

SUMMARY OF THE INVENTION

It is an object of the invention to provide substances which are suitable for the treatment and/or prevention of disorders related to phosphoinositide-3-kinases, PI3Ks.

It is also an object of the present invention to provide substances which are suitable for the treatment and/or prevention of auto-immune and/or inflammatory disorders.

It is also an object of the present invention to provide substances which are suitable for the treatment and/or prevention of cardiovascular diseases.

It is also an object of the present invention to provide substances which are suitable for the treatment and/or prevention of neurodegenerative disorders.

It is also an object of the present invention to provide substances which are suitable for the treatment and/or prevention of a disorder selected from bacterial and viral infections, kidney diseases, platelet aggregation, cancer, transplantation, graft rejection, lung injuries, respiratory diseases and ischemic conditions.

It is notably an object of the present invention to provide chemical compounds which are able to modulate, especially inhibit the activity or function of phosphoinositide-3-kinases, PI3Ks in disease states in mammals, especially in humans.

It is furthermore an object of the present invention to provide a new category of pharmaceutical formulations for the treatment of and/or diseases mediated selected from auto-immune, inflammatory disorders, cardiovascular diseases, neurodegenerative disorders, bacterial and viral infections, kidney diseases, platelet aggregation, cancer, transplantation, graft rejection, lung injuries, respiratory diseases and ischemic conditions.

It is finally an object of the present invention to provide a method for the treatment and/or prevention of disorders selected from auto-immune, inflammatory disorders, cardiovascular diseases, neurodegenerative disorders, bacterial and viral infections, kidney diseases, platelet aggregation, cancer, transplantation, graft rejection or lung injuries, respiratory diseases and ischemic conditions.

In a fast aspect, the invention provides thiazole derivatives of Formula (I):

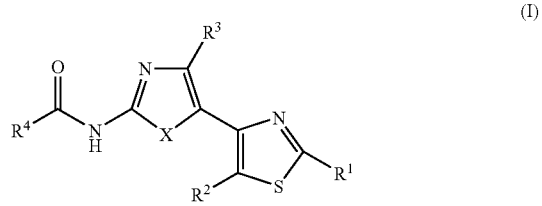

(I)

wherein $R^1$, $R^2$, $R^3$, $R^4$, $R^5$, $R^6$, $R^7$, $R^8$, $R^9$ and X are defined in the detailed description below, for use as a medicament.

In a second aspect, the invention provides a pharmaceutical composition comprising a compound of Formula (I), together with a pharmaceutically acceptable excipient or carrier. In a third aspect, the invention provides a use of a compound of Formula (for the preparation of a pharmaceutical composition useful for a variety of therapies, including alleviating, preventing and/or treating a disorder selected from auto-immune, inflammatory disorders, cardiovascular diseases, neurodegenerative disorders, bacterial and viral infections, kidney diseases, platelet aggregation, cancer, transplantation, graft rejection or lung injuries, respiratory diseases and ischemic conditions and other diseases and disorders associated with the phosphoinositide-3-kinases, PI3Ks.

In a third aspect, the invention provides a method for treating a patient suffering from a disorder selected from auto-immune, inflammatory disorders, cardiovascular diseases, neurodegenerative disorders, bacterial and viral infections, kidney diseases, platelet aggregation, cancer, transplantation, graft rejection or lung injuries, respiratory diseases and ischemic conditions and other diseases and disorders associated with the phosphoinositide-3-kinases, PI3Ks. The method comprises administering a compound according to Formula (I).

In a fourth aspect, the invention provides a use of a thiazole according to the invention for the preparation of a pharmaceutical formulation for the treatment of a disorder selected from auto-immune, inflammatory disorders, cardiovascular diseases, neurodegenerative disorders, bacterial and viral infections, kidney diseases, platelet aggregation, cancer, transplantation, graft rejection or lung injuries, respiratory diseases and ischemic conditions and other diseases and disorders associated with the phosphoinositide-3-kinases, PI3Ks.

In a fifth aspect, the invention provides thiazole derivatives of Formula (I) wherein $R^1$, $R^2$, $R^3$, $R^4$, $R^5$, $R^6$, $R^7$, $R^8$, $R^9$ and X are defined in the detailed description

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl —$CH_2$CH=$CH_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethenyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, 1-methylpiperazine, morpholine, tetrahydrofurane and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, morpholinylmethyl, morpholinylethyl, morpholinylpropyl, piperidinylethyl, tetrahydrofuranylmethyl and the like.

"Carboxy" refers to the group —C(O)OH.

"$C_1$-$C_6$-alkyl carboxy" refers to $C_1$-$C_6$-alkyl groups having a carboxy substituent, including 2-carboxyethyl and the like.

"Aryl carboxy" refers to aryl groups having a carboxy substituent, including carboxylic acid, hydroxamic acid, amide, 1-(4-benzyl-piperazine)-carbonyl, N-(amino-acetic acid methyl ester)carbonyl, N-(amino-acetic acid)carbonyl, N-(3-amino-propionic acid methyl ester)carbonyl, N-(3-amino-propionic acid)carbonyl and the like.

"Acyl" refers to the group —C(O)R where R includes "$C_1$-$C_6$-alkyl", "aryl", "heteroaryl", "$C_3$-$C_8$-cycloalkyl", "Heterocycloalkyl", "$C_1$-$C_6$-alkyl aryl" or "$C_1$-$C_6$-alkyl heteroaryl".

"$C_1$-$C_6$-alkyl acyl" refers to $C_1$-$C_6$-alkyl groups having an acyl substituent, including 2-acetylethyl and the like.

"$C_1$-$C_6$-alkyl acyl" refers to $C_1$-$C_6$-alkyl groups having an acyl substitutent, including acetyl benzoyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-(hetero)cycloalkyl acyl" refers to 3 to 8 membered cycloalkyl or heterocycloalkyl groups having an acyl substituent, including including 4-acetyl piperidine, 4-benzoyl piperidine and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", heterocycloalkyl "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl" and the like.

"$C_1$-$C_6$-alkyl acyloxy" refers to $C_1$-$C_6$-alkyl groups having an acyloxy substituent, including amino-propionic acid ethyl ester and the like.

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"$C_1$-$C_6$-alkyl alkoxy" refers to $C_1$-$C_6$-alkyl groups having an alkoxy substituent, including methoxy, methoxyethyl and the like.

"Alkoxycarbonyl" refers to the group —C(O)OR where R includes H, "$C_1$-$C_6$-alkyl" or "aryl" or "heteroaryl" or "$C_1$-$C_6$-alkyl aryl" or "$C_1$-$C_6$-alkyl heteroaryl" and the like.

"$C_1$-$C_6$-alkyl alkoxycarbonyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl" and the like.

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Aryl aminocarbonyl" refers to aryl groups having an aminocarbonyl substituent, including amino acetyl and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl" and the like.

"$C_1$-$C_6$-alkyl acylamino" refers to $C_1$-$C_6$-alkyl groups having an acylamino substituent, including 2-(propionylamino) ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-akynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_6$-alkyl amino" refers to $C_1$-$C_5$-alkyl groups having an amino substituent, including 2-(1-pyrrolidinyl)ethyl and the like.

"Ammonium" refers to a positively charged group —N$^+$RR'R", where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyloxy" refers to $C_1$-$C_5$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g. an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-akynyl-heteroaryl", "$C_1$-$C_6$-alkyl cycloalkyl", "$C_1$-$C_6$-alkyl heterocycloalkyl".

"$C_1$-$C_6$-alkyl sulfonyl" refers to $C_1$-$C_5$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfinyl" refers to $C_1$-$C_5$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"$C_1$-$C_6$-alkyl sulfanyl" refers to $C_1$-$C_5$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonylamino" refers to $C_1$-$C_5$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl"

or "C₁-C₆-alkyl heteroaryl", "C₂-C₆-alkenyl aryl", "C₂-C₆-alkenyl heteroaryl", "C₂-C₆-alkynyl aryl", "C₂-C₆-alkynyl-heteroaryl", "C₁-C₆-alkyl cycloalkyl", "C₁-C₆-alkyl heterocycloalkyl".

"C₁-C₆-alkyl aminosulfonyl" refers to C₁-C₆-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "C₁-C₆-alkyl", "C₂-C₆-alkenyl", "C₂-C₆-alkynyl", "cycloalkyl", "heterocycloalkyl", "C₁-C₆-alkyl aryl", "C₁-C₆-allyl heteroaryl", "C₁-C₆-alkyl cycloalkyl", "C₁-C₆-alkyl heterocycloalkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Substituted" refers to groups substituted with from 1 to 5 substituents selected from the group consisting of "C₁-C₆-alkyl", "C₂-C₆-alkenyl", "C₂-C₆-alkynyl", "cycloalkyl", "heterocycloalkyl", "C₁-C₆-alkyl aryl", "C₁-C₆-alkyl heteroaryl", "C₁-C₆-alkyl cycloalkyl", "C₁-C₆-alkyl heterocycloalkyl", "amino", "aminosulfonyl", "ammonium", "acyl amino", "amino carbonyl", "aryl", "heteroaryl", "sulfinyl", "sulfonyl", "alkoxy", "alkoxy carbonyl", "carbamate", "sulfanyl", "halogen", trihalomethyl, cyano, hydroxy, mercapto, nitro, and the like "Pharmaceutically acceptable cationic salts or complexes" is intended to define such salts as the alkali metal salts, (e.g. sodium and potassium), alkaline earth metal salts (e.g. calcium or magnesium), aluminium salts, ammonium salts and salts with organic amines such as with methylamine, dimethylamine, trimethylamine, ethylamine, triethylamine, morpholine, N-Me-D-glucamine, N,N'-bis(phenylmethyl)-1,2-ethanediamine, ethanolamine, diethanolamine, ethylenediamine, N-methylmorpholine, piperidine, benzathine (N,N'-dibenzylethylenediamine), choline, ethylene-diamine, meglumine (N-methylglucamine), benethamine (N-benzylphenethylamine), diethylamine, piperazine, thromethamine (2-amino-2-hydroxymethyl-1,3-propanediol), procaine as well as amines of formula —NR,R',R" wherein R, R', R" is independently hydrogen, alkyl or benzyl. Especially preferred salts are sodium and potassium salts.

"Pharmaceutically acceptable salts or complexes" refer to salts or complexes of the below-identified compounds of Formula (I) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quaternary ammonium salt of the formula —NR,R',R"⁺Z⁻, wherein R, R', R" is independently hydrogen, alkyl, or benzyl, C₁-C₆-alkyl, C₂-C₆-alkenyl, C₂-C₆-alkynyl, C₁-C₆-alkyl aryl, C₁-C₆-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

It has now been found that compounds of the present invention are modulators of the Phosphatoinositides 3-kinases (PI3Ks). When the phosphatoinositides 3-kinase (PI3K) enzyme is inhibited by the compounds of the present invention, PI3K is unable to exert its enzymatic, biological and/or pharmacological effects. The compounds of the present invention are therefore useful in the treatment and prevention of autoimmune disorders and/or inflammatory diseases, cardiovascular diseases, neurodegenerative diseases, bacterial or viral infections, kidney diseases, platelet aggregation, cancer, transplantation, graft rejection or lung injuries.

General Formula (I) according to the present invention also comprises its tautomers, its geometrical isomers, its optically active forms as enantiomers, diastereomers and its racemate forms, as well as pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and paratoluenesulfonate salts.

The compounds according to Formula (I) are suitable for the modulation, notably the inhibition of the activity of phosphatoinositides 3-kinases (PI3K). It is therefore believed that the compounds of the present invention are also particularly useful for the treatment and/or prevention of disorders which are mediated by PI3Ks, particularly PI3Kγ. Said treatment involves the modulation—notably the inhibition or the down regulation—of the phosphatoinositides 3-kinases.

The compounds according to Formula (I) are suitable for use as a medicament.

In one embodiment, the invention provides thiazole derivatives of Formula (I) wherein $R^1$ is selected from —NR⁵R⁶ and —SO₂R⁷, preferably —NR⁵R⁶;

$R^2$, $R^3$ and $R^5$ are selected independently from H, optionally substituted C₁-C₆-alkyl, including methyl, optionally substituted C₂-C₆-alkenyl and optionally substituted C₂-C₆-alkynyl;

$R^4$ is selected from H; optionally substituted C₁-C₆-alkyl, including methyl and ethyl; optionally substituted C₂-C₆-alkenyl; optionally substituted C₂-C₆-alkynyl; and —NR⁸R⁹ wherein $R^8$ and $R^9$ are independently selected from H, optionally substituted C₁-C₆-alkyl, optionally substituted C₁-C₆-alkenyl; optionally substituted C₂-C₆-alkynyl; optionally substituted C₁-C₆-alkyl alkoxy carbonyl, including ethyl propanoate; optionally substituted C₁-C₆-alkyl acyloxy, including amino-propionic acid ethyl ester, $R^6$ is selected from optionally substituted C₁-C₆-alkyl, including t-butyl, 2-cyanoethyl, 2-cyanomethyl, 3-hydroxy propyl, 2-hydroxy ethyl, 4-hydroxy butyl, 2-methyl propyl, 2,2-dimethyl propyl and 1-methyl propyl;

optionally substituted C₂-C₆-alkenyl, including allyl and 2-methyl-allyl;

optionally substituted C₂-C₆-alkynyl;

optionally substituted C₁-C₆-alkyl alkoxy, including methoxyethyl, e.g. 2-methoxy ethyl and 3,3-diethoxy-propyl, 2,2-diethoxy-ethyl;

optionally substituted C₁-C₆-alkyl acyl, including methylene phenyl ketone;

optionally substituted $C_1$-$C_6$-alkyl carboxy, including propanoic acid, butanoic acid;
optionally substituted $C_1$-$C_6$-alkyl acylamino, including ethyl-2-acetamide; optionally substituted $C_1$-$C_6$-alkyl amino, including 2-dimethyl amino ethyl, 3-dimethylamino propyl; optionally substituted $C_1$-$C_6$-alkyl aminocarbonyl, including 3-propionamide; optionally substituted $C_1$-$C_6$-alkyl alkoxycarbonyl including 4-butyric acid methyl ester;
optionally substituted aryl, including optionally substituted phenyl such as phenyl, methoxyphenyl (e.g. 2,5-dimethoxy phenyl, 4-methoxy phenyl, 2-methoxy phenyl, 3-methoxy phenyl), acetylamino phenyl (e.g. 4-acetylamino phenyl, 2-acetylamino phenyl), aminophenyl, dimethylamino phenyl (e.g. 4-dimethyl amino phenyl), nitro phenyl (e.g. 3-nitro phenyl, 4-nitrophenyl, 2-nitrophenyl), ethyl phenyl (e.g. 2-ethyl phenyl), methylphenyl (e.g. 2-methylphenyl) bromophenyl (e.g. 4-bromophenyl), chlorophenyl (e.g. 4-chloro phenyl, 2-chlorophenyl, 3-chlorophenyl), hydroxyphenyl (e.g. 3-hydroxyphenyl, 4-hydroxy phenyl, 2-hydroxy phenyl), cyano phenyl (e.g. 4-cyano phenyl, 3-cyano phenyl), 3-(1-hydroxyethyl)phenyl, hydroxamic acid phenyl, 3-(N-hydroxycarbamimidoyl)-phenyl-4-yl, acetyl phenyl (e.g. 3-acetyl phenyl, 2-acetyl phenyl), benzyl piperazine carbonyl phenyl (e.g. 4-benzylpiperazin-1-yl-carbonylphenyl), phenyl optionally substituted with heteroaryl such as oxazolyl phenyl (e.g. 3-(1,3-oxazol-5-yl)phenyl), tetrazolyl phenyl (e.g. 3-(1H-tetrazol-5-yl)phenyl, 4-(1H-tetrazol-5-yl)phenyl), oxadiazolyl phenyl (e.g. 3-(5-hydroxy-1,3,4-oxadiazol-2-yl) phenyl, 3-(5-hydroxy-1,2,4-oxadiazol-3-yl)phenyl), thiadiazolyl phenyl, (e.g. 3-(5-amino-1,3,4-thiadiazol-2-yl)phenyl), 3-(2,4-dioxo-1,3-thiazolidin-5-ylidene)methyl phenyl, 3-hydroxyethyl phenyl, 3-hydroxy methylphenyl, 2-hydroxy ethyl phenyl;
optionally substituted aryl amino sulfonyl, such as dimethylpyrimidin amino sulfonyl phenyl (e.g. 4-{[(4,6-dimethylpyrimidin-2-yl)amino]sulfonyl}phenyl), methyl isoxazol amino sulfonyl phenyl (e.g. 4-[(5-methylisoxazol-3-yl)amino]sulfonyl}phenyl), dimethoxy pyrimidin amino sulfonyl phenyl (e.g. 4{[(2,6-dimethoxypyrimidin-4-yl)amino]sulfonyl}phenyl), pyridinyl aminosulfonyl phenyl (e.g. 4-[(pyridin-2-ylamino)sulfonyl]phenyl), aminosulfonyl phenyl (e.g. 4-(aminosulfonyl)phenyl, 3-(aminosulfonyl)phenyl, 4[(methylamino)sulfonyl]phenyl, 4-[(dimethylamino)sulfonyl]phenyl, 3-[(butylamino) sulfonyl]phenyl, 4-(morpholin-4-yl-sulfonyl)phenyl);
optionally substituted aryl sulfonyl such as 3-[(2-hydroxyethane)sulfonyl]phenyl, 3-(methane sulfonyl)phenyl, 2-(methane sulfonyl)phenyl; 4-[(dimethylamino) sulfonyl] phenyl;
optionally substituted fused phenyl such as benzofuran-5-yl, 2,3-dihydro-benzofuran-5-yl, 1,1-dioxo-benzo[b]thiophen-6-yl; optionally substituted aryl aminocarbonyl e.g. 3-hydroxamic acid phenyl, 3-(aminocarbonyl)phenyl, 4-[N-(3-amino-propionic acid methyl ester)carbonyl]phenyl, 4-[N-(amino-acetic acid methyl ester)carbonyl]phenyl, 4-[N-(3-amino-propionic acid)carbonyl]phenyl, 4-[N-(amino-acetic acid)carbonyl]phenyl;
optionally substituted aryl $C_1$-$C_6$-alkyl carboxy, including 4-(acetic acid)phenyl, 3-(3-propionic acid)phenyl;
optionally substituted aryl $C_1$-$C_6$-alkyl acyl e.g. 4-(acetic acid methyl ester)phenyl, 4-(3-propionic acid methyl ester) phenyl, 3-(acetic acid methyl ester)phenyl, 3-(3-propionic acid methyl ester)phenyl;
optionally substituted heteroaryl, including optionally substituted pyridin such as pyridin (e.g. 2-pyridin, 3-pyridin, 4-pyridin), methoxy pyridine (e.g. 6-methoxy pyridine-3-yl), chloro pyridine (e.g. 6-chloropyridin-3-yl, 2-chloropyridin-3-yl, 2-chloropyridin-4-yl), fluoro pyridine (e.g. 2-fluoropyridin-3-yl, 6-fluoropyridin-3-yl), cyano pyridine (e.g. 6-cyanopyridin-3-yl), acetamide pyridine (e.g. 6-acetamide pyridin-3-yl), optionally substituted fused pyridine such as quinolin-3-yl, quinolin-5-yl, quinolin-6-yl;
optionally substituted $C_3$-$C_8$-cycloalkyl, including optionally substituted cyclohexyl (e.g. 2-(hydroxymethyl)cyclohexyl, cyclohexyl), cyclopentyl, cyclopropyl, cyclobutyl, indan-2-yl; optionally substituted heterocycloalkyl;
optionally substituted $C_1$-$C_6$-alkyl aryl, including benzyl, 2-phenyl ethyl, 2-(4-hydroxyphenyl)ethyl and 2-hydroxy-2-phenyl ethyl;
optionally substituted $C_1$-$C_6$-alkyl heteroaryl, including pyridine-3-yl-methyl, pyridine-4-yl-methyl, 2-(1H-tetrazol-5-yl) ethyl, 2-(2-hydroxy-1,3,4-oxadiazol-5-yl)ethyl, 3-(2-hydroxy-1,3,4-oxadiazol-5-yl)propyl and 3-(1H-imidazol-1-yl) propyl;
optionally substituted $C_1$-$C_6$-alkyl $C_3$-$C_8$-cycloalkyl, including cyclopropyl methyl;
optionally substituted $C_1$-$C_6$-alkyl heterocycloalkyl, including tetrahydrofuran methyl (e.g. tetrahydrofuran-2-yl-methyl), 3-(morpholin-4-yl)propyl 2-(morpholin-4-yl)ethyl, 2-(pyrrolidin-1-yl)ethyl, 2-(piperidin-1-yl)ethyl, 3-(pyrrolidin-1-yl)propyl, 2-(1-methyl-pyrrolidin-2-yl)ethyl, (1-ethyl-pyrrolidin-2-yl)methyl, 3-(1-pyrrolidin-2-one)propyl;
or alternatively $R^5$ and $R^6$, together with the carbon atoms they are linked to, form an optionally substituted 5-8-membered saturated ring or aromatic ring containing optionally one or more heteroatoms selected from O, N and S, including optionally substituted piperidin, such as piperidin, hydroxyethyl piperidin (e.g. 2-hydroxyethyl piperidin-1-yl), piperidin carboxylate (e.g. 3-methyl carboxylate piperidin-1-yl), optionally substituted pyrrolidin, including pyrrolidin, hydroxypyrrolidin (e.g. 3-hydroxypyrrolidin-1-yl), piperazine (e.g. 4-methylpiperazin-1-yl) and morpholine (e.g. morpholin-4-yl);
$R^7$ is selected from optionally substituted $C_1$-$C_6$-alkyl; optionally substituted $C_2$-$C_6$-alkenyl; optionally substituted $C_2$-$C_6$-alkynyl; and $NR^{10}R^{11}$ wherein $R^{10}$ and $R^{11}$ are independently selected from H, optionally substituted $C_1$-$C_6$-alkyl, optionally substituted $C_2$-$C_6$-alkenyl and optionally substituted $C_2$-$C_6$-alkynyl; or alternatively $R^{10}$ and $R^{11}$, together with the carbon atoms they are linked to, form an optionally substituted 5-8-membered saturated, partially unsaturated or aromatic ring containing optionally one or more heteroatoms selected from O, N and S;
X is selected from O and S;
as well as isomers and mixtures of these for use as a medicament.

In a specific embodiment, the invention provides thiazole derivatives of Formula (I) wherein $R^1$ is $-NR^5R^6$.

In another specific embodiment, the invention provides thiazole derivatives of Formula (I) wherein $R^2$ is H.

In another specific embodiment, the invention provides thiazole derivatives of Formula (I) wherein $R^3$ is methyl.

In another specific embodiment, the invention provides thiazole derivatives wherein $R^4$ is selected from optionally substituted $C_1$-$C_6$-alkyl, optionally substituted $C_2$-$C_6$-alkenyl and optionally substituted $C_2$-$C_6$-alkynyl.

In another specific embodiment, the invention provides thiazole derivatives $R^4$ is $-NR^8R^9$ wherein $R^8$ and $R^9$ are independently selected from H, optionally substituted $C_1$-$C_6$-alkyl, optionally substituted $C_2$-$C_6$-alkenyl; optionally substituted $C_2$-$C_6$-alkynyl and optionally substituted $C_1$-$C_6$-alkyl alkoxycarbonyl.

In another specific embodiment, the invention provides thiazole derivatives wherein $R^5$ is H and $R^6$ is selected from optionally substituted —$C_1$-$C_6$-alkyl, optionally substituted $C_2$-$C_6$-alkenyl, optionally substituted $C_2$-$C_6$-alkynyl, optionally substituted $C_1$-$C_6$-alkyl alkoxy, optionally substituted $C_1$-$C_6$-alkyl acyl, optionally substituted $C_1$-$C_6$-alkyl carboxy, optionally substituted $C_1$-$C_6$-alkyl acylamino, optionally substituted $C_1$-$C_6$-alkyl amino, optionally substituted $C_1$-$C_6$-alkyl aminocarbonyl, optionally substituted $C_1$-$C_6$-alkyl alkoxycarbonyl, optionally substituted $C_1$-$C_6$-alkyl $C_3$-$C_8$-cycloalkyl and optionally substituted $C_1$-$C_6$-alkyl heterocycloalkyl.

In another specific embodiment, the invention provides thiazole derivatives wherein wherein $R^5$ is H and $R^6$ is selected from optionally substituted $C_1$-$C_6$-alkyl aryl and optionally substituted $C_1$-$C_6$-alkyl heteroaryl.

In another specific embodiment, the invention provides thiazole derivatives wherein wherein $R^5$ is H and $R^6$ is selected from optionally substituted aryl $C_1$-$C_6$-alkyl and optionally substituted heteroaryl $C_1$-$C_6$-alkyl.

In another specific embodiment, the invention provides thiazole derivatives wherein $R^5$ is H and $R^6$ is selected from optionally substituted aryl and optionally substituted heteroaryl.

In another specific embodiment, the invention provides thiazole derivatives wherein $R^5$ is H and $R^6$ is selected from optionally substituted phenyl.

In another specific embodiment, the invention provides thiazole derivatives wherein $R^5$ is H and $R^6$ is selected from optionally substituted pyridine.

In another specific embodiment, the invention provides thiazole derivatives wherein $R^5$ is H and $R^6$ is selected from optionally substituted heterocycloalkyl and optionally substituted $C_3$-$C_8$-cycloalkyl.

In another specific embodiment, the invention provides thiazole derivatives wherein $R^5$ and $R^6$, together with the carbon atoms they are linked to, form an optionally substituted 5-8-membered saturated or aromatic ring containing optionally one or more heteroatoms selected from O, N and S.

In another specific embodiment, the invention provides thiazole derivatives wherein $R^5$ and $R^6$, together with the carbon atoms they are linked to, form an optionally substituted 5-8-membered saturated ring optionally additionally containing an oxygen atom.

In another specific embodiment, the invention provides bis-thiazole derivatives, i.e. thiazole derivatives of Formula (I) wherein X is S.

In a preferred embodiment, the invention provides thiazole derivatives of Formula a) wherein $R^1$ is —$NR^5R^6$; $R^2$ is H; $R^3$ is methyl; $R^4$ is selected from optionally substituted $C_1$-$C_6$-alkyl, optionally substituted $C_2$-$C_6$-alkenyl; optionally substituted $C_2$-$C_6$-alkynyl and —$NR^8R^9$ wherein $R^8$ and $R^9$ are independently selected from H, optionally substituted $C_1$-$C_6$-alkyl, optionally substituted $C_2$-$C_6$-alkenyl; optionally substituted $C_2$-$C_6$-alkynyl and optionally substituted $C_1$-$C_6$-alkyl alkoxycarbonyl; $R^5$ is H and $R^6$ is selected from optionally substituted $C_1$-$C_6$-alkyl, optionally substituted $C_2$-$C_6$-alkenyl, optionally substituted $C_2$-$C_6$-alkynyl, optionally substituted $C_1$-$C_6$-alkyl alkoxy, optionally substituted $C_1$-$C_6$-alkyl acyl, optionally substituted $C_1$-$C_6$-alkyl carboxy, optionally substituted $C_1$-$C_6$-alkyl acylamino, optionally substituted $C_1$-$C_6$-alkyl amino, optionally substituted $C_1$-$C_6$-alkyl aminocarbonyl, optionally substituted $C_1$-$C_6$-alkyl alkoxycarbonyl, optionally substituted $C_2$-$C_6$-alkyl $C_3$-$C_8$-cycloalkyl and optionally substituted $C_1$-$C_6$-alkyl heterocycloalkyl and X is S.

In another preferred embodiment, the invention provides thiazole derivatives of Formula (I) wherein $R^1$ is —$NR^5R^6$; $R^2$ is H; $R^3$ is methyl; $R^4$ is selected from optionally substituted $C_1$-$C_6$-alkyl, optionally substituted $C_2$-$C_6$-alkenyl; optionally substituted $C_2$-$C_6$-alkynyl and —$NR^8R^9$ wherein $R^8$ and $R^9$ are independently selected from H, optionally substituted $C_1$-$C_6$-alkyl, optionally substituted $C_2$-$C_6$-alkenyl; optionally substituted $C_2$-$C_6$-alynyl and optionally substituted $C_1$-$C_6$-alkyl alkoxycarbonyl; $R^5$ is H and $R^6$ is selected from optionally substituted $C_1$-$C_6$-alkyl aryl and optionally substituted $C_1$-$C_6$-alkyl heteroaryl and X is S.

In another preferred embodiment, the invention provides thiazole derivatives of Formula (I) wherein $R^1$ is —$NR^{56}$; $R^2$ is H; $R^3$ is methyl; $R^4$ is selected from optionally substituted $C_1$-$C_6$-alkyl, optionally substituted $C_2$-$C_6$-alkenyl; optionally substituted $C_2$-$C_6$-alkynyl and —$NR^8R^9$ wherein $R^8$ and $R^9$ are independently selected from H, optionally substituted $C_1$-$C_6$-alkyl, optionally substituted $C_2$-$C_6$-alkenyl; optionally substituted $C_2$-$C_6$-alkynyl and optionally substituted $C_1$-$C_6$-alkyl alkoxycarbonyl; $R^5$ is H and $R^6$ is selected from in another specific embodiment, the invention provides thiazole derivatives wherein $R^5$ is H and $R^6$ is selected from optionally substituted aryl, including optionally substituted phenyl and optionally substituted heteroaryl, including optionally substituted pyridine and X is S.

In another preferred embodiment, the invention provides thiazole derivatives of Formula (I) wherein $R^1$ is —$NR^5R^6$; $R^2$ is H; $R^3$ is methyl; $R^4$ is selected from optionally substituted $C_1$-$C_6$-alkyl, optionally substituted $C_2$-$C_6$-alkenyl; optionally substituted $C_2$-$C_6$-alkynyl and —$NR^8R^9$ wherein $R^8$ and $R^9$ are independently selected from H, optionally substituted $C_1$-$C_6$-alkyl, optionally substituted $C_2$-$C_6$-alkenyl; optionally substituted $C_2$-$C_6$-alkynyl and optionally substituted $C_1$-$C_6$-alkyl alkoxycarbonyl; $R^5$ is H and $R^6$ is selected from optionally substituted heterocycloalkyl and optionally substituted $C_3$-$C_8$-cycloalkyl and X is S.

In another preferred embodiment, the invention provides thiazole derivatives of Formula (I) wherein $R^1$ is —$NR^5R^6$; $R^2$ is H; $R^3$ is methyl; $R^4$ is selected from optionally substituted $C_1$-$C_6$-alkyl, optionally substituted $C_2$-$C_6$-alkenyl; optionally substituted $C_2$-$C_6$-alkynyl and —$NR^8R^9$ wherein $R^8$ and $R^9$ are independently selected from H, optionally substituted $C_1$-$C_6$-alkyl, optionally substituted $C_2$-$C_6$-alkenyl; optionally substituted $C_2$-$C_6$-alkynyl and optionally substituted $C_1$-$C_6$-alkyl alkoxycarbonyl; $R^5$ and $R^6$, together with the carbon atoms they are linked to, form an optionally substituted 5-8-membered saturated or aromatic ring containing optionally one or more heteroatoms selected from O, N and S, and X is S.

In another embodiment, the invention provides a use of a thiazole derivative of Formula (I) wherein $R^1$ is selected from —$NR^5R^6$ and —$SO_2R^7$, preferably —$NR^5R^6$;

$R^2$, $R^3$ and $R^5$ are selected independently from H, optionally substituted $C_1$-$C_6$-alkyl, including methyl, optionally substituted $C_2$-$C_6$-alkenyl and optionally substituted $C_2$-$C_6$-alkynyl;

and —$NR^8R^9$ wherein $R^8$ and $R^9$ are independently selected from H, optionally substituted $C_1$-$C_6$-alkyl, optionally substituted $C_2$-$C_6$-alkenyl; optionally substituted $C_2$-$C_6$-alkynyl; optionally substituted $C_1$-$C_6$-alkyl alkoxy carbonyl, including ethyl propanoate; optionally substituted $C_1$-$C_6$-alkyl acyloxy, including amino-propionic acid ethyl ester;

$R^6$ is selected from H, optionally substituted $C_1$-$C_6$-alkyl, including t-butyl, 2-cyanoethyl, cyanomethyl, 3-hydroxy propyl, 2-hydroxy ethyl, 4-hydroxy butyl, 2-isobutyl, 2,2-dimethyl propyl and 1-methyl propyl;

optionally substituted $C_2$-$C_6$-alkenyl, including allyl and 2-methylprop-2-en-1-yl; optionally substituted $C_2$-$C_6$-alkynyl;

optionally substituted $C_1$-$C_6$-alkyl alkoxy, including methoxyethyl, e.g. 2-methoxy ethyl, 2,2-diethoxy-ethyl and 3,3-diethoxy-propyl;

optionally substituted $C_1$-$C_6$-alkyl acyl, including methylene phenyl ketone;

optionally substituted $C_1$-$C_6$-alkyl carboxy, including propanoic acid, butanoic acid;

optionally substituted $C_1$-$C_6$-alkyl acylamino, including ethyl-2-acetamide;

optionally substituted $C_1$-$C_6$-alkyl amino, including 2-dimethyl amino ethyl, 3-dimethylamino propyl;

optionally substituted $C_1$-$C_6$-alkyl aminocarbonyl, including 3-propionamide;

optionally substituted $C_1$-$C_6$-alkyl alkoxycarbonyl including 4-butyric acid methyl ester;

optionally substituted aryl, including optionally substituted phenyl such as phenyl, methoxyphenyl (e.g. 2,5-dimethoxy phenyl, 4-methoxy phenyl, 2-methoxy phenyl, 3-methoxy phenyl), acetylamino phenyl (e.g. 4-acetylamino phenyl, 2-acetylamino phenyl), aminophenyl, dimethylamino phenyl (e.g. 4-dimethyl amino phenyl), nitro phenyl (e.g. 3-nitro phenyl, 4-nitrophenyl, 2-nitrophenyl), ethyl phenyl (e.g. 2-ethyl phenyl), methylphenyl (e.g. 2-methylphenyl) bromophenyl (e.g. 4-bromophenyl), chlorophenyl (e.g. 4-chloro phenyl, 2-chlorophenyl, 3-chlorophenyl), hydroxyphenyl (e.g. 3-hydroxyphenyl, 4-hydroxy phenyl, 2-hydroxy phenyl), cyano phenyl (e.g. 4-cyano phenyl, 3-cyano phenyl), 3-(1-hydroxyethyl)phenyl, hydroxamic acid phenyl, 3-(N-hydroxycarbamimidoyl)-phenyl-4-yl, acetyl phenyl (e.g. 3-acetyl phenyl, 2-acetyl phenyl), benzyl piperazine carbonyl phenyl (e.g. 4-benzylpiperazin-1-yl-carbonylphenyl), phenyl optionally substituted with heteroaryl such as oxazolyl phenyl (e.g. 3-(1,3-oxazol-5-yl)phenyl), tetrazolyl phenyl (e.g. 3-(1H-tetrazol-5-yl)phenyl, 4-(1H-tetrazol-5-yl)phenyl), oxadiazolyl phenyl (e.g. 3-(5-hydroxy-1,3,4-oxadiazol-2-yl) phenyl, 3-(5-hydroxy-1,2,4-oxadiazol-3-yl)phenyl), thiadiazolyl phenyl (e.g. 3-(5-amino-1,3,4-thiadiazol-2-yl)phenyl), 3-(2,4-dioxo-1,3-thiazolidin-5-ylidene)methyl phenyl, 3-hydroxyethyl phenyl, 3-hydroxy methylphenyl, 2-hydroxy ethyl phenyl, optionally substituted aryl amino sulfonyl, such as dimethylpyrimidin amino sulfonyl phenyl (e.g. 4-{[(4,6-dimethylpyrimidin-2-yl)amino]sulfonyl}phenyl), methyl isoxazol amino sulfonyl phenyl (e.g. 4-{[(5-methyl-isoxazol-3-yl)amino]sulfonyl}phenyl), dimethoxy pyrimidin amino sulfonyl phenyl (e.g. 4-{[(2,6-dimethoxypyrimidin-4-yl) amino]sulfonyl}phenyl), pyridinyl aminosulfonyl phenyl (e.g. 4-[(pyridin-2-ylamino)sulfonyl]phenyl), aminosulfonyl phenyl (e.g. 4-(aminosulfonyl)phenyl, 3-(aminosulfonyl) phenyl, 4-[(methylamino)sulfonyl]phenyl, 4-[(dimethylamino)sulfonyl]phenyl, 3-[(butylamino)sulfonyl]phenyl, 4-(morpholin-4-yl-sulfonyl)phenyl), optionally substituted aryl sulfonyl such as 3-[(2-hydroxyethane)sulfonyl]phenyl, 3-(methane sulfonyl)phenyl, 2-(methane sulfonyl)phenyl; optionally substituted fused phenyl such as benzofuran-5-yl, 2,3-dihydro-benzofuran-5-yl, 1,1-dioxo-benzo[b]thiophen-6-yl; optionally substituted aryl aminocarbonyl e.g. 3-hydroxamic acid phenyl, 3-(aminocarbonyl)phenyl, 4-[N-(3-amino-propionic acid methyl ester)carbonyl]phenyl, 4-[N-(amino-acetic acid methyl ester)carbonyl]phenyl, 4-[N-(3-amino-propionic acid)carbonyl]phenyl, 4-[N-(amino-acetic acid)carbonyl]phenyl; optionally substituted aryl $C_1$-$C_6$-alkyl carboxy, including 4-(acetic acid)phenyl, 3-(3-propionic acid)phenyl;

optionally substituted aryl $C_1$-$C_6$-alkyl acyl e.g. 4-(acetic acid methyl ester)phenyl, 4-(3-propionic acid methyl ester) phenyl, 3-(acetic acid methyl ester)phenyl, 3-(3-propionic acid methyl ester)phenyl;

optionally substituted heteroaryl, including optionally substituted pyridin such as pyridin (e.g. 2-pyridin, 3-pyridin, 4-pyridin), methoxy pyridine (e.g. 6-methoxy pyridine-3-yl), chloro pyridine (e.g. 6-chloropyridin-3-yl, 2-chloropyridin-3-yl, 2-chloropyridin-4-yl), fluoro pyridine (e.g. 2-fluoropyridin-3-yl, 6-fluoropyridin-3-yl), cyano pyridine (e.g. 6-cyanopyridin-3-yl), acetamide pyridine (e.g. 6-acetamide pyridin-3-yl), optionally substituted fused pyridine such as quinolin-3-yl, quinolin-5-yl, quinolin-6-yl; optionally substituted $C_3$-$C_8$-cycloalkyl, including optionally substituted cyclohexyl (e.g. 2-(hydroxymethyl)cyclohexyl, cyclohexyl), cyclopentyl, cyclopropyl, cyclobutyl, indan-2-yl;

optionally substituted heterocycloalkyl;

optionally substituted $C_1$-$C_6$-alkyl aryl, including benzyl, 2-phenyl ethyl, 2-(4-hydroxyphenyl)ethyl and 2-hydroxy-2-phenyl ethyl;

optionally substituted $C_1$-$C_6$-alkyl heteroaryl, including pyridine-3-yl-methyl, pyridine-4-yl-methyl, 2-(1H-tetrazol-5-yl) ethyl, 2-(2-hydroxy-1,3,4-oxadiazol-5-yl)ethyl, 3-(2-hydroxy-1,3,4-oxadiazol-5-yl)propyl and 3-(1H-imidazol-1-yl) propyl;

optionally substituted $C_1$-$C_6$-alkyl $C_3$-$C_8$-cycloalkyl, including cyclopropyl methyl;

optionally substituted $C_1$-$C_6$-alkyl heterocycloalkyl, including tetrahydrofuran methyl (e.g. tetrahydrofuran-2-yl-methyl), 3-(morpholin-4-yl)propyl 2-(morpholin-4-yl)ethyl, 2-(pyrrolidin-1-yl)ethyl, 2-(piperidin-1-yl)ethyl, 3-(pyrrolidin-1-yl)propyl, 2-(1-methyl-pyrrolidin-2-yl)ethyl, (1-ethyl-pyrrolidin-2-yl)methyl, 3-(1-pyrrolidin-2-one)propyl;

or alternatively $R^5$ and $R^6$, together with the carbon atoms they are linked to, form an optionally substituted 5-8-membered saturated ring or aromatic ring containing optionally one or more heteroatoms selected from O, N and S, including optionally substituted piperidin, such as piperidin, hydroxyethyl piperidin (e.g. 2-hydroxyethyl piperidin-1-yl), piperidin carboxylate (e.g. 3-methyl carboxylate piperidin-1-yl), optionally substituted pyrrolidin, including pyrrolidin, hydroxypyrrolidin (e.g. 3-hydroxypyrrolidin-1-yl), piperazine (e.g. 4-methylpiperazin-1-yl) and morpholine (e.g. morpholin-4-yl);

$R^7$ is selected from optionally substituted $C_1$-$C_6$-alkyl; optionally substituted $C_2$-$C_6$-alkenyl; optionally substituted $C_2$-$C_6$-alkynyl; and $NR^{10}R^{11}$ wherein $R^{10}$ and $R^{11}$ are independently selected from H, optionally substituted $C_1$-$C_6$-alkyl, optionally substituted $C_2$-$C_6$-alkenyl and optionally substituted $C_2$-$C_6$-alkynyl; or alternatively $R^{10}$ and $R^{13}$, together with the carbon atoms they are linked to, form an optionally substituted 5-8-membered saturated, partially unsaturated or aromatic ring containing optionally one or more heteroatoms selected from O, N and S;

X is selected from O and S;

as well as isomers and mixtures of these for the preparation of a medicament for the prophylaxis and/or treatment of autoimmune disorders and/or inflammatory diseases, cardiovascular diseases, neurodegenerative diseases, bacterial or viral infections, kidney diseases, platelet aggregation, cancer, transplantation, graft rejection or lung injuries.

In another embodiment, the invention provides thiazole derivatives of Formula (I) wherein $R^1$ is selected from $-NR^5R^6$ and $-SO_2R^7$, preferably $-NR^5R^6$;

$R^2$, $R^3$ and $R^5$ are selected independently from H, optionally substituted $C_1$-$C_6$-alkyl, including methyl, optionally substituted $C_2$-$C_6$-alkenyl and optionally substituted $C_2$-$C_6$-alkynyl;

$R^4$ is selected from H; optionally substituted $C_1$-$C_6$-alkyl, including methyl and ethyl; optionally substituted $C_2$-$C_6$- alkenyl; optionally substituted $C_2$-$C_6$-alkynyl; and —$NR^8R^9$ wherein $R^8$ and $R^9$ are independently selected from H, optionally substituted $C_1$-$C_6$-alkyl, optionally substituted $C_2$-$C_6$-alkenyl; optionally substituted $C_2$-$C_6$-alkynyl; optionally substituted $C_1$-$C_6$-alkyl alkoxy carbonyl, including ethyl propanoate; optionally substituted $C_1$-$C_6$-alkyl acyloxy, including amino-propionic acid ethyl ester;

$R^6$ is selected from optionally substituted $C_1$-$C_6$-alkyl, including t-butyl, 2-cyanoethyl, 2-cyanomethyl, 3-hydroxy propyl, 2-hydroxy ethyl, 4-hydroxy butyl, 2-methyl propyl, 2,2-dimethyl propyl and 1-methyl propyl;

optionally substituted $C_2$-$C_6$-alkynyl;

optionally substituted $C_1$-$C_6$-alkyl alkoxy, including methoxyethyl, e.g. 2-methoxy ethyl and 3,3-diethoxy-propyl, 2,2-diethoxy-ethyl;

optionally substituted $C_1$-$C_6$-alkyl acyl, including methylene phenyl ketone;

optionally substituted $C_1$-$C_6$-alkyl carboxy, including propanoic acid, butanoic acid;

optionally substituted $C_1$-$C_6$-alkyl acylamino, including ethyl-2-acetamide;

optionally substituted $C_1$-$C_6$-alkyl amino, including 2-dimethyl amino ethyl, 3-dimethylamino propyl;

optionally substituted $C_1$-$C_6$-alkyl aminocarbonyl, including 3-propionamide;

optionally substituted $C_1$-$C_6$-alkyl alkoxycarbonyl including 4-butyric acid methyl ester, optionally substituted fused phenyl such as benzofuran-5-yl, 2,3-dihydro-benzofuran-5-yl, 1,1-dioxo-benzo[b]thiophen-6-yl;

optionally substituted aryl aminocarbonyl e.g. 3-hydroxamic acid phenyl, 3-(aminocarbonyl)phenyl, 4-[N-(3-amino-propionic acid methyl ester)carbonyl]phenyl, 4-[N-(amino-acetic acid methyl ester)carbonyl]phenyl, 4-[N-(3-amino-propionic acid) carbonyl]phenyl, 4-[N-(amino-acetic acid) carbonyl]phenyl;

optionally substituted aryl $C_1$-$C_6$-alkyl carboxy, including 4-(acetic acid)phenyl, 3-(3-propionic acid)phenyl;

optionally substituted aryl $C_1$-$C_6$-alkyl acyl e.g. 4-(acetic acid methyl ester)phenyl, 4-(3-propionic acid methyl ester) phenyl, 3-(acetic acid methyl ester)phenyl, 3-(3-propionic acid methyl ester)phenyl;

optionally substituted pyridin such as pyridin (e.g. 2-pyridin, 3-pyridin, 4-pyridin), methoxy pyridine (e.g. 6-methoxy pyridine-3-yl), chloro pyridine (e.g. 6-chloropyridin-3-yl, 2-chloropyridin-3-yl, 2-chloropyridin-4-yl), fluoro pyridine (e.g. 2-fluoropyridin-3-yl, 6-fluoropyridin-3-yl), cyano pyridine (e.g. 6-cyanopyridin-3-yl), acetamide pyridine (e.g. 6-acetamide pyridin-3-yl), optionally substituted fused pyridine such as quinolin-3-yl, quiolin-5-yl, quinolin-6-yl;

optionally substituted $C_3$-$C_8$-cycloalkyl, including optionally substituted cyclohexyl (e.g. 2-(hydroxymethyl)cyclohexyl, cyclohexyl), cyclopentyl, cyclopropyl, cyclobutyl, indan-2-yl;

optionally substituted $C_1$-$C_6$-alkyl aryl, including benzyl, 2-phenyl ethyl, 2-(4-hydroxyphenyl)ethyl and 2-hydroxy-2-phenyl ethyl;

optionally substituted $C_1$-$C_6$-alkyl $C_3$-$C_8$-cycloalkyl, including cyclopropyl methyl;

optionally substituted $C_1$-$C_6$-alkyl heterocycloalkyl, including tetrahydrofuran methyl (e.g. tetrahydrofuran-2-yl-methyl), 3-(morpholin-4-yl)propyl 2-(morpholin-4-yl)ethyl, 2-(pyrrolidin-1-yl)ethyl, 2-(piperidin-1-yl)ethyl, 3-(pyrrolidin-1-yl)propyl, 2-(1-methyl-pyrrolidin-2-yl)ethyl, (1-ethyl-pyrrolidin-2-yl)methyl, 3-(1-pyrrolidin-2-one)propyl;

or alternatively $R^5$ and $R^6$, together with the carbon atoms they are linked to, form an optionally substituted 5-8-membered saturated ring or aromatic ring containing optionally one or more heteroatoms selected from O, N and S, including optionally substituted piperidin, such as piperidin, hydroxyethyl piperidin (e.g. 2-hydroxyethyl piperidin-1-yl), piperidin carboxylate (e.g. 3-methyl carboxylate piperidin-1-yl), optionally substituted pyrrolidin, including pyrrolidin, hydroxypyrrolidin (e.g. 3-hydroxypyrrolidin-1-yl), piperazine (e.g. 4-methylpiperazin-1-yl) and morpholine (e.g. morpholin-4-yl);

$R^7$ is selected from optionally substituted $C_1$-$C_6$-alkyl; optionally substituted $C_2$-$C_6$-alkenyl; optionally substituted $C_2$-$C_6$-alkynyl; and $NR^{10}R^{11}$ wherein $R^{10}$ and $R^{11}$ are independently selected from H, optionally substituted $C_1$-$C_6$-alkyl, optionally substituted $C_2$-$C_6$-alkenyl and optionally substituted $C_2$-$C_6$-alkynyl; or alternatively $R^{10}$ and $R^{11}$, together with the carbon atoms they are linked to, form an optionally substituted 5-8-membered saturated, partially unsaturated or aromatic ring containing optionally one or more heteroatoms selected from O, N and S;

X is selected from O and S;

Compounds of the present invention include in particular those of the group consisting of:

Example No Name 1 3-{[2'-(acetylamino)-4'-methyl-4,5'-bi-1,3-thiazol-2-yl] amino}benzoic acid;

2 4-{[2'-(acetylamino)-4'-methyl-4,5'-bi-1,3-thiazol-2-yl] amino}benzoic acid;

3 N-[2-(benzylamino)-4'-methyl-4,5'-bi-1,3-thiazol-2'-yl] acetamide;

4 N-{4'-methyl-2-[(2-phenylethyl)amino]-4,5'-bi-1,3-thiazol-2'-yl}acetamide;

5 N-(4'-methyl-2-piperidin-1-yl-4,5'-bi-1,3-thiazol-2'-yl)acetamide;

6 N-[2-(allylamino)-4'-methyl-4,5'-bi-1,3-thiazol-2'-yl]acetamide;

7 N-[4'-methyl-2-(pyridin-3-ylamino)-4,5'-bi-1,3-thiazol-2'-yl]acetamide;

8 N-[4'-methyl-2-(pyridin-2-ylamino)-4,5'-bi-1,3-thiazol-2'-yl]acetamide;

9 N-{2-[(4-methoxyphenyl)amino]-4'-methyl-4,5'-bi-1,3-thiazol-2'-yl}acetamide;

10 N-{2-[(4-hydroxyphenyl)amino]-4'-methyl-4,5'-bi-1,3-thiazol-2'-yl}acetamide;

11 N-{4'-methyl-2-[(4-nitrophenyl)amino]-4,5'-bi-1,3-thiazol-2'-yl}acetamide;

12 4-{[2'-(acetylamino)-4'-methyl-4,5'-bi-1,3-thiazol-2-yl] amino}benzamide;

13 N-[2-({4-[(4-benzylpiperazin-1-yl)carbonyl] phenyl}amino)-4'-methyl-4,5'-bi-1,3-thiazol-2'-yl]acetamide;

14 N-(2-amino-4'-methyl-4,5'-bi-1,3-thiazol-2'-yl)acetamide;

15 N-(2-anilino-4'-methyl-4,5'-bi-1,3-thiazol-2'-yl)acetamide;

16 N-(4'-methyl-2-morpholin-4-yl-4,5'-bi-1,3-thiazol-2'-yl) acetamide;

17 N-[4'-methyl-2-(4-methylpiperazin-1-yl)-4,5'-bi-1,3-thiazol-2'-yl]acetamide

18 Methyl 1-[2'-(acetylamino)-4'-methyl-4,5'-bi-1,3-thiazol-2-yl]piperidine-3-carboxylate;

19 N-{2-[4-(2-hydroxyethyl)piperidin-1-yl]-4'-methyl-4,5'-bi-1,3-thiazol-2'-yl}acetamide;

20 N-(4'-methyl-2-pyrrolidin-1-yl-4,5'-bi-1,3-thiazol-2'-yl) acetamide;

21 N-[2-(3-hydroxypyrrolidin-1-yl)-4'-methyl-4,5'-bi-1,3-thiazol-2'-yl]acetamide;

22 N-[2-(tert-butylamino)-4'-methyl-4,5'-bi-1,3-thiazol-2'-yl]acetamide;
23 N-{2-[(6-methoxypyridin-3-yl)amino]-4'-methyl-4,5'-bi-1,3-thiazol-2'-yl}acetamide;
24 N-{2-[(6-chloropyridin-3-yl)amino]-4'-methyl-4,5'-bi-1,3-thiazol-2'-yl}acetamide;
25 N-{2-[(4-cyanophenyl)amino]-4'-methyl-4,5'-bi-1,3-thiazol-2'-yl}acetamide;
26 N-{2-[(4-chlorophenyl)amino]-4'-methyl-4,5'-bi-1,3-thiazol-2'-yl}acetamide:
27 N-{2-[(2-chlorophenyl)amino]-4'-methyl-4,5'-bi-1,3-thiazol-2'-yl}acetamide;
28 N-{2-[(2-methoxyphenyl)amino]-4'-methyl-4,5'-bi-1,3-thiazol-2'-yl}acetamide;
29 N-{2-[(3-chlorophenyl)amino]-4'-methyl-4,5'-bi-1,3-thiazol-2'-yl}acetamide;
30 N-{2-[(3-hydroxyphenyl)amino]-4'-methyl-4,5'-bi-1,3-thiazol-2'-yl}acetamide
31 N-{4'-methyl-2-[(2-morpholin-4-ylethyl)amino]-4,5'-bi-1,3-thiazol-2'-yl}acetamide;
32 N-{4'-methyl-2-[(2-piperidin-1-ylethyl)amino]-4,5'-bi-1,3-thiazol-2'-yl}acetamide;
33 N-{2-[(2-methoxyethyl)amino]-4'-methyl-4,5'-bi-1,3-thiazol-2'-yl}acetamide;
34 N-[2-(cyclohexylamino)-4'-methyl-4,5'-bi-1,3-thiazol-2'-yl]acetamide;
35 N-{4'-methyl-2-[(3-morpholin-4-ylpropyl)amino]-4,5'-bi-1,3-thiazol-2'-yl}acetamide;
36 N-{4'-methyl-2-[(tetrahydrofuran-2-ylmethyl)amino]-4,5'-bi-1,3-thiazol-2'-yl}acetamide;
37 N-{2-[(2-hydroxy-2-phenylethyl)amino]-4'-methyl-4,5'-bi-1,3-thiazol-2'-yl}acetamide;
38 N-[2-(1-benzofuran-5-ylamino)-4'-methyl-4,5'-bi-1,3-thiazol-2'-yl]acetamide;
39 N-{2-[(3-cyanophenyl)amino]-4'-methyl-4,5'-bi-1,3-thiazol-2'-yl}acetamide;
40 [4'-methyl-2-(pyridin-3-ylamino)-4,5'-bi-1,3-thiazol-2'-yl]formamide;
41 Ethyl N-({[2-(allylamino)-4'-methyl-4,5'-bi-1,3-thiazol-2'-yl]amino}carbonyl)-beta-alaninate;
42 N-{4-methyl-5-[2-(pyridin-3-ylamino)-1,3-thiazol-4-yl]-1,3-oxazol-2-yl}acetamide;
43 N-{2-[(2-fluoropyridin-3-yl)amino]-4'-methyl-4,5'-bi-1,3-thiazol-2'-yl}acetamide;
44 N-{2-[(2-cyanoethyl)amino]-4'-methyl-4,5'-bi-1,3-thiazol-2'-yl}acetamide;
45 N-{2-[(3,3-diethoxypropyl)amino]-4'-methyl-4,5'-bi-1,3-thiazol-2'-yl}acetamide;
46 N-{2-[(2,2-diethoxyethyl)amino]-4'-methyl-4,5'-bi-1,3-thiazol-2'-yl}acetamide;
47 N-{4'-methyl-2-[(2-oxo-2-phenylethyl)amino]-4,5'-bi-1,3-thiazol-2'-yl}acetamide;
48 N-{2-[(2-chloropyridin-3-yl)amino]-4'-methyl-4,5'-bi-1,3-thiazol-2'-yl}acetamide;
49 N-(4'-methyl-2-{[3-(1,3-oxazol-5-yl)phenyl]amino}-4,5'-bi-1,3-thiazol-2'-yl)acetamide;
50 N-(4'-methyl-2-{[3-(1H-tetrazol-5-yl)phenyl]amino}-4,5'-bi-1,3-thiazol-2'-yl)acetamide;
51 N-(4'-methyl-2-{[4-(H-tetrazol-5-yl)phenyl]amino}-4,5'-bi-1,3-thiazol-2'-yl)acetamide
52 N-{4'-Methyl-2-[2-(1H-tetrazol-5-yl)-ethylamino]-[4,5]bithiazolyl-2'-yl}-acetamide;
53 N-(2-{[3-(5-hydroxy-1,3,4-oxadiazol-2-yl)phenyl]amino}-4'-methyl-4,5'-bi-1,3-thiazol-2'-yl)acetamide;
54 N-(2-{[3-(5-amino-1,3,4-thiadiazol-2-yl)phenyl]amino}-4'-methyl-4,5'-bi-1,3-thiazol-2'-yl)acetamide;
55 N-[2'-(acetylamino)-4'-methyl-4,5'-bi-1,3-thiazol-2-yl]-beta-alanine;
56 5-(2-{[2'-(acetylamino)-4'-methyl-4,5'-bi-1,3-thiazol-2-yl]amino}ethyl)-1,3,4-oxadiazol-2-olate;
57 4-{[2'-(acetylamino)-4-methyl-4,5'-bi-1,3-thiazol-2-yl]amino}butanoic acid;
58 N-(2-{[3-(5-hydroxy-1,3,4-oxadiazol-2-yl)propyl]amino}-4'-methyl-4,5'-bi-1,3-thiazol-2'-yl)acetamide;
59 3-{[2'-(acetylamino)-4'-methyl-4,5'-bi-1,3-thiazol-2-yl]amino}-N-hydroxy benzamide;
60 3-{[2'-(acetylamino)-4'-methyl-4,5'-bi-1,3-thiazol-2-yl]amino}-N-hydroxy benzenecarboximidic acid;
61 N-(2-{[3-(5-hydroxy-1,2,4-oxadiazol-3-yl)phenyl]amino}-4'-methyl-4,5'-bi-1,3-thiazol-2'-yl)acetamide;
62 N-[2-({3-[(Z) (2,4-dioxo-1,3-thiazolidin-5-ylidene)methyl]phenyl}amino)-4'-methyl-4,5'-bi-1,3-thiazol-2'-yl]acetamide;
63 N-[4'-methyl-2-({4-[(pyridin-2-ylamino)sulfonyl]phenyl}amino)-4,5'-bi-1,3-thiazol-2'-yl]acetamide;
64 N-(2-{[2-(2-hydroxyethyl)phenyl]amino}-4'-methyl-4,5'-bi-1,3-thiazol-2'-yl)acetamide;
65 N-(2-{[3-(hydroxymethyl)phenyl]amino}-4'-methyl-4,5'-bi-1,3-thiazol-2'-yl)acetamide;
66 N-(2-{[4-(2-hydroxyethyl)phenyl]amino}-4'-methyl-4,5'-bi-1,3-thiazol-2'-yl)acetamide;
67 N-[2-({3-[(2-hydroxyethyl)sulfonyl]phenyl}amino)-4'-methyl-4,5'-bi-1,3-thiazol-2'-yl]acetamide;
68 N-[2-({4-[(dimethylamino)sulfonyl]phenyl}amino)-4'-methyl-4,5'-bi-1,3-thiazol-2'-yl]acetamide;
69 N-(2-{[3-(aminosulfonyl)phenyl]amino}-4'-methyl-4,5'-bi-1,3-thiazol-2'-yl)acetamide;
70 N-{2-[(2-chloropyridin-4-yl)amino]-4'-methyl-4,5'-bi-1,3-thiazol-2'-yl}acetamide;
71 N-[4'-methyl-2-({4-[(methylamino)sulfonyl]phenyl}amino)-4,5'-bi-1,3-thiazol-2'-yl]acetamide;
72 N-(5-{[2'-(acetylamino)-4'-methyl-4,5'-bi-1,3-thiazol-2-yl]amino}pyridin,—2-yl)acetamide;
73 N-[2-(2,3-dihydro-1-benzofuran-5-ylamino)-4'-methyl-4,5'-bi-1,3-thiazol-2'-yl]acetamide;
74 N-(4'-methyl-2-{[2-(1-methylpyrrolidin-2-yl)ethyl]amino}-4,5'-bi-1,3-thiazol-2'-yl)acetamide;
75 N-{4'-methyl-2-[(2-pyrrolidin-1-ylethyl)amino]-4,5'-bi-1,3-thiazol-2'-yl}acetamide;
76 N-(4'-methyl-2-{[3-(2-oxopyrrolidin-1-yl)propyl]amino}-4,5'-bi-1,3-thiazol-2'-yl)acetamide;
77 N-(2-{[2-(acetylamino)ethyl]amino}-4'-methyl-4,5'-bi-1,3-thiazol-2'-yl)acetamide;
78 N-(2-{[2-(dimethylamino)ethyl]amino}-4'-methyl-4,5'-bi-1,3-thiazol-2'-yl)acetamide;
79 N-{2-[(2-hydroxyethyl)amino]-4'-methyl-4,5'-bi-1,3-thiazol-2'-yl}acetamide;
80 N-(2-{[2-(4-hydroxyphenyl)ethyl]amino}-4'-methyl-4,5'-bi-1,3-thiazol-2'-yl)acetamide;
81 N-(2-{[3-(dimethylamino)propyl]amino}-4'-methyl-4,5'-bi-1,3-thiazol-2'-yl)acetamide;
82 N-{2-[(3-hydroxypropyl)amino]-4'-methyl-4,5'-bi-1,3-thiazol-2'-yl}acetamide;
83 N-(2-{[3-(1H-imidazol-1-yl)propyl]amino}-4'-methyl-4,5'-bi-1,3-thiazol-2'-yl)acetamide;
84 N~3~-[2'-(acetylamino)-4'-methyl-4,5'-bi-1,3-thiazol-2-yl]-beta-alaninamide;
85 N-{4'-methyl-2-[(2-methylprop-2-en-1-yl)amino]-4,5-bi-1,3-thiazol-2'-yl}acetamide;
86 N-{2-[(2-hydroxyphenyl)amino]-4'-methyl-4,5'-bi-1,3-thiazol-2'-yl}acetamide;
87 N-{2-[(6-fluoropyridin-3-yl)amino]-4'-methyl-4,5'-bi-1,3-thiazol-2'-yl}acetamide;

88 N-{2-[(4-cyanophenyl)amino]-4'-methyl-4,5'-bi-1,3-thiazol-2'-yl}acetamide;
89 N-{2-[(6-cyanopyridin-3-yl)amino]-4'-methyl-4,5'-bi-1,3-thiazol-2'-yl}acetamide;
90 N-{2-[(3-methoxyphenyl)amino]-4'-methyl-4,5'-bi-1,3-thiazol-2'-yl}acetamide;
91 3-{[2'-(acetylamino)-4'-methyl-4,5'-bi-1,3-thiazol-2-yl]amino}benzamide;
92 N-{4'-methyl-2-[(2-nitrophenyl)amino]-4,5'-bi-1,3-thiazol-2'-yl}acetamide;
93 N-{4'-methyl-2-[(3-nitrophenyl)amino]-4,5'-bi-1,3-thiazol-2'-yl}acetamide;
94 N-[4'-methyl-2-(quinolin-3-ylamino)-4,5'-bi-1,3-thiazol-2'-yl]acetamide;
95 N-[4'-methyl-2-(quinolin-5-ylamino)-4,5'-bi-1,3-thiazol-2'-yl]acetamide;
96 N-[4'-methyl-2-(quinolin-6-ylamino)-4,5'-bi-1,3-thiazol-2'-yl]acetamide;
97 N-[2-(cyclopentylamino)-4'-methyl-4,5'-bi-1,3-thiazol-2'-yl]acetamide;
98 N-[2-(cyclopropylamino)-4'-methyl-4,5'-bi-1,3-thiazol-2-yl]acetamide;
99 N-{4'-methyl-2-[(pyridin-3-ylmethyl)amino]-4,5'-bi-1,3-thiazol-2'-yl}acetamide;
100 N-{2-[(4-hydroxybutyl)amino]-4'-methyl-4,5'-bi-1,3-thiazol-2'-yl}acetamide;
101 N-(4'-methyl-2-{[3-(methylsulfonyl)phenyl]amino}-4,5'-bi-1,3-thiazol-2'-yl)acetamide;
102 N-{4'-methyl-2-[(3-pyrrolidin-1-ylpropyl)amino]-4,5'-bi-1,3-thiazol-2'-yl}acetamide;
103 N-{2-[(1,1-dioxido-1-benzothien-6-yl)amino]-4'-methyl-4,5'-bi-1,3-thiazol-2'-yl}acetamide;
104 N-(2-{[(1-ethylpyrrolidin-2-yl)methyl]amino}1'-methyl-4,5'-bi-1,3-thiazol-2'-yl)acetamide;
105 N-{2-[(cyanomethyl)amino]-4'-methyl-4,5'-bi-1,3-thiazol-2'-yl acetamide;
106 N-[2-(isobutylamino)-4'-methyl-4,5'-bi-1,3-thiazol-2'-yl]acetamide;
107 N-{2-[(2,2-dimethylpropyl)amino]-4'-methyl-4,5'-bi-1,3-thiazol-2'-yl}acetamide;
108 N-(2-{[(cis)-2-(hydroxymethyl)cyclohexyl]amino})-4'-methyl-4,5'-bi-1,3-thiazol-2'-yl)acetamide;
109 N-(2-{[(trans)-2-(hydroxymethyl)cyclohexyl]amino}-4'-methyl-4,5'-bi-1,3-thiazol-2'-yl)acetamide;
110 N-[2-(sec-butylamino)-4'-methyl-4,5'-bi-1,3-thiazol-2'-yl]acetamide;
111 N-{4'-methyl-2-[(pyridin-4-ylmethyl)amino]-4,5'-bi-1,3-thiazol-2'-yl}acetamide;
112 N-(4'-methyl-2-{[4-(morpholin-4-ylsulfonyl)phenyl]amino}-4,5'-bi-1,3-thiazol-2'-yl)acetamide;
113 N-[2-({3-[(butylamino)sulfonyl]phenyl}amino)-4'-methyl-4,5'-bi-1,3-thiazol-2'-yl]acetamide;
114 N-{2-[(cyclopropylmethyl)amino]-4'-methyl-4,5'-bi-1,3-thiazol-2'-yl}acetamide;
115 N-[2-(cyclobutylamino)-4'-methyl-4,5'-bi-1,3-thiazol-2'-yl]acetamide;
116 N-[2-(2,3-dihydro-1H-inden-2-ylamino)-4'-methyl-4,5'-bi-1,3-thiazol-2'-yl]acetamide;
117 N-(4'-methyl-2-{[2-(methylsulfonyl)phenyl]amino}-4,5'-bi-1,3-thiazol-2'-yl)acetamide;
118 N-(4'-methyl-2-{[2-(1H-1,2,4-triazol-1-yl)ethyl]amino}-4,5'-bi-1,3-thiazol-2'-yl)acetamide;
119 N-(2-{[3-(1-hydroxyethyl)phenyl]amino}-4'-methyl-4,5'-bi-1,3-thiazol-2'-yl)acetamide;
120 Methyl (4-{[2'-(acetylamino)-4'-methyl-4,5'-bi-1,3-thiazol-2-yl]amino}phenyl)acetate;
121 Methyl N-(4-f{[2'-(acetylamino)-4'-methyl-4,5'-bi-1,3-thiazol-2-yl]amino}benzoyl)-beta-alaninate;
122 Methyl N-(4-{[2'-(acetylamino)-4'-methyl-4,5'-bi-1,3-thiazol-2-yl]amino}benzoyl)glycinate;
123 Methyl 3-(3-{[2'-(acetylamino)-4'-methyl-4,5'-bi-1,3-thiazol-2-yl]amino}phenyl)propanoate;
124 3-(4-{[2'-(acetylamino)-4'-methyl-4,5'-bi-1,3-thiazol-2-yl]amino}phenyl) propanoic acid;
125 Methyl 4-{[2'-(acetylamino)-4'-methyl-4,5'-bi-1,3-thiazol-2'-yl]amino}butanoate;
126 Methyl (3-{[2'-(acetylamino)-4'-methyl-4,5'-bi-1,3-thiazol-2-yl]amino}phenyl)acetate;
127 N-[2-(allylamino)-4'-methyl-4,5'-bi-1,3-thiazol-2'-yl]urea;
128 N-[4'-methyl-2-(pyridin-3-ylamino)-4,5'-bi-1,3-thiazol-2'-yl]urea;
129 N-(4'-methyl-2-piperidin-1-yl-4,5'-bi-1,3-thiazol-2'-yl)urea;
130 N-(2-anilino-4'-methyl-4,5'-bi-1,3-thiazol-2'-yl)urea;
131 N-{2-[(4-hydroxyphenyl)amino]-4'-methyl-4,5'-bi-1,3-thiazol-2'-yl}urea;
132 N-[2-(pyridin-3-ylamino)-4,5'-bi-1,3-thiazol-2'-yl]acetamide;
133 (4-{[2'-(acetylamino)-4'-methyl-4,5'-bi-1,3-thiazol-2-yl]amino}phenyl)acetic acid;
134 N-(4-{[2'-(acetylamino)-4'-methyl-4,5'-bi-1,3-thiazol-2-yl]amino}benzoyl)-beta-alanine;
135 N-(4-{[2'-(acetylamino)-4'-methyl-4,5'-bi-1,3-thiazol-2-yl]amino}benzoyl)glycine;
136 3-(3-{[2'-(acetylamino)-4'-methyl-4,5'-bi-1,3-thiazol-2-yl]amino}phenyl) propanoic acid;
N-{2-[(4-ethoxyphenyl)amino]-4'-methyl-4,5'-bi-1,3-thiazol-2'-yl}acetamide;
N-{4'-methyl-2-[(4-methylphenyl)amino]-4,5'-bi-1,3-thiazol-2'-yl}acetamide;
N-{2-[(4-{[(4,6-dimethylpyrimidin-2-yl)amino]sulfonyl}phenyl)amino]-4'-methyl-4,5'-bi-1,3-thiazol-2'-yl}acetamide;
N-{4'-methyl-2-[(4-{[(5-methylisoxazol-3-yl)amino]sulfonyl}phenyl)amino]-4,5'-bi-1,3-thiazol-2'-yl}acetamide;
N-[2-(allylamino)-4'-methyl-4,5'-bi-1,3-thiazol-2'-yl]propanamide;
N-{2-[(4-{[(2,6-dimethoxypyrimidin-4-yl)amino]sulfonyl}phenyl)amino]-4'-methyl-4,5'-bi-1,3-thiazol-2'-yl}acetamide;
N-{4'-methyl-2-[(4-{[(5-methylisoxazol-3-yl)amino]sulfonyl}phenyl)amino]-4,5'-bi-1,3-thiazol-2'-yl}propanamide;
N-{2-[(4-{[(4,6-dimethylpyrimidin-2-yl)amino]sulfonyl}phenyl)amino]-4'-methyl-4,5'-bi-1,3-thiazol-2'-yl}propanamide;
N-(4-[{2'-(acetylamino)-4'-methyl-4,5'-bi-1,3-thiazol-2-yl]amino}phenyl)acetamide;
N-{2-[(4-aminophenyl)amino]-4'-methyl-4,5'-bi-1,3-thiazol-2'-yl}acetamide;
N-{2-[(2-ethylphenyl)amino]-4'-methyl-4,5'-bi-1,3-thiazol-2'-yl}acetamide;
N-{4'-methyl-2-[(2-methylphenyl)amino]-4,5'-bi-1,3-thiazol-2'-yl}acetamide;
N-{2-[(4-bromophenyl)amino]-4'-methyl-4,5'-bi-1,3-thiazol-2'-yl}acetamide;
N-(2-{[4-(aminosulfonyl)phenyl]amino}-4'-methyl-4,5'-bi-1,3-thiazol-2'-yl)acetamide;
N-{2-[(2,5-dimethoxyphenyl)amino]-4'-methyl-4,5'-bi-1,3-thiazol-2'-yl}acetamide;

N-{2-[(3-acetylphenyl)amino]-4'-methyl-4,5'-bi-1,3-thiazol-2'-yl}acetamide;
N-(2-{[4-(dimethylamino)phenyl]amino}-4'-methyl-4,5'-bi-1,3-thiazol-2'-yl)acetamide.

In a particular embodiment, the invention provides compounds according to Formula selected from the following group:

5  N-(4'-methyl-2-piperidin-1-yl-4,5'-bi-1,3-thiazol-2'-yl)acetamide;
7  N-[4'-methyl-2-(pyridin-3-ylamino)-4,5'-bi-1,3-thiazol-2'-yl]acetamide;
8  N-[4'-methyl-2-(pyridin-2-ylamino)-4,5'-bi-1,3-thiazol-2'-yl]acetamide;
16  N-(4'-methyl-2-morpholin-4-yl-4,5'-bi-1,3-thiazol-2'-yl)acetamide;
17  N-[4'-methyl-2-(4-methylpiperazin-1-yl)-4,5'-bi-1,3-thiazol-2'-yl]acetamide;
18  Methyl 1-[2-(acetylamino)-4'-methyl-4,5'-bi-1,3-thiazol-2-yl]piperidine-3-carboxylate;
19  N-{2-[4-(2-hydroxyethyl)piperidin-1-yl]-4'-methyl-4,5'-bi-1,3-thiazol-2'-yl}acetamide;
20  N-(4'-methyl-2-pyrrolidin-1-yl-4,5'-bi-1,3-thiazol-2'-yl)acetamide;
21  N-[2-(3-hydroxypyrrolidin-1-yl)-4'-methyl-4,5'-bi-1,3-thiazol-2'-yl]acetamide;
22  N-[2-(tert-butylamino)-4'-methyl-4,5'-bi-1,3-thiazol-2'-yl]acetamide;
23  N-{2-[(6-methoxypyridin-3-yl)amino]-4'-methyl-4,5'-bi-1,3-thiazol-2'-yl}acetamide;
24  N-{2-[(6-chloropyridin-3-yl)amino]-4'-methyl-4,5'-bi-1,3-thiazol-2'-yl}acetamide;
31  N-{4-methyl-2-[(2-morpholin-4-ylethyl)amino]-4,5'-bi-1,3-thiazol-2'-yl}acetamide;
32  N-{4'-methyl-2-[(2-piperidin-1-ylethyl)amino]-4,5'-bi-1,3-thiazol-2'-yl}acetamide;
33  N-{2-[(2-methoxyethyl)amino]-4'-methyl-4,5'-bi-1,3-thiazol-2'-yl}acetamide;
34  N-[2-(cyclohexylamino)-4'-methyl-4,5'-bi-1,3-thiazol-2'-yl]acetamide;
35  N-{4'-methyl-2-[(3-morpholin-4-ylpropyl)amino]-4,5'-bi-1,3-thiazol-2'-yl}acetamide
36  N-{4'-methyl-2-[(tetrahydrofuran-2-ylmethyl)amino]-4,5'-bi-1,3-thiazol-2'-yl}acetamide;
38  N-[2-(1-benzofuran-5-ylamino)-4'-methyl-4,5'-bi-1,3-thiazol-2'-yl]acetamide;
40  [4'-methyl-2-(pyridin-3-ylamino)-4,5'-bi-1,3-thiazol-2'-yl]formamide;
42  N-{4-methyl-5-[2-pyridin-3-ylamino)-1,3-thiazol-4-yl]-1,3-oxazol-2-yl}acetamide;
43  N-{2-[(2-fluoropyridin-3-yl)amino]-4'-methyl-4,5'-bi-1,3-thiazol-2'-yl}acetamide;
44  N-{2-[(2-cyanoethyl)amino]-4'-methyl-4,5'-bi-1,3-thiazol-2'-yl}acetamide;
45  N-{2-[(3,3-diethoxypropyl)amino]-4'-methyl-4,5'-bi-1,3-thiazol-2'-yl}acetamide;
46  N-{2-[(2,2-diethoxyethyl)amino]-4'-methyl-4,5'-bi-1,3-thiazol-2'-yl}acetamide;
47  N-{4'-methyl-2-[(2-oxo-2-phenylethyl)amino]-4,5'-bi-1,3-thiazol-2'-yl}acetamide;
48  N-{2-[(2-chloropyridin-3-yl)amino]-4'-methyl-4,5'-bi-1,3-thiazol-2'-yl}acetamide;
55  N-[2'-(acetylamino)-4'-methyl-4,5'-bi-1,3-thiazol-2-yl]-beta-alanine;
57  4-f{[2'-(acetylamino)-4'-methyl-4,5'-bi-1,3-thiazol-2-yl]amino}butanoic acid;
70  N-{2-[(2-chloropyridin-4-yl)amino]-4'-methyl-4,5'-bi-1,3-thiazol-2'-yl}acetamide;
72  N-(5-{[2'-acetylamino)-4'-methyl-4,5'-bi-1,3-thiazol-2-yl]amino}pyridin-2-yl)acetamide;
73  N-[2-(2,3-dihydro-1-benzofuran-5-ylamino)-4'-methyl-4,5'-bi-1,3-thiazol-2'-yl]acetamide;
74  N-(4'-methyl-2-{[2-(1-methylpyrrolidin-2-yl)ethyl]amino}-4,5'-bi-1,3-thiazol-2'-yl)acetamide;
75  N-{4'-methyl-2-[(2-pyrrolidin-1-ylethyl)amino]-4,5'-bi-1,3-thiazol-2'-yl}acetamide;
76  N-(4'-methyl-2-{[3-(2-oxopyrrolidin-1-yl)propyl]amino}-4,5'-bi-1,3-thiazol-2'-yl)acetamide;
77  N-(2-{[2-(acetylamino)ethyl]amino}-4'-methyl-4,5'-bi-1,3-thiazol-2'-yl)acetamide;
78  N-(2-{[2-(dimethylamino)ethyl]amino}-4'-methyl-4,5-bi-1,3-thiazol-2'-yl)acetamide;
79  N-{2-[(2-hydroxyethyl)amino]-4'-methyl-4,5'-bi-1,3-thiazol-2'-yl}acetamide;
81  N-(2-([3-(dimethylamino)propyl]amino 4'-methyl-4,5'-bi-1,3-thiazol-2'-yl)acetamide;
82  N-{2-[(3-hydroxypropyl)amino]-4'-methyl-4,5'-bi-1,3-thiazol-2'-yl}acetamide;
84  N~3~-[2'-(acetylamino)-4'-methyl-4,5'-bi-1,3-thiazol-2-yl]-beta-alaninamide;
89  N-{2-[(6-cyanopyridin-3-yl)amino]-4'-methyl-4,5'-bi-1,3-thiazol-2'-yl}acetamide;
94  N-[4'-methyl-2-(quinolin-3-ylamino)-4,5'-bi-1,3-thiazol-2'-yl]acetamide;
95  N-[4'-methyl-2-(quinolin-5-ylamino)-4,5'-bi-1,3-thiazol-2'-yl]acetamide;
96  N-[4'-methyl-2-(quinolin-6-ylamino)-4,5'-bi-1,3-thiazol-2'-yl]acetamide;
97  N-[2-(cyclopentylamino)-4'-methyl-4,5'-bi-1,3-thiazol-2'-yl]acetamide;
98  N-[2-(cyclopropylamino)-4'-methyl-4,5'-bi-1,3-thiazol-2'-yl]acetamide;
100  N-{2-[(4-hydroxybutyl)amino]-4'-methyl-4,5'-bi-1,3-thiazol-2'-yl}acetamide;
102  N-{4'-methyl-2-[(3-pyrrolidin-1-ylpropyl)amino]-4,5'-bi-1,3-thiazol-2'-yl}acetamide;
103  N-{2-[(1,1-dioxido-1-benzothien-6-yl)amino]-4'-methyl-4,5'-bi-1,3-thiazol-2'-yl}acetamide;
104  N-(2-{[(1-ethylpyrrolidin-2-yl)methyl]amino}-4'-methyl-4,5'-bi-1,3-thiazol-2'-yl)acetamide;
105  N-{2-[(cyanomethyl)amino]-4'-methyl-4,5'-bi-1,3-thiazol-2'-yl}acetamide;
106  N-[2-(isobutylamino)-4'-methyl-4,5'-bi-1,3-thiazol-2'-yl]acetamide;
107  N-{2-[(2,2-dimethylpropyl)amino]-4'-methyl-4,5'-bi-1,3-thiazol-2'-yl}acetamide;
108  N-(2-{[(cis)-2-(hydroxymethyl)cyclohexyl]amino}-4'-methyl-4,5'-bi-1,3-thiazol-2'-yl)acetamide;
109  N-(2-{[(trans)-2-(hydroxymethyl)cyclohexyl]amino}-4'-methyl-4,5'-bi-1,3-thiazol-2'-yl)acetamide;
110  N-[2-(sec-butylamino)-4'-methyl-4,5'-bi-1,3-thiazol-2'-yl]acetamide;
114  N-{2-[(cyclopropylmethyl)amino]-4-methyl-4,5'-bi-1,3-thiazol-2'-yl}acetamide;
115  N-[2-(cyclobutylamino)-4'-methyl-4,5'-bi-1,3-thiazol-2'-yl]acetamide;
116 N-[2-(2,3-dihydro-1H-inden-2-ylamino)-4'-methyl-4,5'-bi-1,3-thiazol-2'-yl]acetamide;
125  methyl 4-{[2'-(acetylamino)-4-methyl-4,5'-bi-1,3-thiazol-2-yl]amino}butanoate;
128  N-[4'-methyl-2-(pyridin-3-ylamino)-4,5'-bi-1,3-thiazol-2'-yl]urea;
129  N-(4'-methyl-2-piperidin-1-yl-4,5'-bi-1,3-thiazol-2'-yl)urea;

In another embodiment, the invention provides compounds according to Formula (I) selected from the following group:

3  N-[2-(benzylamino)-4'-methyl-4,5'-bi-1,3-thiazol-2'-yl]acetamide;
4  N-{4'-methyl-2-[(2-phenylethyl)amino]-4,5'-bi-1,3-thiazol-2'-yl}acetamide;
12  4-{[2'-(acetylamino)-4'-methyl-4,5'-bi-1,3-thiazol-2'-yl]amino}benzamide
13  N-[2-({4-[(4-benzylpiperazin-1-yl)carbonyl]phenyl}amino)-4'-methyl-4,5'-bi-1,3-thiazol-2'-yl]acetamide
25 N-{2-[(4-cyanophenyl)amino]-4'-methyl-4,5'-bi-1,3-thiazol-2'-yl}acetamide
27  N-{2-[(2-chlorophenyl)amino]-4'-methyl-4,5'-bi-1,3-thiazol-2'-yl}acetamide;
29  N-{2-[(3-chlorophenyl)amino]-4'-methyl-4,5'-bi-1,3-thiazol-2'-yl}acetamide
37  N-{2-[(2-hydroxy-2-phenylethyl)amino]-4'-methyl-4,5'-bi-1,3-thiazol-2'-yl}acetamide;
39 N-{2-[(3-cyanophenyl)amino]-4'-methyl-4,5'-bi-1,3-thiazol-2'-yl}acetamide
41  Ethyl N-({[2-(allylamino)-4'-methyl-4,5'-bi-1,3-thiazol-2'-yl]amino}carbonyl)-beta-alaninate;
49  N-(4'-methyl-2-{[3-(1,3-oxazol-5-yl)phenyl]amino})-4,5'-bi-1,3-thiazol-2'-yl)acetamide;
50  N-(4'-methyl-2-{[3-(1H-tetrazol-5-yl)phenyl]amino}-4,5'-bi-1,3-thiazol-2'-yl)acetamide;
51  N-(4'-methyl-2-f{[4-(1H-tetrazol-5-yl)phenyl]amino}-4,5'-bi-1,3-thiazol-2'-yl)acetamide
52  N-{4'-Methyl-2-[2-(1H-tetrazol-5-yl)-ethylamino]-[4,5]bithiazolyl-2'-yl}-acetamide
53  N-(2-{[3-(5-hydroxy-1,3,4-oxadiazol-2-yl)phenyl]amino}-4'-methyl-4,5'-bi-1,3-thiazol-2'-yl)acetamide;
54 N-(2-{[3-(5-amino-1,3,4-thiadiazol-2-yl)phenyl]amino}-4'-methyl-4,5'-bi-1,3-thiazol-2'-yl)acetamide;
56  5-(2-{[2'-(acetylamino)-4'-methyl-4,5'-bi-1,3-thiazol-2-yl]amino}ethyl)-1,3,4-oxadiazol-2-olate;
58  N-(2-{[3-(5-hydroxy-1,3,4-oxadiazol-2-yl)propyl]amino}-4'-methyl-4,5'-bi-1,3-thiazol-2'-yl)acetamide;
59  3-{[2'-(acetylamino)-4'-methyl-4,5'-bi-1,3-thiazol-2'-yl]amino}-N-hydroxy benzamide;
60  3-{[2'-(acetylamino)-4'-methyl-4,5'-bi-1,3-thiazol-2'-yl]amino}-N-hydroxy benzene carboximidic acid;
61  N-(2-{[3-(5-hydroxy-1,2,4-oxadiazol-3-yl)phenyl]amino}-4'-methyl-4,5'-bi-1,3-thiazol-2'-yl)acetamide;
62  N-[2-({3-[(Z)-(2,4-dioxo-1,3-thiazolidin-5-ylidene)methyl]phenyl}amino)-4'-methyl-4,5'-bi-1,3-thiazol-2'-yl]acetamide;
63  N-[4'-methyl-2-({4-[(pyridin-2-ylamino)sulfonyl]phenyl}amino)-4,5'-bi-1,3-thiazol-2'-yl]acetamide;
64  N-(2-{[2-(2-hydroxyethyl)phenyl]amino}-4'-methyl-4,5'-bi-1,3-thiazol-2'-yl)acetamide;
65  N-(2-{[3-(hydroxymethyl)phenyl]amino}-4'-methyl-4,5'-bi-1,3-thiazol-2'-yl)acetamide;
66  N-(2-{[4-(2-hydroxyethyl)phenyl]amino}-4'-methyl-4,5'-bi-1,3-thiazol-2'-yl)acetamide
67  N-[2-({3-[(2-hydroxyethyl)sulfonyl]phenyl}amino)-4'-methyl-4,5-bi-1,3-thiazol-2'-yl]acetamide;
68  N-[2-({4-[(dimethylamino)sulfonyl]phenyl}amino)-4'-methyl-4,5'-bi-1,3-thiazol-2'-yl]acetamide;
71  N-[4'-methyl-2-({4-[(methylamino)sulfonyl]phenyl}amino)-4,5'-bi-1,3-thiazol-2'-yl]acetamide;
80  N-(2-{[2-(4-hydroxyphenyl)ethyl]amino}-4'-methyl-4,5'-bi-1,3-thiazol-2'-yl)acetamide;
83 N-(2-{[3-(1H-imidazol-1-yl)propyl]amino}-4'-methyl-4,5'-bi-1,3-thiazol-2'-yl)acetamide;
85  N-{4'-methyl-2-[(2-methylprop-2-en-1-yl)amino]-4,5'-bi-1,3-thiazol-2'-yl}acetamide;
86  N-{2-[(2-hydroxyphenyl)amino]-4'-methyl-4,5'-bi-1,3-thiazol-2'-yl}acetamide;
88 N-{2-[(4-cyanophenyl)amino]-4'-methyl-4,5'-bi-1,3-thiazol-2'-yl}acetamide;
90  N-{2-[(3-methoxyphenyl)amino]-4'-methyl-4,5'-bi-1,3-thiazol-2'-yl}acetamide;
91  3-f{[2'-(acetylamino)-4'-methyl-4,5'-bi-1,3-thiazol-2-yl]amino}benzamide;
92  N-{4'-methyl-2-[(2-nitrophenyl)amino]-4,5'-bi-1,3-thiazol-2'-yl}acetamide;
99  N-{4'-methyl-2-[din-3-ylmethyl)amino]-4,5'-bi-1,3-thiazol-2'-yl}acetamide;
101  N-(4'-methyl-2-{[3-(methylsulfonyl)phenyl]amino}-4,5'-bi-1,3-thiazol-2'-yl)acetamide;
111  N-{4-methyl-2-[(pyridin-4-ylmethyl)amino]-4,5'-bi-1,3-thiazol-2'-yl}acetamide;
112  N-(4'-methyl-2-{[4-(morpholin-4-ylsulfonyl)phenyl]amino}-4,5'-bi-1,3-thiazol-2'-yl)acetamide;
113  N-[2-({3-[(butylamino)sulfonyl]phenyl}amino)-4'-methyl-4,5'-bi-1,3-thiazol-2'-yl]acetamide;
117  N-(4'-methyl-2-{[2-(methylsulfonyl)phenyl]amino}-4,5'-bi-1,3-thiazol-2'-yl)acetamide;
118  N-(4'-methyl-2-{[2-(1H-1,2,4-triazol-1-yl)ethyl]amino}-4,5'-bi-1,3-thiazol-2'-yl)acetamide;
119  N-(2-{[3-(1-hydroxyethyl)phenyl]amino}-4'-methyl-4,5'-bi-1,3-thiazol-2'-yl)acetamide;
120 Methyl (4-{[2'-(acetylamino)-4'-methyl-4,5'-bi-1,3-thiazol-2'-yl]amino}phenyl)acetate;
121  Methyl N-(4-{[2'-(acetylamino)-4'-methyl-4,5'-bi-1,3-thiazol-2-yl]amino}benzoyl)-beta-alaninate;
122  Methyl N-(4-{[2'-(acetylamino)-4'-methyl-4,5'-bi-1,3-thiazol-2-yl]amino}benzoyl)glycinate;
123  Methyl 3-(3-{[2'-(acetylamino)-4'-methyl-4,5'-bi-1,3-thiazol-2-yl]amino}phenyl)propanoate;
124  3-(4-{[2'-(acetylamino)-4'-methyl-4,5'-bi-1,3-thiazol-2-yl]amino}phenyl) propanoic acid;
126 Methyl (3-{[2'-(acetylamino)-4'-methyl-4,5'-bi-1,3-thiazol-2-yl]amino}phenyl)acetate;
127  N-[2-(allylamino)-4'-methyl-4,5'-bi-1,3-thiazol-2'-yl]urea;
130 N-(2-anilino-4-methyl-4,5'-bi-1,3-thiazol-2'-yl)urea;
131  N-{2-[(4-hydroxyphenyl)amino]-4'-methyl-4,5'-bi-1,3-thiazol-2'-yl}urea;
133  (4-{[2'-(acetylamino)-4'-methyl-4,5'-bi-1,3-thiazol-2-yl]amino}phenyl)acetic acid;
134  N-(4-{[2'-(acetylamino)-4'-methyl-4,5'-bi-1,3-thiazol-2-yl]amino}benzoyl)-beta-alanine;
135  N-(4-{[2'-(acetylamino)-4'-methyl-4,5'-bi-1,3-thiazol-2-yl]amino}benzoyl)glycine;
136  3-(3-{[2'-(acetylamino)-4'-methyl-4,5'-bi-1,3-thiazol-2-yl]amino}phenyl) propanoic acid The compounds of the present invention are useful as medicaments. They may be used for the preparation of a medicament for the prophylaxis and/or treatment of autoimmune disorders and/or inflammatory diseases, cardiovascular diseases, neurodegenerative diseases, bacterial or viral infections, kidney diseases, platelet aggregation, cancer, transplantation, graft rejection or lung injuries.

In one embodiment, the compounds of Formula (I) are useful for the treatment and/or prophylaxis of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

In another embodiment, the compounds of Formula (I) are useful for the treatment and/or prophylaxis of neurodegenerative diseases including multiple sclerosis, Alzheimer's disease, Huntington's disease, CNS trauma, stroke or ischemic conditions.

In still a further embodiment according to the invention, the compounds of Formula a) are useful for the treatment and/or prophylaxis of cardiovascular diseases such as athero-sclerosis, heart hypertrophy, cardiac myocyte dysfunction, elevated blood pressure or vasoconstriction.

In still another embodiment according to the invention, the compounds of Formula (I) are useful for the treatment and/or prophylaxis of chronic obstructive pulmonary disease, anaphylactic shock fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastasis, in particular melanoma, Karposi's sarcoma, acute and chronic bacterial and viral infections, sepsis, transplantation, graft rejection, glomerulo sclerosis, glomerulo nephritis, progressive renal fibrosis, endothelial and epithelial injuries in the lung or in general lung airways inflammation.

The thiazole derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

Synthesis of Compounds of the Invention:

The novel bis-thiazole or oxazole-thiazole derivatives according to Formula (I) can be prepared from readily available starting materials by several synthetic approaches, using both solution-phase and solid-phase chemistry protocols (Pirrung et al., *J Comb. Chem.* 2001, 3, 90-96). Examples of synthetic pathways for the will be described.

The following abbreviations refer respectively to the definitions below:

min (minute), hr (hour), g (gram), MHz (Megahertz), ml (milliliter), mmol (millimole), mM (millimolar), rt (room temperature), ATP (Adenoside Triphospbate), BSA (Bovine Serum Albumin), CDI (N,N'-carbonyldiimidazole), DCM (dichloromethane), DCC (dicyclohexylcarbodiimide), DIEA (di-isopropyl ethylamine), DMSO (Dimethyl Sulfoxide), EDC (1-(3-dimethylaminopropyl)-3-ethylcarbodiimide hydrochloride), HPLC (High Performance Liquid Chromatography), Ins1P (D-myo-inositol-1-phosphate), mCPBA (m-chloroperoxybenzoic acid), MS (mass spectrometry), NMR (Nuclear Magnetic Resonance), PBS (Phosphate Buffered Saline), PIs (Phosphoinositides), PI3Ks (Phosphoinositide 3-kinases), PI(3)P (Phosphatidylinositol 3-monophosphate), PI(3,4)$P_2$ (Phosphatidylinositol 3,4-bisphosphate), PI(3,4,5)$P_3$ (Phosphatidylinositol 3,4,5-triphosphate), PI(4)P (Phosphatidylinositol-4-phosphate), PI(4,5)$P_2$ (Phosphatidylinositol-4,5-biphosphate), PtdIns (Phosphatidylinositol), SPA (Scintillation Proximity Assay), TEA (triethylamine), THF (tetrahydrofuran), TLC (Thin Layer Chromatography), UV (Ultraviolet).

One synthetic approach (Scheme 1 below) consists in reacting approximately equimolar amounts of an α-bromoketone reactant (P1) with a thiourea, a dithiocarbamate or a dithiocarbamic acid alkyl, alkenyl or alkynyl ester (P2), mixed in a solvent, preferably polar such as alcoholic solvent, to afford a compound of Formula (M). The temperature of the reaction depends on the nature of (P1) and (P2), ranging between –20° C. and reflux.

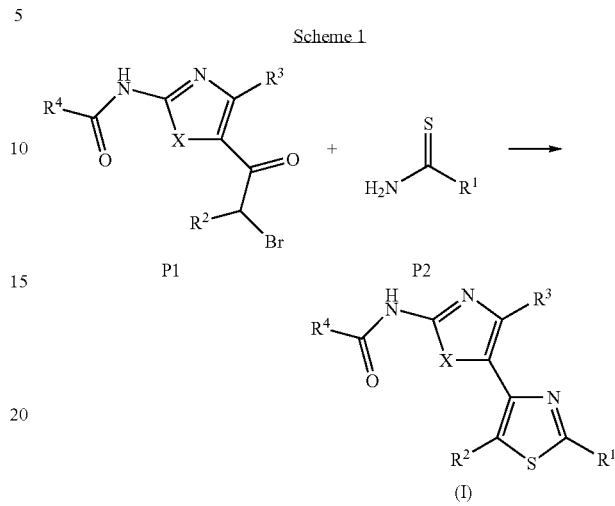

Another synthetic approach, described on Scheme 2 below, consists in reacting in the same way a free amine derivative (P1a), with a thiourea or a dithiocarbamate (P2), affording the corresponding bis-thiazole or oxazole-thiazole of Formula (Ia).

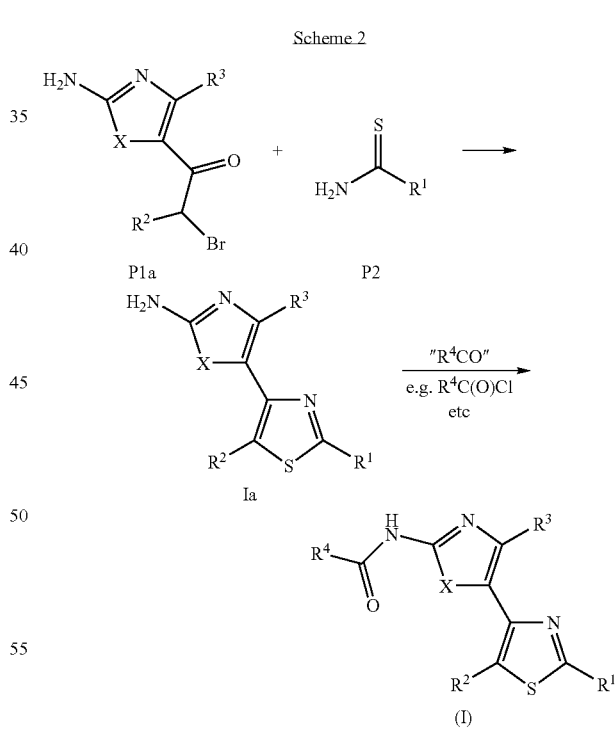

Derivative (Ia) can be further substituted by a group —C(O)$R^4$ to lead to a compound of Formula (I) using conditions known by the person skilled in the art.

When the group —C(O)$R^4$ is an acyl group, the corresponding acyl chloride is added to intermediate (Ia) in the presence of a base, e.g. pyridine, DIEA, TEA, etc. The corresponding carboxylic acid can be also added in the presence of an activating agent such as DCC, EDC, etc.

A formyl group, i.e. —C(O)R$^4$=—C(O)H, can be introduced by heating intermediate (Ia) in formic acid or in any alkyl formate, with or without a cosolvent. A substituted urea is formed by addition of an isocyanate, R$^8$R$^9$NC(O), to intermediate (Ia) in the presence of a base, e.g. DIEA, TEA, etc. The sequential addition of CDI and ammonia to intermediate (Ia) affords a compound of Formula (I) with —C(O)R$^4$=—C(O)NH$_2$.

Other —C(O)R$^4$ functionalities can be added to intermediate (Ia), to give a compound of Formula (I) as defined above in the description, using reaction conditions known to the person skilled in the art.

In the case of compounds of the invention of Formula a) wherein R$^1$=NR$^5$R$^6$, i.e. of Formula (Ib), the same processes as described above may be used and wherein derivatives of formula (P2) are thiourea of formula (P2a) (Scheme 3 below).

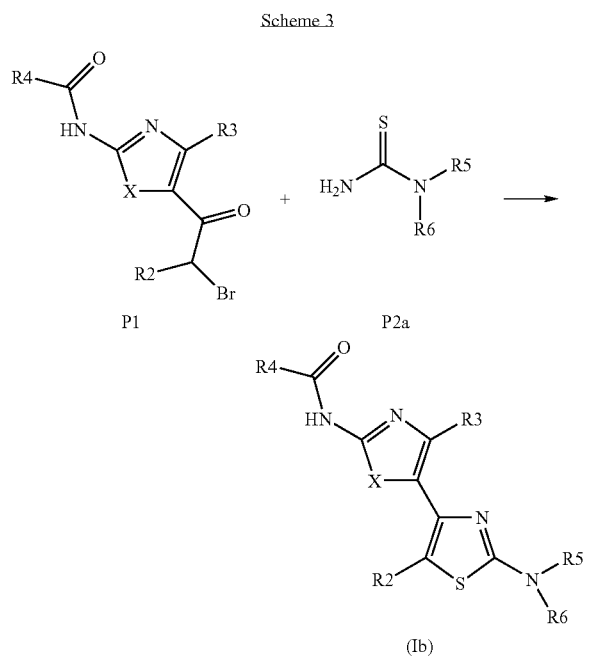

Scheme 3

For the preparation of compounds of Formula (Ib), approximately equimolar amounts of the α-bromoketone reactant (P1) and N-substituted thiourea (P2a) are stirred as a solution or a suspension in a solvent, preferably polar such as alcoholic solvent. When reagents (PI) or (P2a) are used as salt, an excess of base, preferably triethylamine or pyridine (about 3 equivalents), is added to the reaction mixture. The temperature chosen for this reaction depends on the nature of (P1) and (P2a), varying between −20° C. and reflux.

The desired bis-thiazole or oxazole-thiazole of Formula (Ib) is then isolated as HBr salt by filtration, in case it precipitates out of the reaction mixture upon cooling, or by evaporation of the solvents to obtain the crude product. This crude product can be then purified, if desired, e.g. by crystallization or by standard chromatographic methods. When R$^5$ and R$^6$ form a ring, the same processes as described above may be used.

Alternatively the HBr liberated during the reaction can be first neutralized by addition of an excess of base, preferably triethylamine or pyridine (about 3 equivalents). The desired bis-thiazole or oxazole-thiazole of Formula (Ib) is then isolated by filtration, in case it precipitates out of the reaction mixture upon cooling, and washed with water to remove the HBr salt of the base added. It can also be precipitated by addition of water and isolated by filtration or be extracted with an organic solvents, such as EtOAc or DCM. The resulting crude product can be then purified, if desired, e.g. by crystallization or by standard chromatographic methods.

These reaction conditions described above and detailed in the Examples below can be also applied on when using compounds (P1a) as starting material. In this case, compounds of Formula (Ib) can be then obtained with an additional step for the introduction of the group —C(O)R$^4$, as defined above in the description, using conditions known to the person skilled in the art.

When —C(O)R$^4$ is an acyl group, the corresponding acyl chloride is added to intermediate (Ia), wherein R$^1$=NR$^5$R$^6$, in the presence of a base, e.g. pyridine, DIEA, TEA, etc. The corresponding carboxylic acid can also be added in the presence of an activating agent such as DCC, EDC, etc.

A formyl group, i.e. —C(O)R$^4$=—C(O)H, can be introduced by heating (Ia), wherein R$^1$=NR$^5$R$^6$, in formic acid or in any alkyl formate with or without a cosolvent. A substituted urea is formed by addition of an isocyanate, R$^8$R$^9$NC(O), to intermediate (Ia), wherein R$^1$=NR$^5$R$^6$, in the presence of a base, e.g. DIEA, TEA, etc. The sequential addition of CDI and ammonia to intermediate (Ia), wherein R$^1$=NR$^5$R$^6$, affords compound of the invention according to Formula (Ib) with —C(O)R$^4$=—C(O)NH$_2$.

Other —C(O)R$^4$ functionalities can be added to intermediate (Ia), wherein R$^1$=NR$^5$R$^6$, to give a compound of the invention according to Formula (Ib) as defined above in the description, using reaction conditions known to the person skilled in the art.

Thioureas (P2a) used in synthetic Scheme 3 above are either commercially available from various sources or synthesized using conditions known to the person skilled in the art.

For example, thioureas (P2a) can be obtained by coupling a salt of an amine NHR$^5$R$^6$, preferably HCl salt, with potassium thiocyanate used in equimolarity in THF under reflux (Herr et al., *J. Synthesis*, 2000, 1569-1574) as shown on Scheme 4 below, Pathway A.

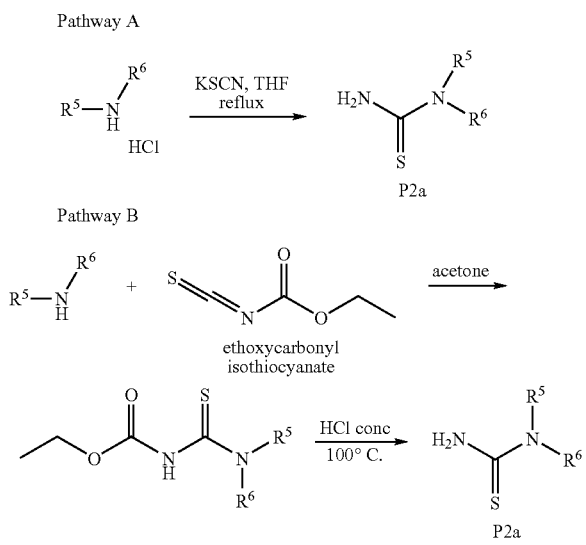

Scheme 4

Pathway C

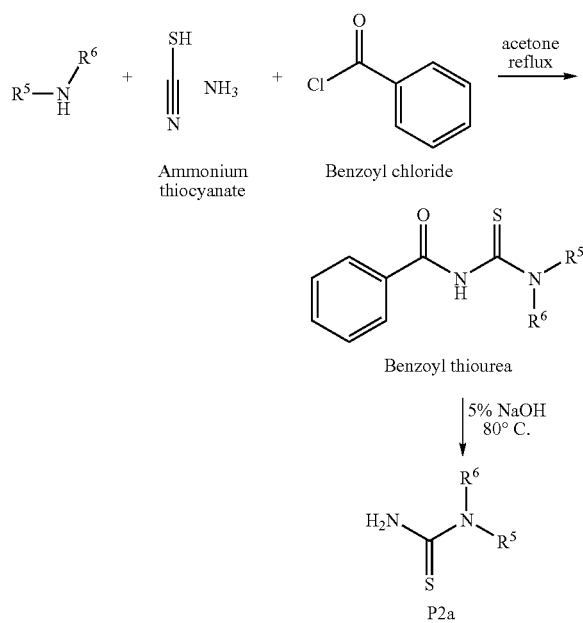

Pathway D

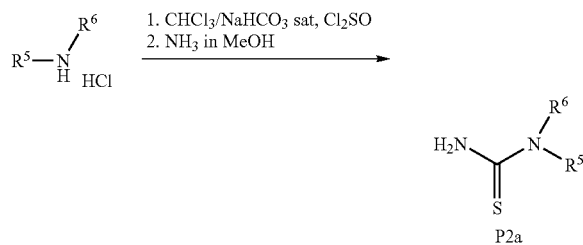

Pathway E

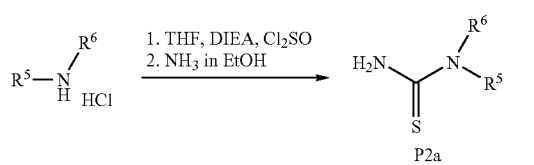

The amine NHR⁵R⁶ can be first activated with ethoxycarbonyl isothiocyanate affording an ethoxycarbonyl thiourea intermediate, as presented above on Scheme 4, Pathway B (Hartmann et al., *Prakt. Chem.* 1973, 315, 144-148). Upon deprotection under acidic conditions, e.g. concentrated HCl, the desired thiourea (P2a) is released. The amine NHR⁵R⁶ can be also activated with benzoyl isothiocyanate, obtained by addition of benzoyl chloride to ammonium thiocyanate, giving a benzoyl thiourea intermediate, as shown above on Scheme 4, Pathway C (Rasmussen et al., *Synthesis*, 1988, 456-459). Upon deprotection under basic conditions, e.g. NaOH, the desired thiourea (P2a) is released. Alternatively, the amine NHR⁵R⁶ can be reacted with thiophogene, followed by the addition of ammonia, as presented above on Scheme 4, Pathway D (Wilson et al., *J. Bioorg. Med. Chem. Lett.* 2001, 11, 915-918; Feldman et al., *Tetrahedron Lett.* 1991, 32, 875). If the above set of synthetic methods are not applicable to obtain N-substituted thiourea (P2a), suitable methods of preparation known by a person skilled in the art should be used.

The amine NHR⁵R⁶ used in synthetic Scheme 4 above are either commercially available from various sources or synthesized, as it will be detailed below in the examples, using conditions known to the person skilled in the art.

The thioureas (P2a) synthesized under conditions described in pathways A, B, C and D, or any other method reported in the literature, are either used directly in the synthesis of his-thiazole or oxazole-thiazole of Formula (I) or first purified, if desired, e.g. by crystallization or by standard chromatographic methods.

Bis-thiazole or oxazole-thiazole derivatives of the invention according to Formula (I) wherein R¹ is SO₂R⁷, i.e. compounds of Formula (ac), can be obtained by several synthetic approaches. An example of such a process is described hereinafter.

Bis-thiazole or oxazole-thiazole derivatives of the invention according to Formula (I) wherein R¹ is SO₂R⁷, i.e. compounds of Formula (Ic) and wherein R⁷ is selected from optionally substituted $C_1$-$C_6$-alkyl, optionally substituted $C_2$-$C_6$-alkenyl and optionally substituted-alkynyl can be obtained by the oxidation of the corresponding alkyl, alkenyl or alkynyl sulfur (P3) as shown below on Scheme 5 below.

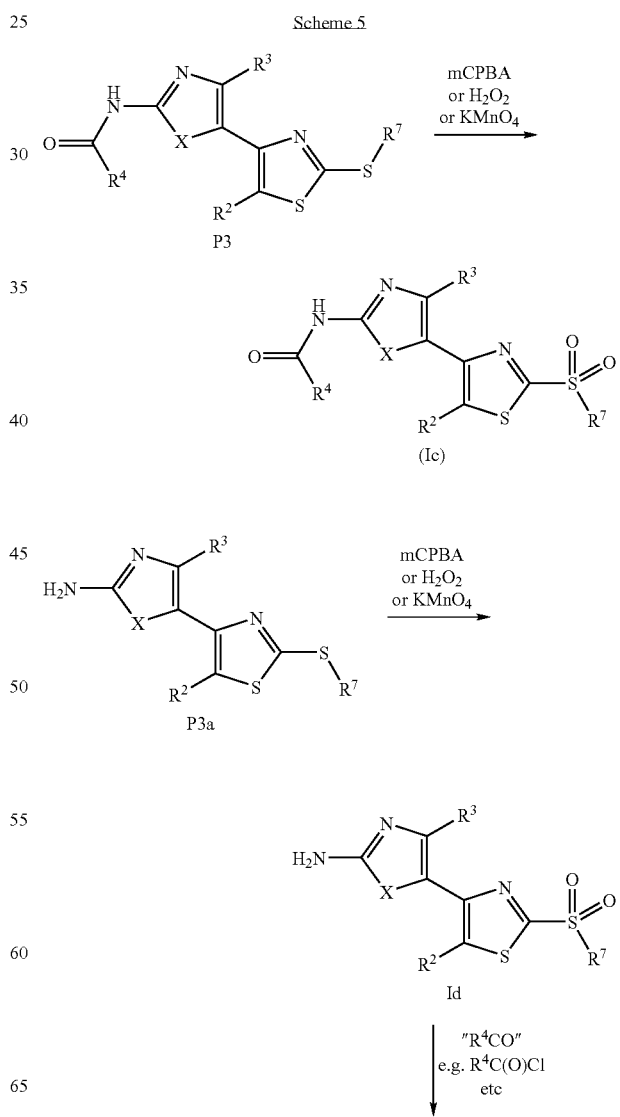

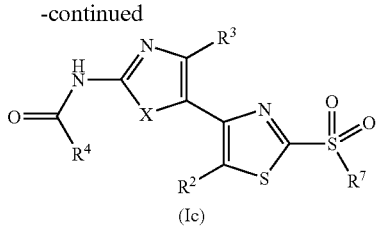

Oxidative agents used in this transformation can be selected from m-chloroperoxybenzoic acid, mCPBA, (Alvarez-Ibarra et al., *Heterocycles* 1991, 32, 2127-2137), KMnO$_4$ (Konno et al., *Yakugaku* 1990, 110, 105-114), H$_2$O$_2$ (Fukatsu et al., *Heterocycles,* 1989, 29, 1517-1528) and any other oxidative agents known by the person skilled in the art.

The oxidation reaction can also be performed on the free amine (P3a) to lead to the corresponding bis-thiazole or oxazole-thiazole intermediate (Id) that can be further substituted by a group —C(O)R$^4$ into a compound of the invention of Formula (Ic), using conditions known to the person skilled in the art.

When —C(O)R$^4$ is an acyl group, the corresponding acyl chloride is added to intermediate (Id) in the presence of a base, e.g. pyridine, DIEA, TEA, etc. The corresponding carboxylic acid can be also added in the presence of an activating agent such as DCC, EDC, etc.

A formyl group, —(O)R$^4$=—C(O)H, can be introduced by heating intermediate (Id) in formic acid or in any alkyl formate, with or without a cosolvent. A substituted urea is formed by addition of an isocyanate, R$^8$R$^9$NC(O), to intermediate (Id) in the presence of a base, e.g. DIEA, TEA, etc. The sequential addition of CDI and ammonia to intermediate (Id) affords a compound of the invention of Formula (Ic) with —C(O)R$^4$=—C(O)NH$_2$.

Other —C(O)R$^4$ functionalities can be added to intermediate ad), to lead to a compound of the invention according to Formula ac) as defined above in the description, using reaction conditions known to the person skilled in the art.

Bis-thiazole or oxazole-thiazole derivatives of the invention according to Formula (I) wherein R$^1$ is —SO$_2$NR$^{10}$R$^{11}$, i.e. compounds of Formula (Ie) can be obtained in two steps, starting with an oxidative chlorination step with Cl$_2$ for the transformation of a sulfure derivative (P4) into the corresponding sulfonyl chloride (P6) as shown on Scheme 6 below.

The second step is the addition of a suitable amine HNR$^{10}$R$^{11}$ to the sulfonyl chloride (P6) in the presence of a base, e.g. DIEA, TEA, pyridine, etc, affording sulfonamide derivatives of the invention according to Formula (Ie), as shown on Scheme 6 below. When R$^{10}$ and R$^{11}$ form a ring, the same processes as described above may be used.

Scheme 6

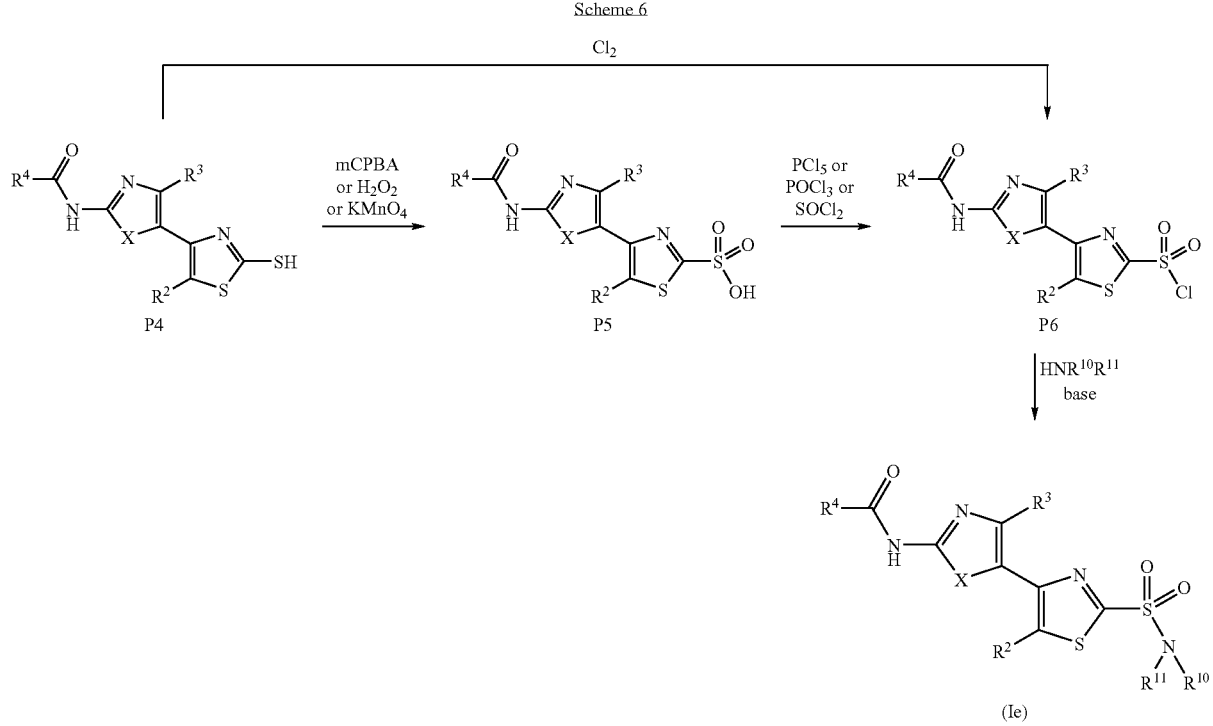

The oxidative chlorination step can be replaced by a two steps process, involving the oxydation of a sulfure (P4) into the corresponding sulfonic acid (P5) (Mazzone et al. *Il Farmaco Ed. Sc.* 1980, 36, 181-196), followed by its chlorination into a sulfonyl chloride (P6).

Different chlorination reagents can be used, as for example PCl$_5$, POCl$_3$ or SOCl$_2$ (Chan et al., *Bioorg. Med. Chem.* 1998, 6, 2301-2316; Kropf et al., *J. Chem. Eng. Data* 1988, 33, 537-538; El-Maghraby et al., *Indian Journal of Chemistry, Section B: Organic Chemistry Including Medicinal Chemistry* 1981, 20B, 256-257).

Methods of Preparing Intermediates of Compounds of Formula (I).

Intermediates (P3) and (P4) are obtained by the reaction of approximately equimolar amounts of the α-bromoketone (P1) with Ammonium dithiocarbamate (P2b) or dithiocarbamic acid alkyl, alkenyl or alkynyl ester (P2c) respectively as shown below on Scheme 7 below.

Scheme 7

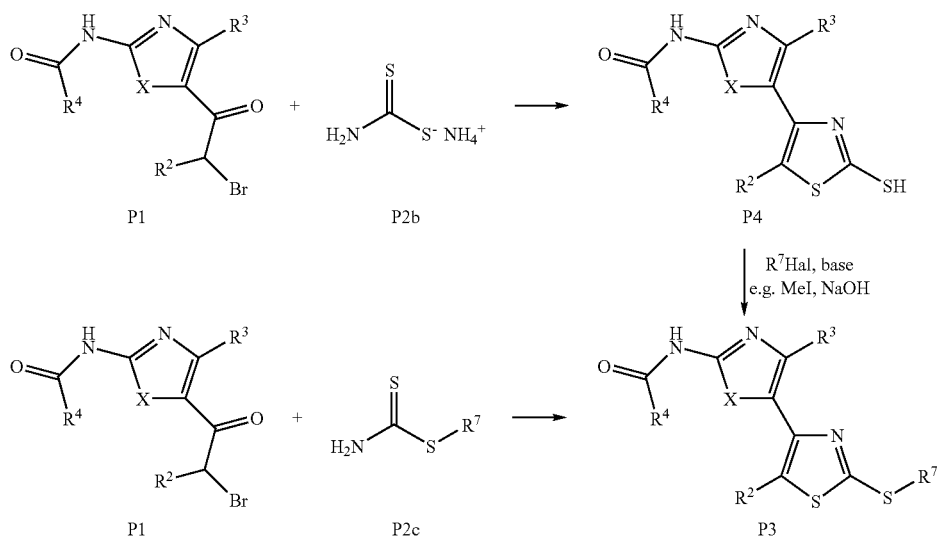

The mixture is stirred as a suspension or solution in a polar solvent, preferably an alcoholic solvent, at a temperature depending on the nature of (P1), (P2b) and (P2c) (Pattan et al., *J. Indian Drugs* 2002, 429-433). The desired bis-thiazole or oxazole-thiazole of formula (P3) or (P4) respectively is isolated by filtration, in case it precipitated out of the reaction mixture upon cooling, or by evaporation of the solvents to obtain the crude product. This crude product can be purified, if desired, e.g. by crystallization or by standard chromatographic methods.

Compound (P3) can be also obtained by direct alkylation of (P4) with $R^7$Hal (where Hal is any leaving group such halides (e.g. Cl, Br, I), alkyl sulfonyloxy or aryl sulfonyloxy groups (e.g. tosyloxy group) in the presence of a base, e.g. MeI or any other alkyl, alkenyl or alkynyl halide, alkyl, alkenyl or alkynyl sulfonyloxy alkyl or aryl in the presence of NaOH (Nair et al., *J. Org. Chem.* 1975, 40, 1348-1349).

Ammonium dithiocarbamate (P2b) can be obtained by addition of ammonia to a carbon disulfide solution in a solvent such as THF as shown on Scheme 8 below. It can be further transformed into (P2c) using $R^7$Hal, e.g. dimethyl sulfate (Brandsma et al., *Synthesis* 1985, 948-949).

Scheme 8

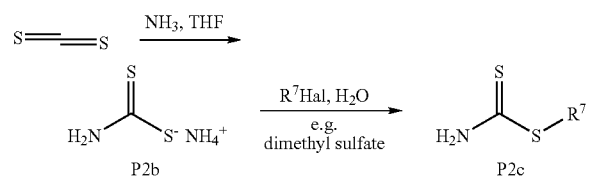

α-bromoketone (P1) can be obtained in two steps, from substituted 5-acetyl-2-amino thiazole (P5) as shown on Scheme 9 below.

Scheme 9

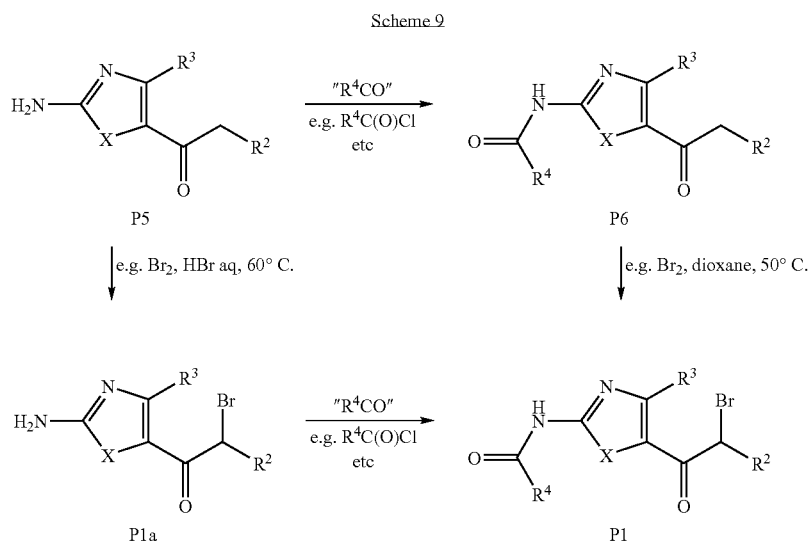

Functionalization of the primary amine in (P5) with a group —C(O)R⁴ as defined above in the description can be performed first, using conditions known to the person skilled in the art to afford (P6).

When —C(O)R⁴ is an acyl group, the corresponding acyl chloride is added to (P5) in the presence of a base, e.g. pyridine, DIEA, TEA, etc. The corresponding carboxylic acid can be also added in the presence of an activating agent such as DCC, EDC, etc.

A formyl group, —C(O)R⁴=—C(O)H, can be introduced by heating (P5) in formic acid or in any alkyl formate, with or without a cosolvent A substituted urea is formed by addition of an isocyanate, R⁸R⁹NC(O), to intermediate (P5) in the presence of a base, e.g. DIEA, TEA, etc. The sequential addition of CDI and ammonia to (P5) affords (P6) with —C(O)R⁴=—C(O)NH₂.

Other —C(O)R⁴ functionalities can be added to intermediate (P5), to give an intermediate of formula (P6) as defined above in the description, using reaction conditions known to the person skilled in the art. This step is then followed by a α-bromination of the 5-acetyl group to afford intermediate (P1). These two steps can be done in the reverse order, performing first the bromination on intermediate (P5) in the presence of the unprotected primary amine, affording an intermediate (P1a), and then the introduction of —(O)R⁴ group as defined above in the description using conditions known to the person skilled in the art to afford an intermediate (P1).

In both synthetic pathways, different bromination agents can be used, such as Br₂ (Bhatti et al., *Indian J. Heterocyclic Chem.* 2000, 10, 81-84), in the optional presence of HBr (Lipinski et al., *J. Med. Chem.* 1986, 29, 2154-2163), NBS (Sayed et al., *Heteroatom Chemistry* 1999, 10, 385-390).

Intermediates according to formula (P5) are either commercially available from various sources or can be obtained by several synthetic approaches, using both solution-phase and solid-phase chemistry protocols (Kodomari et al., *Tetrahedron Lett.* 2002, 43, 1717-1720).

An example of a synthetic approach for obtaining intermediate (P5) is illustrated on Scheme 10 hereinafter.

A substituted bi-ketone (P7) is halogenated, using for example Br₂ for a bromination or thionyl chloride for a chlorination, affording an intermediate (P8). "Hal" in intermediate (P8) can be as well a tosyloxy group, which is introduced with suitable reagents such as hydroxy(tosyloxy)iodobenzene. Intermediate (P8) is then added to a solution of thiourea or urea in a suitable solvent, preferably a polar solvent, e.g. EtOH to lead to an intermediate (P5).

The specific reaction conditions, temperature, time, etc, depend on the nature of X and substituents R² and R³, according to the literature and as it will be detailed below in the examples (Sayed et al., 1999, above; Dahiya et al., *Indian J. Chem.* 1986, 25B, 966; Lipinski et al., *J. Org. Chem.* 1984, 49, 566-570; WO95/01979; EP0117082; JP11209284; Öhler et al., *Chem. Ber.* 1985, 118, 4099-4130).

Intermediate (P6) can be directly obtained from the reaction of (P8) with the suitable thiourea or urea (P9), substituted with a —C(O)R⁴ group as it has been defined above in the description. Thiourea or urea (P9) are either commercially available or obtained by functionalization of urea H₂NC(O)NH₂ or thiourea H₂NC(S)NH₂ with —C(O)R⁴, as defined above in the description, using conditions known to the person skilled in the art.

When R³=H, P7a is prepared in one step, as sodium salt, by the condensation of a methyl ketone with ethyl formate, as described on Scheme 11 below. It is then directly brominated, affording intermediate P8a, according to the literature and as it will be detailed below in the examples (Lipinski et al., *J. Org. Chem.* 1984, 49, 566-570).

Scheme 11

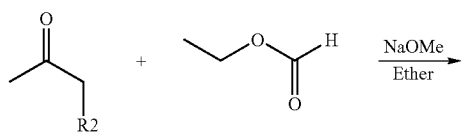

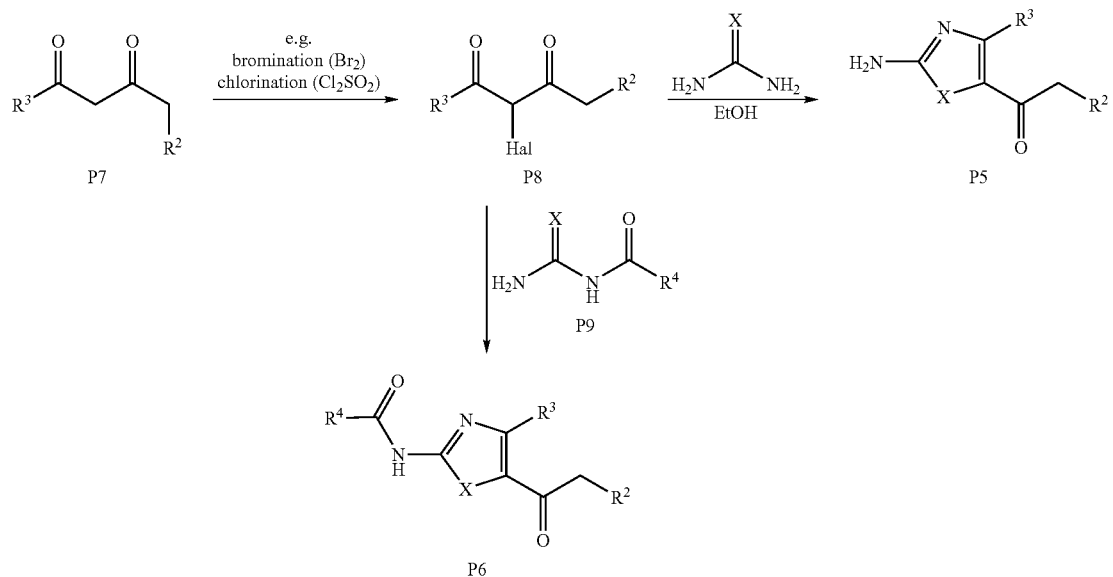

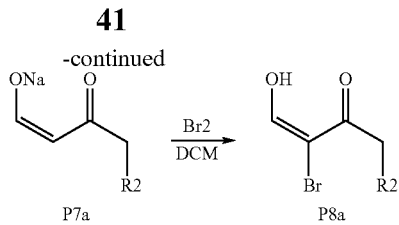

According to a further general process, compounds of Formula (I) can be converted to alter-native compounds of Formula (I), employing suitable interconversion techniques well known by a person skilled in the art.

If the above set of general synthetic methods are not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula M) will depend on the specific substitutents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart New York, 1994 and, Theodora W. Greene and Peter G. M. Wuts in "*Protective Groups in Organic Synthesis*", Wiley Interscience, $3^{rd}$ Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

When employed as pharmaceuticals, the compounds of the present invention are typically administered in the form of a pharmaceutical composition. Hence, pharmaceutical compositions comprising a compound of Formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing thiazole derivatives of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the thiazole derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the bisthoiazole derivatives derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences, $20^{th}$ Edition*, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples, which are not construed to be viewed as limiting the scope of the invention.

EXAMPLES

The Following Intermediate Commercially Available were Used

5-Acetyl-2-amino-4-methylthiazole and 2,4-pentandione have been used from commercial source.

The commercial amines which have been used as starting material for thiourea synthesis are the following:
4-aminobenzamide, {4-[(4-benzylpiperazin-1-yl)carbonyl]phenyl}amine, morpholine, 1-methylpiperazine, ethyl piperidine-3-carboxylate, 2-piperidin-4-ylethanol, pyrrolidine, pyrrolidin-3-ol, 6-methoxypyridin-3-amine, 6-chloropyridin-3-amine, beta-alanine, 3-amino-2-fluoropyridine, N-(2-cyanoethyl)amine, 1-amino-3,3-diethoxypropane, aminoacetaldehyde diethyl acetal, 2-aminoacetophenone, 3-amino-2-chloropyridine, 5-(3-aminophenyl)oxazole, 5-(3-aminophenyl)tetrazole, methyl 3-aminobutanoate, hydrochloride salt, 3-aminobenzyldehyde ethylene acetal, (4-aminophenyl)acetic acid, N-(4-aminobenzoyl)-beta-alanine, N-(4-aminobenzoyl)glycine, 3-(3-aminophenyl)propanoic acid, 3-(4-aminophenyl)propanoic acid, (3-aminophenyl)acetic acid, 4-amino-N-pyridin-2-ylbenzenesulfonamide, 2-(2-aminophenyl)ethanol, (3-aminophenyl)methanol, 2-(4-aminophenyl)ethanol, 2-[(3-aminophenyl)sulfonyl]ethanol, hydrochloride salt, 4-amino-N,N-dimethylbenzenesulfonamide, 3-aminobenzenesulfonamide, 2-chloropyridin-4-amine, 4-amino-N-methylbenzenesulfonamide, N-(5-aminopyridin-2-yl)acetamide, 2,3-dihydro-1-benzofuran-5-amine, [2-(1-methylpyrrolidin-2-yl)ethyl]amine, (2-pyrrolidin-1-ylethyl) amine, 1-(3-aminopropyl)pyrrolidin-2-one, N-(2-aminoethyl)acetamide, N,N-dimethyl ethane-1,2-diamine, 2-aminoethanol, 4-(2-aminoethyl)phenol, N,N-dimethylpropane-1,3-diamine, 3-aminopropan-1-ol, [3-(1H-imidazol-1-yl)propyl]amine, beta-alaninamide, hydro chloride salt, (2-methylprop-2-en-1-yl)amine, 2-aminophenol, 3-aminophenol, 6-fluoro pyridin-3-amine, 2-fluoropyridin-3-amine, 5-aminopyridine-2-carbonitrile, (3-methoxy phenyl)amine, (4-chlorophenyl)amine, 3-aminobenzamide, (2-nitrophenyl)amine, quinolin-3-amine, quinolin-5-amine, quinolin-6-amine, cyclopentanamine, cyclopropanamine, (pyridin-3-ylmethyl)amine, 4-aminobutan-1-ol, [3-(methylsulfonyl)phenyl]amine, hydro chloride salt, 3-aminopropanenitrile, (3-pyrrolidin-1-ylpropyl)amine, (1,1-dioxido-1-benzo thien-6-yl)amine, [(1-ethylpyrrolidin-2-yl)methyl]amine, aminoacetonitrile, 2-methyl propan-1-amine, (2,2-dimethylpropyl)amine, cis-(2-aminocyclohexyl)methanol, hydro chloride salt, trans-(2-aminocyclohexyl)methanol hydrochloride salt, sec-butylamine, (pyridin-4-ylmethyl)amine, [4-(morpholin-4-ylsulfonyl)phenyl]amine, 3-amino-N-butyl benzenesulfonamide, (cyclopropylmethyl)amine, cyclobutanamine, 2,3-dihydro-1H-inden-2-ylamine, [2-(methylsulfonyl)phenyl]amine, hydrochloride salt, [2-(1H-1,2,4-triazol-1-yl)ethyl]amine, 1-(3-aminophenyl)ethanol, methyl 4-aminobutanoate.

Commercial thiourea used in the examples disclosed below are the following: 3-[(aminocarbonothioyl)amino]benzoic acid, 4-[(aminocarbonothioyl)amino]benzoic acid, N-benzylthiourea, N-(2-phenylethyl)thiourea, piperidine-1-carbothioamide, N-allyl thiourea, N-pyridin-3-ylthiourea, N-pyridin-2-ylthiourea, N-(4-methoxyphenyl)thiourea, N-(4-hydroxyphenyl)thiourea, N-(4-nitrophenyl)thiourea, N-(4-cyanophenyl)thiourea, N-(4-chlorophenyl)thiourea, N-(2-chlorophenyl)thiourea, N-(2-methoxyphenyl)thiourea, N-(3-chlorophenyl)thiourea, N-(3-hydroxyphenyl)thiourea, N-(2-morpholin-4-ylethyl)thiourea, N-(2-piperidin-1-ylethyl)thiourea, N-(2-methoxyethyl)thiourea, N-cyclohexylthiourea, N-(3-morpholin-4-ylpropyl)thiourea, N-(tetrahydrofuran-2-ylmethyl)thiourea, N-1-benzofuran-5-ylthiourea, N-1-benzofuran-5-ylthiourea, N-(4-cyanophenyl)thiourea, N-(3-nitrophenyl)thiourea, N-allylthiourea, N-pyridin-3-ylthiourea, piperidine-1-carbothioamide, N-phenylthiourea, N-(4-hydroxyphenyl)thiourea, N-pyridin-3-ylthiourea.

The HPLC, NMR and MS data provided in the examples described below are obtained as followed: HPLC: column Waters Symmetry C8 50×4.6 mm, Conditions: MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The preparative HPLC purifications are performed with HPLC Waters Prep LC 4000 System equipped with columns Prep Nova-Pak®HR C186 μm 60 Å, 40×30 mm (up to 100 mg) or with XTerra® Prep MS C8, 10 μm, 50×300 mm (up to 1 g). All the purifications are performed with a gradient of MeCN/H$_2$O 0.09% TFA. The semi-preparative reverse-phase HPLC are performed with the Biotage Parallex Flex System equipped with columns Supelcosil™ ABZ+Plus (25 cm×21.2 mm, 12 μm); UV detection at 254 nm and 220 nm; flow 20 mL/min (up to 50 mg). TLC Analysis is performed on Merck Precoated 60 F$_{254}$ plates. Purifications by flash chromatography are performed on SiO$_2$ sup port, using cyclohexane/EtOAc or DCM/MeOH mixtures as eluents.

The microwave chemistry is performed on a single mode microwave reactor Emrys™ Optimiser from Personal Chemistry.

Intermediate 1

Preparation of N-[5-(bromoacetyl)-4-methyl-1,3-thiazol-2-yl]acetamide, hydrobromide Salt (Intermediate (P1) Wherein $R^2$ is H, $R^3$ and $R^4$ are Methyl and X is S)

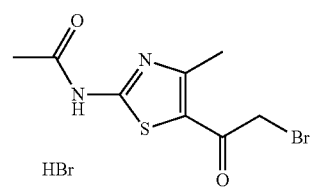

Intermediate 1

Step I

N-(5-acetyl-4-methyl-1,3-thiazol-2-yl)acetamide (Intermediate (P6) wherein $R^2$ is H, $R^3$ and $R^4$ are methyl and X is S)

5-Acetyl-2-amino-4-methylthiazole (P5) (12.35 g, 79 mmol) is suspended in THF/DCM 3:2 mixture (150 mL). The mixture was cooled down to 0° C. and pyridine (16 mL) is added, followed by the dropwise addition of acetyl chloride (8.43 mL, 119 mmol, 1.5 eq). The mixture was stirred 2 hours at 0° C. As the acetylation is complete, the reaction is quenched with addition of water (70 mL) and diluted with EtOAc (100 mL). The two phases are separated and the organic phase is washed with one portion of 10% citric acid solution. Organic layer is dried over MgSO$_4$, filtrated and evaporated. The resulting crude mass is purified by crystallization in EtOAc/Cyclohexane mixture, to obtain N-(5-acetyl-4-methyl-1,3-thiazol-2-yl)acetamide (P6) as a colorless powder (13.13 g, 83.6% yield). $^1$H NMR (DMSO-$d_6$) δ: 2.17 (s, 3H), 2.47 (s, 3H), 2.56 (s, 3H), 12.44 (br s, 1H). M$^-$ (ESI): 197.3; M$^+$ (ESI): 199.3. HPLC, Rt: 1.7 min (purity: 99.7%).

Step II

N-[5-(bromoacetyl)-4-methyl-1,3-thiazol-2-yl]acetamide, hydrobromide salt

Intermediate 1

A solution of Br$_2$ (3.36 mL, 65.6 mmol) in 75 mL dioxane is added dropwise to a solution of N-(5-acetyl-4-methyl-1,3-thiazol-2-yl)acetamide (P6), obtained in Step I as described above, (10.40 g, 52.5 mmol) in 200 mL dioxane. The resulting mixture is heated at 50° C. for 19 hours. The solution turns from dark red to beige and remains a heterogeneous mixture. By analytical HPLC, only 2.8% of starting material is detected. The suspension is filtered, washed with a 1:2 EtOAc/hexanes mixture (50 mL) and air dried for 15 min, to give Intermediate 1 as a beige solid (11.2 g, 60%). It is used in bis-thiazol synthesis as HBr salt or as parent, after 5 min treatment with Amberlyst A21 in DCM/MeOH mixture. $^1$H NE (DMSO-$d_6$) δ: 2.04 (s, 3H), 2.44 (s, 3H), 4.52 (s, 2H), 12.44 (br s, 1H). M$^-$ (ESI): 276; M$^+$ (ESI): 278. HPLC, Rt: 2.2 min (purity: 97.4%).

Intermediate 2

Preparation of 1-(2-amino-4-methyl-1,3-thiazol-5-yl)-2-bromo ethanone, hydrobromide Salt (Intermediate (P1a) Wherein $R^2$ is H, $R^3$ is Methyl and X is S)

Intermediate 2

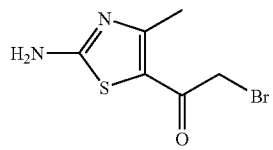

5-Acetyl-2-amino-4-methylthiazole (P5) (1.0 g, 6.4 mmol) is suspended in 48% HBr solution in water (20 mL, 6.4 mmol). The mixture is warmed to 60° C. and a solution of Br$_2$ (0.262 mL, 5.12 mmol, 0.8 eq) in dioxane (20 mL) is added dropwise. The mixture is stirred at 60° C. for 3 hours. The progression of the reaction is followed by LC/MS. When it is complete, the solvents are evaporated, and the water is removed by azeotropic distillation with toluene. The resulting solid is recrystallized in isopropanol/Et$_2$O mixture, affording Intermediate 2 as colorless solid (890 mg, 74% yield). $^1$H NMR (DMSO-$d_6$) δ: 2.46 (s, 3H), 4.50 (s, 3H), 6.90 (br s, 1H), 9.18 (br s, 2H). M$^-$ (ESI): 234.1; M$^+$ (ESI): 236.1.

Intermediate 3

Preparation of N-[5(bromoacetyl-4-methyl-1,3-oxazol-2-yl]acetamide (Intermediate (P1) Wherein $R^2$ is H, $R^3$ and $R^4$ are Methyl and X is O)

Intermediate 3

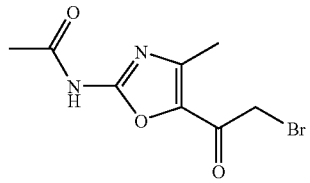

Step I

3-Bromo-2,4-pentandione (Intermediate (P8) wherein $R^2$ is H, $R^3$ is methyl and Hal is Br)

A solution of bromine (55.9 g, 0.35 mol, 18 mL) in CCl$_4$ (135 mL) is added over 80 min to a bi-phasic solution of 2,4-pentanedione (P7) (35 g, 0.35 mol, 36 mL) in 1:1 CCl$_4$/water mixture (400 mL), keeping the temperature at 3-4° C. 40 min after the addition, both layers are separated and the organic phase is dried over MgSO$_4$. Evaporation under reduced pressure gives 3-bromo-2,4-pentandione (P8) as a slightly yellowish liquid (54.01 g, 86%). $^1$H NMR (DMSO-$d_6$) δ: 2.32 (s, 6H), 5.64 (s, 1H).

Step II 1-(2-amino-4-methyl-1,3-oxazol-5-yl)ethanone (Intermediate (P5) wherein $R^2$ is H, $R^3$ is methyl and X is O)

3-Bromo-2,4-pentandione (P8) (26.66 g, 148.93 mmol) obtained in Step I as described above, is dissolved in acetone (87 mL). This mixture is added to a solution of urea (22.36 g, 372 mmol, 2.5 eq) in water (20 mL). The resulting mixture is heated in order to obtain a clear solution and is distributed into 38 microwave tubes (3 ml each). The vials are heated to 100° C. for 1200 s each in the microwave oven. All vials are combined, NaHCO$_3$ sat (100 ml) and EtOAc (100 ml) are added, the aqueous phase is saturated with NaCl and the phases are separated. The aqueous phase is extracted with EtOAc (4 times 100 ml). Combined organic layers are dried over MgSO$_4$, filtrated and evaporated under reduced pressure to give 1-(2-amino-4-methyl-1,3-oxazol-5-yl)ethanone (P5) as an orange solid (12.09 g). It is further recrystallized in MeOH, affording a brownish solid (5.56 g, 27%). $^1$H NMR (DMSO-d) δ: 2.22 (s, 3H), 2.25 (s, 3H), 7.51 (s, 2H).

Step III

N-(5-acetyl-4-methyl-1,3-oxazol-2-yl)acetamide (Intermediate (P6) Wherein $R^2$ is H, $R^3$ and $R^4$ are methyl and X is O)

1-(2-amino-4-methyl-1,3-oxazol-5-yl)ethanone (P5) obtained in Step II as described above (12.55 g, 89.58 mmol, 1.00 eq.) is dissolved in pyridine (300 ml). The solution is cooled to 0° C., and acetyl chloride (9.55 ml; 134.37 mmol; 1.50 eq.) is added dropwise at such a rate that the temperature did not exceed 5° C. The mixture is stirred at r.t. overnight HCl solution (1.0 M, 250 mL) is added and the desired product is extracted with EtOAc (5 times, 100 mL). Combined organic layers are dried over MgSO4, filtrated and evaportated, affording the N-(5-acetyl-4-methyl-1,3-oxazol-2-yl) acetamide (P6) as beige/brownish solid (15.18 g, 93%). $^1$H NMR (DMSO-$d_6$) δ: 2.12 (s, 3H), 2.34 (s, 3H), 2.35 (s, 3H), 11.64 (s, 1H).

Step IV

N-[5-(bromoacetyl)-4-methyl-1,3-oxazol-2-yl]acetamide (Intermediate 3)

N-(5-acetyl-4-methyl-1,3-oxazol-2-yl)acetamide (P6) obtained in Step III above (13.29 g, 72.95 mmol, 1.00 eq.) is dissolved in glacial acetic acid (250 ml) and 10 drops of hydrobromic acid 62% are added. To the resulting solution, bromine (3.74 ml, 72.95 mmol, 1.00 eq.) is added dropwise and the mixture is stirred at r.t. for 2.5 h. A beige precipitate is formed. It is filtrated off, washed with cyclohexane and dried under reduced pressure to lead to Intermediate 3 as beige solid (14.89 g, 78%). $^1$H NMR (DMSO-$d_6$) δ: 2.14 (s, 3H), 2.38 (s, 3H), 4.46 (s, 2H), 11.78 (s, 1H). M$^-$ (ESI): 259.8; M$^+$ (ESI): 261.9. HPLC, Rt: 1.3 min (purity: 97.6%).

Intermediate 4

Preparation of N-[5-(2-bromo-acetyl)-thiazol-2-yl]-acetamide (Intermediate (P1) Wherein $R^2$ and $R^3$ are H, $R^4$ is Methyl and X is S)

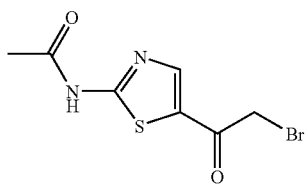

Intermediate 4

Step I

Sodium acetoacetaldehyde (Intermediate (P7a) wherein $R^2$ is H)

Ethylformate (5 g, 0.067 mol) is added slowly to a solution of NaOMe (3.64 g, 0.067 mol) in diethyl ether (30 mL) and acetone (5 mL). The mixture is stirred for 30 min. The resulting solid is collected by filtration, washed with ether, and then dried under vacuo, affording sodium acetoacetaldehyde (P7a) as a white solid (4.5 g, 61%).

Step II

2-Bromoacetoacetaldehyde (Intermediate (P8a) Wherein $R^2$ is H)

Sodium acetoacetaldehyde (P7a) (4.5 g, 0.041 mol) obtained in Step I as described above, is dissolved in DCM (45 mL). The resulting solution is cooled to −78° C. and bromine (6.6 g, 0.041 mol) in DCM (3 mL) is added dropwise. The reaction mixture is stirred at −78° C. for 24 h and is warmed up to RT. The resulting solid is collected by filtration and recrystallised with ethylacetate and petroleum ether, affording 2-bromo acetoacetaldehyd (P8a) as a pale yellow solid (5.4 g, 78%).

Step III 1-(2-Amino-1,3-thiazol-5-yl)ethanone (Intermediate (P5) Wherein $R^2$ and $R^3$ are H and X is S)

2-Bromoacetoacetaldehyde, obtained in Step II as described above, (5 g, 0.03 mol) is dissolved in ethanol (50 mL). Thiourea (2.76 g, 0.03 mol) is added and the reaction mixture is stirred 24 h at RT and 3 h under reflux. It is cooled to RT and the resulting solid is isolated by filtration, washed with EtOH and dried under vacuo. 1-(2-Amino-1,3-thiazol-5-yl)ethanone (P5) is recovered as a white solid (2.5 g, 40%).

Step IV

N-(5-acetyl-1,3-thiazol-2-yl)acetamide (Intermediate (P6) Wherein $R^2$ and $R^3$ are H, $R^4$ is methyl and X is S)

1-(2-Amino-1,3-thiazol-5-yl)ethanone, obtained in Step III as described above (2 g, 9.66 mmol) is dissolved in a mixture of THF (15 mL) and DCM (10 mL). The resulting solution is cooled down to 0° C. Acetyl chloride (1.1 g, 14.4 mmol) is added and the mixture is stirred at RT overnight. It is then diluted with water (50 mL), extracted with ethyl acetate (3×50 mL). The combined organic phase is washed with water, brine, dried over MgSO$_4$, filtrated and evaporated, affording N-(5-acetyl-1,3-thiazol-2-yl)acetamide (P6) as a white solid (2.1 g, 87%).

Step V

N-[5-(2-bromo-acetyl)-thiazol-2-yl]-acetamide (Intermediate 4)

N-(5-acetyl-1,3-thiazol-2-yl)acetamide, obtained in Step IV as described above (1.5 g, 6 mmol), is dissolved in dioxane (50 mL). Bromine (0.96 g, 6 mmol) is added and the mixture is heated at 60° C. for 24 h. The reaction mixture is concentrated. The resulting solid is isolated by filtration and recrystallised in ethyl acetate and petroleum ether, affording Intermediate 4 as white-off solid (1.2 g, 60%). $^1$H NMR (DMSO-$d_6$) δ: 2.17 (s, 3H), 4.76 (s, 2H), 8.47 (s, 1H), 12.67 (br s, 1H). M$^-$ (ESI): 261.09; M$^+$ (ESI): 263.14. HPLC, Rt: 1.79 min (purity: 94.32%).

Intermediate 5

Preparation of N-[5-(2-bromo-acetyl)-4-trifluoromethyl-thiazol-2-yl]-acetamide (Intermediate (P1) Wherein $R^2$ is H, $R^3$ is $CF_3$ and $R^4$ is Methyl and X is S)

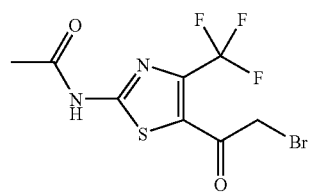

Intermediate 5

Step I

1-[2-amino-4-(trifluoromethyl)-1,3-thiazol-5-yl]ethanone (Intermediate (P5) Wherein $R^2$ is H and $R^3$ is $CF_3$)

Hydroxy(tosyloxy)iodobenzene (3 g, 7.7 mmol) is added to a solution of 1,1,1,-trifluoro pentane-2,4-dione (1 g, 6.4 mmol) in ACN (10 mL). The resulting mixture is heated under reflux for 45 minutes, then cooled down to RT, and thiourea (0.59 g, 7.7 mmol) is added. The mixture is heated under reflux for 4 hours and then left to stand overnight. The reaction mixture is concentrated and the residue is recrystallised in ethylacetate and petroleum ether, affording 1-[2-amino-4-(trifluoromethyl)-1,3-thiazol-5-yl]ethanone (P8) as white solid (1.2 g, 79%).

Step II

N-[5-acetyl-4-(trifluoromethyl)-1,3-thiazol-2-yl)acetamide (Intermediate (P6) Wherein $R^2$ is H, $R^3$ is $CF_3$, $R^4$ is methyl and X is S)

1-[2-amino-4-(trifluoromethyl)-1,3-thiazol-5-yl]ethanone, obtained in Step I as described above (1 g, 5.7 mmol), is dissolved in a mixture of THF (7.5 mL), DCM (7.5 mL) and pyridine (1 g, 12.8 mmol). The resulting solution is cooled down to 0° C. and acetylchloride (0.6 g, 7.7 mmol) is added. The mixture is stirred overnight at RT. It is diluted with water (10 mL) and extracted with DCM (3×25 mL). The combined organic phase is washed with water, brine, dried over $MgSO_4$, filtrated and concentrated. The resulting crude product, N-[5-acetyl-4-(trifluoromethyl)-1,3-thiazol-2-yl)acetamide, is used in the next step without further purification (1.1 g, 90%).

Step III

2-Acetylamino-4-(trifluoromethyl)-5-bromoacetyl thiazole (Intermediate 5)

N-[5-acetyl-4-(trifluoromethyl)-1,3-thiazol-2-yl)acetamide, obtained in Step II as described above (1 g, 4.2 mmol), is dissolved in dioxane (50 mL). Bromine (0.67 g, 4.2 mmol) is added and the mixture is heated at 60° C. for 24 h. The reaction mixture is concentrated. The crude compound obtained is recrystallised in ethyl acetate and petroleum ether, affording Intermediate 5 (0.8 g, 60%) which is mixed with bis-brominated intermediate in 4:6 ratio. However, it is used as such in the reactions described hereafter. $^1$H NMR (DMSO-$d_6$) δ: 2.22 (s, 3H), 2.38 (s, 3H), 4.73 (s, 2H), 13.08 (s, 1H). $^{19}$F NMR (DMSO-$d_6$) δ: −61.22. M$^{-1}$ (ESI): 329.1; M$^+$ (ESI): 331.3. HPLC, Rt: 2.90 min (purity: 41.47%).

Intermediate 6

Preparation of Ethyl 2-(acetylamino)-5-(bromoacetyl)-1,3-thiazole-4-carboxylate (Intermediate (P1) Wherein $R^2$ is H, $R^3$ is COOEt and $R^4$ is Methyl and X is S)

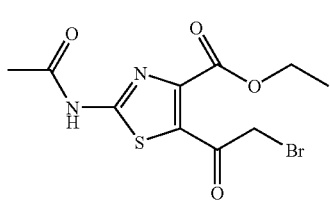

Intermediate 6

Step I

Ethyl 5-acetyl-2-amino-1,3-thiazole-4-carboxylate (Intermediate (P5) Wherein $R^2$ is H and $R^3$ is COOEt)

Dioxovalerate (2 g, 12.6 mmol) is dissolved in $CCL_4$ (20 mL) and cooled down to 0° C. $SOCl_2$ (1.7 g, 17.7 mmol) is added and the mixture is stirred at RT for 1 h. The reaction mixture is concentrated. The resulting residue is dissolved in absolute ethanol (20 mL). Thiourea (1.4 g, 18.9 mmol) is added and the mixture is stirred overnight RT. The reaction mixture is diluted with water and extracted with ethyl acetate (3×25 mL). Combined organic phase are washed with water, brine and dried over $MgSO_4$. Filtration and evaporation of the solvents afford ethyl 5-acetyl-2-amino-1,3-thiazole-4-carboxylate as white solid (0.8 g, 29%). It is used in the next step without further purification.

Step II

Ethyl 5-acetyl-2-(acetylamino)-1,3-thiazole-4-carboxylate (Intermediate (P6) Wherein $R^2$ is H, $R^3$ is COOEt, $R^4$ is methyl and X is S)

Ethyl 5-acetyl-2-amino-1,3-thiazole-4-carboxylate, obtained in Step I as described above (0.8 g, 3.7 mmol), is dissolved in a mixture of THF (10 mL) and DCM (5 mL) and pyridine (0.73 g, 9.3 mmol). The resulting solution is cooled down to 0° C. and acetylchloride (0.43 g, 5.6 mmol) is added. The mixture is stirred overnight at RT. It is diluted with ethyl acetate (25 mL). The organic phase is washed with water, brine, dried over $MgSO_4$, filtrated and concentrated. The resulting crude product is crystallized in ethyl acetate and petroleum ether, affording ethyl 5-acetyl-2-(acetylamino)-1,3-thiazole-4-carboxylate as white solid (0.6 g, 62%).

Step III

Ethyl 2-(acetylamino)-5-(bromoacetyl)-1,3-thiazole-4-carboxylate (Intermediate 6)

Ethyl 5-acetyl-2-(acetylamino)-1,3-thiazole-4-carboxylate, obtained in Step II as described above (0.6 g, 2.3 mmol) is dissolved in dioxane (50 mL). Bromine (0.37 g, 2.33 mol) is added and the mixture is stirred at 60° C. for 24 h. The reaction mixture is concentrated. The resulting crude compound is recrystallised in ethyl acetate and petroleum ether mixture, affording Intermediate 6 as white solid (0.7 g, 90%). It is contaminated with 19% of bis-brominated intermediate. However, it is used as such in the reactions described hereafter. $^1$H NMR (DMSO-$d_6$) δ: 1.27 (m, 3H), 2.19 (s, 3H), 4.31 (m, 2H), 4.74 (s, 2H), 12.90 (br s, 1H). M$^−$ (ESI): 333.1; M$^+$ (ESI): 335.1. HPLC, Rt: 2.66 min (purity: 70.54%).

Intermediate 7

Preparation of N-[5-(bromoacetyl)-4-methyl-1,3-thiazol-2-yl]urea (Intermediate (P1) Wherein $R^2$ is H, $R^3$ and $R^4$ are Methyl and X is S)

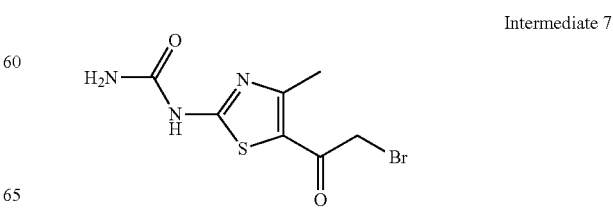

Intermediate 7

Step I

N-(5-acetyl-4-methyl-1,3-thiazol-2-yl)urea (Intermediate (P6) Wherein $R^2$ is H, $R^3$ is methyl, $R^4$ is NH3 and X is S)

2-Amino-4-methyl-5-acetylthiazole (3 g, 19.2 mmol) is dissolved in DMF (30 mL). CDI (3.5 g, 21.1 mmol) is added and the mixture is stirred at RT for 3 h. Ammonia 0.5 N in dioxane is added (60 mL, 30 mmol) is added and the mixture is stirred for 2 days in a closed system. The resulting precipitate is recovered by filtration, washed with petroleum ether and dried under vacuo, affording N-(5-acetyl-4-methyl-1,3-thiazol-2-yl)urea as colorless solid (1.5 g, 39%).

Step II

N-[5-(bromoacetyl)-4-methyl-1,3-thiazol-2-yl]urea (Intermediate 7)

A solution of (5-acetyl-4-methyl-thiazol-2-yl)urea, obtained in Step I as described above (1.5 g, 7.5 mmol), is dissolved in dioxane (200 mL). Bromine (1.2 g, 7.5 mmol) is added and the mixture is heated to 60° C. overnight. The reaction mixture is concentrated and the resulting crude product is recrystallised in ethyl acetate and petroleum ether mixture, affording Intermediate 7 as colorless solid (0.55 g, 26%). It is mixed with 7% of bis-brominated intermediate and 55% of starting material. However, it is used as such in the reactions described hereafter. $M^-$ (ESI): 277.81; $M^+$ (ESI): 279.89. HPLC, Rt: 1.78 min (purity: 36.29%).

Amine 1

Preparation of 5(3-aminophenyl)-1,3,4-oxadiazol-2-ol (Amine (NHR$^5$R$^6$) Wherein R$^5$ is H and R$^6$ is 5-Phenyl-[1,3,4]oxadiazol-2-ol)

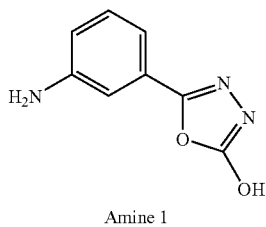 [SMILES: Nc1cccc(-c2nnc(O)o2)c1]

Amine 1

Step I

Methyl 3-nitrobenzoate

3-Nitrobenzoic acid (1.00 g; 5.98 mmol; 1.00 eq.) is dissolved in toluene (15 ml). Timethylsilyl diazomethane in toluene and MeOH (1/1) (8.98 ml; 2.00 M; 17.95 mmol; 3.00 eq.) is added dropwise. The solution is stirred at RT for 1.5 h. Solvents are removed affording methyl 3-nitrobenzoate as a yellow powder (940.70 mg; 86.79%).

$^1$H NMR (DMSO-d$_6$) δ: 3.92 (s, 3H), 7.84 (m, 1H), 8.35 (m, 1H), 8.50 (m, 1H), 8.62 (m, 1H). HPLC, Rt: 1.8 min (purity: 99.1%).

Step II

3-Nitrobenzohydrazide

Methyl 3-nitrobenzoate (940.70 mg; 5.19 mmol; 1.00 eq.) is dissolved in EtOH (24.00 ml). Hydrazine hydrate (4.04 ml; 83.09 mmol; 16.00 eq.) is added and the mixture is stirred 1 hour at RT. It is stirred at 60° C. for 6 hours and RT overnight. The precipitate formed is filtrated and dried under vacuo, affording 3-nitrobenzohydrazide as white-off solid (815.90 mg; 86.73%). $^1$H NMR (DMSO-d$_6$) δ: 4.62 (s, 2H), 7.76 (m, 1H), 8.24 (m, 1H), 8.36 (m, 1H), 8.63 (s, 1H), 10.15 (s, 1H).

Step III 5-(3-nitrophenyl)-1,3,4-oxadiazol-2-ol 1,1'-Carbonyldiimidazole (641.18 mg; 3.95 mmol; 1.00 eq.) is added to a 0° C. solution of 3-nitrobenzohydrazide (715.90 mg; 3.95 mmol; 1.00 eq.) and triethylamine (822.18 μl; 5.93 mmol; 1.50 eq.) in DMF (30.00 ml). The reaction mixture is stirred between 0° C. and RT for 4 hours. Solvents are removed under vacuo affording an orange oil which is solubilized in DCM and washed with HCl 0.1 M. The organic phase is concentrated. The resulting precipitate is recovered by filtration, affording 5-(3-nitrophenyl)-1,3,4-oxadiazol-2-ol as a white solid (469.90 mg; 58%).

$^1$H NMR (DMSO-d$_6$) δ: 7.84 (s, 1H), 8.19 (m, 1H), 8.41 (m, 2H), 12.91 (s, 1H). HPLC, Rt: 2.06 min (purity: 97.5%).

Step IV 5-(3-aminophenyl)-1,3,4-oxadiazol-2-ol (Amine 1)

In a flask, is dissolved 5-(3-nitrophenyl)-1,3,4-oxadiazol-2-ol (369.90 mg; 1.79 mmol; 1.00 eq.) in MeOH (20.00 ml) under innert atmosphere. Palladium 10% on charcoal (190.03 mg; 0.18 mmol; 0.10 eq.) is added and the reaction mixture is stirred 5 minutes at RT. The mixture is then put under atmospheric pressure of hydrogen. The reaction is completed after 2 hours. The mixture is filtrated on celite and rinced with MeOH. The solvents are evaporated under vacuo, affording 5-(3-aminophenyl)-1,3,4-oxadiazol-2-ol as a white powder (283.30 mg; 89.55%). $^1$H NMR (DMSO-d$_6$) δ: 5.43 (s, 2H), 6.70 (m, 1H), 6.89 (m, 1H), 7.08 (s, 1H), 7.14 (m, 1H), 12.44 (s, 1H).

Amine 2

Preparation of 5-(3-aminophenyl)-1,3,4-thiadiazol-2-amine (Amine (NHR$^5$R$^6$) Wherein R$^5$ is H and R$^6$ is 5-Phenyl-[1,3,4]thiadiazol-2-ylamine)

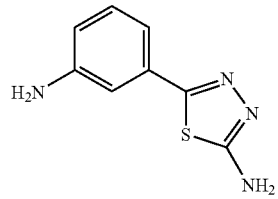

Amine 2

Thiosemicarbazide (455.69 mg; 5.00 mmol; 1.00 eq.) and 3-aminobenzonitrile (590.69 mg; 5.00 mmol; 1.00 eq.) are heated in TFA (2.50 ml) at 60° C. for 4 h00. The mixture become a thick yellowish solution. The reaction mixture is poured into ice-water (15 mL) and neutralized with saturated NaHCO$_3$ aqueous solution. The resulting precipitate is filtered, affording 5-(3-aminophenyl)-1,3,4-thiadiazol-2-amine as white-off solid (291.00 mg; 30.27%).

The aqueous layers are extracted with ethyl acetate (3×15 mL). The combined organic layers is washed with saturated NaCl solution, dried over sodium sulfate, filtered and concentrated to give a 1:1 mixture of 5-(3-aminophenyl)-1,3,4-thiadiazol-2-amine and N-[3-(5-Amino-[1,3,4]thiadiazol-2-yl)-phenyl]-2,2,2-trifluoro-acetamide (526.00 mg). The undesired trifluoroacetamide can be deprotected in quantitative yield by dissolving it in 2N solution of ammonia methanol (30 eq.) and stirred at room temperature for 3 hours. $^1$H NMR (DMSO-d$_6$) δ: 5.29 (br s, 2H), 6.59 (m, 1H), 6.85 (m, 1H), 6.96 (m, 1H), 7.06 (t, J=8 Hz, 1H), 7.28 (br s, 2H). M$^-$ (ESI): 191.3; M$^+$ (ESI): 193.3.

Amine 3

General Procedure for Esterification of Amino Acid of Formula (NHR$^5$R$^6$) Wherein R$^5$ is H and R$^6$ Contains a carboxylic Acid: e.g. Preparation of Methyl 3-Aminopropanoate (Amine (NHR$^5$R$^6$) Wherein R$^5$ is H and R$^6$ is Methyl Propanoate)

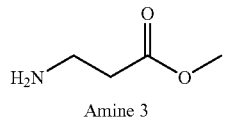

Amine 3

A mixture of beta-alanine (2.00 g; 22.45 mmol; 1.00 eq.) in MeOH (20.00 ml) is cooled to 5° C. Thionyl chloride (3.26 ml; 44.90 mmol; 2.00 eq.) is slowly added over 15 minutes under rigorous stirring. After the completion of the addition, the reaction mixture is heated under reflux overnight. The reaction mixture is concentrated under vacuum. The resulting oil is treated with dry ether, affording methyl 3-aminopropanoate as a white solid (2.48 g; 79.08%). $^1$H NMR (DMSO-d$_6$) δ: 2.71 (m, 2H), 2.97 (s, 2H), 3.62 (s, 3H), 8.22 (s, 2H, NH$_2$).

Thiourea (P2a) Preparation: Procedure A

The appropriate amine R$^5$R$^6$NH (1 eq) as HCl salt and KSCN (1.5 eq) are heated under reflux in THF (0.5 M). When the reaction is complete, the mixture was diluted with H$_2$O and extracted with EtOAc (3 portions). Combined organic phases was washed with HCl 1N, brine and dried over Na$_2$SO$_4$. After filtration and concentration, the isolated thiourea (P2a) is used in bis-thiazol or oxazole-thiazole synthesis, following general procedure 1 described below.

Thiourea (P2a) Preparation: Procedure B

The appropriate amine R$^5$R$^6$NH (1 eq) is dissolved in acetone (1 M). This solution is added to a mixture of ethoxycarbonyl isothiocyanate (0.8 eq) in acetone (0.5 M). The reaction progression is followed by LC-MS. When it is complete, aqueous HCl 18% is added and the mixture is extracted with two portions of EtOAc. Combined organic phases are dried over MgSO$_4$, filtrated and evaporated. The products are usually sufficiently pure to be used directly for hydrolysis into the thioureas or eventually purified by flash chromatography. The resulting N-ethoxycarbonyl thiourea is heated at 100° C. in conc. HCl (0.1 M). When the deprotection was complete, the mixture is diluted with water, basified with NH$_4$OH solution and extracted with EtOAc (3 portions). Combined organic phases are dried over MgSO$_4$. Filtrated and evaporated isolated thiourea (P2a) is then used in bis-thiazol or oxazole-thiazole synthesis, following general procedure 1 described below.

Thiourea (P2a) Preparation: Procedure C

Benzoyl chloride (1.1-1.4 eq.) is added over 5 min to a freshly prepared solution of NH$_4$SCN (1.1-1.4 eq.) in reagent-grade acetone (0.1 M, endothermic) and the mixture is heated under reflux for about 15 min. Heating is stopped and the appropriate amine R$^5$R$^6$NI (1 eq.), either neat or in acetone, is added as rapidly as possible maintaining a vigorous reflux. Following the addition, the mixture is heated under reflux for 15 to 30 min, then poured onto excess cracked ice with vigorous stirring. The resulting solid is collected and liberally washed with H$_2$O, followed by cold H$_2$O/MeOH (1:1) or MeOH. The products are usually sufficiently pure to be used directly for hydrolysis into the thioureas or eventually purified by flash chromatography.

The resulting N-benzoylthiourea is added in one portion to a preheated (about 80° C.) stirring solution of 5% aqueous NaOH (0.5 M). When the deprotection is complete, the mixture is poored onto ice containing excess aqueous HCl. The pH is adjusted to 8-8.5 with NH$_4$OH. The desired thiourea is filtrated and washed with NH$_4$OH and water, or extracted with EtOAc (3 portions) and dried over MgSO$_4$. Isolated thiourea (P2a) is then used in the bis-thiazol or oxazole-thiazole synthesis, following general procedure 1 described below.

Thiourea (P2a) Preparation: Procedure D

The appropriate amine R$^5$R$^6$NH (1 eq.) is added to a 1:1 chloroform/water mixture (0.1 M). Saturated NaHCO$_3$ solution in water (3 eq) followed by thiophosgene (1.1 eq.) are added dropwise at 0° C. The bi-phasic mixture is stirred overnight at rt. The reaction progression is followed by TLC. After completion, the organic phase is separated, washed with water and dried over MgSO$_4$. A saturated solution of ammonia in ethanol (1 vol) is added to the chloroform solution, and stirred overnight at r.t. The reaction mixture is concentrated affording the expected thiourea, which is kept as crude product or recrystallized in a suitable solvent. Isolated thiourea is used in the bis-thiazole or oxazole-thiazole synthesis, following general procedure 1 described below.

Thiourea (P2a) Preparation: Procedure E

The appropriate amine R$^5$R$^6$NH (1 eq.) is dissolved in THF (0.05 to 0.1 M). N,N-diisopropylethylamine (1 eq.) is added and the mixture is cooled down to 0° C. Thiophosgene (1 eq.) is added dropwise. The reaction is kept at 0° C. Its progression is followed by LC-MS. After completion, ammonia 2M in ethanol (5 eq.) is added and the reaction mixture is stirred at RT. When the conversion is complete, solvents are removed under reduced pressure, affording the expected thiourea (P2a), which is kept as crude product or recrystallized in a suitable solvent Isolated thiourea is used in the bis-thiazole or oxazole-thiazole synthesis, following general procedure 1 described below.

Bis-Thiazole or Oxazole-Thiazole Synthesis: General Procedure 1

Intermediate P1 or P1a is dissolved in EtOH (0.5 M) and the appropriate thiourea is added (1 eq). When P1 or P1a is used as salt, TEA (3 eq) is added before the addition of the thiourea. The mixture is stirred for 1 to 24 h at temperatures ranging from −20° C. to reflux. When the reaction is complete, TEA (2-3 eq) is added. The desired product (Ia) or (Ib) is isolated as indicated in the examples below.

Example 1

3-{[2-acetylamino)-4-methyl-4,5-bi-1,3-thiazol-2-yl]amino}benzoic acid, hydrobromide salt

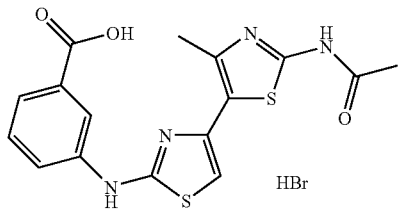

(1)

According to the general procedure 1,3-[(aminocarbonothioyl)amino]benzoic acid (Aldrich) is added to a solution of N-[5-(bromoacetyl)-4-methyl-1,3-thiazol-2-yl]acetamide (Intermediate 1) in EtOH. The mixture is stirred at r.t. for 30 min. The desired product is filtrated off the reaction mixture and washed with cold EtOH. Compound (1) is isolated as a kaki solid (68%). $^1$H NMR (DMSO-$d_6$, 300 MHz) δ 2.13 (s, 3H), 2.51 (s, 3H), 6.93 (s, 1H), 7.44 (m, 1H), 7.49 (m, 1H), 7.92 (m, 1H), 8.25 (m, 1H), 10.49 (s, 1H), 11.83 (br s, 1H). M$^-$ (ESI): 373; M$^+$ (ESI): 375. HPLC, Rt: 2.6 min (purity: 92.8%).

Example 2

4-{[2-(acetylamino)-4-methyl-4,5-bi-1,3-thiazol-2-yl]amino}benzoic acids hydrobromide salt

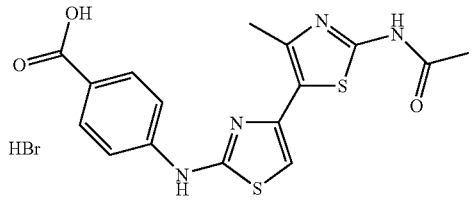

(2)

According to the general procedure 1,4-[(aminocarbonothioyl)amino]benzoic acid (Lancaster) is added to a solution of N-[5-(bromoacetyl)-4-methyl-1,3-thiazol-2-yl]acetamide (Intermediate 1) in EtOH.

The mixture is stirred at r.t for 30 min. The desired product is filtrated off the reaction mixture and washed with cold EtOH. Compound (2) is isolated as a white solid (67%). $^1$H NMR (DMSO-$d_6$, 300 MHz) δ 2.13 (s, 3H), 2.49 (m, 3H), 7.00 (s, 1H), 7.73 (d, J=9 Hz, 2H), 7.90 (d, J=9 Hz, 2H), 10.71 (s, 1H), 12.07 (s, 1H). M$^-$ (ESI): 373; M$^-$ (ESI): 375. HPLC, Rt: 3 min (purity: 95%).

Example 3

N-[2-(benzylamino)-4-methyl-4,5-bi-1,3-thiazol-2-yl]acetamide

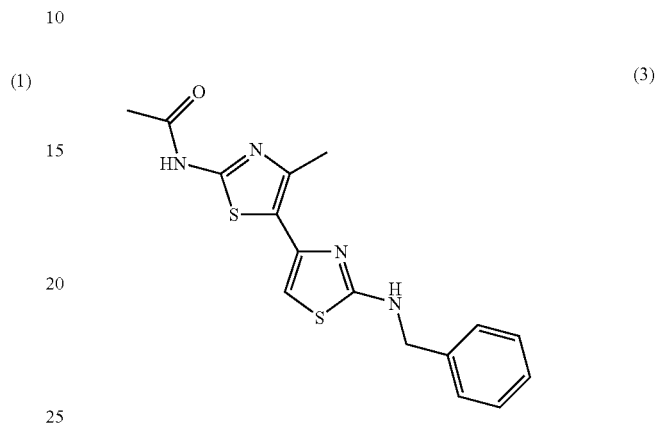

(3)

According to the general procedure 1, N-benzylthiourea (Lancaster) is added to a solution of N-[5-(bromoacetyl)-4-methyl-1,3-thiazol-2-yl]acetamide (Intermediate 1) in EtOH. The mixture is stirred at reflux for 1.5 h TEA (2 eq) is then added. The solvents are evaporated and the desired product is purified by flash chromatography. Compound (3) is isolated as a light yellow solid (34%). $^1$H NMR (DMSO-$d_6$, 300 MHz) δ 2.27 (s, 3H), 2.56 (s, 3H), 4.61 (m, 2H), 6.78 (s, 1H), 7.49 (m, 5H), 8.40 (m, 1H), 12.14 (s, 1H). M$^-$ (ESI): 343; M$^+$ (ESI): 345. HPLC, Rt: 2.79 min (purity: 99.6%).

Example 4

N-{4-methyl-2-[(2-phenylethyl)amino]-4,5-bi-1,3-thiazol-2-yl}acetamide

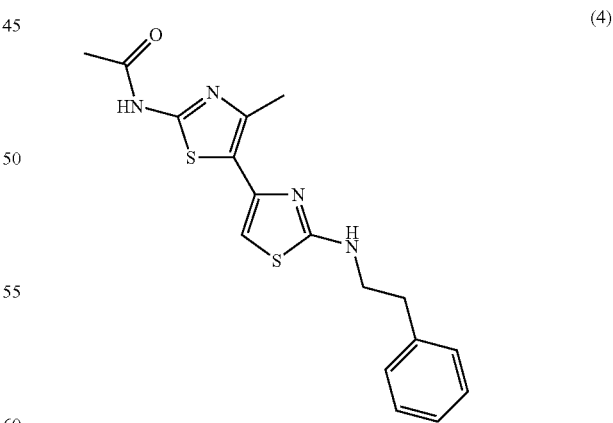

(4)

According to the general procedure 1, N-(2-phenylethyl)thiourea (Lancaster) is added to a solution of N-[5-(bromoacetyl)-4-methyl-1,3-thiazol-2-yl]acetamide (Intermediate 1) in EtOH. The mixture is stirred at reflux for 1.5 h. TEA (2 eq) is then added. The solvents are evaporated and the desired product is purified by flash chromatography. Compound (4) was isolated is a light yellow solid (74%). $^1$H NMR (DMSO-d$_6$, 300 MHz) δ 1.93 (s, 3H), 2.25 (s, 3H), 2.70 (t, J=7.5 Hz, 2H), 3.26 (m, 2H), 6.43 (s, 1H), 7.07 (m, 5H), 7.64 (m, 1H), 11.79 (s, 1H). M$^-$ (ESI): 357; M$^+$ (ESI): 359. HPLC, Rt: 2.79 min (purity: 93.3%).

Example 5

N-(4-methyl-2-piperidin-1-yl-4,5-bi-1,3-thiazol-2-yl)acetamide

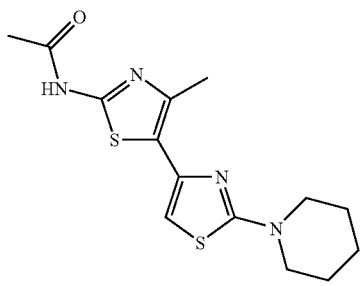

(5)

According to the general procedure 1, piperidine-1-carbothioamide (Lancaster) is added to a solution of N-[5-(bromoacetyl)-4-methyl-1,3-thiazol-2-yl]acetamide (Intermediate 1) in EtOH. The mixture is stirred at reflux for 1.5 h. TEA (2 eq) is then added. The solvents are evaporated and the desired product is purified by flash chromatography. Compound (5) is isolated as a colorless solid (82%). $^1$H NMR (DMSO-d$_6$, 300 MHz) δ 1.46 (m, 6H), 1.98 (s, 3H), 2.29 (s, 3H), 3.29 (m, 4H), 6.64 (s, 1H), 11.86 (s, 1H). M$^-$ (ESI): 321; M$^+$ (ESI): 323. HPLC, Rt: 2.73 min (purity: 95.2%).

Example 6

N-[2-(allylamino)-4-methyl-4,5-bi-1,3-thiazol-2-yl]acetamide

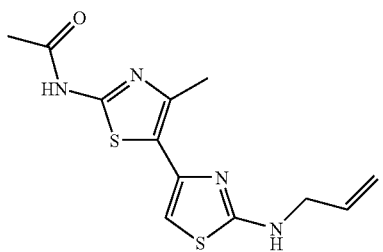

(6)

According to the general procedure 1, N-allylthiourea (Fluka) is added to a solution of N-[5-(bromoacetyl)-4-methyl-1,3-thiazol-2-yl]acetamide (Intermediate 1) in EtOH. The mixture is stirred at reflux for 1.5 h. TEA (2 eq) is then added. The solvents are evaporated and the desired product is purified by flash chromatography. Compound (6) is isolated as a light green solid (65%). $^1$H NMR (DMSO-d$_6$, 300 MHz) δ 2.14 (s, 3H), 2.44 (s, 3H), 3.90 (m, 2H), 5.13 (dd, J=3 Hz, J=12 Hz, 1H), 5.28 (dd, J=3 Hz, J=18 Hz, 1H), 5.94 (m, 1H), 6.65 (s, 1H), 7.89 (m, 1H), 11.99 (s, 1H). M$^-$ (ESI): 293; M$^+$ (ESI): 295. HPLC, Rt: 1.99 min (purity: 98.7%).

Example 7

N-[4-methyl-2-(Pyridin-3-ylamino)-4,5-bi-1,3-thiazol-2-yl]acetamid

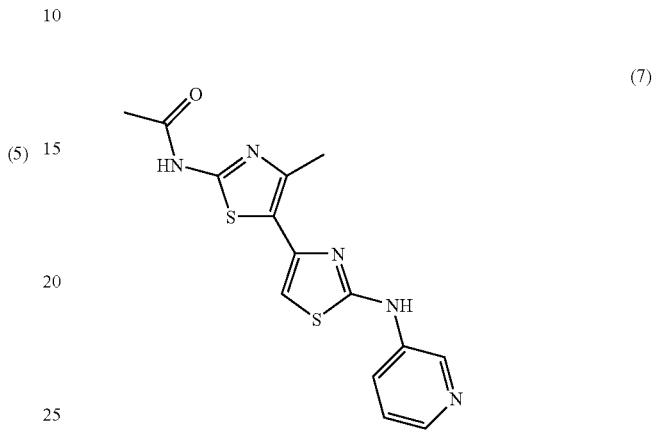

(7)

According to the general procedure 1, N-pyridin-3-ylthiourea (Lancaster) is added to a solution of N-[5-(bromoacetyl)-4-methyl-1,3-thiazol-2-yl]acetamide (Intermediate 1) in EtOH. The mixture is stirred at reflux for 1 h. TEA (2 eq) is then added. After addition of water, the desired product is filtrated off and washed with water. Compound (7) is isolated as a yellow orange solid (91%). $^1$H NMR (DMSO-d$_6$, 300 MHz) δ 2.18 (s, 3H), 2.53 (m, 3H), 7.01 (s, 1H), 7.41 (m, 1H), 8.17 (m, 1H), 8.22 (m, 1H), 8.89 (d, J=3 Hz, 1H), 10.57 (s, 1H), 12.11 (s, 1H). M$^-$ (ESI): 330; M$^+$ (ESI): 332. HPLC, Rt: 1.97 min (purity: 98%).

Example 8

N-[4-methyl-2-(Pyridin-2-ylamino)-4,5-bi-1,3-thiazol-2-yl]acetamide

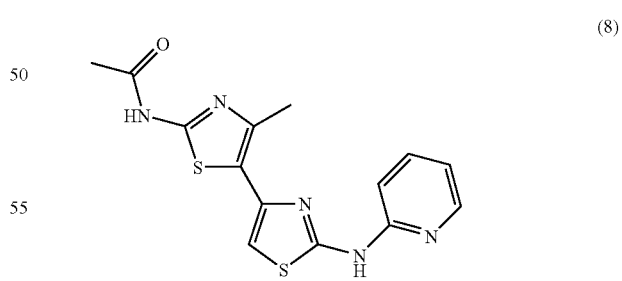

(8)

According to the general procedure 1, N-pyridin-2-ylthiourea (Lancaster) is added to a solution of N-[5-(bromoacetyl)-4-methyl-1,3-thiazol-2-yl]acetamide (Intermediate 1) in EtOH. The mixture is stirred at reflux for 2 h. TEA (2 eq) is then added. The solvents are evaporated and the desired product is purified by flash chromatography. Compound (8) is isolated as a beige yellow solid (51%). $^1$H NMR (DMSO-d$_6$, 300 MHz) δ 2.17 (s, 3H), 2.51 (s, 3H), 6.98 (m, 1H), 7.05 (s, 1H), 7.12 (m, 1H), 7.75 (m, 1H), 8.35 (m, 1H), 11.49 (s, 1H), 12.07 (br s, 1H). M⁻ (ESI): 330; M⁺ (ESI): 332. HPLC, Rt: 2.07 min (purity: 98.2%).

Example 9

N-{2-[(4-methoxyphenyl)amino]-4-methyl-4,5-bi-1,3-thiazol-2-yl}acetamide

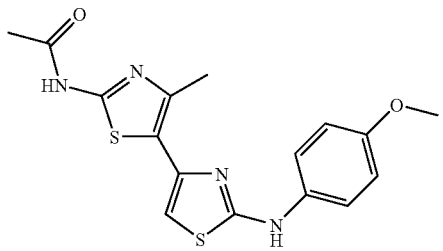

(9)

According to the general procedure 1, N-(4-methoxyphenyl)thiourea (Lancaster) is added to a solution of N-[5-(bromoacetyl)-4-methyl-1,3-thiazol-2-yl]acetamide (Intermediate 1) in EtOH. The mixture is stirred at reflux for 2 h. TEA (2 eq) is then added. The solvents are evaporated and the desired product is purified by flash chromatography. Compound (9) is isolated as a brown solid (60%). ¹H NMR (DMSO-d₆, 300 MHz) δ 2.25 (s, 3H), 2.54 (s, 3H), 3.82 (s, 3H), 6.68 (s, 1H), 6.94 (m, 2H), 7.57 (m, 2H). M⁻ (ESI): 359; M⁺ (ESI): 361. HPLC, Rt: 3.29 min (purity: 96.3%).

Example 10

N-{2-[(4-hydroxyphenyl)amino]-4-methyl-4,5-bi-1,3-thiazol-2-yl}acetamide

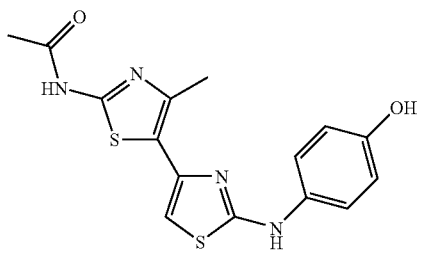

(10)

According to the general procedure 1, N-(4-hydroxyphenyl)thiourea (Lancaster) is added to a solution of N-[5-(bromoacetyl)-4-methyl-1,3-thiazol-2-yl]acetamide (Intermediate 1) in EtOH. The mixture was stirred at reflux for 2 h. TEA (2 eq) is then added. The solvents are evaporated and the desired product is purified by flash chromatography. Compound (10) is isolated as a light pink solid (50%). ¹H NMR (DMSO-d₆, 300 MHz) δ 2.17 (s, 3H), 2.50 (s, 3H), 6.79 (m, 3H), 7.43 (m, 2H), 9.19 (s, 1H), 9.98 (s, 1H), 12.07 (s, 1H). M⁻ (ESI): 345; M⁺ (ESI): 347. HPLC, Rt: 2.52 min (purity: 99%).

Example 11

N-{4-methyl-2-[(4-nitrophenyl)amino]-4,5-bi-1,3-thiazol-2-yl}acetamide

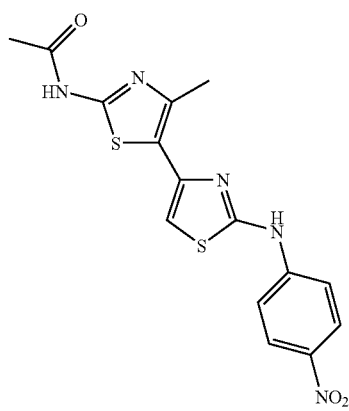

(11)

According to the general procedure 1, N-(4-nitrophenyl)thiourea (Aldrich) is added to a solution of N-[5-(bromoacetyl)-4-methyl-1,3-thiazol-2-yl]acetamide (Intermediate 1) in EtOH. The mixture is stirred at reflux for 20 h. TEA (2 eq) is then added. The solvents are evaporated and the desired product is purified by flash chromatography. Compound (11) is isolated as an orange solid (40%). ¹H NMR (DMSO-d₆, 300 MHz) δ 2.13 (s, 3H), 2.49 (s, 3H), 7.10 (s, 1H), 7.83 (1,2H), 8.23 (m, 2H), 11.10 (s, 1H), 12.09 (s, 1H). M⁻ (ESI): 374; M⁺ (ESI): 376. HPLC, Rt: 3.69 min (purity: 100%).

Example 12

4-{[2-(acetylamino)-4-methyl-4,5-bi-1,3-thiazol-2-yl]amino}benzamide

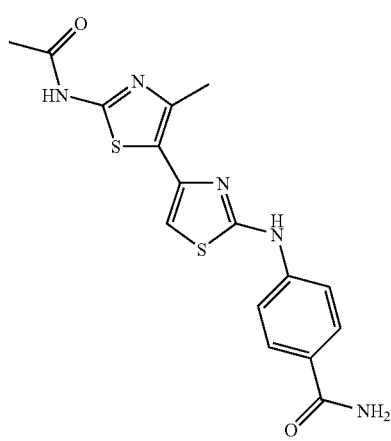

(12)

According to the general procedure 1, 4-[(aminocarbonothioyl)amino]benzamide (obtained from 4-aminobenzamide from Aldrich following procedure C) is added to a solution of N-[5-(bromoacetyl)-4-methyl-1,3-thiazol-2-yl]acetamide (Intermediate 1) in EtOH. The mixture is stirred at reflux for 1.5 h. TEA (2 eq) is then added. After addition of water, the desired product is filtrated off and washed with water. It is then purified by flash chromatography. Compound (12) is isolated as a light beige solid (29%). $^1$H NMR (DMSO-$d_6$, 300 MHz) δ 2.14 (s, 3H), 2.49 (s, 3H), 6.97 (s, 1H), 7.16 (br s, 1H), 7.70 (m, 2H), 7.85 (m, 3H), 10.60 (s, 1H), 12.07 (s, 1H). M$^-$ (ESI): 372; M$^+$ (ESI): 374. HPLC, Rt: 2.73 min (purity: 99.5%).

Example 13

N-[2-({4-[(4-benzylpiperazin-1-yl)carbonyl]phenyl}amino)-4-methyl-4,5-bi-1,3-thiazol-2-yl]acetamide, trifluoroacetate Salt

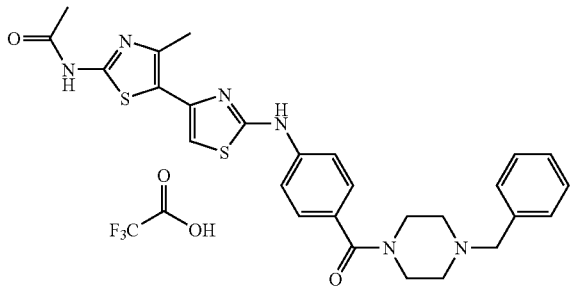

(13)

According to the general procedure 1, N-{4-[(4-benzylpiperazin-1-yl)carbonyl]phenyl}thiourea (obtained from commercial {4-[(4-benzylpiperazin-1-yl)carbonyl]phenyl}amine following procedure C) is added to a solution of N-[5-(bromoacetyl)-4-methyl-1,3-thiazol-2-yl]acetamide (Intermediate 1) in EtOH. The mixture is stirred at reflux for 2 h. TEA (2 eq) is then added. The solvents are evaporated and the desired product is purified by preparative HPLC. Compound (13) is isolated as a beige solid (42%). $^1$H NMR (DMSO-$d_6$, 300 MHz) δ 2.13 (s, 3H), 2.49 (s, 3H), 3.25 (m, 6H), 3.88 (m, 2H), 4.36 (m, 2H), 6.98 (s, 1H), 7.47 (m, 7H), 7.73 (m, 2H), 9.90 (br s, 1H), 10.60 (s, 1H), 12.08 (s, 1H). M$^-$ (ESI): 531; M$^+$ (ESI): 533. HPLC, Rt: 2.76 min (purity: 99.9%).

Example 14

N-(2-amino-4-methyl-4,5-bi-1,3-thiazol-2-yl)acetamide

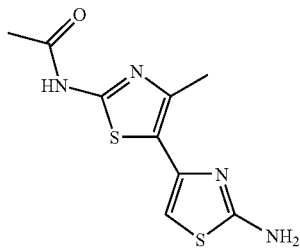

(14)

According to the general procedure 1, thiourea (Fluka) is added to a solution of N-[5-(bromoacetyl)-4-methyl-1,3-thiazol-2-yl]acetamide (Intermediate 1) in EtOH. The mixture is stirred at r.t. for 1.5 h. TEA (2 eq) is then added. The solvents are evaporated and the desired product is purified by flash chromatography. Compound (14) is isolated as a beige solid (81%). $^1$H NMR (DMSO-$d_6$, 300 MHz) δ 2.17 (s, 3H), 2.47 (s, 3H), 6.62 (s, 1H), 7.18 (br s, 2H), 12.02 (s, 1H). M$^-$ (ESI): 253; M$^+$ (ESI): 255. HPLC, Rt: 1.21 min (purity: 99.9%).

Example 15

N-(2-anilino-4-methyl-4,5-bi-1,3-thiazol-2-yl)acetamide

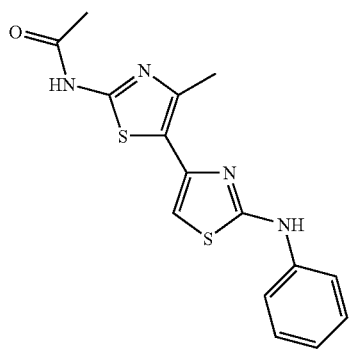

(15)

According to the general procedure 1, N-phenylthiourea (Aldrich) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 1 h. TEA (3 eq) is then added. After addition of water, the desired product is extracted with EtOAc (3 fractions) and dried over MgSO$_4$. Compound (15) is isolated as a brown green solid (quantitative). $^1$H NMR (DMSO-$d_6$, 300 MHz) δ 2.13 (s, 3H), 2.48 (s, 3H), 6.68 (s, 1H), 6.96 (m, 1H), 7.32 (m, 2H), 7.63 (m, 2H), 10.29 (s, 1H), 12.00 (s, 1H). M$^-$ (ESI): 329; M$^+$ (ESI): 331. HPLC, Rt: 3.45 min (purity: 96.6%).

Example 16

N-(4-methyl-2-morpholin-4-yl-4,5-bi-1,3-thiazol-2-yl)acetamide

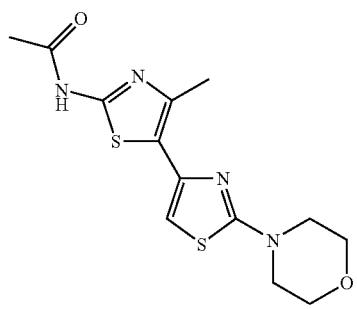

(16)

According to the general procedure 1, morpholine-4-carbothioamide (obtained from morpholine from Fluka following procedure B) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 1 h. TEA (3 eq) is then added. After addition of water, the desired product is extracted with EtOAc (3 fractions) and dried over MgSO$_4$. It is then purified by flash chromatography. Compound (16) is isolated as a light beige solid (74%). $^1$H NMR (DMSO-d$_6$, 300 MHz) δ 2.14 (s, 3H), 2.46 (s, 3H), 3.42 (m, 4H), 3.74 (m, 4H), 6.89 (s, 1H), 12.03 (s, 1H). M$^-$ (ESI): 323; M$^+$ (ESI): 325. HPLC, Rt: 2.5 min (purity: 99.5%).

Example 17

N-[4-methyl-2-(4-methylpiperazin-1-yl)-4,5-bi-1,3-thiazol-2-yl]acetamide, trifluoroacetate salt

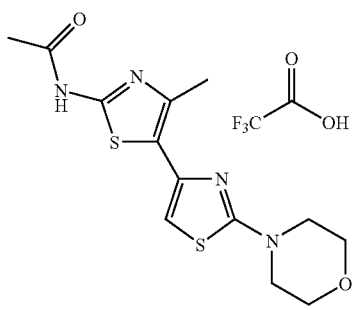

(17)

According to the general procedure 1, 4-methylpiperazine-1-carbothioamide (obtained from 1-methylpiperazine from Fluka following procedure B) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 2 h. TEA (3 eq) is then added. After addition of water, the desired product is extracted with EtOAc (3 fractions) and dried over MgSO$_4$. It is then purified by preparative HPLC. Compound (17) isolated as a green oil (67%). $^1$H NMR (CDCl$_3$, 300 MHz) δ 2.36 (s, 3H), 2.58 (s, 3H), 2.86 (s, 3H), 3.10 (m, 2H), 3.83 (m, 6H), 6.71 (s, 1H), 14.92 (br s, 1H). M$^+$ (ESI): 336; M$^+$ (ESI): 338. HPLC, Rt: 1.71 min (purity: 93%).

Example 18

Methyl 1-[2-(acetylamino)-4-methyl-4,5-bi-1,3-thiazol-2-yl]piperidine-3-carboxylate

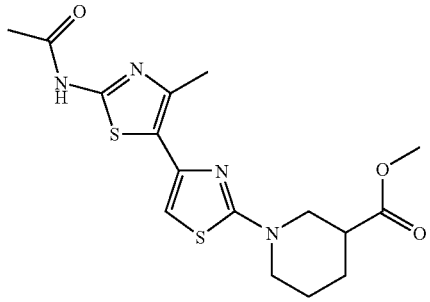

(18)

According to the general procedure 1, ethyl 1-(aminocarbonothioyl)piperidine-3-carboxylate (obtained from methyl piperidine-3-carboxylate from Fluka following procedure B) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 1 h. TEA (3 eq) is then added. After addition of water, the desired product is extracted with EtOAc (3 fractions) and dried over MgSO$_4$. It is then purified by flash chromatography. Compound (18) is isolated as a light yellow solid (61%). $^1$H NMR (DMSO-d$_6$, 300 MHz) δ 1.72 (m, 3H), 2.01 (m, 1H), 2.16 (s, 3H), 2.47 (s, 3H), 2.73 (m, 1H), 3.22 (m, 1H), 3.37 (m, 1H), 3.68 (s, 3H), 3.71 (m, 1H), 4.00 (m, 1H), 6.86 (s, 1H), 12.05 (s, 1H). M$^-$ (ESI): 379; M$^+$ (ESI): 381. HPLC, Rt: 3.11 min (purity: 90.8%).

Example 19

N-{2-[4-(2-hydroxyethyl)piperidin-1-yl]-4-methyl-4,5-bi-1,3-thiazol-2-yl}acetamide

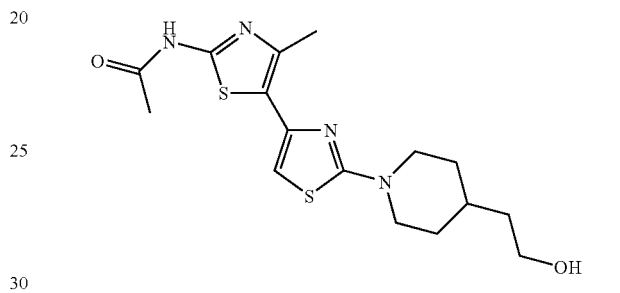

(19)

According to the general procedure 1, 4-(2-hydroxyethyl)piperidine-1-carbothioamide (obtained from 2-piperidin-4-ylethanol from Aldrich following procedure B) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 1 h. TEA (3 eq) is then added. After addition of water, the desired product is extracted with EtOAc (3 fractions) and dried over MgSO$_4$. It is then purified by flash chromatography. Compound (19) is isolated as a beige solid (48%). $^1$H NMR (DMSO-d$_6$, 300 MHz) δ 1.25 (m, 2H), 1.44 (m, 2H), 1.68 (m, 1H), 1.79 (m, 2H), 2.16 (s, 3H), 2.47 (s, 3H), 3.05 (m, 2H), 3.51 (m, 2H), 3.92 (m, 2H), 4.43 (t, J=6 Hz, 1H), 6.82 (s, 1H), 12.04 (s, 1H). M$^-$ (ESI): 365; M$^+$ (ESI): 367. HPLC, Rt: 2.25 min (purity: 95.9%).

Example 20

N-(4-methyl-2-pyrrolidin-1-yl-4,5-bi-1,3-thiazol-2-yl)acetamide

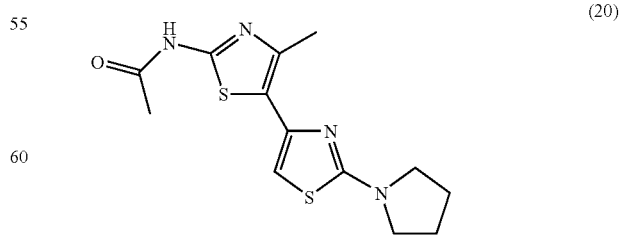

(20)

According to the general procedure 1, pyrrolidine-1-carbothioamide (obtained from pyrrolidine from Fluka following procedure B) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 1 h. TEA (3 eq) is then added. After addition of water, the desired product is extracted with EtOAc (3 fractions) and dried over MgSO$_4$. It is then purified by flash chromatography. Compound (20) is isolated as a light yellow solid (50%). $^1$H NMR (DMSO-d$_6$, 300 MHz) δ 2.00 (m, 4H), 2.14 (s, 3H), 2.45 (s, 3H), 3.41 (m, 4H), 6.72 (s, 1H), 12.00 (s, 1H). M$^-$ (ESI): 307; M$^+$ (ESI): 309. HPLC, Rt: 1.83 min (purity: 98.8%).

Example 21

N-[2-(3-hydroxypyrrolidin-1-yl)-4-methyl-4,5-bi-1,3-thiazol-2-yl]acetamide

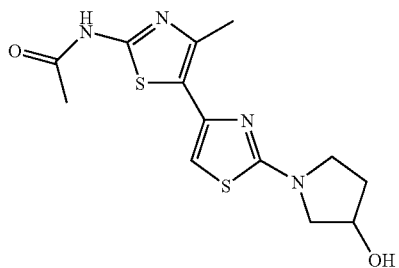

(21)

According to the general procedure 1,3-hydroxypyrrolidine-1-carbothioamide (obtained from pyrrolidin-3-ol from Aldrich following procedure B) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 1 h. TEA (3 eq) is then added.

After addition of water, the desired product is extracted with EtOAc (3 fractions) and dried over MgSO$_4$. It is then purified by flash chromatography. Compound (21) is isolated as a light beige solid (54%). $^1$H NMR (DMSO-d$_6$, 300 MHz) δ 1.85-1.96 (m, 1H), 2.0-2.14 (m, 1H), 2.11 (s, 3H), 2.42 (s, 3H), 3.27 (m, 1H), 3.41-3.56 (m, 3H), 4.40 (br s, 1H), 5.05 (d, J=3 Hz, 1H), 6.69 (s, 1H), 11.97 (br s, 1H). M$^-$ (ESI): 323.2; M$^+$ (ESI): 325.2. HPLC, Rt: 1.4 mm (purity: 98.4%).

Example 22

N-[2-(tert-butylamino)-4-methyl-4,5-bi-1,3-thiazol-2-yl]acetamide

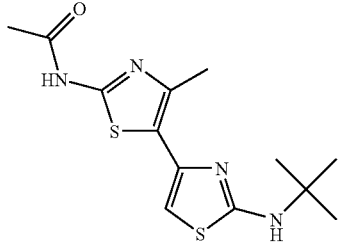

(22)

According to the general procedure 1, N-(tert-butyl)thiourea (Lancaster) is added to a solution of N-[5-(bro-
moacetyl)-4-methyl-1,3-thiazol-2-yl]acetamide, hydrobromide salt (Intermediate 1) and TEA (3 eq) in EtOH. The mixture is stirred at r.t. for 1.5 h. TEA (3 eq) is then added. After addition of water, the desired product is extracted with EtOAc (3 fractions) and dried over MgSO$_4$. Compound (22) is isolated as a dark yellow solid (quantitative). $^1$H NMR (DMSO-d$_6$, 300 MHz) δ 1.38 (s, 9H), 2.10 (s, 3H), 2.42 (s, 3H), 6.55 (s, 1H), 7.43 (s, 1H), 11.70 (s, 1H). M$^-$ (ESI): 309.3; M$^+$ (ESI): 311.3. HPLC, Rt: 2.5 min (purity: 96.7%).

Example 23

N-{2-[(6-methoxypyridin-3-yl)amino]-methyl-4,5-bi-1,3-thiazol-2-yl}acetamide

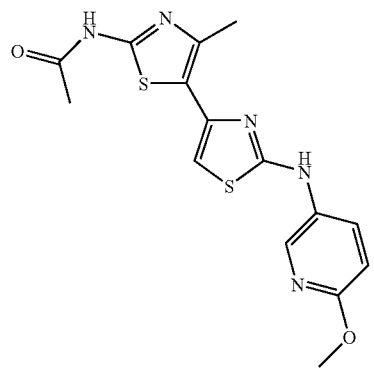

(23)

According to the general procedure 1, N-6-methoxypyridin-3-yl)thiourea (obtained from 6-methoxypyridin-3-amine from Aldrich following procedure C) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 2 h. TEA (3 eq) is then added. After addition of water, the desired product is filtrated off and washed with water. Compound (23) is isolated as a brown-beige solid (73%). $^1$H NMR (DMSO-d$_6$, 300 MHz) δ 2.15 (s, 3H), 2.49 (s, 3H), 3.85 (s, 3H), 6.86 (d, J=9 Hz, 1H), 6.89 (s, 1H), 7.91 (dd, J=3, 9 Hz, 1H), 8.63 (d, J=3 Hz, 1H), 10.24 (s, 1H), 12.06 (s, 1H). M$^-$ (ESI): 360.3; M$^+$ (ESI): 362.2. HPLC, Rt: 2.6 min (purity: 97.6%).

Example 24

N-{2-[(6-chloropyridin-3-yl)amino]-4-methyl-4,5-bi-1,3-thiazol-2-yl}acetamide

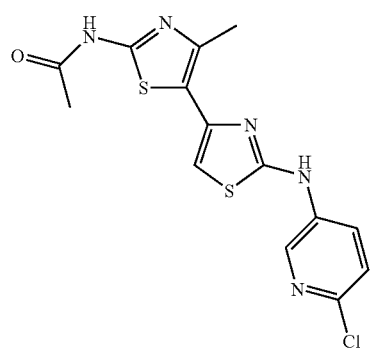

(24)

According to the general procedure 1, N-(6-chloropyridin-3-yl)thiourea (obtained from 6-chloropyridin-3-amine from Aldrich following procedure C) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 2 h. TEA (3 eq) is then added. After addition of water, the desired product is filtrated off and washed with water. Compound (24) is isolated as a light beige solid (72%). $^1$H NMR (DMSO-d$_6$, 300 MHz) δ 2.16 (s, 3H), 2.50 (s, 3H), 7.02 (s, 1H), 7.51 (d, J=9 Hz, 1H), 8.13 (dd, J=3, 9 Hz, 1H), 8.79 (d, J=3 Hz, 1H), 10.70 (s, 1H), 12.09 (s, 1H). M$^-$ (ESI): 364; M$^+$ (ESI): 366. HPLC, Rt: 3.3 min (purity: 98.7%).

Example 25

N-{2-[(4-cyanophenyl)amino]-4-methyl-4,5-bi-1,3-thiazol-2-yl}acetamide

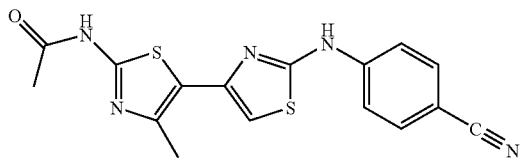

(25)

According to the general procedure 1, N-(4-cyanophenyl)thiourea (Lancaster) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 2 h. TEA (3 eq) is then added. After addition of water, the desired product is filtrated off and washed with water. Compound (25) is isolated as a beige solid (72%). $^1$H NMR (DMSO-d$_6$, 300 MHz) δ 2.13 (s, 3H), 2.50 (s, 3H), 7.05 (s, 1H), 7.78 (m, 4H), 10.85 (s, 1H), 11.95 (s, 1H). M$^-$ (ESI): 354.3; M$^+$ (ESI): 356.3. HPLC, Rt: 3.5 min (purity: 99.5%).

Example 26

N-{2-[(4-chlorophenyl)amino]-4-methyl-4,5-bi-1,3-thiazol-2-yl}acetamide

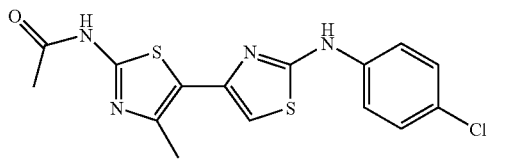

(26)

According to the general procedure 1, N-(4-chlorophenyl)thiourea (Lancaster) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 2 h. TEA (3 eq) is then added. After addition of water, the desired product is filtrated off and washed with water. Compound (26) is isolated as a beige solid (47%). $^1$H NMR (DMSO-(L, 300 MHz) δ 2.13 (s, 3H), 2.47 (s, 3H), 6.92 (s, 1H), 7.37 (m, J=9 Hz, 2H), 7.66 (m, J=9 Hz, 2H), 10.43 (s, 1H), 11.85 (s, 1H). M$^-$ (ESI): 363; M$^+$ (ESI): 365. HPLC, Rt: 3.9 min (purity: 99.9%).

Example 27

N-{2-[(2-chlorophenyl)amino]-4-methyl-4,5-bi-1,3-thiazol-2-yl}acetamide

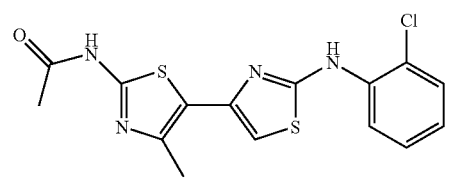

(27)

According to the general procedure 1, N-(2-chlorophenyl)thiourea (Lancaster) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 2 h. TEA (3 eq) is then added. After addition of water, the desired product is filtrated off and washed with water. Compound (27) is isolated as a brown solid (59%). $^1$H NMR (DMSO-d$_6$, 300 MHz) δ 2.12 (s, 3H), 2.45 (s, 3H), 6.93 (s, 1H), 7.06 (m, 1H), 7.34 (m, 1H), 7.48 (m, 1H), 8.30 (m, 1H), 9.73 (s, 1H), 12.10 (s, 1H). M$^-$ (ESI): 363; M$^+$ (ESI): 365. HPLC, Rt: 3.8 min (purity: 97.7%).

Example 28

N-{2-[(2-methoxyphenyl)amino]-4-methyl-4,5-bi-1,3-thiazol-2-yl}acetamide

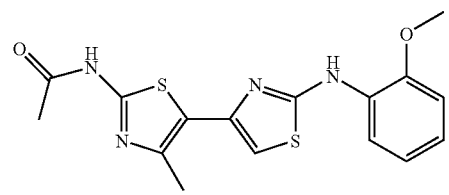

(28)

According to the general procedure 1, N-(2-methoxyphenyl)thiourea (Lancaster) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 2 h. TEA (3 eq) is then added. After addition of water, the desired product is filtrated off and washed with water. Compound (28) is isolated as a white solid (69%). $^1$H NMR (DMSO-d$_6$, 300 MHz) δ 2.12 (s, 3H), 2.46 (s, 3H), 3.85 (s, 3H), 6.84 (s, 1H), 6.91-7.05 (m, 3H), 8.33 (m, 1H), 9.59 (s, 1H), 11.85 (s, 1H). M$^-$ (ESI): 359; M$^+$ (ESI): 361. HPLC, Rt: 3.5 min (purity: 100%).

Example 29

N-{2-[(3-chlorophenyl)amino]-4-methyl-4,5-bi-1,3-thiazol-2-yl}acetamide

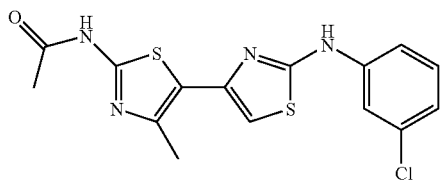

(29)

According to the general procedure 1, N-(3-chlorophenyl)thiourea (Lancaster) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 2 h. TEA (3 eq) is then added. After addition of water, the desired product is filtrated off and washed with water. Compound (29) is isolated as a beige solid (81%). $^1$H NMR (DMSO-$d_6$, 300 MHz) δ 2.13 (s, 3H), 2.50 (s, 3H), 6.95 (s, 1H), 7.00 (m, 1H), 7.33 (m, 1H), 7.40 (m, 1H), 8.00 (s, 1H), 10.52 (s, 1H), 12.10 (s, 1H). M$^-$ (ESI): 363; M$^+$ (ESI): 365. HPLC, Rt: 3.9 min (purity: 99.8%).

Example 30

N-{2-[(3-hydroxyphenyl)amino]-4-methyl-4,5-bi-1,3-thiazol-2-yl}acetamide

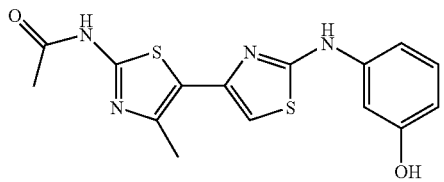

(30)

According to the general procedure 1, N-(3-hydroxyphenyl)thiourea (Lancaster) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 2 h. TEA (3 eq) is then added. After addition of water, the desired product is filtrated off and washed with water. Compound (30) is isolated as a kaki solid (79%). $^1$H NMR (DMSO-$d_6$, 300 MHz) δ 2.12 (s, 3H), 2.47 (s, 3H), 6.38 (m, 1H), 6.86 (s, 1H), 7.01-7.09 (m, 3H), 9.36 (s, 1H), 10.15 (s, 1H), 11.85 (s, 1H). M$^-$ (ESI): 345; M$^+$ (ESI): 347. HPLC, Rt: 2.9 min (purity: 99.6%).

Example 31

N-{4-methyl-2-[(2-morpholin-4-ylethyl)amino]-4,5-bi-1,3-thiazol-2-yl}acetamide, hydrochloride salt

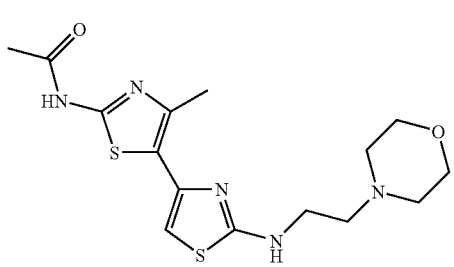

(31)

According to the general procedure 1, N-(2-morpholin-4-ylethyl)thiourea (Transwld) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at r.t. for 4 h. TEA (3 eq) is then added. After addition of water, the desired product is extracted with EtOAc (3 fractions) and dried over MgSO$_4$. It is then precipitated as HCl salt. Compound (31) is isolated as a pastel pink solid (42%). $^1$H NMR (DMSO-$d_6$, 300 MHz) δ 2.14 (s, 3H), 2.45 (s, 3H), 3.18 (m, 2H), 3.39 (m, 3H), 3.73 (m, 3H), 3.81 (m, 2H), 3.98 (m, 2H), 6.74 (s, 1H), 8.04 (br s, 1H), 10.56 (br s, 1H), 12.04 (s, 1H). M$^-$ (ESI): 366; M$^+$ (ESI): 368. HPLC, Rt: 1.6 min (purity: 96.8%).

Example 32

N-{4-methyl-2-[(2-piperidin-1-ylethyl)amino]-4,5-bi-1,3-thiazol-2-yl}acetamide, hydrochloride salt

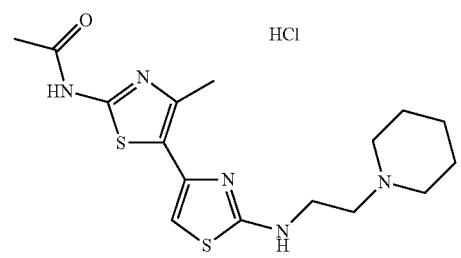

(32)

According to the general procedure 1, N-(2-piperidin-1-ylethyl)thiourea (Transwld) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at r.t. for 4 h. TEA (3 eq) is then added. After addition of water, the desired product is extracted with EtOAc (3 fractions) and dried over MgSO$_4$. It is then precipitate as HCl salt. Compound (32) is isolated as a mauve solid (74%). $^1$H NMR (DMSO-$d_6$, 300 MHz) δ 1.33 (m, 1H), 1.62-1.87 (m, 5H), 2.08 (s, 3H), 2.39 (s, J=S Hz, 3H), 2.92 (m, 2H), 3.23 (m, 2H), 3.49 (m, 2H), 3.6-3.8 (m, 2H), 6.68 (s, 1H), 7.98 (br s, 1H), 9.74 (br s, 1H), 11.98 (s, 1H). M$^-$ (ESI): 364; M$^+$ (ESI): 366. HPLC, Rt: 1.8 min (purity: 97.4%).

Example 33

N-{2-[(2-methoxyethyl)amino]-4-methyl-4,5-bi-1,3-thiazol-2-yl}acetamide

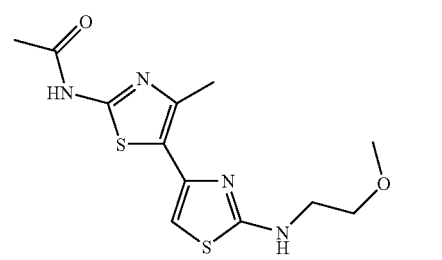

(33)

According to the general procedure 1, N-(2-methoxyethyl)thiourea (Transwld) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at r.t. for 4 h. TEA (3 eq) is then added. After addition of water, the desired product is extracted with EtOAc (3 fractions) and dried over MgSO$_4$. Compound (33) is isolated as a dark green oil (quantitative). $^1$H NMR (CDCl$_3$, 300 MHz) δ 2.16 (s, 3H), 2.50 (s, 3H), 3.37 (s, 3H), 3.52 (m, 2H), 3.60 (m, 2H), 5.82 (br s, 1H), 6.40 (s, 1H), 10.97 (br s, 1H). M$^-$ (ESI): 311; M$^+$ (ESI): 313. HPLC, Rt: 1.6 min (purity: 97.7%).

Example 34

N-[2-(cyclohexylamino)-4-methyl-4,5-bi-1,3-thiazol-2-yl]acetamide

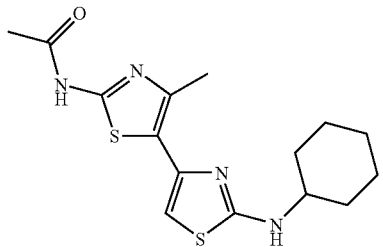

(34)

According to the general procedure 1, N-cyclohexylthiourea (Transwld) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at r.t. for 4 h. TEA (3 eq) is then added. After addition of water, the desired product is extracted with EtOAc (3 fractions) and dried over MgSO$_4$. Compound (34) is isolated as a green foam (89%). $^1$H NMR (CDCl$_3$, 300 MHz) δ 1.16-1.44 (m, 5H), 1.55-1.83 (m, 3H), 2.07 (m, 2H), 2.13 (s, 3H), 2.49 (s, 3H), 3.30 (m, 1H), 5.52 (d, J=9 Hz, 1H), 6.39 (s, 1H), 10.98 (br s, 1H). M$^-$ (ESI): 335; M$^+$ (ESI): 337. HPLC, Rt: 2.5 min (purity: 93%).

Example 35

N-{4-methyl-2-[(3-morpholin-4-ylpropyl)amino]-4,5-bi-1,3-thiazol-2-yl}acetamide, hydrochloride salt

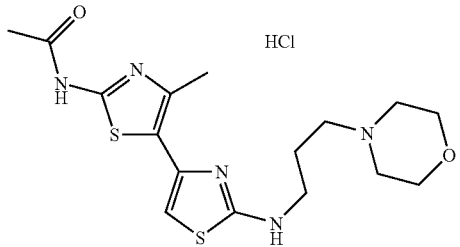

(35)

According to the general procedure 1, N-(3-morpholin-4-ylpropyl)thiourea (Transwld) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at r.t. for 4 h. TEA (3 eq) is then added. After addition of water, the desired product is extracted with EtOAc (3 fractions) and dried over MgSO$_4$. It is then precipitated as HCl salt Compound (35) is isolated as a purple solid (82%). $^1$H NMR (DMSO-d$_6$, 300 MHz) δ 2.05 (m, 2H), 2.14 (s, 3H), 2.44 (s, 3H), 2.98-3.26 (m, 4H), 3.31-3.54 (m, 4H), 3.79 (m, 2H), 3.98 (m, 2H), 6.69 (s, 1H), 8.00 (br s, 1H), 10.70 (br s, 1H), 12.04 (s, 1H). M$^-$ (ESI): 380; M$^+$ (ESI): 382. HPLC, Rt: 1.3 min (purity: 98.5%).

Example 36

N-{4-methyl-2-[(tetrahydrofuran-2-ylmethyl)amino]-4,5-bi-1,3-thiazol-2-yl}acetamide

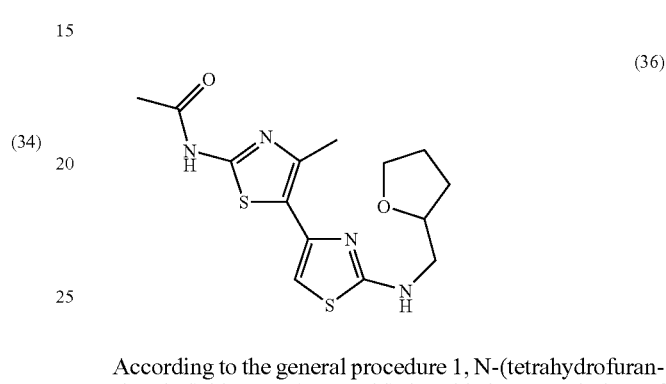

(36)

According to the general procedure 1, N-(tetrahydrofuran-2-ylmethyl)thiourea (Transwld) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at r.t. for 4 h. TEA (3 eq) is then added. After addition of water, the desired product is extracted with EtOAc (3 fractions) and dried over MgSO$_4$. Compound (36) is isolated as a light green solid (quantitative). $^1$H NMR (CDCl$_3$, 300 MHz) δ 1.59-1.70 (m, 1H), 1.86-2.07 (m, 3H), 2.15 (s, 3H), 2.24 (s, 3H), 3.28 (m, 1H), 3.56 (m, 1H), 3.76 (m, 1H), 3.87 (m, 1H), 4.14 (m, 1H), 5.96 (br s, 1H), 6.38 (s, 1H), 11.01 (br s, 1H). M$^-$ (ESI): 337.3; M$^+$ (ESI): 339.3. HPLC, Rt: 1.8 min (purity: 94.4%).

Example 37

N-{2-[(2-hydroxy-2-phenylethyl)amino]-4-methyl-4,5-bi-1,3-thiazol-2-yl}acetamide, trifluoroacetate salt

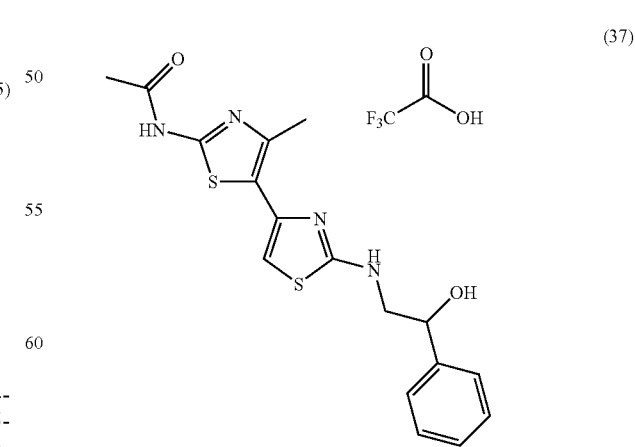

(37)

According to the general procedure 1, N-(2-hydroxy-2-phenylethyl)thiourea (prepared from 2-amino-1-phenylethanol (Fluka), following procedure C) is added to a solution of N-[5-(bromoacetyl)-4-methyl-1,3-thiazol-2-yl]acetamide, hydrobromide salt (Intermediate 1) and TEA (3 eq) in EtOH. The mixture is stirred at reflux for 2 h. TEA (3 eq) is then added. The solvents are evaporated and the desired product is purified by preparative HPLC. Compound (37) is isolated as a yellow solid (32%). $^1$H NMR (DMSO-$d_6$, 300 MHz) δ 2.14 (s, 3H), 2.45 (s, 3H), 3.31 (d, J=9 Hz, 1H), 3.51 (d, J=6 Hz, 1H), 4.48 (br s, 1H), 4.88 (d, J=6 Hz, 1H), 6.64 (s, 1H), 7.22-7.47 (m, 6H), 7.98 (br s, 1H), 12.01 (s, 1H). M$^-$ (ESI): 373; M$^+$ (ESI): 375. HPLC, Rt: 2.3 min (purity: 97.2%).

Example 38

N-[2-(1-benzofuran-5-ylamino)-4-methyl-4,5-bi-1,3-thiazol-2-yl]acetamide, trifluoroacetate salt

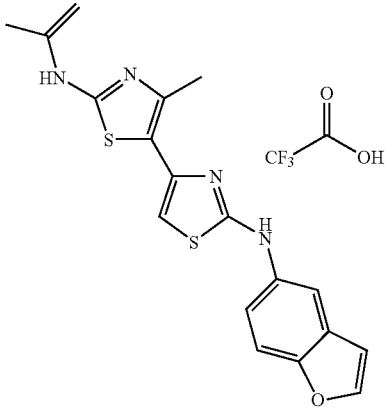

(38)

According to the general procedure 1, N-1-benzofuran-5-ylthiourea (Bionet) is added to a solution of N-[5-(bromoacetyl)-4-methyl-1,3-thiazol-2-yl]acetamide, hydrobromide salt (Intermediate 1) and TEA (3 eq) in EtOH. The mixture was stirred at r.t. for 1 h. TEA (3 eq) is then added. The solvents are evaporated and the desired product is purified by preparative HPLC. Compound (38) is isolated as a light rose solid (36%). $^1$H NMR (DMSO-$d_6$, 300 MHz) δ 2.13 (s, 3H), 2.49 (s, 3H), 6.84 (s, 1H), 6.89 (m, 1H), 7.45 (m, 1H), 7.55 (m, 1H), 7.95 (m, 1H), 8.01 (m, 1H), 10.26 (s, 1H), 12.04 (br s, 1H). M$^-$ (ESI): 369; M$^+$ (ESI): 371. HPLC, Rt: 3.5 min (purity: 99.8%).

Example 39

N-{2-[(3-cyano benzyl)amino]-4-methyl-4,5-bi-3-thiazol-2-yl}acetamide

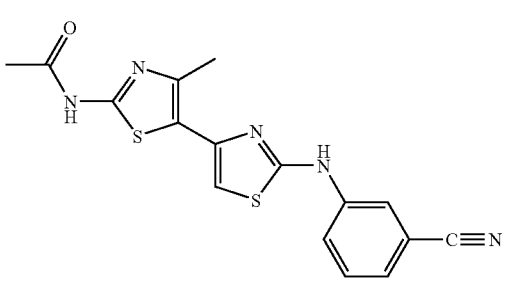

(39)

According to the general procedure 1,1-(3-cyanophenyl)-2-thiourea (Transwld) is added to a solution of N-[5-(bromoacetyl)-4-methyl-1,3-thiazol-2-yl]acetamide (Intermediate 1) in EtOH. The mixture is stirred at r.t. for 17 h. TEA (3 eq) is then added. The solvents are evaporated and the desired product is purified by flash chromatography. Compound (39) is isolated as light yellow solid (430%). $^1$H NMR (DMSO-$d_6$) δ: 2.13 (s, 3H), 2.49 (s, 3H), 6.99 (s, 1H), 7.40 (m, 1H), 7.53 (m, 1H), 7.80 (m, 1H), 8.24 (m, 1H), 10.70 (s, 1H), 12.07 (s, 1H). M$^-$ (ESI): 356; M$^+$ (ESI): 354. HPLC, Rt: 3.5 min (purity: 95.79%).

Example 40

[4-methyl-2-(Pyridin-3-ylamino)-4,5-bi-1,3-thiazol-2-yl]formamide

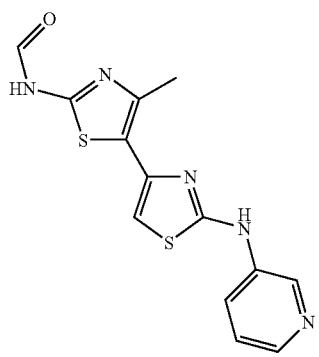

(40)

Step I 4-methyl-N-2-pyridin-3-yl-4,5-bi-1,3-thiazole-2,2-diamine

According to the general procedure 1,3-pyridylthiourea (Lancaster) is added to a solution of 1-(2-amino-4-methyl-1,3-thiazol-5-yl)-2-bromoethanone, hydrobromide salt (Intermediate 2) and TEA (3 eq) in EtOH. The mixture is stirred at r.t. for 2 hours. TEA (3 eq) is then added. After addition of water, the desired product is extracted with EtOAc (3 fractions) and dried over MgSO$_4$. It is then purified by flash chromatography. 4-methyl-N-2-pyridin-3-yl-4,5-bi-1,3-thiazole-2,2-diamine is isolated as light yellow solid in 95% yield. M$^-$ (ESI): 288.2; M$^+$ (ESI): 290.1. HPLC, Rt: 1.2 min (purity: 99.6%).

Step II

[4-methyl-2-(pyridin-3-ylamino)-4,5-bi-1,3-thiazol-2-yl]formamide (40)

In a microwave tube, 4-methyl-N-2-pyridin-3-yl-4,5-bi-1,3-thiazole-2,2-diamine obtained in Step I as described above (58.0 mg; 0.20 mmol; 1.00 eq.) is dissolved in formic acid (2.00 ml). The mixture is heated twice to 130° C. for 30 min in the microwave. A conversion of 50% is afforded. Solvents are evaporated and the desired product is isolated by preparative HPLC. Compound (40) is isolated as dark yellow solid (13 mg, 21% yield). $^1$H NMR (DMSO-$d_6$, 300 MHz) δ 2.53 (s, 3H), 7.06 (s, 1H), 7.55 (m, 1H), 8.20 (m, 1H), 8.27 (m, 1H), 8.48 (s, 1H), 9.01 (s, 1H), 10.77 (s, 1H), 12.00 (s, 1H). M⁻ (ESI): 316.3; M⁺ (ESI): 318.3. HPLC, Rt: 1.9 min (purity: 97.4%).

Example 41

Ethyl N-({[2-(allylamino)-4-methyl-4,5-bi-1,3-thiazol-2-yl]amino}carbonyl)-beta-alaninate

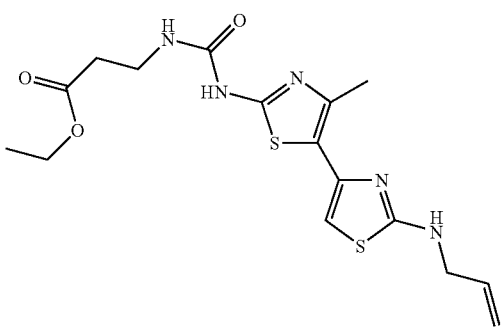

(41)

Step I

N-2-allyl-4-methyl-4,5-bi-1,3-thiazole-2,2-diamine

According to the general procedure 1, N-allylthiourea (Fluka) is added to a solution of 1-(2-amino-4-methyl-1,3-thiazol-5-yl)-2-bromoethanone, hydrobromide salt (Intermediate 2) and TEA (3 eq) in EtOH. The mixture is stirred at r.t. for 1 h. TEA (3 eq) is then added. After addition of water, the desired product is extracted with EtOAc (3 fractions) and dried over MgSO₄. It is then purified by flash chromatography. N-2-allyl-4-methyl-4,5-bi-1,3-thiazole-2,2-diamine is isolated as colorless solid (175 mg, 70% yield). M⁺ (ESI): 253.1. HPLC, Rt: 1.5 min (purity: 92.0%).

Step II ethyl N-({[2-(allylamino)-4-methyl-4,5-bi-1,3-thiazol-2-yl]amino}carbonyl)-beta-alaninate (41)

To a solution of N-2-allyl-4-methyl-4,5-bi-1,3-thiazole-2,2-diamine obtained in Step I as described above (60.60 mg; 0.18 mmol; 1.00 eq.) in DCM (2.00 ml) is added to commercial N-ethyldiisopropylamine (0.07 ml; 0.40 mmol; 2.20 eq.) and commercial ethyl 3-isocyanatopropionate (26.03 mg; 0.18 mmol; 1.00 eq.). The mixture is stirred under reflux for 5 hours, and the solvents are evaporated. The resulting product is purified by preparative HPLC. The purified fraction is diluted with EtOAc and washed with NaHCO₃, affording compound (41) as dark oil (28.2 mg; 39%). ¹H NMR (DMSO-d₆) δ: 1.18 (m, 3H), 2.35 (s, 3H), 2.50 (m, 2H), 3.36 (m, 2H), 3.86 (m, 2H), 4.04 (m, 2H), 5.11 (m, 1H), 5.24 (m, 1H), 5.90 (m, 1H), 6.52 (s, 1H), 6.68 (m, 1H), 7.83 (m, 1H), 10.29 (br s, 1H). M⁻ (ESI): 394; M⁺ (ESI): 396. HPLC, Rt: 2.5 min (purity: 98.36%).

Example 42

N-{4-methyl-5-[2-(pyridin-3-ylamino)-1,3-thiazol-4-yl]-1,3-oxazol-2-yl}acetamide, trifluoroacetate salt

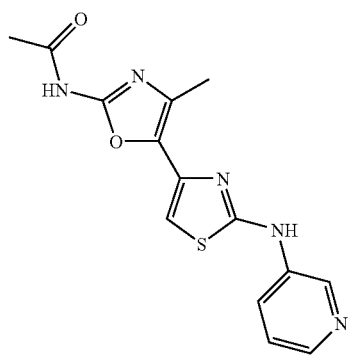

(42)

According to the general procedure 1,3-pyridylthiourea (Lancaster) is added to a solution of N-[5-(bromoacetyl)-4-methyl-1,3-oxazol-2-yl]acetamide (Intermediate 3) in EtOH. The mixture is stirred 17 h at −20° C., then 5 h at r.t. The desired product is filtrated off the reaction mixture. It is further purified by preparative HPLC. Compound (42) is isolated as a yellow solid (5%). ¹H NMR (Methanol-d₄) δ: 2.21 (s, 3H), 2.52 (s, 3H), 7.07 (s, 1H), 7.93 (m, 1H), 8.43 (m, 3H), 9.55 (s, 1H). M⁻ (ESI): 314; M⁺ (ESI): 316. HPLC, Rt: 1.5 min (purity: 96.03%).

Example 43

N-{2-[(2-fluoropyridin-3-yl)amino]-4'-methyl-4,5'-bi-1,3-thiazol-2'-yl}acetamide, bis-hydrochloride salt

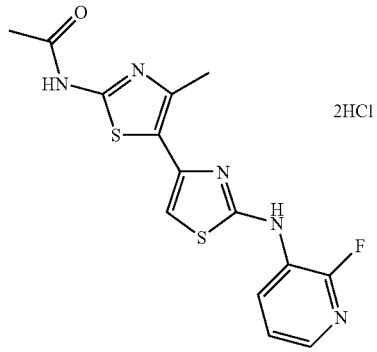

(43)

According to the general procedure 1, N-(2-fluoropyridin-3-yl)thiourea (prepared from 3-amino-2-fluoropyridine (Asymchem), following procedure D) is added to a solution of N-[5-(bromoacetyl)-4-methyl-1,3-thiazol-2-yl]acetamide, hydrobromide salt (Intermediate 1) and TEA (3 eq) in EtOH. The mixture is stirred for 2 h at RT. After addition of water, the desired product is filtrated off and washed with water. N-{2-[(2-fluoropyridin-3-yl)amino]-4'-methyl-4,5'-bi-1,3-thiazol-2'-yl}acetamide is isolated as a pale yellow solid (57%). The hydrochloride salt of a batch of N-{2-[(2- fluoropyridin-3-yl)amino]-4'-methyl-4,5'-bi-1,3-thiazol-2'-yl}acetamide (200.00 mg; 0.57 mmol; 1.00 eq.) is prepared. It is suspended in MeOH (10.00 ml) and hydrogen chloride (2.29 ml; 1.25 M; 2.86 mmol; 5.00 eq.) in methanol is added. The mixture is stirred during 20 minutes at RT and filtered. The yellow powder obtained is washed with diethyl ether and dried under vacuo, affording compound (43) in 79% yield. $^1$H NMR (DMSO-d$_6$, 300 MHz) δ 2.13 (s, 3H), 2.47 (s, 3H), 3.15 (s, 2H), 7.01 (s, 1H), 7.36 (m, 1H), 7.77 (m, 1H), 8.94 (m, 1H), 10.39 (s, 1H), 12.07 (s, 1H). M$^-$ (ESI): 347.8; M$^+$ (ESI): 349.8. HPLC, Rt: 3.0 min (purity: 100%).

Example 44

N-{2-[(2-cyanoethyl)amino]-4'-methyl-4,5'-bi-1,3-thiazol-2'-yl}acetamide (44)

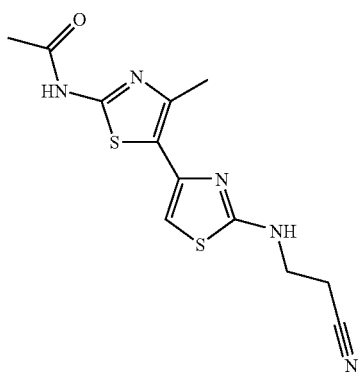

According to the general procedure 1, N-(2-cyanoethyl)thiourea (prepared from N-(2-cyanoethyl)amine (Lancaster), following procedure D) is added to a solution of N-[5-(bromoacetyl)-4-methyl-1,3-thiazol-2-yl]acetamide (Intermediate 1) in EtOH. The mixture is stirred for 30 min at RT. The solvents are evaporated and the desired product is purified by flash chromatography. Compound (44) is isolated as a light orange solid (29%). $^1$H NMR (DMSO-d, 300 MHz) δ 2.11 (s, 3H), 2.42 (s, 3H), 2.84 (m, 2H), 3.51 (m, 2H), 6.68 (s, 1H), 8.06 (t, J=3 Hz, 1H), 11.98 (s, 1H). M$^-$ (ESI): 306; M$^+$ (ESI): 308. HPLC, Rt: 1.86 min (purity: 97.5%).

Example 45

N-{2-[(3,3-diethoxypropyl)amino]-4'-methyl-4,5'-bi-1,3-thiazol-2'-yl}acetamide (45)

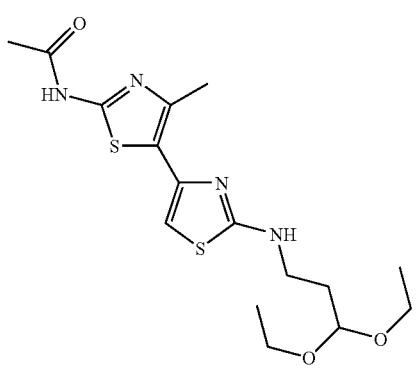

According to the general procedure 1, N-(3,3-diethoxypropyl)thiourea (prepared from 1-amino-3,3-diethoxypropane (Acros), following procedure D) is added to a solution of N-[5-(bromoacetyl)-4-methyl-1,3-thiazol-2-yl]acetamide, hydrobromide salt (Intermediate 1) and TEA (3 eq) in EtOH. The mixture is stirred for 60 min at RT. The solvents are evaporated and the desired product is purified by preparative HPLC. Compound (45) is isolated as a dark yellow foam (56%). $^1$H NMR (DMSO-d$_6$, 300 MHz) δ 1.22 (t, 6H), 2.03 (m, 2H), 2.20 (s, 3H), 2.50 (s, 3H, COCH$_3$), 3.50 (m, 4H), 3.67 (m, 2H), 4.62 (t, J=9 Hz, 1H), 5.73 (m, 1H), 6.41 (s, 1H). M$^-$ (ESI): 383; M$^+$ (ESI): 385. HPLC, Rt: 2.42 min purity: 97.7%).

Example 46

N-{2-[(2,2-diethoxyethyl)amino]-4'-methyl-4,5'-bi-1,3-thiazol-2'-yl}acetamide (46)

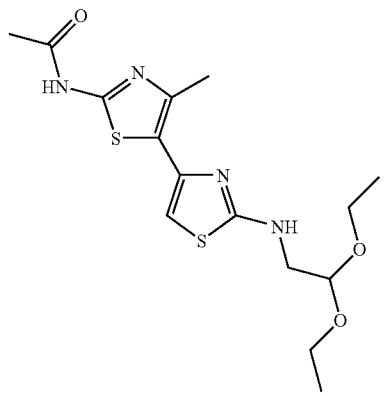

According to the general procedure 1, N-(3,3-diethoxypropyl)thiourea (prepared from aminoacetaldehyde diethyl acetal (Fluka), following procedure D) is added to a solution of N-[5-(bromoacetyl)-4-methyl-1,3-thiazol-2-yl]acetamide, hydrobromide salt (Intermediate 1) and TEA (3 eq) in EtOH. The mixture is stirred for 3 hours at RT. The solvents are evaporated. DCM is added and washed with saturated solution of NH$_4$Cl and brine. This organic phase is dried over MgSO$_4$, filtrated and evaporated. The desired product is purified by flash chromatography, affording compound (46) as an orange solid (44%). $^1$H NMR (DMSO-d, 300 MHz) δ 1.25 (m, 6H), 2.22 (s, 3H), 2.53 (s, 3H), 3.48 (m, 2H), 3.60 (m, 2H), 3.76 (m, 2H), 4.70 (m, 1H), 5.50 (m, 1H), 6.44 (s, 1H). M$^-$ (ESI): 369; M$^+$ (ESI): 371. HPLC, Rt: 2.45 min (purity: 95.3%).

Example 47

N-{4'-methyl-2-[(2-oxo-2-phenylethyl)amino]-4,5'-bi-1,3-thiazol-2'-yl}acetamide (47)

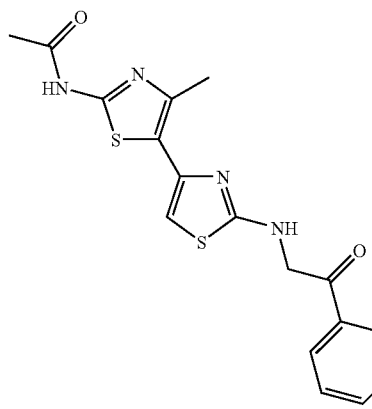

According to the general procedure 1, N-(2-oxo-2-phenylethyl)thiourea (prepared from 2-aminoacetophenone (Fluka), following procedure D) is added to a solution of N-[5-(bromoacetyl)-4-methyl-1,3-thiazol-2-yl]acetamide, hydrobromide salt (Intermediate 1) and TEA (3 eq) in EtOH. The mixture is stirred for 1 hour at RT. The solvents are evaporated and the desired product is purified by flash chromatography. Compound (47) is isolated as a colorless solid (71%). $^1$H NMR (DMSO-d$_6$, 300 MHz) δ 2.18 (s, 3H), 2.61 (s, 3H), 4.83 (s, 2H), 7.33 (m, 1H), 7.43 (m, 2H), 7.63 (m, 2H), 7.67 (s, 1H), 12.56 (s, 1H). M$^-$ (ESI): 372; M$^+$ (ESI): 374. HPLC, Rt: 3.72 min (purity: 99.2%).

Example 48

N-{2-[(2-chloropyridin-3-yl)amino]-4'-methyl-4,5'-bi-1,3-thiazol-2'-yl}acetamide

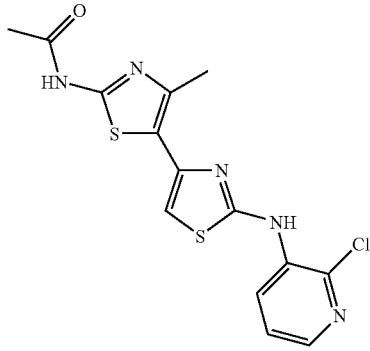

(48)

According to the general procedure 1, N-(2-chloro-3-pyridinyl)thiourea (prepared from 3-amino-2-chloropyridine (Fluka), following procedure D) is added to a solution of N-[5-(bromoacetyl)-4-methyl-1,3-thiazol-2-yl]acetamide, hydrobromide salt (Intermediate 1) and TEA (3 eq) in EtOH. The mixture is stirred for 1 hour at RT. The solvents are evaporated and the desired product is purified by flash chromatography. Compound (48) is isolated as a pink solid (64%). $^1$H NMR (DMSO-d, 300 MHz) δ 2.12 (s, 3H), 2.45 (s, 3H), 7.02 (s, 1H), 7.6 5 (m, 1H), 8.03 (m, 1H), 8.83 (m, 1H), 9.96 (s, 1H), 12.06 (s, 1H). M$^-$ (ESI): 364; M$^+$ (ESI): 366. HPLC, Rt: 3.16 min (purity: 99.8%).

Example 49

N-(4'-methyl-2-{[3-(1,3-oxazol-5-yl)phenyl]amino}-4,5'-bi-1,3-thiazol-2'-yl)acetamide

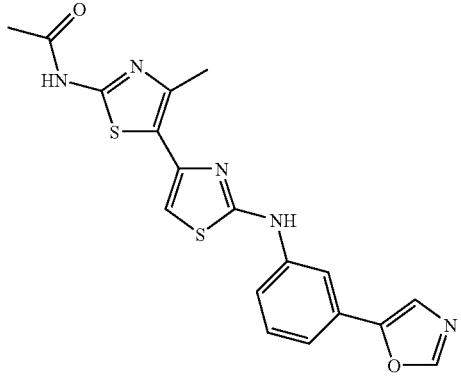

(49)

According to the general procedure 1, N-[3-(1,3-oxazol-5-yl)phenyl]thiourea (prepared from 5-(3-aminophenyl)oxazole (Maybridge), following procedure D) is added to a solution of N-[5-(bromoacetyl)-4-methyl-1,3-thiazol-2-yl]acetamide, hydrobromide salt (Intermediate 1) and TEA (3 eq) in EtOH/Acetone 2:1 mixture. The mixture is stirred for 5 hours at RT. The solvents are evaporated and the desired product is purified by preparative HPLC. Compound (49) is isolated as a beige solid (11%). $^1$H NMR (DMSO-d$_6$, 300 MHz) δ 2.15 (s, 3H), 2.48 (s, 3H), 6.93 (s, 1H), 7.38 (m, 3H), 7.65 (s, 1H), 8.47 (s, 1H), 8.50 (s, 1H), 10.50 (s, 1H), 12.06 (s, 1H). M$^-$ (ESI): 396; M$^+$ (ESI): 398. HPLC, Rt: 3.59 min (purity: 99.1%).

Example 50

N-(4'-methyl-2-{[3-(1H-tetrazol-5-yl)phenyl]amino}-4,5'-bi-1,3-thiazol 2'-yl)acetamide, potassium salt

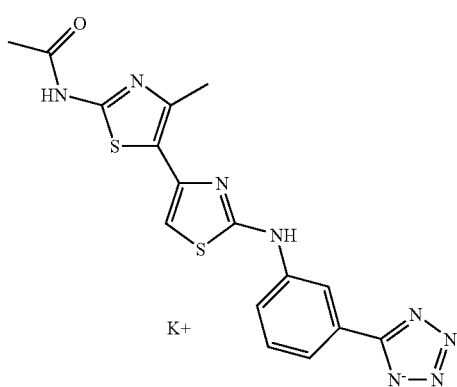

(50)

According to the general procedure 1, N-[3-(1H-tetrazol-5-yl)phenyl]thiourea (prepared from 5-(3-aminophenyl)tetrazole (Avocado), following procedure E) is added to a solution of N-[5-(bromoacetyl)-4-methyl-1,3-thiazol-2-yl]acetamide (Intermediate 1) in EtOH. The mixture is stirred for 5 hours at RT. The solvents are evaporated and the desired product is purified by preparative HPLC. N-(4'-methyl-2-{[3-(1H-tetrazol-5-yl)phenyl]amino}-4,5'-bi-1,3-thiazol-2'-yl)acetamide is isolated as TFA salt. A sample (120.20 mg; 0.30 mmol; 1.00 eq.) is dissolved in THF (5.00 ml)/MeOH (2 mL) mixture. PS-DEA (Argonaut, 78.76 mg; 0.30 mmol; 1.00 eq.) is added and the mixture is shaken for 15 min. The resine is filtrated and rinced with DCM/MeOH 2:1 mixture. The filtrate is evaporated, affording (50) as parent (105.3 mg, 88%). It is dissolved in THF (5.00 ml) and water (5.00 ml) and potassium hydroxide solution in water is added (469.07 μl; 0.50 M; 0.23 mmol; 1.00 eq.). The mixture is filtered over cotton and freeze-dried, affording compound (50) as beige powder (103.6 mg, quantitative yield). $^1$H NMR (DMSO-d$_6$, 300 MHz) δ 2.12 (s, 3H), 2.50 (s, 3H, COCH$_3$), 6.87 (s, 1H), 7.31 (m, 1H), 7.56 (m, 1H), 7.76 (m, 1H), 7.99 (s, 1H), 10.31 (s, 1H), 12.07 (s, 1H). M$^-$ (ESI): 397; M$^+$ (ESI): 399. HPLC, Rt: 2.98 min (purity: 98.3%).

Example 51

N-(4'-methyl-2-{[4-(1H-tetrazol-5-yl)phenyl]amino}-4,5'-bi-1,3-thiazol-2'-yl)acetamide

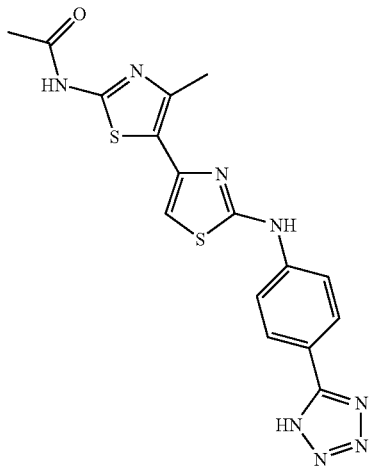

(51)

N-{2-[(4-cyanophenyl)amino]-4-methyl-4,5-bi-1,3-thiazol-2'-yl}acetamide (25) obtained in Example 25 as described above (150.00 mg; 0.42 mmol; 1.00 eq.) is dissolved in anhydrous DMF (10.00 ml). Tributyltin chloride (457.89 µl; 1.69 mmol; 4.00 eq.) and sodium azide (109.74 mg; 1.69 mmol; 4.00 eq.) are added successively. The mixture is heated at 130° C. for two days. After cooling down to RT, the black solution is poored on ice/water mixture and is acidified with 5N HCl solution. The solvents are evaporated. The resulting solid is washed with $Et_2O$ to remove the excess of $Bu_3SnCl$. It is finally purified by preparative HPLC, affording (51) as a brown powder (12.0 mg; 7.14%). $^1$H NMR (DMSO-$d_6$, 300 MHz) δ2.09 (s, 3H), 2.45 (s, 3H), 6.99 (s, 1H), 7.86 (d, J=8 Hz, 2H), 7.99 (d, J=8 Hz, 2H), 10.72 (s, 1H), 12.07 (s, 1H). M$^-$ (ESI): 397; M$^+$ (ESI): 399. HPLC, Rt: 2.97 rain (purity: 93.2%).

Example 52

N-{4'-Methyl-2-[2-(1H-tetrazol-5-yl)ethylamino]-[4,5']bithiazolyl-2'-yl}-acetamide, potassium salt

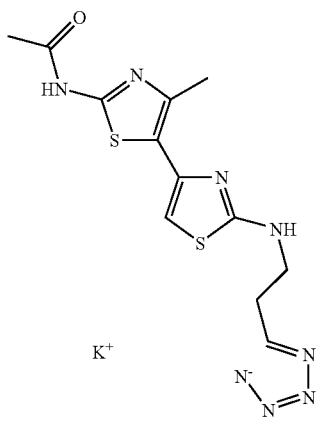

(52)

N-{2-[(2-cyanoethyl)amino]-4'-methyl-4,5'-bi-1,3-thiazol-2'-yl}acetamide (44) obtained in Example 44 as described above (225.00 mg; 0.73 mmol; 1.00 eq.) is suspended in dry toluene (5.00 ml). Trimethylsilyl azide (481.33 µl; 3.66 mmol; 5.00 eq.) and dibutyltin oxide (91.10 mg; 0.37 mmol; 0.50 eq.) are added. The mixture is heated overnight under reflux. As the reaction is not complete, dibutyltin oxide (18.22 mg; 0.07 mmol; 0.10 eq.) and trimethylsilyl azide (192.53 µl; 1.46 mmol; 2.00 eq.) are added and the mixture is further refluxed for 24 hours. Solvents are evaporated and the crude mixture is purified by preparative HPLC, affording N-{4'-Methyl-2-[2-(1H-tetrazol-5-yl)-ethylamino]-[4,5']bithiazolyl-2'-yl}-acetamide (52) as TFA salt (192.30 mg; 56.57%). It is dissolved in THF (22.00 ml). PS-DIEA (Argonaut, 118.91 mg; 0.46 mmol; 1.10 eq.) is added and the mixture is shaken for 1 h15. The resine is filtrated and rinced with THF/MeOH 2:1 mixture. The filtrate is evaporated, affording (52) as parent (145.2 mg, quantitative). It is dissolved in THF/water 1:1 mixture (20.00 ml) and potassium hydroxide (800.00 µl; 0.50 M; 0.40 mmol; 0.97 eq.) is added. The mixture is filtred over cotton and freeze-dried, affording (52) as light yellow powder (133.2 mg; 82.8%). $^1$H NMR (DMSO-$d_6$, 300 MHz) δ 2.09 (s, 3H, $CH_3$), 2.42 (s, 3H, $COCH_3$), 2.92 (t, J=6, 2H), 3.47 (m, 2H), 6.57 (s, 1H), 7.73 (t, J=6, 1H), 11.90 (br s, 1H). M$^-$ (ESI): 349; M$^+$ (ESI): 351. HPLC, Rt: 1.54 min (purity: 98.6%).

Example 53

N-(2-{[3-(5-hydroxy-1,3,4-oxadiazol-2-yl)phenyl]amino}-4'-methyl-4,5'-bi-1,3-thiazol-2'-yl)acetamide, potassium salt

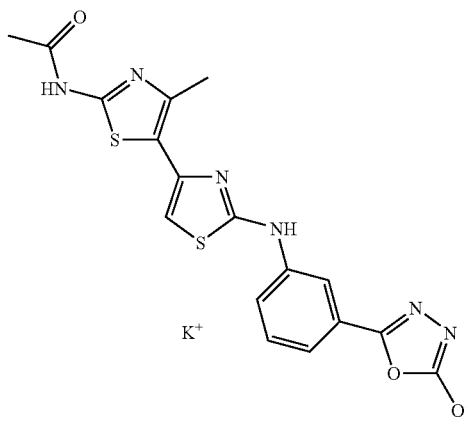

(53)

According to the general procedure 1, N-[3-(5-hydroxy-1,3,4-oxadiazol-2-yl)phenyl]thiourea (prepared from 5-(3-aminophenyl)-1,3,4-oxadiazol-2-ol (Amine 1), following procedure E) is added to a solution of N-[5-(bromoacetyl)-4-methyl-1,3-thiazol-2-yl]acetamide (Intermediate 1) in EtOH. The mixture is stirred for 5 hours at RT. A precipitate is formed. It is filtered, affording N-(2-{[3-(5-hydroxy-1,3,4-oxadiazol-2-yl)phenyl]amino}-4'-methyl-4,5'-bi-1,3-thiazol-2'-yl)acetamide (53) as parent (pale yellow solid; 139.70 mg; 29.86%). It is disolved in a mixture of THF (4.00 ml) and water (4.00 ml). Potassium hydroxide solution (660.63 µl; 0.50 M; 0.33 mmol; 0.98 eq.) is added and the reaction mixture is stirred for 20 minutes at RT. It is finally freeze-dried, affording (53) as pale yellow solid (152.54 mg; quantitative yield). $^1$H NMR (DMSO-$d_6$, 300 MHz) δ 2.11 (t, 3H), 2.48 (s, 3H), 6.87 (s, 1H), 7.21 (m, 1H), 7.31 (m, 1H), 7.72 (m, 2H), 10.35 (s, 1H), 12.04 (s, 1H). M⁻ (ESI): 413; M⁺ (ESI): 415. HPLC, Rt: 3.25 min (purity: 99.4%).

Example 54

N-(2-{[3-(5-amino-1,3,4-thiadiazol-2-yl)phenyl]amino}-4'-methyl-4,5'-bi-1,3-thiazol-2'-yl)acetamide, trifluoroacetate salt

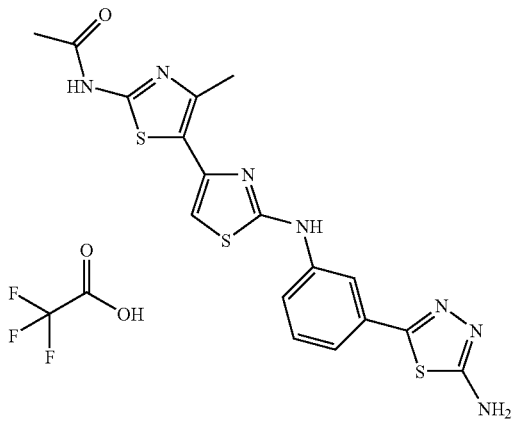

(54)

According to the general procedure 1, N-[3-(5-amino-1,3,4-thiadiazol-2-yl)phenyl]thiourea (prepared from 5-(3-aminophenyl)-1,3,4-thiadiazol-2-amine (Amine 2), following procedure E) is added to a solution of N-[5-(bromoacetyl)-4-methyl-1,3-thiazol-2-yl]acetamide (Intermediate 1) in EtOH. The mixture is stirred for 5 hours at RT. The solvents are evaporated and the desired product is purified by preparative HPLC, affording (54) as light beige solid (75.00 mg; 33%).
¹H NMR (DMSO-d₆, 300 MHz) δ 2.15 (s, 3H), 2.51 (s, 3H), 6.95 (s, 1H), 7.39 (m, 4H), 7.54 (m, 1H), 8.31 (br s, 1H), 8.71 (br s, 1H), 10.52 (br s, 1H), 12.10 (br s, 1H). M⁻ (ESI): 428; M⁺ (ESI): 430. HPLC, Rt: 2.97 min (purity: 95.13%).

Example 55

N-[2'-(acetylamino)-4'-methyl-4,5'-bi-3-thiazol-2-yl]-beta-alanine trifluoroacetate salt

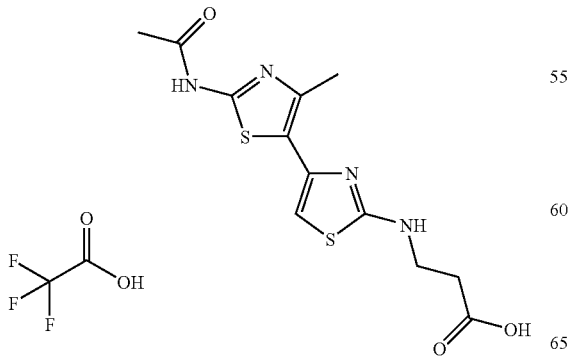

(55)

Step 1

Preparation of methyl N-[2'-(acetylamino)-4'-methyl-4,5'-bi-1,3-thiazol-2-yl]-beta-alaninate According to the general procedure 1, methyl N-(aminocarbonothioyl)-beta-alaninate (prepared from methyl 3-aminopropanoate (amine 3), following procedure D) is added to a solution of N-[5-(bromoacetyl)-4-methyl-1,3-thiazol-2-yl]acetamide, hydrobromide salt (Intermediate 1) and TEA (3 eq) in EtOH/Acetone 2:1 mixture. The mixture is stirred for 5 hours at RT. The solvents are evaporated and methyl N-[2'-(acetylamino)-4'-methyl-4,5'-bi-1,3-thiazol-2-yl]-beta-alaninate is used in the next step without further purification.

Step 2

Preparation of N-[2'-(acetylamino)-4'-methyl-4,5'-bi-1,3-thiazol-2-yl]-beta-alanine, trifluoroacetate salt (55)

To a solution of methyl N-[2'-(acetylamino)-4'-methyl-4,5'-bi-1,3-thiazol-2-yl]-beta-alaninate obtained above (300.00 mg; 0.88 mmol; 1.00 eq.) in MeOH (10.00 ml) is added sodium hydroxide (17.62 ml; 1.00 M; 17.62 mmol; 20.00 eq.) and the mixture is stirred at RT. After 3 hours, the reaction mixture is acidified to pH=1 with HCl 1N solution and extracted with AcOEt (3 times). Combined organic layers are washed with water, brine and dried over magnesium sulfate. After filtration and evaporation of the solvents, the crude product is purified by preparative HPLC, affording (55) as a colorless solid (22.6 mg; 8%).
¹H NMR (DMSO-d₆, 300 MHz) δ 2.11 (s, 3H), 2.42 (s, 3H), 2.56 (m, 2H), 2.43 (m, 2H), 3.90 (s, 2H), 6.62 (s, 1H), 7.78 (s, 1H), 11.98 (s, 1H). M⁻ (ESI): 325; M⁺ (ESI): 327. HPLC, Rt: 1.49 min (purity: 93.3%).

Example 56

5-(2-{[2'-(acetylamino)-4'-methyl-4,5'-bi-1,3-thiazol-2-yl]amino}ethyl)-1,3,4-oxadiazol-2-olate, potassium salt

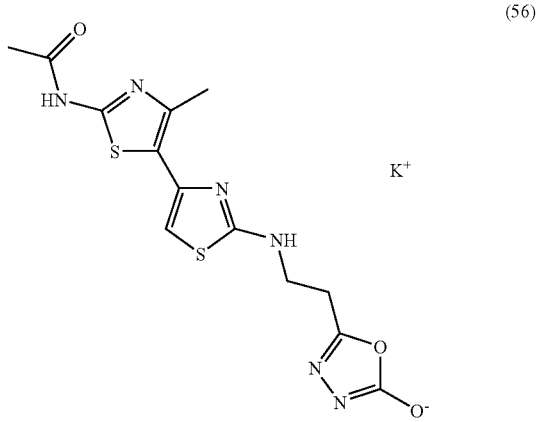 [SMILES: CC(=O)Nc1nc(C)c(-c2csc(NCCc3nnc([O-])o3)n2)s1 ; [K+]]

(56)

Step 1

Preparation of N-(3-hydrazino-3-oxopropyl)thiourea

Methyl 3-[(aminocarbothioyl)amino]propanoate (500.00 mg; 3.08 mmol; 1.00 eq.) (prepared from methyl 3-aminopropanoate (Amine 3), following procedure D) is dissolved in MeOH (25.00 ml). Hydrazine hydrate (2.38 ml; 48.89 mmol; 15.86 eq.) is added and the mixture is stirred under reflux for 5 hours, then at RT overnight. A white precipitate is formed. It is filtrated and washed with MeOH, affording N-(3-hydrazino-3-oxopropyl)thiourea as colorless solid (490.7 mg; 98%).

Step 2

Preparation of N-{2-[(4-hydrazino-4-oxobutyl)amino]-4'-methyl-4,5'-bi-1,3-thiazol-2-yl}acetamide N-(3-hydrazino-3-oxopropyl)thiourea obtained in Step I as described above (200.00 mg; 1.23 mmol; 1.00 eq.) is dissolved in MeOH (30.00 ml) with triethylamine (512.02 µl; 3.70 mmol; 3.00 eq.). The resulting solution is cooled down to 0° C. Intermediate 1 (340.23 mg; 1.23 mmol; 1.00 eq.) dissolved in MeOH (2 mL) is added. The reaction mixture is stirred overnight at 0° C. Solvents are evaporated, affording N-{2-[(4-hydrazino-4-oxobutyl)amino]-4'-methyl-4,5'-bi-1,3-thiazol-2'-yl}acetamide as yellow solid, which is used in the next step without further purification. M$^-$ (ESI): 339; M$^+$ (ESI): 341. HPLC, Rt: 1.15 min (purity: 81.5%).

Step 3

Preparation of 5-(2-{[2'-(acetylamino)-4'-methyl-4,5'-bi-1,3-thiazol-2-yl]amino}ethyl)-1,3,4-oxadiazol-2-olate, potassium salt (56)

N-{2-[(4-hydrazino-4-oxobutyl)amino]-4'-methyl-4,5'-bi-1,3-thiazol-2'-yl}acetamide obtained in Step 2 as described above (419.73 mg; 1.23 mmol; 1.00 eq.) is dissolved in a 1:1 THF/DMF mixture (18 mL). Triethylamine (0.26 ml; 1.85 mmol; 1.50 eq.) is added and the resulting solution is cooled down to 0° C. 1,1'-Carbonyldiimidazole (399.85 mg; 2.47 mmol; 2.00 eq.) is added in THF (8.00 ml). The reaction is stirred at 0° C. for 5 hours. Solvents are evaporated and the resulting crude product is purified by preparative HPLC, affording 5-(2-{[2'-(acetylamino)-4'-methyl-4,5'-bi-1,3-thiazol-2-yl]amino}ethyl)-1,3,4-oxadiazol-2-olate (56) as TFA salt (227.1 mg; 50% yield).

$^1$H NMR (DMSO-d$_6$, 300 MHz) δ 2.11 (s, 3H), 2.42 (s, 3H), 2.86 (m, 2H), 2.54 (m, 2H), 6.64 (s, 1H), 11.98 (s, 1H), 12.07 (s, 1H). M$^-$ (ESI): 365; M$^+$ (ESI): 367. HPLC, Rt: 1.67 min (purity: 95.3%).

5-(2-{[2'-(acetylamino)-4'-methyl-4,5'-bi-1,3-thiazol-2-yl]amino}ethyl)-1,3,4-oxadiazol-2-olate, trifluoroacetate salt (227.1 mg; 0.473 mmol) is dissolved in DMF. PS-DIEA (Argonaut, 123.00 mg; 0.65 mmol; 1.37 eq.) is added and the mixture is shaken for 1 hour. The reaction mixture is filtered, rinced with DMF and evaporated to give (56) as parent (173 mg; quantitative yield). M$^-$ (ESI): 365; M$^+$ (ESI): 367. HPLC, Rt: 1.73 min (purity: 97.5%).

It is dissolved in a 1:1 mixture THF/water (173 mg; 0.473 mmol in 10 mL). Potassium hydroxide solution (1 047.33 µl; 0.50 M; 0.52 mmol; 0.98 eq.) is added and the reaction mixture is stirred for 20 minutes at RT. The reaction mixture is filtered over cotton and freeze-dried, affording (56) as pale pink solid (216.4 mg, 90.37%). $^1$H NMR (DMSO-d$_6$, 300 MHz) δ 2.10 (s, 3H), 2.43 (s, 3H), 2.66 (t, J=8 Hz, 2H), 3.47 (m, 2H), 6.63 (s, 1H), 7.79 (t, J=8 Hz, 1H), 12.06 (s, 1H). M$^-$ (ESI): 365; M$^+$ (ESI): 367. HPLC, Rt: 1.88 min (purity: 95.0%).

Example 57

4-{[2'-(acetylamino)-4'-methyl-4,5'-bi-1,3-thiazol-2-yl]amino}butanoic acid, potassium salt

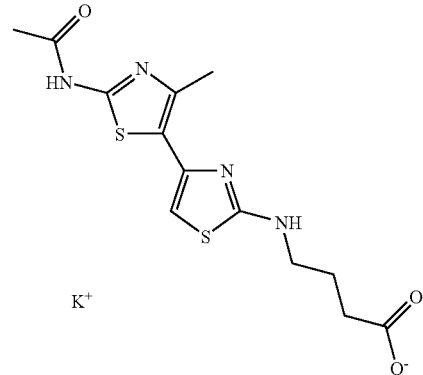

(57)

Step 1

Preparation of methyl 4-([2'-(acetylamino)-4'-methyl-4,5'-bi-1,3-thiazol-2-yl]amino/butanoate According to the general procedure 1, methyl 4-[(aminocarbothioyl)amino]butanoate (prepared from methyl 3-aminobutanoate, hydrochloride salt (Fluka), following procedure D) is added to a solution of N-[5-(bromoacetyl)-4-methyl-1,3-thiazol-2-yl]acetamide, hydrobromide salt (Intermediate 1) and TEA (3 eq) in EtOH/Acetone 2:1 mixture. The mixture is stirred for 5 hours at RT. The solvents are evaporated and the desired product is suspended in water, filtrated and dried under vacuo. Methyl 4-{[2'-(acetylamino)-4'-methyl-4,5'-bi-1,3-thiazol-2-yl]amino}butanoate is isolated as a yellow solid (166.00 mg; 83.63%). $^1$H NMR (DMSO-d$_6$, 300 MHz) δ 1.82 (m, 2H), 2.10 (s, 3H) 2.37 (m, 2H), 2.41 (s, 3H), 3.22 (m, 2H), 3.58 (s, 3H), 6.60 (s, 1H), 7.74 (m, 1H), 11.98 (s, 1H). M$^-$ (ESI): 353; M$^+$ (ESI): 355. HPLC, Rt: 1.92 min (purity: 90.2%).

Step 2

Preparation of 4-{[2'-(acetylamino)-4'-methyl-4,5'-bi-1,3-thiazol-2-yl]amino}butanoic acid, potassium salt (57)

To a solution of methyl 4-{[2'-(acetylamino)-4,5'-bi-1,3-thiazol-2-yl]amino}butanoate obtained above (164.00 mg; 0.46 mmol; 1.00 eq.) in MeOH (5.00 ml) is added sodium hydroxide (9.25 ml; 1.00 M; 9.25 mmol; 20.00 eq.) and the mixture is stirred at 35° C. After 2 hours, the reaction mixture is acidified to pH=1 with HCl 1N solution and the solvents are removed by freeze-dried. The resulting solid is dissolved in DMF and filtrated to remove NaCl salt. After evaporation of DMF and treatment with ether, 4-{[2'-(acetylamino)-4'-methyl-4,5'-bi-1,3-thiazol-2-yl]amino}butanoic acid is obtained as a solid (73.00 mg; 46.35%). It is suspended in water/THF 1:1 mixture (4.00 ml)

and potassium hydroxide (428.87 μl; 0.50 M; 0.21 mmol; 1.00 eq.) is added. The resulting solution is filtered through cotton and freeze-dried, affording (57) as light orange powder (78.70 mg; 96.96%). $^1$H NMR (DMSO-$d_6$, 300 MHz) δ 1.69 (m, 2H), 1.97 (m, 2H), 2.10 (s, 3H), 2.40 (s, 3H), 3.11 (m, 2H), 6.53 (s, 1H), 8.94 (s, 1H), 12.01 (s, 1H). M$^-$ (ESI): 339; M$^+$ (ESI): 341. HPLC, Rt: 1.58 min (purity: 98.8%).

Example 58

N-2-{[3-(5-hydroxy-1,3,4-oxadiazol-2-yl)propyl]amino}-4'-methyl-4,5'-bi-1,3-thiazol-2'-yl)acetamide, potassium salt

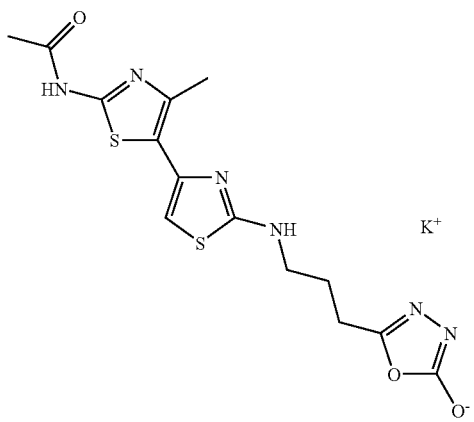

Step 1

Preparation of N-(4-hydrazino-4-oxobutyl)thiourea

Methyl 4-[(aminocarbothioyl)amino]butanoate (176.24 mg; 1.00 mmol; 1.00 eq.) (prepared from methyl 3-aminobutanoate, hydrochloride salt (Fluka), following procedure D) is dissolved in MeOH (10.00 ml). Hydrazine hydrate (2.97 ml; 48.89 mmol; 48.89 eq.) is added. The reaction mixture is stirred 5 hours under reflux and overnight at RT. Solvents are evaporated. The resulting oil is dissolved in MeOH and EtOH is added. A white product precipitates. It is filtrated and washed with EtOH, affording N-(4-hydrazino-4-oxobutyl)thiourea (128.5 mg; 72.91%). HPLC, Rt: 6.50 min (purity: 86.9%).

Step 2

Preparation of N-{2-[(4-hydrazino-4-oxobutyl)amino]-4'-methyl-4,5'-bi-1,3-thiazol-2'-yl}acetamide N-(4-hydrazino-4-oxobutyl)thiourea (128.50 mg; 0.73 mmol; 1.00 eq.) is dissolved in MeOH (7.00 ml) and triethylamine (0.30 ml; 2.19 mmol; 3.00 eq.). The solution is cooled down to 0° C. and intermediate 1 (201.20 mg; 0.73 mmol; 1.00 eq.) is added as a solid. The mixture is stirred 2 hours at RT. Solvents are evaporated and N-{2-[(4-hydrazino-4-oxobutyl)amino]-4'-methyl-4,5'-bi-1,3-thiazol-2'-yl}acetamide is used in the next step without further purification. M$^-$ (ESI): 353; M$^+$ (ESI): 355. HPLC, Rt: 1.19 min (purity: 95.3

Step 3

Preparation of N-(2-{[3-(5-hydroxy-1,3,4-oxadiazol-2-yl)propyl]amino}-4'-methyl-4,5'-bi-1,3-thiazol-2'-yl)acetamide, potassium salt (58)

CDI (236.74 mg; 1.46 mmol; 2.00 eq.) is added to a 0° C. solution of N-{2-[(4-hydrazino-4-oxobutyl)amino]-4'-methyl-4,5'-bi-1,3-thiazol-2'-yl}acetamide (258.75 mg; 0.73 mmol; 1.00 eq.) in DMF (5.00 ml) and triethylamine (0.15 ml; 1.10 mmol; 1.50 eq.). The mixture is stirred at 0° C. for 3 hours. As the reaction is complete, solvents are evaporated. The crude mixture is purified by prepative HPLC, affording N-(2-{[3-(5-hydroxy-1,3,4-oxadiazol-2-yl)propyl]amino}-4'-methyl-4,5'-bi-1,3-thiazol-2'-yl)acetamide (58) as TFA salt (white-off solid; 259 mg; 71.8%). M$^-$ (ESI): 379; M$^+$ (ESI): 381. HPLC, Rt: 1.72 min (purity: 99.3%). It is dissolved in DCM. PS-DIEA (150.43 mg; 0.58 mmol; 1.10 eq.) is added and the mixture is shaken for 15 min. The resin is filtered off and washed with DCM and DCM/MeOH mixture. The filtrate is evaporated, affording (58) as parent (192 mg; 96%). It is suspended in water and potassium hydroxide (1.01 ml; 0.50 M; 0.50 mmol; 0.96 eq.) is added. The mixture is stirred for 5 min and is freeze-dried, affording (58) as beige solid (189.4 mg; 86.4%). $^1$H NMR (DMSO-$d_6$, 300 MHz) δ 1.88 (m, 2H), 2.14 (s, 3H, CH3), 2.44 (s, 311, CH$_3$), 2.56 (s, 2H), 3.28 (m, 2H), 6.64 (s, 1H), 7.81 (m, 1H, NHCH$_2$), 12.04 (s, 1H, NHCOCH$_3$). M$^-$ (ESI): 379; M$^+$ (ESI): 381. HPLC, Rt: 1.73 min (purity: 99.5%).

Example 59

3-{[2'-(acetylamino)-4'-methyl-4,5'-bi-1,3-thiazol-2-yl]amino}-N-hydroxybenzamide

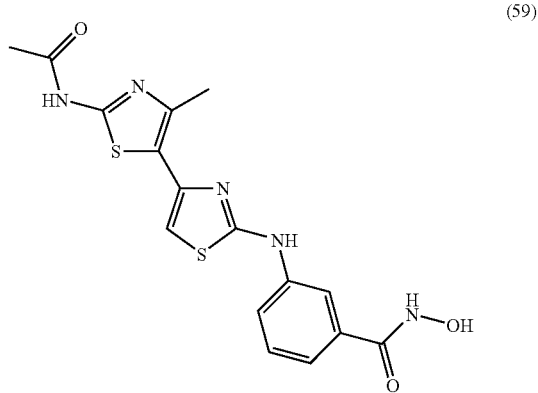 [SMILES: CC(=O)Nc1nc(C)c(-c2csc(Nc3cccc(C(=O)NO)c3)n2)s1]

3-{[2-(Acetylamino)-4-methyl-4,5-bi-1,3-thiazol-2-yl]amino}benzoic acid, hydrobromide salt (1) obtained as described above in example 1 (81.80 mg; 0.22 mmol; 1.00 eq.) is dissolved in dry DMF (3.00 ml). N-Ethyldiisopropylamine (201.68 μl; 1.09 mmol; 5.00 eq.), HATU (99.68 mg; 0.26 mmol; 1.20 eq.) and hydroxylamine hydrochloride (30.36 mg; 0.44 mmol; 2.00 eq.) are added and the mixture is stirred at RT. After 3 hours, the reaction is complete. The solvents are evaporated and the crude mixture is purified by preparative HPLC, affording (59) as beige solid (19.60 mg; 23.04%). $^1$H NMR (DMSO-$d_6$, 300 MHz) δ 2.13 (s, 3H), 2.52 (s, 3H, COCH$_3$), 6.92 (s, 1H), 7.36 (m, 2H), 7.91 (m, 2H), 10.44 (s, 1H), 11.16 (s, 1H), 12.06 (s, 1H). M$^-$ (ESI): 388; M$^+$ (ESI): 390. HPLC, Rt: 2.41 min (purity: 89.8%).

Example 60

3-{[2'-(acetylamino)-4'-methyl-4,5'-bi-1,3-thiazol-2-yl]amino}-N-hydroxybenzenecarboximidic acid

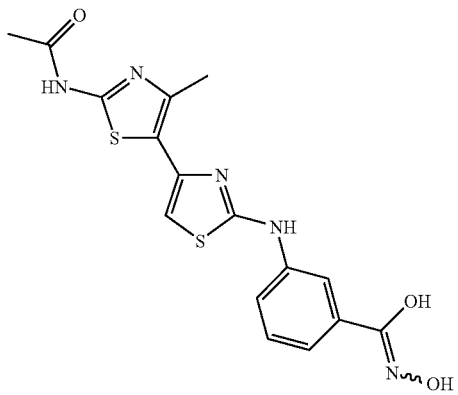

(60)

Triethylamine (0.99 ml; 7.03 mmol; 5.00 eq.) is added to a suspension of hydroxylamine hydrochloride (488.76 mg; 7.03 mmol; 5.00 eq.) in DMSO (10.00 ml). After 15 min, an insoluble material (Et3N.HCl) is filtered off and washed with THF. The filtrate is concentrated in vaccuo, to remove THF. N-{2-[(4-cyanophenyl)amino]-4-methyl-4,5-bi-1,3-thiazol-2-yl}acetamide (25) obtained as described above in Example 25 (500.00 mg; 1.41 mmol; 1.00 eq.) is added and the mixture is stirred overnight at 75° C. The reaction mixture is diluted with water and extracted with EtOAc. The aqueous phase is freeze-dried. Water is added and the resulting precipitate is filtered, washed with ether, affording (60) as beige powder (425.20 mg; 65.67%). $^1$H NMR (DMSO-$d_6$, 300 MHz) δ 2.09 (s, 3H), 2.45 (s, 3H), 5.68 (br s, 2H), 6.85 (m, 1H), 7.28 (m, 2H), 7.77 (m, 2H), 9.58 (s, 1H), 10.35 (s, 1H), 12.02 (s, 1H). M$^-$ (ESI): 387; M$^+$ (ESI): 389. HPLC, Rt: 2.07 min (purity: 84.4%).

Example 61

N-(2-{[3-(5-hydroxy-1,2,4-oxadiazol-3-yl)phenyl]amino}-4'-methyl-4,5'-bi-1,3-thiazol-2'-yl)acetamide, potassium salt

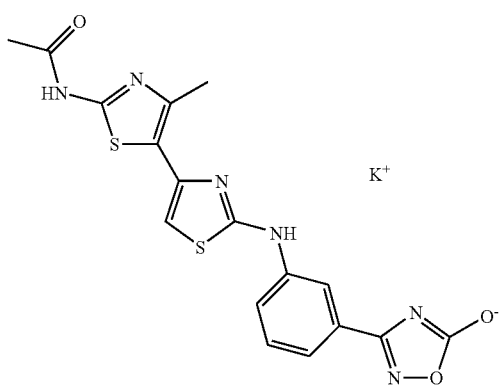

(61)

2-Ethylhexyl chloroformate (101.22 µl; 0.51 mmol; 1.00 eq.) is added dropwise to an ice cooling mixture of 3-{[2'-(acetylamino)-4'-methyl-4,5'-bi-1,3-thiazol-2-yl]amino}-N-hydroxybenzenecarboximidic acid (60) obtained as described above in Example 60 (200.00 mg; 0.51 mmol; 1.00 eq.) and anhydrous pyridine (41.56 µl; 0.51 mmol; 1.00 eq.) in DMF (2.00 ml). The resulting mixture is stirred at 0° C. for 30 min. It is diluted with water and extracted with EtOAc (3 times). The extracts are washed with water and dried over Na2SO4. Solvents are evaporated and the resulting crude intermediate is suspended in xylene (2 mL) and heated at 150° C. for 2 hours. The solvents are evaporated and the resulting crude product is purified by flash chromatography, affording N-(2-{[3-(5-hydroxy-1,2,4-oxadiazol-3-yl)phenyl]amino}-4'-methyl-4,5'-bi-1,3-thiazol-2'-yl)acetamide (61) as parent (134.90 mg; 64.70%). A sample (88.00 mg; 0.21 mmol; 1.00 eq.) is suspended in water (2.50 ml) and THF (2.50 ml) and potassium hydroxide solution (416.15 µl; 0.50 M; 0.21 mmol; 0.98 eq.) is added. The resulting solution is filtered through cotton and freeze-dried, affording (61) as brown powder (82.8 mg; 91.58%). $^1$H NMR (DMSO-$d_6$, 300 MHz) δ 2.12 (s, 3H), 2.52 (s, 3H, COCH$_3$), 6.88 (s, 1H), 7.34 (m, 2H), 7.84 (m, 2H), 10.34 (s, 1H). M$^-$ (ESI): 413; M$^+$ (ESI): 415. HPLC, Rt: 3.09 min (purity: 97.6%).

Example 62

N-[2-({3-[(Z)-(2,4-dioxo-1,3-thiazolidin-5-ylidene)methyl]phenyl}amino)-4'-methyl-4,5'-bi-1,3-thiazol-2'-yl]acetamide, acetate salt

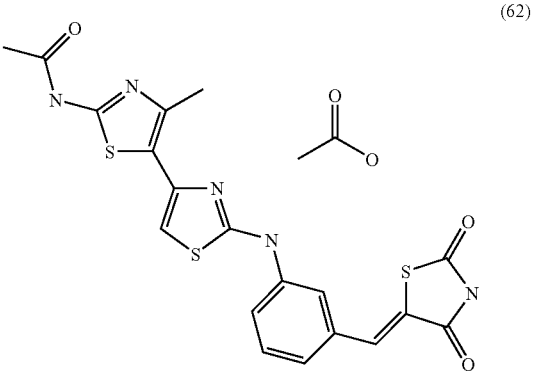

(62)

Step 1

Preparation of N-(2-([3-(1,3-dioxolan-2-yl)phenyl]amino)-4'-methyl-4,5'-bi-1,3-thiazol-2'-yl)acetamide According to the general procedure 1, N-[3-(1,3-dioxolan-2-yl)phenyl]thiourea (prepared from 3-aminobenzyldehyde ethylene acetal (Alfa), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. N-(2-{[3-(1,3-dioxolan-2-yl)phenyl]amino}-4'-methyl-4,5'-bi-1,3-thiazol-2'-yl)acetamide is isolated as a beige solid (320 mg; 88%). HPLC, Rt: 3.26 min (purity: 90.29%).

Step 2

Preparation of N-[2-({3-[(Z)-(2,4-dioxo-1,3-thiazolidin-5-ylidene)methyl]phenyl}amino)-4'-methyl-4,5'-bi-1,3-thiazol-2'-yl]acetamide, acetate salt (62)

A solution of N-(2-{[3-(1,3-dioxolan-2-yl)phenyl]amino}-4'-methyl-4,5'-bi-1,3-thiazol-2'-yl)acetamide obtained in Step 1 as described above (290.00 mg; 0.72 mmol; 1.00 eq.), 2,4-thiazolidinedione (151.90 mg; 1.30 mmol; 1.80 eq.) and beta-alanine (115.55 mg; 1.30 mmol; 1.80 eq.) in AcOH (6.00 ml) are heated at 100° C. for 1 h30. Water is added and the precipitate is filtered and washed with Et$_2$O, affording (62) as a yellow solid (35 mg; 9%). $^1$H NMR (DMSO-d$_6$, 300 MHz) δ 1.92 (s, 3H), 2.14 (s, 3H), 2.50 (s, 3H), 6.98 (s, 1H), 7.22 (d, J=7.91 Hz, 1H), 7.50 (t, J=7.91 Hz, 1H), 7.73 (s, 1H), 7.80 (d, J=7.91 Hz, 1H), 7.85 (s, 1H), 10.59 (s, 1H), 11.92 (s, 1H), 12.06 (s, 1H), 12.60 (s, 1H). M−(ES): 456; M+(ESI): 458. HPLC, Rt: 3.52 min (purity: 93.0%).

Example 63

N-[4'-methyl-2-({4-[(pyridin-2-ylamino)sulfonyl]phenyl}amino)-4,5'-bi-1,3-thiazol-2'-yl]acetamide

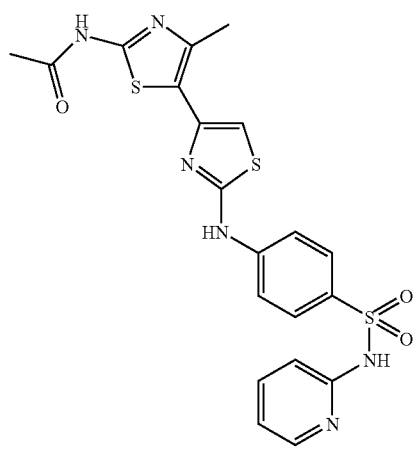

(63)

According to the general procedure 1,4-[(aminocarbonothioyl)amino]-N-pyridin-2-ylbenzenesulfonamide (prepared from 4-amino-N-pyridin-2-ylbenzenesulfonamide (Sigma), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (63) is isolated as a beige solid (25.25 mg; 25%).

M$^+$ (ESI): 487.2. HPLC, Rt: 6.89 min (purity: 85.8%).

Example 64

N-(2-{[2-(2-hydroxyethyl)phenyl]amino}-4'-methyl-4,5'-bi-1,3-thiazol-2'-yl)acetamide

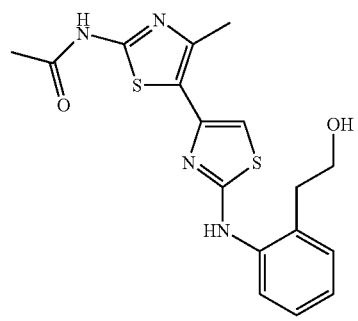

(64)

According to the general procedure 1, N-[2-(2-hydroxyethyl)phenyl]thiourea (prepared from 2-(2-aminophenyl)ethanol (Aldrich), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (64) is isolated as a beige solid (43.71 mg; 56%). M$^+$ (ESI): 375.2. HPLC, Rt: 8.21 min (purity: 90.26%).

Example 65

N-(2-{[3-(hydroxymethyl)phenyl]amino}-4'-methyl-4,5'-bi-1,3-thiazol-2'-yl)acetamide

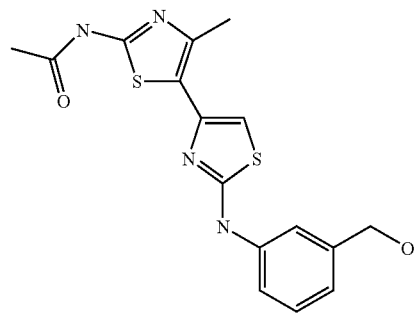

(65)

According to the general procedure 1, N-[3-(hydroxymethyl)phenyl]thiourea (prepared from (3-aminophenyl)methanol (Aldrich), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (65) is isolated as a beige solid (18.89 mg; 18%). M+ (ESI): 361. HPLC, Rt: 7.13 min (purity: 96.88%).

Example 66

N-(2-{[4-(2-hydroxyethyl)phenyl]amino}-4'-methyl-4,5'-bi-1,3-thiazol-2'-yl)acetamide

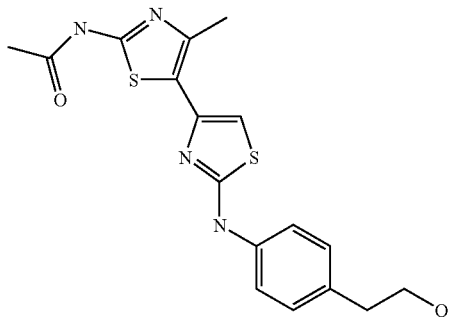

(66)

According to the general procedure 1, N-[4-(2-hydroxyethyl)phenyl]thiourea (prepared from 2-(4-aminophenyl)ethanol (Aldrich), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (66) is isolated as a beige solid (57.25 mg; 52%). M+ (ESI): 375.2. HPLC, Rt: 7.08 min (purity: 98.7%).

Example 67

N-[2-({3-[(2-hydroxyethyl)sulfonyl]phenyl}amino)-4'-methyl-4,5'-bi-1,3-thiazol-2'-yl]acetamide

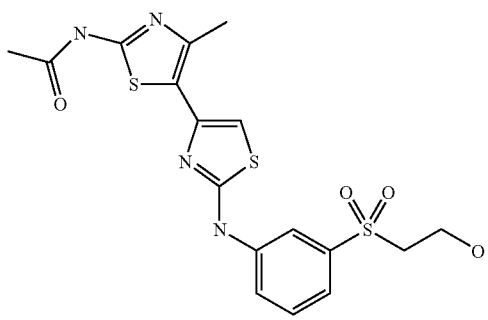

(67)

According to the general procedure 1, N-{3-[(2-hydroxyethyl)sulfonyl]phenyl}thiourea (prepared from 2-[(3-aminophenyl)sulfonyl]ethanol, hydrochloride salt (Aldrich), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (67) is isolated as a beige solid (21.50 mg; 35%). M+ (ESI): 439. HPLC, Rt: 6.57 min (purity: 95.3%).

Example 68

N-[2-({4-[(dimethylamino)sulfonyl]phenyl}amino)-4'-methyl-4,5'-bi-1,3-thiazol-2'-yl]acetamide

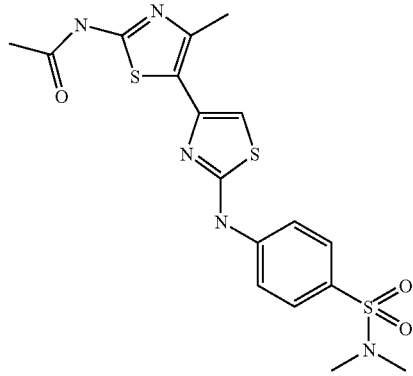

(68)

According to the general procedure 1, 4-[(aminocarbonothioyl)amino]-N,N-dimethylbenzenesulfonamide (prepared from 4-amino-N,N-dimethylbenzenesulfonamide (Bionet), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (68) is isolated as a beige solid (36.04 mg; 28%). M+ (ESI): 438. HPLC, Rt: 8.972 min (purity: 94.344%).

Example 69

N-(2-{[3-aminosulfonyl)phenyl]amino}-4'-methyl-4,5'-bi-1,3-thiazol-2'-yl)acetamide

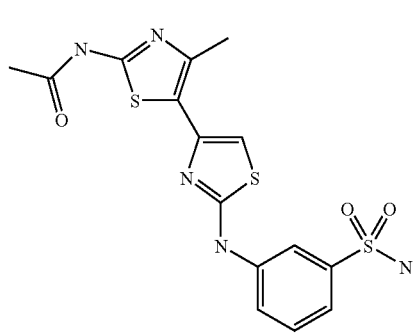

(69)

According to the general procedure 1,3-[(aminocarbonothioyl)amino]benzenesulfonamide (prepared from 3-aminobenzenesulfonamide (Maybridge), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound

(69) is isolated as a beige solid (25.11 mg; 44%). M⁺ (ESI): 410. HPLC, Rt: 6.9 min (purity: 96.9%).

Example 70

N-{2-[(2-chloropyridin-4-yl)amino]-4'-methyl-4,5'-bi-1,3-thiazol-2'-yl}acetamide

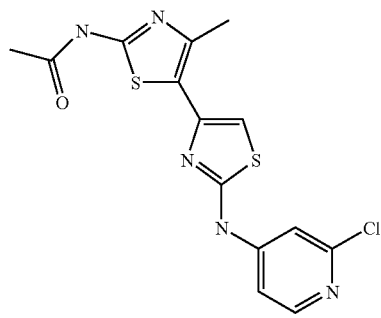

(70)

According to the general procedure 1, N-(2-chloropyridin-4-yl)thiourea (prepared from 2-chloropyridin-4-amine (Aldrich), following procedure A) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (70) is isolated as a beige solid (57.51 mg; 6%). M⁺ (ESI): 366. HPLC, Rt: 7.37 min (purity: 91.5%).

Example 71

N-[4'-methyl-2-({4-[(methylamino)sulfonyl]phenyl}amino)-4,5'-bi-1,3 thiazol-2'-yl]acetamide

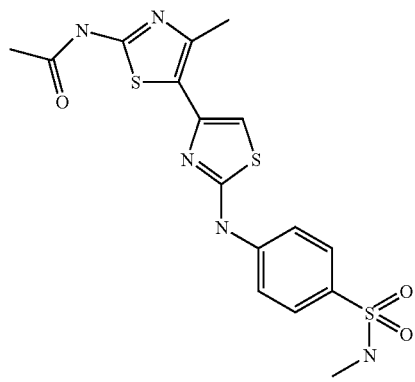

(71)

According to the general procedure 1,4-[(aminocarbonothioyl)amino]-N-methylbenzenesulfonamide (prepared from 4-amino-N-methylbenzenesulfonamide (Fluorochem), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (71) is isolated as a beige solid (25.14 mg; 21%). M⁺ (ESI): 424. HPLC, Rt: 6.9 min (purity: 96.9%).

Example 72

N-(5-{[2'-(acetylamino)-4-methyl-4,5'-bi-1,3-thiazol-2-yl]amino}pyridin-2-yl)acetamide

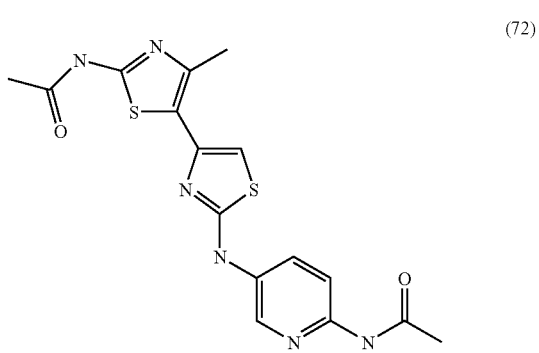 [SMILES: CC(=O)Nc1ccc(Nc2nc(-c3sc(NC(C)=O)nc3C)cs2)cn1]

(72)

According to the general procedure 1, N-{5-[(aminocarbonothioyl)amino]pyridin-2-yl}acetamide (prepared from N-(5-aminopyridin-2-yl)acetamide (Fluorochem), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (72) is isolated as a beige solid (29.20 mg; 22%). M⁺ (ESI): 389.2. HPLC, Rt: 6.13 min (purity: 96.13%).

Example 73

N-[2-(2,3-dihydro-1-benzofuran-5-ylamino)-4'-methyl-4,5'-bi-1,3-thiazol-2'-yl]acetamide

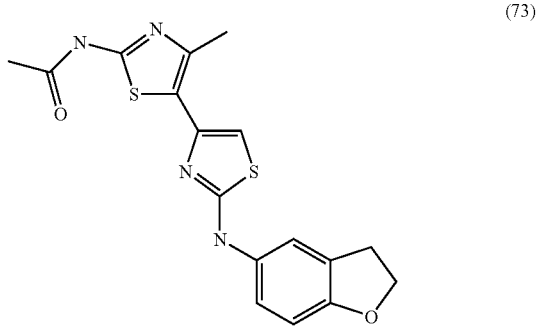 [SMILES: CC(=O)Nc1nc(C)c(-c2csc(Nc3ccc4c(c3)CCO4)n2)s1]

(73)

According to the general procedure 1, N-(2,3-dihydro-1-benzofuran-5-yl)thiourea (prepared from 2,3-dihydro-1-benzofuran-5-amine (Bionet), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (73) is iso-

Example 74

N-(4'-methyl-2-{[2-(1-methylpyrrolidin-2-yl)ethyl]amino}-4,5'-bi-1,3-thiazol-2'-yl) acetamide

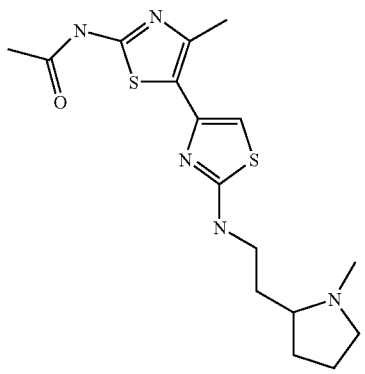

(74)

According to the general procedure 1, N-[2-(1-methylpyrrolidin-2-yl)ethyl]thiourea (prepared from [2-(1-methylpyrrolidin-2-yl)ethyl]amine (Aldrich), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (74) is isolated as a beige solid (6.82 mg; 5%). M⁺ (ESI): 366. HPLC, Rt: 5.77 min (purity: 93.52%).

Example 75

N-{4'-methyl-2-[(2-pyrrolidin-1-ylethyl)amino]-4,5'-bi-1,3-thiazol-2'-yl}acetamide

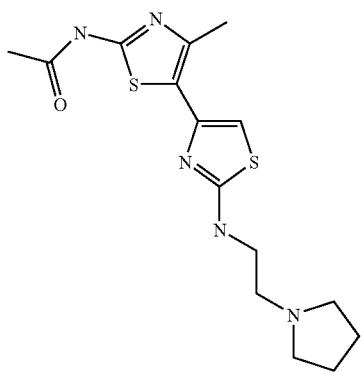

(75)

According to the general procedure 1, N-(2-pyrrolidin-1-ylethyl)thiourea (prepared from (2-pyrrolidin-1-ylethyl)amine (Aldrich), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (75) is isolated as a beige solid (22.99 mg; 31%). M⁺ (ESI): 352. HPLC, Rt: 6.05 min (purity: 94.7%).

Example 76

N-(4'-methyl-2-{[3-(2-oxopyrrolidin-1-yl)propyl]amino}-4,5'-bi-1,3-thiazol-2'-yl)acetamide

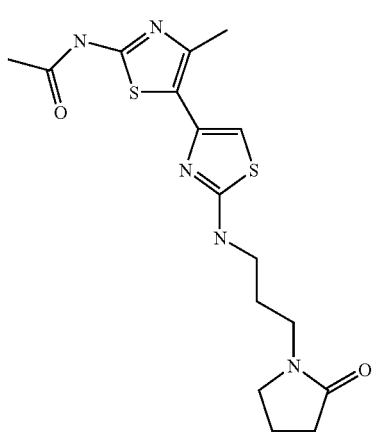

(76)

According to the general procedure 1, N-[3-(2-oxopyrrolidin-1-yl)propyl]thiourea (prepared from 1-(3-aminopropyl)pyrrolidin-2-one (Lancaster), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (76) is isolated as a beige solid (12.72 mg; 12%). M⁺ (ESI): 380. HPLC, Rt: 5.89 min (purity: 91.2%).

Example 77

N-(2-{[2-(acetylamino)ethyl]amino}-4'-methyl-4,5'-bi-1,3-thiazol-2'-yl)acetamide

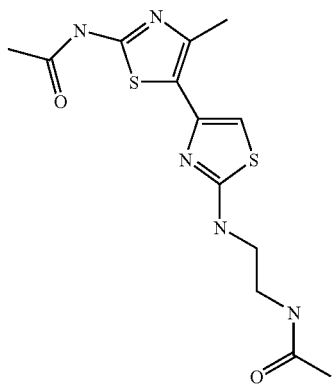

(77)

According to the general procedure 1, N-{2-[(aminocarbonothioyl)amino]ethyl}acetamide (prepared from N-(2-aminoethyl)acetamide (Lancaster), following procedure D) is added to a solution of N-[5-(bromoacetyl)-4-methyl-1,3- thiazol-2-yl]acetamide (Intermediate 1) in EtOH. The mixture is stirred 5 hours at RT. After addition of water, the desired product is extracted with EtOAc (3 fractions) and dried over MgSO$_4$. Combined organic phases is filtrated and evaporated. Compound (77) is isolated as a light yellow oil (31.28 mg; 65%). M$^+$ (ESI): 340. HPLC, Rt: 5.56 min (purity: 64%).

Example 78

N-(2-{[2-(dimethylamino)ethyl]amino}-4'-methyl-4,5'-bi-1,3-thiazol-2'-yl)acetamide

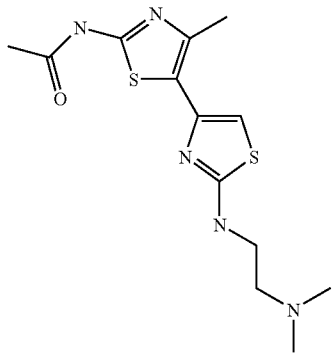

(78)

According to the general procedure 1, N-[2-(dimethylamino)ethyl]thiourea (prepared from N,N-dimethylethane-1,2-diamine (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (78) is isolated as a beige solid (34.30 mg; 38%). M$^+$ (ESI): 326. HPLC, Rt: 5.93 min (purity: 95.7%).

Example 79

N-{2-[(2-hydroxyethyl)amino]-4'-methyl-4,5'-bi-1,3-thiazol-2'-yl}acetamide

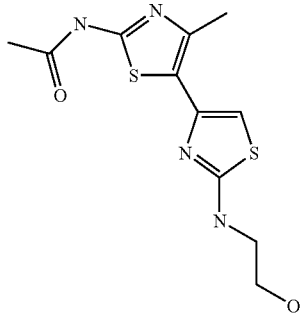

(79)

According to the general procedure 1, N-(2-hydroxyethyl)thiourea (prepared from 2-aminoethanol (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evapo-rated and the desired product is purified by crystallization. Compound (79) is isolated as a beige solid (5 mg; 43%). M$^+$ (ESI): 299.2. HPLC, Rt: 5.6 min (purity: 94.9%).

Example 80

N-(2-{[2-(4-hydroxyphenyl)ethyl]amino}-4'-methyl-4,5'-bi-1,3-thiazol-2'-yl)acetamide

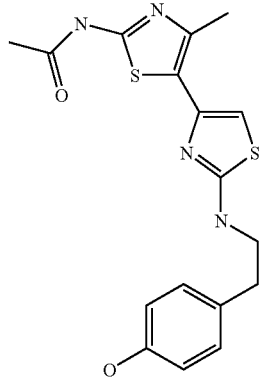

(80)

According to the general procedure 1, N-[2-(4-hydroxyphenyl)ethyl]thiourea (prepared from 4-(2-aminoethyl)phenol (Fluka), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (80) is isolated as a beige solid (49.18 mg; 47%). M$^+$ (ESI): 375.2. HPLC, Rt: 6.84 min (purity: 97.9%).

Example 81

N-(2-{[3-dimethylamino)propyl]amino}-4'-methyl-4,5'-bi-1,3-thiazol-2'-yl)acetamide

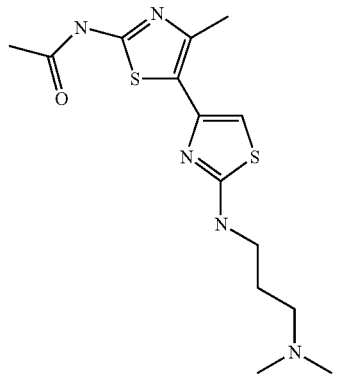

(81)

According to the general procedure 1, N-[3-(dimethylamino)propyl]thiourea (prepared from N,N-dimethylpropane-1,3-diamine (Fluka), following procedure D) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO$_4$. Combined organic phases is filtrated and evaporated. Compound (81) is isolated as a light yellow oil (35.39 mg; 34%). M$^+$ (ESI): 340. HPLC, Rt: 5.595 min (purity: 94.41%).

Example 82

N-{2-[(3-hydroxypropyl)amino]-4'-methyl 4,5'-bi-3-thiazol-2'-yl}acetamide

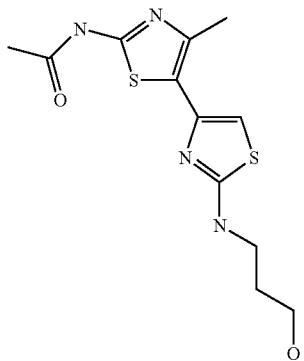

(82)

According to the general procedure 1, N-(3-hydroxypropyl)thiourea (prepared from 3-aminopropan-1-ol (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (82) is isolated as a beige solid (38.17 mg; 4%). M$^+$ (ESI): 313.2. HPLC, Rt: 5.67 min (purity: 97.1%).

Example 83

N-(2-{[3-(1H-imidazol-1-yl)propyl]amino}-4'-methyl-4,5'-bi-1,3-thiazol-2'-yl)acetamide

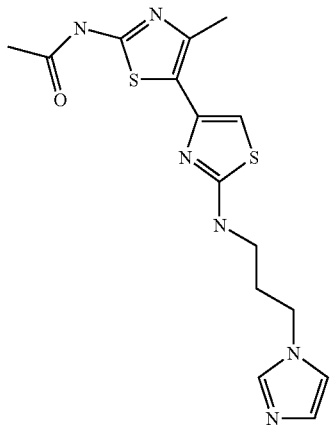

(83)

According to the general procedure 1, N-[3-(1H-imidazol-1-yl)propyl]thiourea (prepared from [3-(1H-imidazol-1-yl)propyl]amine (Aldrich), following procedure D) is added to a solution of N-[5-(bromoacetyl)-4-methyl-1,3-thiazol-2-yl] acetamide (Intermediate 1) in EtOH. The mixture is stirred 5 hours at RT. After addition of water, the desired product is extracted with EtOAc (3 fractions) and dried over MgSO$_4$. Combined organic phases is filtrated and evaporated. Compound (83) is isolated as a light yellow oil (50.3 mg; 50%). M$^+$ (ESI): 363.2. HPLC, Rt: 5.6 min (purity: 94.336%).

Example 84

N~3~-[2'-(acetylamino-4'-methyl-4,5'-bi-1,3-thiazol-2-yl]-beta-alaninamide

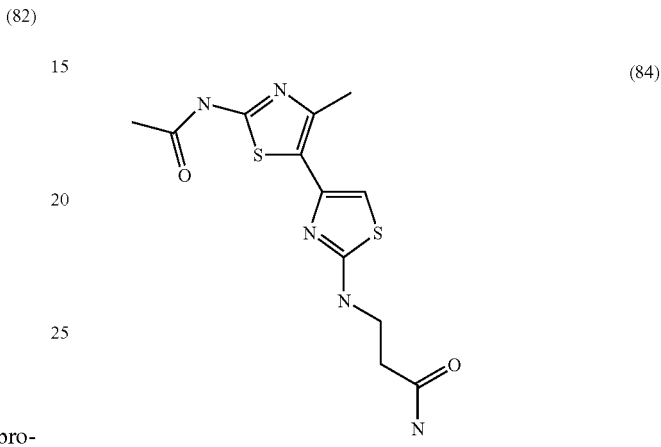

(84)

According to the general procedure 1, N~3~-(aminocarbonothioyl)-beta-alaninamide (prepared from beta-alaninamide, hydrochloride salt (Novabio), following procedure D) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO$_4$. Combined organic phases is filtrated and evaporated. Compound (84) is isolated as a light yellow oil (11.25 mg; 13%). M$^+$ (ESI): 323. HPLC, Rt: 6.62 min (purity: 65.495%).

Example 85

N-{4'-methyl-2-[(2-methylprop-2-en-1-yl)amino]-4,5'-bi-1,3-thiazol-2'-yl}acetamide

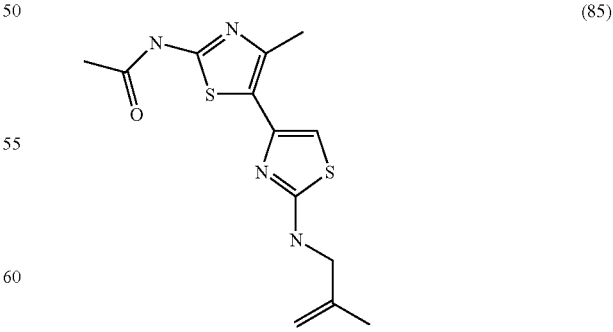

(85)

According to the general procedure 1, N-(2-methylprop-2-en-1-yl)thiourea (prepared from (2-methylprop-2-en-1-yl)amine (Acros), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (85) is isolated as a beige solid (15.75 mg; 70%). M+ (ESI): 309.2. HPLC, Rt: 7.54 nm in (purity: 97.43%).

Example 86

N-{2-[(2-hydroxyphenyl)amino]-4'-methyl-4,5'-bi-1,3-thiazol-2'-yl}acetamide

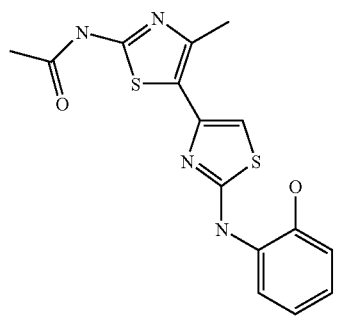

(86)

According to the general procedure 1, N-(2-hydroxyphenyl)thiourea (prepared from 2-aminophenol (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO4. Combined organic phases is filtrated and evaporated. Compound (86) is isolated as a light yellow oil (23.66 mg; 49%). M+ (ESI): 347.2. HPLC, Rt: 8.04 min (purity: 91.8%).

Example 87

N-{2-[(6-fluoropyridin-3-yl)amino]-4'-methyl-4,5'-bi-1,3-thiazol-2'-yl}acetamide

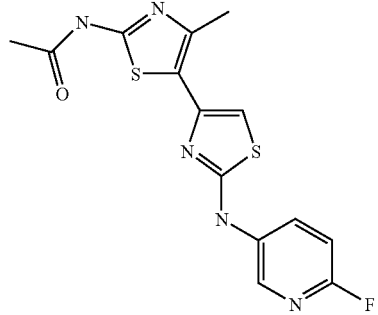

(87)

According to the general procedure 1, N-(6-fluoropyridin-3-yl)thiourea (prepared from 6-fluoropyridin-3-amine (Asymchem), following procedure D) is added to a solution of N-[5-(bromoacetyl)-4-methyl-1,3-thiazol-2-yl]acetamide (Intermediate 1) in EtOH. The mixture is stirred 5 hours at RT.

The solvents are evaporated and the desired product is purified by crystallization. Compound (87) is isolated as a beige solid (34.15 mg; 33%). M+ (ESI): 350. HPLC, Rt: 8.25 min (purity: 96.053%).

Example 88

N-{2-[(4-cyanophenyl)amino]-4'-methyl-4,5'-bi-1,3-thiazol-2'-yl}acetamide

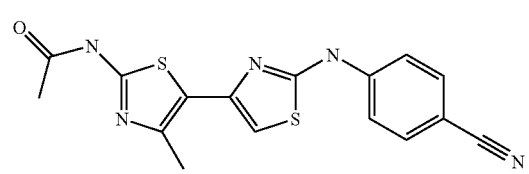

(88)

According to the general procedure 1, N-(4-cyanophenyl)thiourea (Fluka) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (88) is isolated as a beige solid (17.23 mg; 5%). M+ (ESI): 356. HPLC, Rt: 9.13 min (purity: 93.3%).

Example 89

N-{2-[(6-cyanopyridin-3-yl)amino]-4'-methyl-4,5'-bi-1,3-thiazol-2'-yl}acetamide

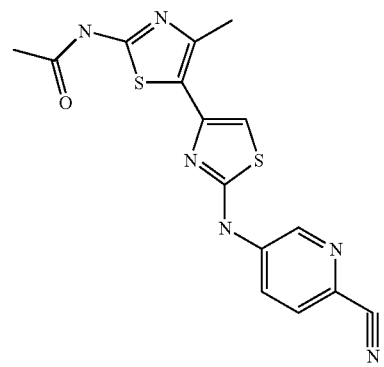

(89)

According to the general procedure 1, N-(6-cyanopyridin-3-yl)thiourea (prepared from 5-aminopyridine-2-carbonitrile (Aldrich), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (89) is isolated as a beige solid (28.71 mg; 29%). M⁺ (ESI): 357.2. HPLC, Rt: 7.96 min (purity: 92.6%).

Example 90

N-{2-[(3-methoxy phenyl)amino]-4-methyl-4,5'-bi-1,3-thiazol-2'-yl}acetamide

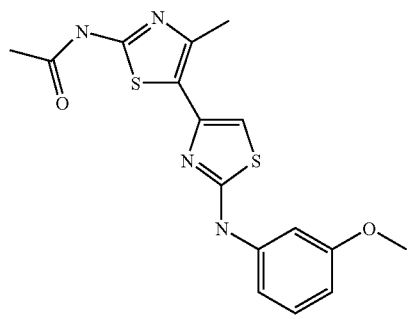

(90)

According to the general procedure 1, N-(3-methoxyphenyl)thiourea (prepared from (3-methoxyphenyl)amine (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (90) is isolated as a beige solid (19.63 mg; 12%). M⁺ (ESI): 361.2. HPLC, Rt: 10.03 min (purity: 94.8%).

Example 91

3-{[2'-(acetylamino)-4'-methyl-4,5'-bi-1,3-thiazol-2-yl]amino}benzamide

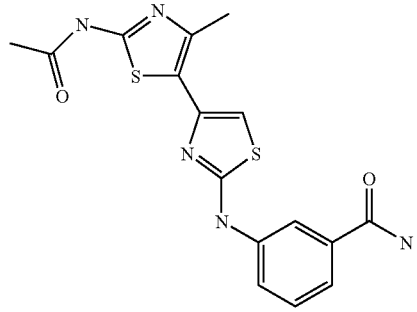

(91)

According to the general procedure 1,3-[(aminocarbonothioyl)amino]benzamide (prepared from 3-aminobenzamide (Fluka), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (91) is isolated as a beige solid (25.49 mg; 33%). M⁺ (ESI): 374. HPLC, Rt: 15.27 min (purity: 97.8%).

Example 92

N-{4'-methyl-2-[(2-nitrophenyl)amino]-4,5-bi-1,3-thiazol-2'-yl}acetamide

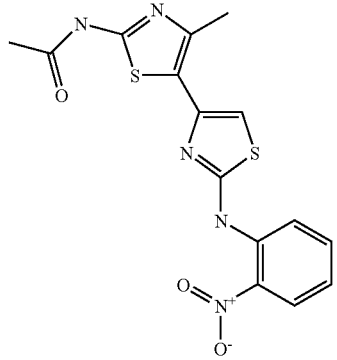

(92)

According to the general procedure 1, N-(2-nitrophenyl)thiourea (prepared from (2-nitrophenyl)amine (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (92) is isolated as a beige solid (12.69 mg; 15%). M⁺ (ESI): 376. HPLC, Rt: 11.55 min (purity: 94.5%).

Example 93

N-{4'-methyl-2-[(3-nitrophenyl)amino]-4,5'-bi-1,3-thiazol-2'-yl}acetamide

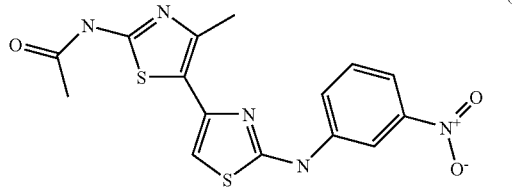

(93)

According to the general procedure 1, N-(3-nitrophenyl)thiourea (Fluka) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (93) is isolated as a beige solid (67.80 mg; 63%). M+ (ESI): 376. HPLC, Rt: 9.94 min (purity: 93.93%).

Example 94

N-[4'-methyl-2-(quinolin-3-ylamino)-4,5'-bi-1,3-thiazol-2'-yl]acetamide

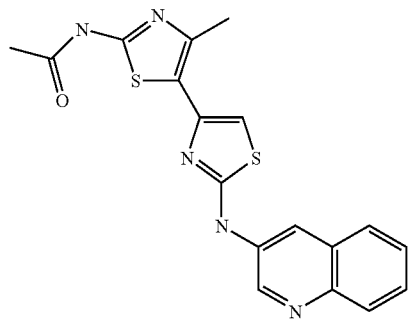

(94)

According to the general procedure 1, N-quinolin-3-ylthiourea (prepared from quinolin-3-amine (Aldrich), following procedure A) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (94) is isolated as a beige solid (29.83 mg; 25%). M+ (ESI): 382. HPLC, Rt: 7 min (purity: 98.2%).

Example 95

N-[4'-methyl-2-(quinolin-5-ylamino)-4,5'-bi-1,3-thiazol-2'-yl]acetamide

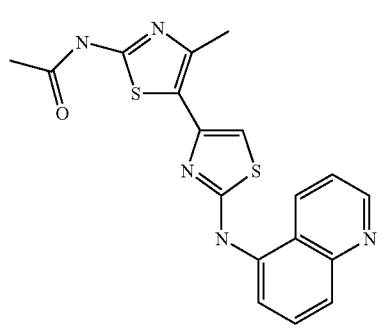

(95)

According to the general procedure 1, N-quinolin-5-ylthiourea (prepared from quinolin-5-amine (Fluka), following procedure A) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (95) is isolated as a beige solid (15.45 mg; 19%). M+ (ESI): 382. HPLC, Rt: 6.11 min (purity: 95.3%).

Example 96

N-[4'-methyl-2-(quinolin-6-ylamino)-4,5'-bi-1,3-thiazol-2'-yl]acetamide

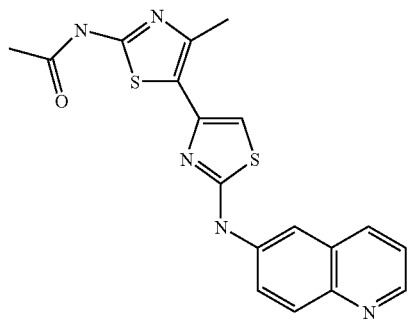

(96)

According to the general procedure 1, N-quinolin-6-ylthiourea (prepared from quinolin-6-amine (Fluka), following procedure A) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by preparative HPLC. Compound (96) is isolated as a beige solid (39.67 mg; 45%). M+ (ESI): 382. HPLC, Rt: 6.37 min (purity: 98.9%).

Example 97

N-[2-(cyclopentylamino)-4'-methyl-4,5'-bi-1,3-thiazol-2'-yl]acetamide

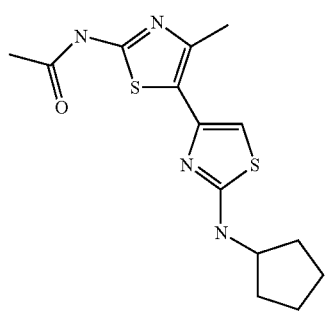

(97)

According to the general procedure 1, N-cyclopentylthiourea (prepared from cyclopentanamine (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization.

Compound (97) is isolated as a beige solid (44.41 mg; 54%). M+ (ESI): 323.2. HPLC, Rt: 8.14 min (purity: 91.8%).

Example 98

N-[2-(cyclopropylamino)-4'-methyl-4,5'-bi-3-thiazol-2'-yl]acetamide

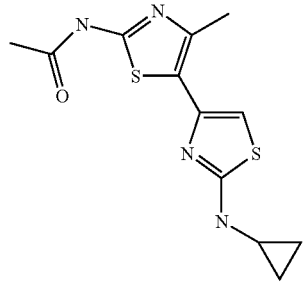
(98)

According to the general procedure 1, N-cyclopropylthiourea (prepared from cyclopropanamine (Aldrich), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (98) is isolated as a beige solid (65.7 mg; 62%). M+ (ESI): 295.2. HPLC, Rt: 6.86 min (purity: 98%).

Example 99

N-{4'-methyl-2-[(Pyridin-3-ylmethyl)amino]-4,5'-bi-1,3-thiazol-2'-yl}acetamide

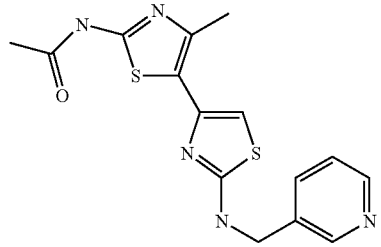
(99)

According to the general procedure 1, N-(pyridin-3-ylmethyl)thiourea (prepared from (pyridin-3-ylmethyl)amine (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO4. Combined organic phases is filtrated and evaporated. Compound (99) is isolated as a light yellow oil (10 mg; 12%). M+ (ESI): 346. HPLC, Rt: 5.69 min (purity: 86.5%).

Example 100

N-{2-[(4-hydroxybutyl)amino]-4'-methyl-4,5-bi-1,3-thiazol-2'-yl}acetamide

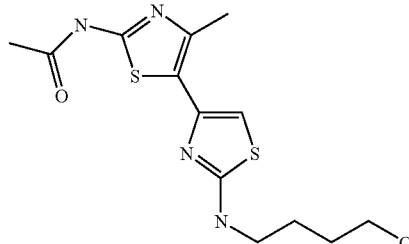
(100)

According to the general procedure 1, N-(4-hydroxybutyl)thiourea (prepared from 4-aminobutan-1-ol (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO4. Combined organic phases is filtrated and evaporated. Compound (100) is isolated as a light yellow oil (26.2 mg; 16%). M+ (ESI): 327.2. HPLC, Rt: 5.71 min (purity: 92.9%).

Example 101

N-(4'-methyl-2-{[3-(methylsulfonyl)phenyl]amino}-4,5'-bi-3-thiazol-2'-yl)acetamide

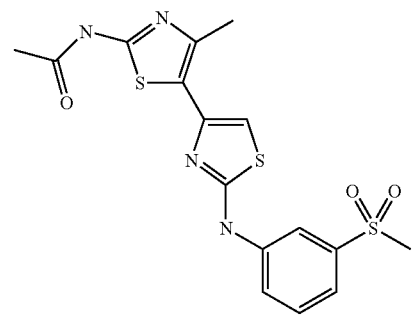
(101)

According to the general procedure 1, N-[3-(methylsulfonyl)phenyl]thiourea (prepared from [3-(methylsulfonyl)phenyl]amine, hydrochloride salt (Acros), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (101) is isolated as a beige solid (24.2 mg; 20%). M⁺ (ESI): 409.2. HPLC, Rt: 7.87 min (purity: 93.13%).

Example 102

N-{4'-methyl-2-[(3-pyrrolidin-1-ylpropyl)amino]-4,5'-bi-1,3-thiazol-2'-yl}acetamide

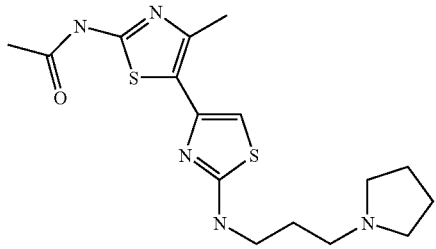

(102)

According to the general procedure 1, N-(3-pyrrolidin-1-ylpropyl)thiourea (prepared from (3-pyrrolidin-1-ylpropyl)amine (Lancaster), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (102) is isolated as a beige solid (14.18; 16%). M⁺ (ESI): 366. HPLC, Rt: 5.85 min (purity: 94.398%).

Example 103

N-{2-[(1,1-dioxido-1-benzothien-6-yl)amino]-4'-methyl-4,5'-bi-1,3-thiazol-2'-yl}acetamide

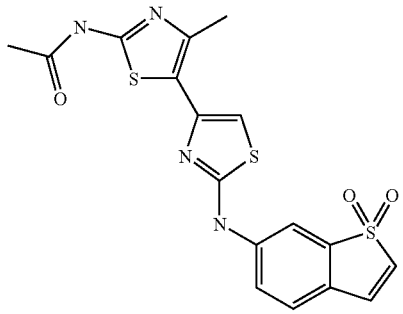

(103)

According to the general procedure 1, N-(1,1-dioxido-1-benzothien-6-yl)thiourea (prepared from (1,1-dioxido-1-benzothien-6-yl)amine (Maybridge), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (103) is isolated as a beige solid (58.6 mg; 40%). M⁺ (ESI): 419.2. HPLC, Rt: 8.1 min (purity: 93.69%).

Example 104

N-(2-{[(1-ethylpyrrolidin-2-yl)methyl]amino}-4'-methyl-4,5'-bi-1,3-thiazol-2'-yl)acetamide

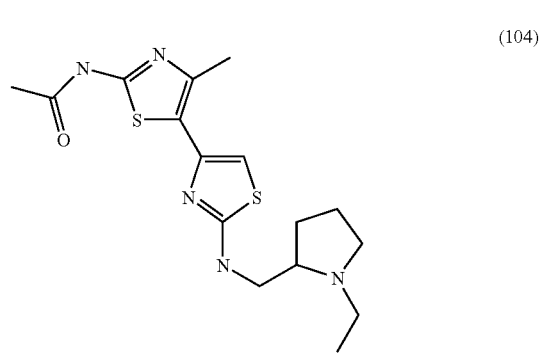 [SMILES: CCN1CCCC1CNc1nc(-c2sc(NC(C)=O)nc2C)cs1]

(104)

According to the general procedure 1, N-[(1-ethylpyrrolidin-2-yl)methyl]thiourea (prepared from [(1-ethylpyrrolidin-2-yl)methyl]amine (Acros), following procedure D) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO₄. Combined organic phases is filtrated and evaporated. Compound (104) is isolated as a light yellow oil (47.24 mg; 46%). M⁺ (ESI): 366. HPLC, Rt: 6.227 min (purity: 97.59%).

Example 105

N-{2-[(cyanomethyl)amino]-4'-methyl-4,5'-bi-1,3-thiazol-2'-yl}acetamide

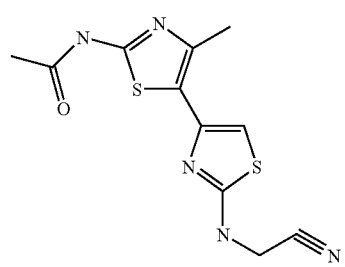

(105)

According to the general procedure 1, N-(cyanomethyl)thiourea (prepared from aminoacetonitrile (Sigma), following procedure D) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO₄. Combined organic phases is filtrated and evaporated. Compound (105) is isolated as a light yellow oil (3.96 mg; 5%). M+ (ESI): 294. HPLC, Rt: 6.86 min (purity: 85%).

Example 106

N-[2-(isobutylamino)-4'-methyl-4,5'-bi-1,3-thiazol-2'-yl]acetamide

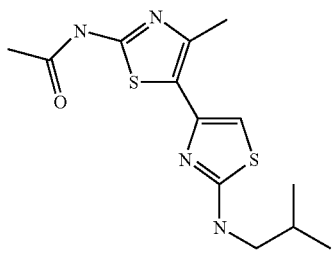

(106)

According to the general procedure 1, N-isobutylthiourea (prepared from 2-methylpropan-1-amine (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (106) is isolated as a beige solid (50.82 mg; 57%). M+ (ESI): 311.2. HPLC, Rt: 7.9 min (purity: 90.6%).

Example 107

N-{2-[(2,2-dimethylpropyl)amino]-4'-methyl-4,5'-bi-1,3-thiazol-2'-yl}acetamide

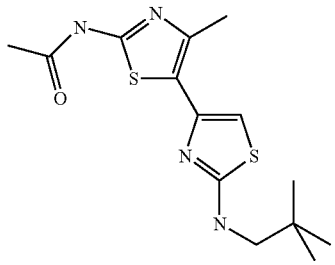

(107)

According to the general procedure 1, N-(2,2-dimethylpropyl)thiourea (prepared from (2,2-dimethylpropyl)amine (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (107) is isolated as a beige solid (35.87 mg; 38%). M+ (ESI): 325.2. HPLC, Rt: 8.8 min (purity: 97.7%).

Example 108

N-(2-{[(cis)-2-(hydroxymethyl)cyclohexyl]amino}-4'-methyl-4,5'-bi-3-thiazol-2'-yl)acetamide

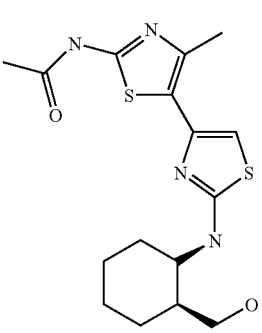

(108)

According to the general procedure 1, N-[(cis)-2-(hydroxymethyl)cyclohexyl]thiourea (prepared from cis-(2-aminocyclohexyl)methanol, hydrochloride salt (Acros), following procedure D) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO4. Combined organic phases is filtrated and evaporated. Compound (108) is isolated as a light yellow oil (24.3 mg; 5%). M+ (ESI): 367.2. HPLC, Rt: 6.23 min (purity: 75%).

Example 109

N-(2-{[(trans)-2-(hydroxymethyl)cyclohexyl]amino}-4'-methyl-45'-bi-1,3-thiazol-2'-yl)acetamide

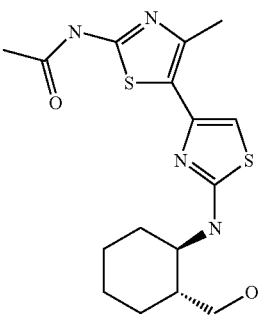

(109)

According to the general procedure 1, N-[(trans)-2<hydroxymethyl)cyclohexyl]thiourea (prepared from trans-(2-aminocyclohexyl)methanol, hydrochloride salt (Acros), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (109) is isolated as a beige solid (34.5 mg; 61%). M+ (ESI): 367.2. HPLC, Rt: 6.79 min (purity: 94.4%).

Example 110

N-[2-(sec-butylamino)-4'-methyl-4,5'-bi-1,3-thiazol-2'-yl]acetamide

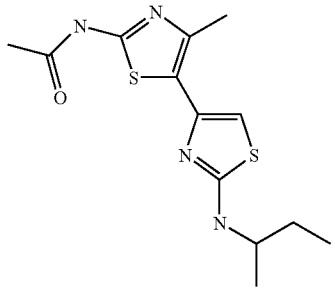

(110)

According to the general procedure 1, N-(sec-butyl)thiourea (prepared from sec-butylamine (Avocado), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (110) is isolated as a beige solid (67.01 mg; 75%). M+ (ESI): 311.2. HPLC, Rt: 7.68 min (purity: 90.2%).

Example 111

N-{4'-methyl-2-[(Pyridin-4-ylmethyl)amino]-4,5'-bi-1,3-thiazol-2'-yl}acetamide

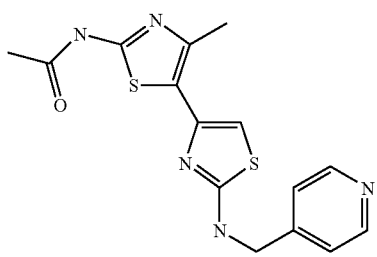

(111)

According to the general procedure 1, N-(pyridin-4-ylmethyl)thiourea (prepared from (pyridin-4-ylmethyl)amine (Aldrich), following procedure D) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO4. Combined organic phases is filtrated and evaporated. Compound (111) is isolated as a light yellow oil (38.54 mg; 7%). M+ (ESI): 346. HPLC, Rt: 5.72 min (purity: 91.8%).

Example 112

N-(4'-methyl-2-{[4(morpholin-4-ylsulfonyl)phenyl]amino}-4,5'-bi-13 thiazol-2'-yl)acetamide

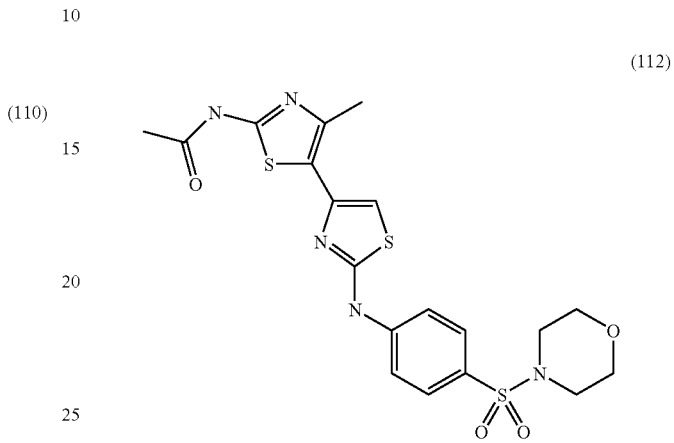

(112)

According to the general procedure 1, N-[4-(morpholin-4-ylsulfonyl)phenyl]thiourea (prepared from [4-(morpholin-4-ylsulfonyl)phenyl]amine (Maybridge), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization Compound (112) is isolated as a beige solid (24.82 mg; 19%). M+ (ESI): 480. HPLC, Rt: 8.55 min (purity: 96%).

Example 113

N-[2-({3-[(butylamino)sulfonyl]phenyl}amino)-4'-methyl-4,5'-bi-1,3-thiazol-2'-yl]acetamide

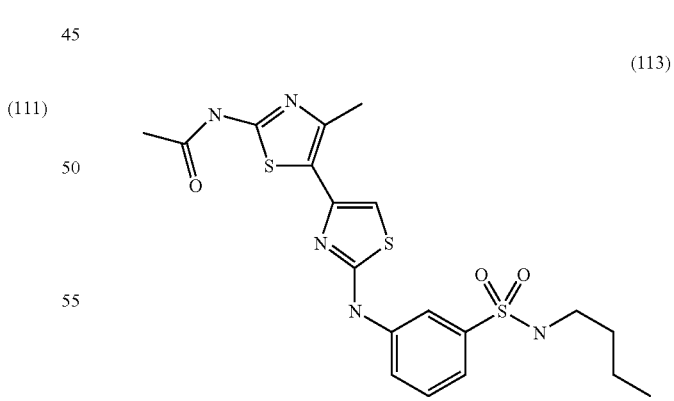

(113)

According to the general procedure 1,3-[(aminocarbonothioyl)amino]-N-butylbenzene sulfonamide (prepared from 3-amino-N-butylbenzenesulfonamide (Aldrich), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by preparative HPLC. Compound (113) is isolated as a beige solid (26.42 mg; 20%). M+ (ESI): 466. HPLC, Rt: 10.31 min (purity: 99.1%).

Example 114

N-{2-[(cyclopropylmethyl)amino]-4'-methyl-4,5'-bi-1,3-thiazol-2'-yl}acetamide

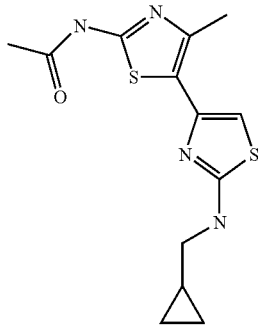

(114)

According to the general procedure 1, N-(cyclopropylmethyl)thiourea (prepared from (cyclopropylmethyl)amine (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (114) is isolated as a beige solid (39.26; 32%). M+ (ESI): 309.2. HPLC, Rt: 7.3 min (purity: 97.5%).

Example 115

N-[2-(cyclobutylamino)-4'-methyl-4,5'-bi-1,3-thiazol-2'-yl]acetamide

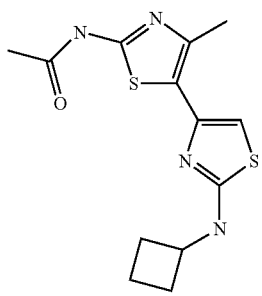

(115)

According to the general procedure 1, N-cyclobutylthiourea (prepared from cyclobutanamine (Fluka), following procedure C) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (115) is isolated as a beige solid (73.20 mg; 84%). M+ (ESI): 309.2. HPLC, Rt: 7.68 min (purity: 90.2%).

Example 116

N-[2-(2,3-dihydro-1H-inden-2-ylamino)-4'-methyl-4,5'-bi-1,3-thiazol-2'-yl]acetamide

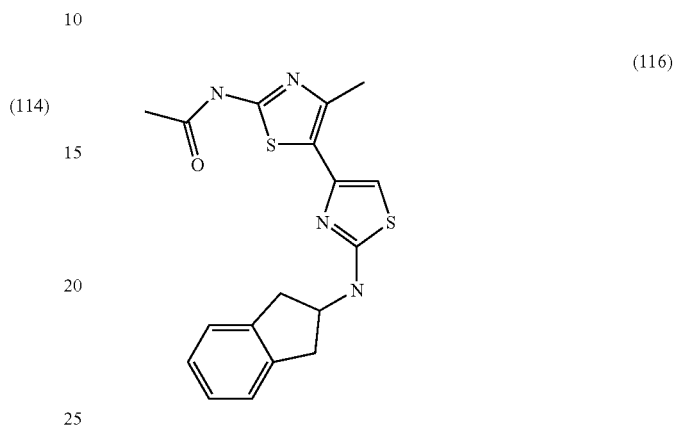

(116)

According to the general procedure 1, N-(2,3-dihydro-1H-inden-2-yl)thiourea (prepared from 2,3-dihydro-1H-inden-2-ylamine (Maybridge), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (116) is isolated as a beige solid (6 mg; 6%). M+ (ESI): 371.2. HPLC, Rt: 9.83 min (purity-90.8%).

Example 117

N-(4'-methyl-2-{[2-(methylsulfonyl)phenyl]amino}4,5'-bi-1,3-thiazol-2'-yl)acetamide

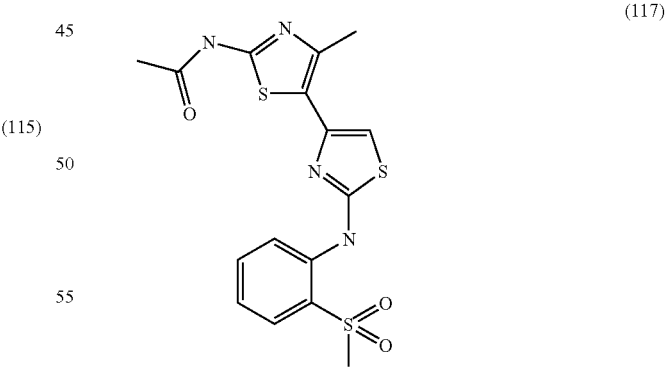

(117)

According to the general procedure 1, N-[2-methylsulfonyl)phenyl]thiourea (prepared from [2-(methylsulfonyl)phenyl]amine, hydrochloride salt (Acros), following procedure A) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO4. Combined organic phases is filtrated and evaporated. Compound (117) is isolated as a light yellow oil (5.93 mg; 10%). M+ (ESI): 409. HPLC, Rt: 9.5 min (purity: 83.4%).

Example 118

N-(4'-methyl-2-{[2-(1H-1,2,4-triazol-1-yl)ethyl]amino}-4,5-bi-1,3 thiazol-2'-yl acetamide number

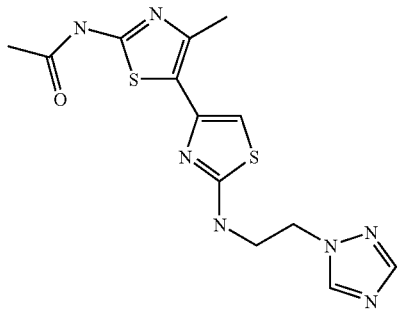

(118)

According to the general procedure 1, N-[2-(1H-1,2,4-triazol-1-yl)ethyl]thiourea (prepared from [2-(1H-1,2,4-triazol-1-yl)ethyl]amine (Ostwest), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (118) is isolated as a beige solid (6.51 mg; 30%). M+ (ESI): 350. HPLC, Rt: 5.699 min (purity: 91.43%).

Example 119

N-(2-{[3-(1-hydroxyethyl)phenyl]amino}-4'-methyl-4,5'-bi-1,3-thiazol-2'-yl)acetamide

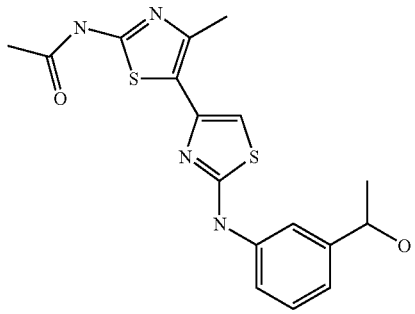

(119)

According to the general procedure 1, N-[3-(1-hydroxyethyl)phenyl]thiourea (prepared from 1-(3-aminophenyl)ethanol (Aldrich), following procedure D) is added to a solution of N-[5-(bromoacetyl)-4-methyl-1,3-thiazol-2-yl]acetamide (Intermediate 1) in EtOH. The mixture is stirred 5 hours at RT. After addition of water, the desired product is extracted with EtOAc (3 fractions) and dried over MgSO4. Combined organic phases is filtrated and evaporated. Compound (119) is isolated as a light yellow oil (41.06 mg; 50%). M+ (ESI): 375.2. HPLC, Rt: 7.62 min (purity: 88.4%).

Example 120

Methyl (4-{[2'-(acetylamino)-4'-methyl-4,5'-bi-1,3-thiazol-2-yl]amino}Phenyl)acetate

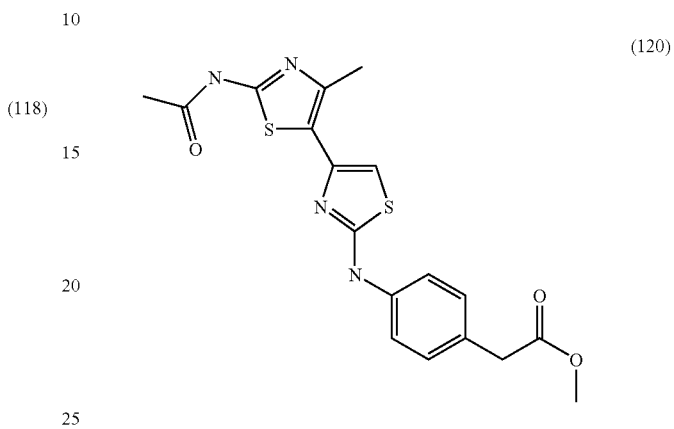

(120)

Methyl ester of (4-aminophenyl)acetic acid (Lancaster) is obtained using the etherification conditions described above for amines (NHR$^5$R$^6$) wherein R$^5$ is H and R$^6$ contains a carboxylic acid. It is transformed into its corresponding thiourea, following the procedure D. The resulting thiourea, methyl {4-[(aminocarbonothioyl)amino]phenyl}acetate, is added to a solution of N-[5-(bromoacetyl)-4-methyl-1,3-thiazol-2-yl]acetamide (Intermediate 1) in EtOH, according to the general procedure 1. The mixture is stirred 5 hours at RT. The solvents are evaporated and the desired product is purified by crystallization. Compound (120) is isolated as a beige solid (10 mg; 9%). M+ (ESI): 403. HPLC, Rt: 9.3 min (purity: 90.7%).

Example 121

Methyl N-(4-{[2'-(acetylamino)-4'-methyl-4,5'-bi-1,3-thiazol-2-yl]amino}benzoyl)-beta-alaninate

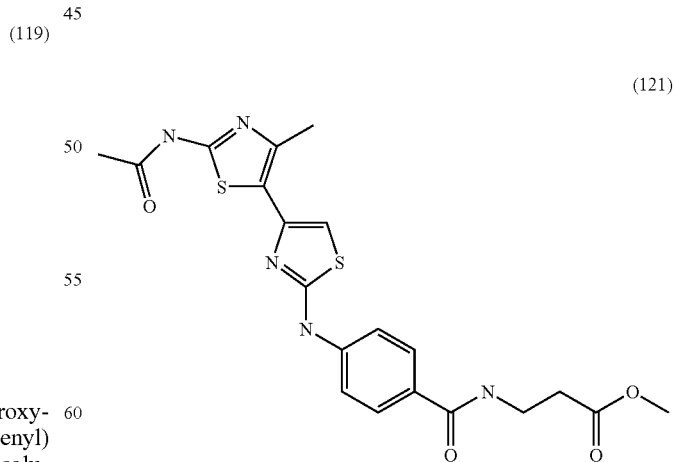

(121)

Methyl ester of N-(4-aminobenzoyl)-beta-alanine (Aldrich) is obtained using the etherification conditions described above for amines (NHR$^5$R$^6$) wherein R$^5$ is H and R$^6$ contains a carboxylic acid. It is transformed into its corresponding thiourea, following the procedure D. The resulting thiourea, methyl N-(4-aminobenzoyl)-beta-alaninate, is added to a solution of N-[5-(bromoacetyl)-4-methyl-1,3-thiazol-2-yl] acetamide (Intermediate 1) in EtOH, according to the general procedure 1. The mixture is stirred 5 hours at RT. The solvents are evaporated and the desired product is purified by crystallization. Compound (121) is isolated as a beige solid (22.39 mg; 23%). M+ (ESI): 460. HPLC, Rt: 7.2 min (purity: 90%).

Example 122

Methyl N-(4-{[2'-(acetylamino)-4'-methyl-4,5'-bi-1,3-thiazol-2-yl]amino}benzoyl)glycinate

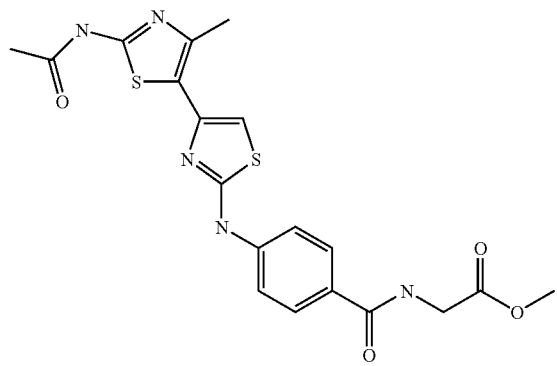

(122)

Methyl ester of N-(4-aminobenzoyl)glycine (Aldrich) is obtained using the etherification conditions described above for amines (NHR⁵R⁶) wherein R⁵ is H and R⁶ contains a carboxylic acid. It is transformed into its corresponding thiourea, following the procedure D. The resulting thiourea, methyl N-{4-[(aminocarbonothioyl)amino]benzoyl}glycinate, is added to a solution of N-[5-(bromoacetyl)-4-methyl-1,3-thiazol-2-yl]acetamide (Intermediate 1) in EtOH, according to the general procedure 1. The mixture is stirred 5 hours at RT. The solvents are evaporated and the desired product is purified by crystallization. Compound (122) is isolated as a beige solid (35.35 mg; 18%). M+ (ESI): 446. HPLC, Rt: 7.05 nm in (purity: 91.5%).

Example 123

Methyl 3-(3-{[2'-(acetylamino)-4'-methyl-4,5'-bi-1,3-thiazol-2-yl]amino}phenyl)propanoate

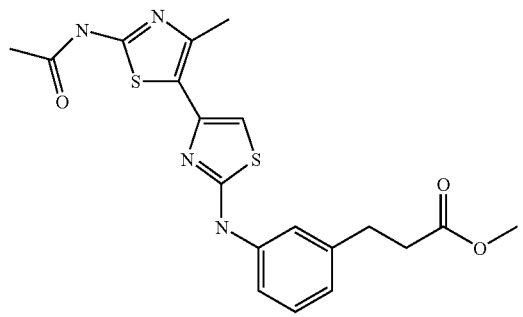

(123)

Methyl ester of 3-(3-aminophenyl)propanoic acid (Lancaster) is obtained using the etherification conditions described above for amines (NHR⁵R⁶) wherein R⁵ is H and R⁶ contains a carboxylic acid. It is transformed into its corresponding thiourea, following the procedure D. The resulting thiourea, methyl 3-{3-[(aminocarbonothioyl)amino]phenyl}propanoate, is added to a solution of N-[5-(bromoacetyl)-4-methyl-1,3-thiazol-2-yl]acetamide (Intermediate 1) in EtOH, according to the general procedure 1. The mixture is stirred 5 hours at RT. The solvents are evaporated and the desired product is purified by crystallization. Compound (123) is isolated as a beige solid (12.3 mg; 11%). M+ (ESI): 417.2. HPLC, Rt: 10.285 min (purity: 93%).

Example 124

3-(4-{[2'-(acetylamino)-4'-methyl-4,5'-bi-1,3-thiazol-2-yl]amino}phenyl) propanoic acid

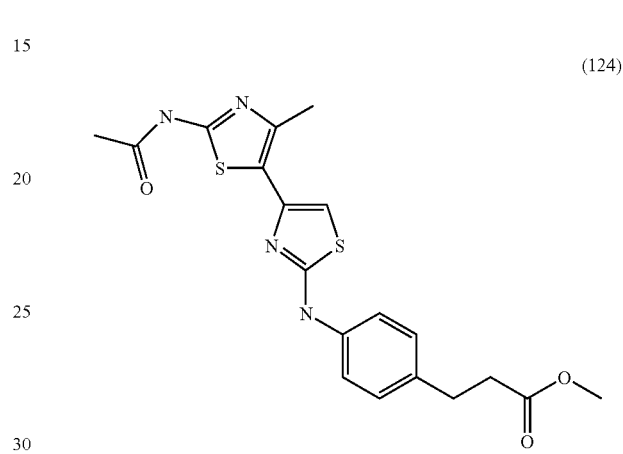

(124)

Methyl ester of 3-(4-aminophenyl)propanoic acid (Lancaster) is obtained using the etherification conditions described above for amines (NHR⁵R⁶) wherein R⁵ is H and R⁶ contains a carboxylic acid. It is transformed into its corresponding thiourea, following the procedure D. The resulting thiourea, methyl 3-{4-[(aminocarbonothioyl)amino]phenyl}propanoate, is added to a solution of N-[5-(bromoacetyl)-4-methyl-1,3-thiazol-2-yl]acetamide (Intermediate 1) in EtOH, according to the general procedure 1. The mixture is stirred 5 hours at RT. The resulting ester is hydrolysed under the reaction condition. The solvents are evaporated and the desired product is purified by crystallization. Compound (124) is isolated as a beige solid (11 mg; 8%). M+ (ESI): 403. HPLC, Rt: 10.09 min (purity: 91.40%).

Example 125

Methyl 4-{[2'-(acetylamino)-4'-methyl-4,5'-bi-1,3-thiazol-2-yl]amino}butanoate

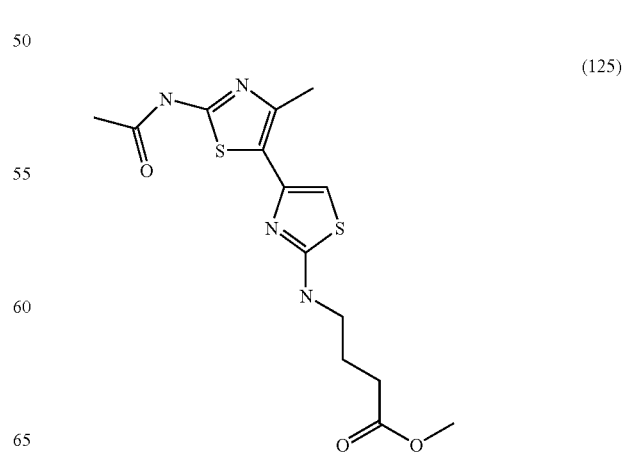

(125)

According to the general procedure 1, methyl 4-[(aminocarbonothioyl)amino]butanoate (prepared from methyl 4-aminobutanoate (Fluka), following procedure D) is added to a solution of N-[5-(bromoacetyl)-4-methyl-1,3-thiazol-2-yl]acetamide (Intermediate 1) in EtOH. The mixture is stirred 5 hours at RT. The solvents are evaporated and the desired product is purified by crystallization. Compound (125) is isolated as a beige solid (9.61 mg; 5%). M⁺ (ESI): 356. HPLC, Rt: 7.678 min (purity: 96.506%).

Example 126

Methyl (3-{[2'-(acetylamino)-4'-methyl-4,5'-bi-1,3-thiazol-2-yl]amino}henyl)acetate

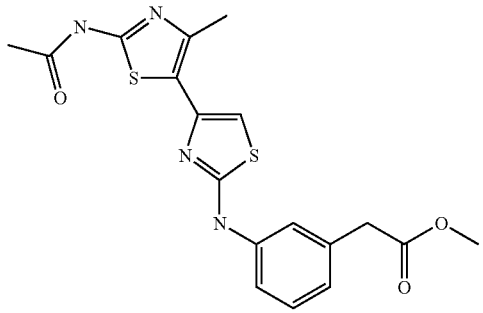
(126)

Methyl ester of (3-aminophenyl)acetic acid (Aldrich) is obtained using the etherification conditions described above for (NHR⁵R⁶) wherein R⁵ is H and R⁶ contains a carboxylic acid. It is transformed into its corresponding thiourea, following the procedure D. The resulting thiourea, methyl {3-[(aminocarbonothioyl)amino]phenyl}acetate, is added to a solution of N-[5-(bromoacetyl)-4-methyl-1,3-thiazol-2-yl] acetamide (Intermediate 1) in EtOH, according to the general procedure 1. The mixture is stirred 5 hours at RT. The solvents are evaporated and the desired product is purified by crystallization. Compound (126) is isolated as a beige solid (4.47 mg; 6%). M⁺ (ESI): 403.2. HPLC, Rt: 7.7 min (purity: 90%).

Example 127

N-[2-(allylamino)-4'-methyl-4,5'-bi-1,3-thiazol-2'-yl] urea

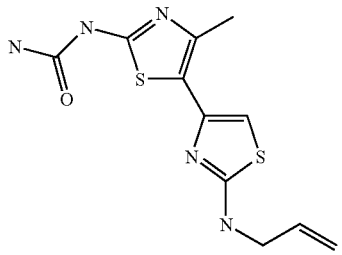
(127)

According to the general procedure 1, N-allylthiourea (Lancaster) is added to a solution of N-[5-(bromoacetyl)-4-methyl-1,3-thiazol-2-yl]urea (Intermediate 7) in EtOH. The mixture is stirred 5 hours at RT. The solvents are evaporated and the desired product is purified by crystallization. Compound (127) is isolated as a beige solid (14.3 mg; 18%). M⁺ (ESI): 296. HPLC, Rt: 8.95 min (purity: 93.08%).

Example 128

N-[4'-methyl-2-(pyridin-3-ylamino)-4,5'-bi-1,3-thiazol-2'-yl]urea

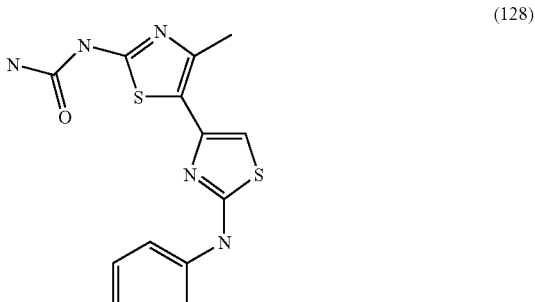
(128)

According to the general procedure 1, N-pyridin-3-ylthiourea (Fluka) is added to a solution of N-[5-(bromoacetyl)-4-methyl-1,3-thiazol-2-yl]urea (Intermediate 7) in EtOH. The mixture is stirred 5 hours at RT. The solvents are evaporated and the desired product is purified by crystallization. Compound (128) is isolated as a beige solid (32.63 mg; 35%). M⁺ (ESI): 333.2. HPLC, Rt: 5.71 min (purity: 98.09%).

Example 129

N-(4'-methyl-2-piperidin-1-yl-4,5'-bi-1,3-thiazol-2'-yl)urea

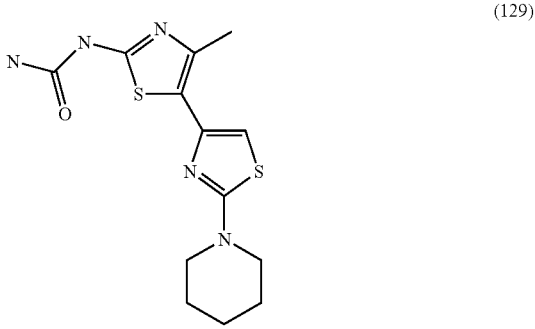 [SMILES: Cc1nc(NC(N)=O)sc1-c1csc(N2CCCCC2)n1]
(129)

According to the general procedure 1, piperidine-1-carbothioamide (Transwld) is added to a solution of N-[5-(bromoacetyl)-4-methyl-1,3-thiazol-2-yl]urea (Intermediate 7) in EtOH. The mixture is stirred 5 hours at RT. The solvents are evaporated and the desired product is purified by crystalliza-

Example 130

N-(2-anilino-4'-methyl-4,5'-bi-1,3-thiazol-2'-yl)urea

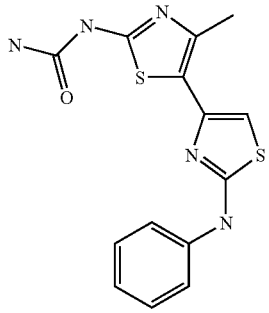

(130)

According to the general procedure 1, N-phenylthiourea (Transwld) is added to a solution of N-[5-(bromoacetyl)-4-methyl-1,3-thiazol-2-yl]urea (Intermediate 7) in EtOH. The mixture is stirred 5 hours at RT. The solvents are evaporated and the desired product is purified by crystallization. Compound (130) is isolated as a beige solid (30.17 mg; 32%). M$^+$ (ESI): 332. HPLC, Rt: 8.37 min (purity: 94.42%).

Example 131

N-{2-[(4-hydroxyphenyl)amino]-4'-methyl-4,5'-bi-1,3-thiazol-2'-yl}urea

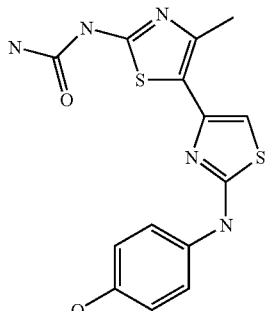

(131)

According to the general procedure 1, N-(4-hydroxyphenyl)thiourea (Aldrich) is added to a solution of N-[5-(bromoacetyl)-4-methyl-1,3-thiazol-2-yl]urea (Intermediate 7) in EtOH. The mixture is stirred 5 hours at RT. The solvents are evaporated and the desired product is purified by crystallization. Compound (131) is isolated as a beige solid (70.42 mg; 68%). M$^+$ (ESI): 348. HPLC, Rt: 6.14 min (purity: 96.82%).

Example 132

N-[2-pyridin-3-ylamino)-4,5'-bi-1,3-thiazol-2'-yl] acetamide

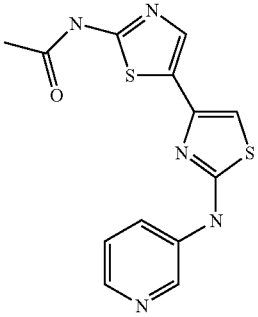

(132)

According to the general procedure 1, N-pyridin-3-ylthiourea (Lancaster) is added to a solution of N-[5-(2-bromoacetyl)-thiazol-2-yl]-acetamide (Intermediate 4) in EtOH. The mixture is stirred 5 hours at RT. The solvents are evaporated and the desired product is purified by crystallization Compound (132) is isolated as a beige solid (37.28 mg; 42%). M$^+$ (ESI): 318. HPLC, Rt: 6 min (purity: 94.96%).

Example 133

(4-{[2'-(acetylamino)-4'-methyl-4,5'-bi-1,3-thiazol-2-yl]amino}phenyl) cetic acid

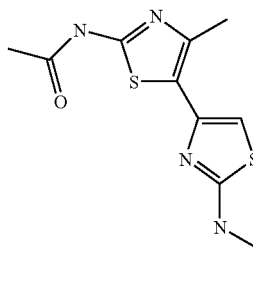

(133)

Methyl (4-{[2'-(acetylamino)-4'-methyl-4,5'-bi-1,3-thiazol-2-yl]amino}phenyl)acetate (122) is dissolved in a mixture MeOH/NaOH 1N (0.1M) and is stirred 4 hours at RT. The reaction mixture is concentrated and acidified to pH 4 with HCl 1.5N. The resulting solid is filtered, washed with water and dried under vacuo. Compound (133) is isolated as a beige solid (6.72 mg; 50%). M⁺ (ESI): 389.2. HPLC, Rt: 7.19 min (purity: 80.67%).

Example 134

N-(4-{[2'-(acetylamino)-4'-methyl-4,5'-bi-1,3-thiazol-2-yl]amino}benzoyl)-beta-alanine

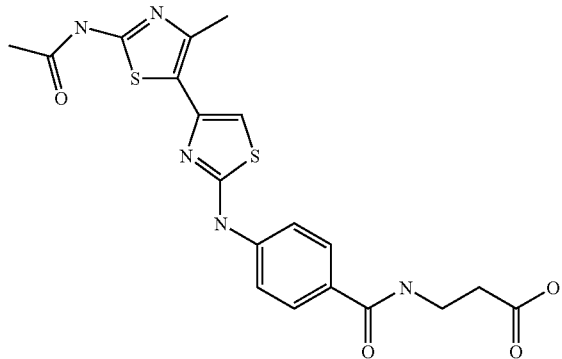

(134)

Methyl N-(4-{[2'-(acetylamino)-4'-methyl-4,5'-bi-1,3-thiazol-2-yl]amino}benzoyl)-beta-alaninate (123) is dissolved in a mixture MeOH/NaOH 1N (0.1 M) and is stirred 4 hours at RT. The reaction mixture is concentrated and acidified to pH 4 with HCl 1.5N. The desired product is extracted with EtOAc (3 fractions) and dried over MgSO₄. Combined organic phases is filtrated and evaporated. Compound (134) is isolated as a light yellow oil (5.77 mg; 48%). M⁺ (ESI): 446. HPLC, Rt: 6.07 min (purity: 68.2%).

Example 135

N-(4-{[2'-(acetylamino)-4'-methyl-4,5'-bi-1,3-thiazol-2-yl]amino}benzoyl)glycine

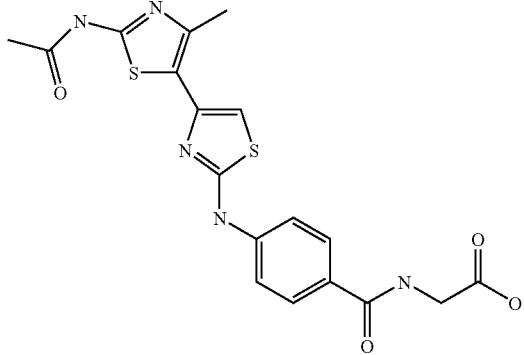

(135)

Methyl N-(4-f{[2'-(acetylamino)-4'-methyl-4,5'-bi-1,3-thiazol-2-yl]amino}benzoyl)glycinate (124) is dissolved in a mixture MeOH/NaOH 1N (0.1M) and is stirred 4 hours at RT. The reaction mixture is concentrated and acidified to pH 4 with HCl 1.5N. The resulting solid is filtered, washed with water and dried under vacuo. Compound (135) is isolated as a beige solid (12.02 mg; 82%). M⁺ (ESI): Not ionising. HPLC, Rt: 14.49 min (purity: 98.5%).

Example 136

3-(3-{[2'-(acetylamino)-4'-methyl-4,5'-bi-1,3-thiazol-2-yl]amino}phenyl) propanoic acid

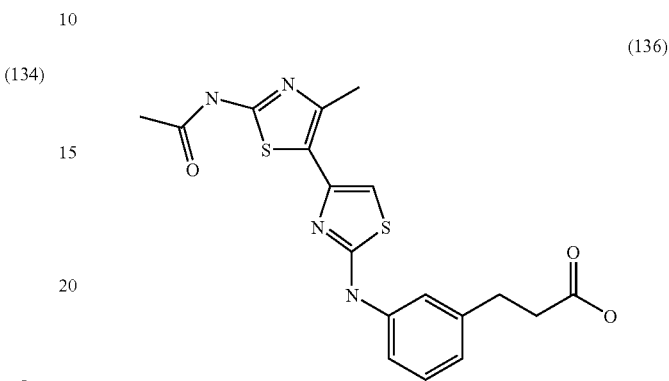

(136)

Methyl 3-(3-{[2'-(acetylamino)-4'-methyl-4,5'-bi-1,3-thiazol-2-yl]amino}phenyl) propanoate (125) is dissolved in a mixture MeOH/NaOH 1N (0.1M) and is stirred 4 hours at RT. The reaction mixture is concentrated and acidified to pH 4 with HCl 1.5N. The resulting solid is filtered, washed with water and dried under vacuo. Compound (136) is isolated as a beige solid (7.84 mg; 63%). M⁺ (ESI): 403.2. HPLC, Rt: 7.94 min (purity: 94.21%).

The following compounds can be synthesized according to the general schemes proposed herein and are commercially available:

N-{2-[(4-ethoxyphenyl)amino]-4'-methyl-4,5'-bi-1,3-thiazol-2'-yl}acetamide;
N-{4'-methyl-2-[(4-methylphenyl)amino]-4,5'-bi-1,3-thiazol-2'-yl}acetamide;
N-{2-[(4-{[(4,6-dimethylpyrimidin-2-yl)amino]sulfonyl}phenyl)amino]-4'-methyl-4,5'-bi-1,3-thiazol-2'-yl}acetamide;
N-{4'-methyl-2-[(4-{[(5-methylisoxazol-3-yl)amino]sulfonyl}phenyl)amino]-4,5'-bi-1,3-thiazol-2'-yl}acetamide;
N-[2-(allylamino)-4'-methyl-4,5'-bi-1,3-thiazol-2'-yl]propanamide;
N-{2-[(4-{[(2,6-dimethoxypyrimidin-4-yl)amino]sulfonyl}phenyl)amino]-4'-methyl-4,5'-bi-1,3-thiazol-2'-yl}acetamide;
N-{4'-methyl-2-[(4-{[(5-methylisoxazol-3-yl)amino]sulfonyl}phenyl)amino]-4,5'-bi-1,3-thiazol-2'-yl}propanamide;
N-{2-[(4-{[(4,6-dimethylpyrimidin-2-yl)amino]sulfonyl}phenyl)amino]-4'-methyl-4,5'-bi-1,3-thiazol-2'-yl}propanamide;
N-(4-{[2'-(acetylamino)-4'-methyl-4,5'-bi-1,3-thiazol-2-yl]amino}phenyl)acetamide;
N-{2-[(4-aminophenyl)amino]-4'-methyl-4,5-bi-1,3-thiazol-2'-yl}acetamide;
N-{2-[(2-ethylphenyl)amino]-4'-methyl-4,5'-bi-1,3-thiazol-2'-yl}acetamide;
N-{4'-methyl-2-[(2-methylphenyl)amino]-4,5'-bi-1,3-thiazol-2'-yl}acetamide;
N-{2-[(4-bromophenyl)amino]-4'-methyl-4,5'-bi-1,3-thiazol-2'-yl}acetamide;

N-(2-{[4-(aminosulfonyl)phenyl]amino}-4'-methyl-4,5'-bi-1,3-thiazol-2'-yl)acetamide;

N-{2-[(2,5-dimethoxyphenyl)amino]-4'-methyl-4,5'-bi-1,3-thiazol-2'-yl}acetamide;

N-{2-[(3-acetylphenyl)amino]-4'-methyl-4,5'-bi-1,3-thiazol-2'-yl}acetamide;

N-(2-f{[4-(dimethylamino)phenyl]amino}-4'-methyl-4,5'-bi-1,3-thiazol-2'-yl)acetamide.

N-{4'-methyl-2-[(3-nitrophenyl)amino]-4,5'-bi-1,3-thiazol-2'-yl}acetamide;

3-{[2'-(acetylamino)-4-methyl-4,5'-bi-1,3-thiazol-2-yl]amino}benzoic acid;

Example 137

Biological Assays

The compounds of the present invention may be subjected to the following assays:

a) High Throughput PI3K Lipid Kinase Assay (Binding Assay):

The efficacy of compounds of the invention in inhibiting the PI3K induced-lipid phosphorylation may be tested in the following binding assay.

The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin.

To a 384 wells MTP containing 5 µl of the test compound of Formula (I) (solubilized in 6% DMSO; to yield a concentration of 100, 30, 10, 3, 1, 0.3, 0.1, 0.03, 0.01, 0.001 µM of the test compound), the following assay components are added. 1) 5 µl (58 ng) of Human recombinant GST-PI3Kγ (in Hepes 40 mM, pH 7.4, DTT 1 mM and ethylenglycol 5%) 2) 10 µl of lipid micelles and 3) 10 µl of Kinase buffer ([$^{33}$P]γ-ATP 45 µM60nCi, MgCl$_2$ 30 nM, DTT 1 mM, β-Glycerophosphate 1 mM, Na$_3$VO$_4$ 100 µM, Na Cholate 0.3%, in Hepes 40 mM, pH 7.4). After incubation at room temperature for 180 minutes, with gentle agitation, the reaction is stopped by addition of 60 µl of a solution containing 100 µg of neomycin-coated PVT SPA beads in PBS containing ATP 10 mM and EDTA 5 mM. The assay is further incubated at room temperature for 60 minutes with gentle agitation to allow binding of phospholipids to neomycin-SPA beads. After precipitation of the neomycin-coated PVT SPA beads for 5 minutes at 1500×g, radioactive PtdIns(3)P is quantified by scintillation counting in a Wallac MicroBeta™ plate counter.

The values indicated in Table I below refer to the IC$_{50}$ (nM) with respect to PI3Kγ, i.e. the amount necessary to achieve 50% inhibition of said target. Said values show a considerable inhibitory potency of thiazole compounds with regard to PI3Kγ.

Examples of inhibitory activities for compounds of the invention are set out in Table I below.

TABLE I

IC$_{50}$ values of thiazole derivatives against PI3Kγ.

| Example No | PI3Kγ · IC$_{50}$(nM) |
|---|---|
| 1 | 10 |
| 5 | 630 |
| 6 | 202 |
| 7 | 94 |
| 14 | 575 |
| 16 | 844 |
| 22 | 314 |
| 31 | 871 |
| 33 | 355 |
| 37 | 70 |
| 43 | 38 |
| 45 | 612 |
| 50 | 9 |
| 56 | 377 |
| 77 | 189 |
| 84 | 64 |
| 136 | 64 | b) Cell Based ELISA to Monitor PI3K Inhibition:

The efficacy of compounds of the invention in inhibiting the PI3K induced AKt/PKB phosphorylation may be tested in the following cell based assay.

Measurement of Akt/PKB phosphorylation in macrophages after stimulation with Complement 5a: Raw 264: Raw 264-7 macrophages (cultured in DMEM-F12 medium containing 10% Fetal Calf serum and antibiotics) are plated at 20'000 cells/well in a 96 MTP 24 h before cell stimulation. Previous to the stimulation with 50 nM of Complement 5a during 5 minutes, Cells are serum starved for 2 h, and pretreated with inhibitors for 20 minutes. After stimulation cells are fixed in 4% formaldehyde for 20 minutes and washed 3 times in PBS containing 1% Triton X-100 (PBS/Triton). Endogenous peroxidase is blocked by a 20 minutes incubation in 0.6% H$_2$O$_2$ and 0.1% Sodium Azide in PBS/Triton and washed 3 times in PBS/Triton. Cells are then blocked by 60 minutes incubation with 10% fetal calf serum in PBS/Triton. Next, phosphorylated AKt/PKB is detected by an overnight incubation at 4° C. with first antibody (anti phospho Serine 473 Akt IHC, Cell Signaling) diluted 800-fold in PBS/Triton, containing 5% bovine serum albumin (BSA). After 3 washes in PBS/Triton, cells are incubated for 60 minutes with a peroxidase conjugated goat-anti-rabbit antibody (1/400 dilution in PBS/Triton, containing 5% BSA), washed 3 times in PBS/Triton, and 2 times in PBS and further incubated in 100 µl of substrate reagent solution (R&D) for 20 minutes. The reaction is stopped by addition of 50 µl of 1 M SO$_4$H$_2$ and absorbance is read at 450 nm.

The values indicated in Table II below reflect the percentage of inhibition of AKT phoshorylation as compared to basal level. Said values show a clear effect of the thiazole compounds on the activation of AKT phosphorylation in macrophages.

Examples of inhibitory activities for compounds of the invention are set out in Table II below.

TABLE II

IC$_{50}$ values of thiazole derivatives in Cell Assay

| Example No | Cell Assay (P-Akt, Elisa) IC50 [µM] |
|---|---|
| 1 | 3.18 |
| 7 | 1.64 |
| 24 | 0.66 |

131

TABLE II-continued

IC$_{50}$ values of thiazole derivatives in Cell Assay

| Example No | Cell Assay (P-Akt, Elisa) IC50 [μM] |
|---|---|
| 53 | 1.51 |
| 84 | 1.84 |

Example 138

Thioglycollate-Induced Peritoneal Cavity Cell Recruitment Model

The in vivo efficacy of compounds of the invention in inhibiting the migration of leukocytes upon intraperitoneal challenge of thioglycollate may be tested with the following assay.

Experimental Protocol:

8-10 weeks old female C3H mice were fasted during 18 hours. 15 minutes prior the intraperitoneal injection of thioglycollate (1.5%, 40 ml/kg), the mice were treated orally with Pyridin methylene thiazolidindiones of formula (I). Control mice received CMC/Tween as vehicle (10 ml/kg). The mice were then sacrificed by $CO_2$ inhalation and the peritoneal cavity was washed two times with 5 ml of ice-cold PBS/1 mM EDTA. The lavages were done 4 hrs or 48 hrs after thioglycollate challenge to evaluate neutrophils or macrophages recruitment, respectively. The white blood cells (neutrophils, lymphocytes or macrophages) were counted using a Beckman Coulter® A$^c$T 5Diff™. Dexamethasone was used as reference drug.

Example 139

Preparation of a Pharmaceutical Formulation

The following formulation examples illustrate representative pharmaceutical compositions according to the present invention being not restricted thereto.

Formulation 1—Tablets

A compound of Formula (I) is admixed as a dry powder with a dry gelatin binder in an approximate 1:2 weight ration. A minor amount of magnesium stearate is added as a lubricant. The mixture is formed into 240-270 mg tablets (80-90 mg) of active thiazole compound per tablet) in a tablet press.

Formulation 2—Capsules

A compound of Formula (I) is admixed as a dry powder with a starch diluent in an approximate 1:1 weight ratio. The mixture is filled into 250 mg capsules (125 mg of active thiazole compound per capsule).

Formulation 3—Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active thiazole compound) in a tablet press.

132

Formulation 5—Injection

A compound of Formula (I) is dissolved in a buffered sterile saline injectable aqueous medium to a concentration of approximately 5 mg/ml.

The invention claimed is:

1. A thiazole according to Formula (I),

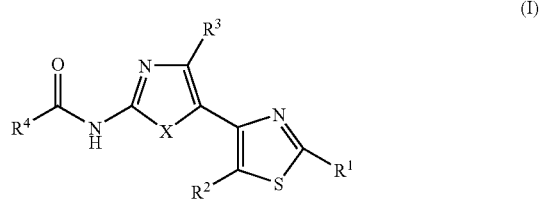

(I)

wherein $R^1$ is a moiety of the formula —$NR^5R^6$;

$R^2$, $R^3$ and $R^5$ are selected independently from the group consisting of H, $C_1$-$C_6$-alkyl, $C_2$-$C_6$-alkenyl and $C_2$-$C_6$-alkynyl;

$R^4$ is selected from the group consisting of H, $C_1$-$C_6$-alkyl, $C_2$-$C_6$-alkenyl, $C_2$-$C_6$-alkynyl and $NR^8R^9$, wherein $R^8$ and $R^9$ are independently selected from the group consisting of H, $C_1$-$C_6$-alkyl, $C_2$-$C_6$-alkenyl, $C_2$-$C_6$-alkynyl, $C_1$-$C_6$-alkyl alkoxy carbonyl and $C_1$-$C_6$-alkyl acyloxy;

$R^6$ is an unsubstituted group selected from the group consisting of $C_2$-$C_6$-alkenyl,
$C_2$-$C_6$-alkynyl,
$C_1$-$C_6$-alkyl alkoxy,
$C_1$-$C_6$ alkyl acyl,
$C_1$-$C_6$-alkyl carboxy,
$C_1$-$C_6$ alkyl $C_3$-$C_8$ cycloalkyl,
$C_1$-$C_6$ alkyl heterocycloalkyl,
$C_1$-$C_6$-alkyl acylamino,
$C_1$-$C_6$-alkyl amino,
$C_1$-$C_6$-alkyl aminocarbonyl,
$C_1$-$C_6$-alkyl alkoxycarbonyl,
2-acetylamino-phenyl,
3-nitro phenyl,
2-nitrophenyl,
2-methylphenyl,
2-chlorophenyl,
3-chlorophenyl,
2-hydroxyphenyl,
4-hydroxyphenyl,
cyanophenyl,
3-(1-hydroxyethyl)phenyl,
hydroxamic acid phenyl,
3-(N-hydroxycarbamimidoyl)-phenyl-4-yl,
benzyl piperazine carbonyl phenyl,
phenyl substituted with heteroaryl,
dimethylpyrimidine amino sulfonyl phenyl,
methyl isoxazol amino sulfonyl phenyl,
dimethoxy pyrimidine amino sulfonyl phenyl,
pyridinyl amino sulfonyl phenyl,
3-(aminosulfonyl)phenyl,
4[(methylamino)sulfonyl]phenyl,
4-[(dimethylamino)sulfonyl]phenyl,
3 [(butylamino)sulfonyl]phenyl,
4-(morpholin-4-yl-sulfonyl)phenyl,
aryl sulfonyl,
fused phenyl,
3-pyridine, 4-pyridine,
methoxy pyridine,
chloro pyridine,
fluoro pyridine,
cyano pyridine,
acetamide pyridine,
fused pyridine,
$C_3$-$C_8$ cycloalkyl,
pyridine-3-yl-methyl,
pyridine-4-yl-methyl,
2-(1H-tetrazol-5-yl)ethyl,
2-(2-hydroxy-1,3,4-oxadiazol-5-yl)ethyl,
3-(2-hydroxy-1,3,4-oxadiazol-5-yl)propyl, and
3-(1H-imidazol-1-yl)propyl;
  or $R^5$ and $R^6$, together with the carbon atoms they are linked to, form an unsubstituted 5-8-membered saturated ring or aromatic ring containing optionally one or more heteroatoms selected from the group consisting of O, N and S; and
X is S;
as well as isomers thereof.

2. The thiazole according to claim 1; wherein $R^2$ is H.

3. The thiazole according to claim 1; wherein $R^3$ is methyl.

4. The thiazole according to claim 1; wherein $R^4$ is selected from the group consisting of $C_1$-$C_6$-alkyl, $C_2$-$C_6$-alkenyl and $C_2$-$C_6$-alkynyl.

5. The thiazole according to claim 1; wherein $R^5$ is H and $R^6$ is unsubstituted and selected from the group consisting of $C_2$-$C_6$-alkenyl, $C_2$-$C_6$-alkynyl, and $C_1$-$C_6$-alkyl alkoxy.

6. The thiazole according to claim 1; wherein $R^5$ is H.

7. The thiazole according to claim 1; wherein $R^5$ is H and $R^6$ is unsubstituted and selected from the group consisting of 2-hydroxyphenyl, 4-hydroxyphenyl, 2-acetylamino-phenyl, dimethylpyrimidine amino sulfonyl phenyl, pyridinyl amino sulfonyl phenyl, 3-(aminosulfonyl)phenyl, 4[(methylamino)sulfonyl]phenyl, 4-[(dimethylamino)sulfonyl]phenyl, 3[(butylamino)sulfonyl]phenyl, 4-(morpholin-4-yl-sulfonyl)phenyl, 2-chlorophenyl, 3-chlorophenyl, 2-methylphenyl, 3-nitro phenyl, 2-nitrophenyl, cyanophenyl, 3-(1-hydroxyethyl)phenyl, hydroxamic acid phenyl, 3-(N-hydroxycarbamimidoyl)-phenyl-4-yl, benzyl piperazine carbonyl phenyl, and phenyl substituted with heteroaryl.

8. The thiazole according to claim 1; wherein $R^5$ and $R^6$, together with the carbon atoms they are linked to, form a 5-8-membered saturated or aromatic ring containing optionally one or more heteroatoms selected from the group consisting of O, N and S.

9. The thiazole according to claim 1; wherein $R^1$ is —$NR^5R^6$; $R^2$ is H; $R^3$ is methyl; $R^4$ is selected from the group consisting of $C_1$-$C_6$-alkyl, $C_2$-$C_6$-alkenyl, $C_2$-$C_6$-alkynyl and —$NR^8R^9$; wherein $R^8$ and $R^9$ are independently selected from the group consisting of H, $C_1$-$C_6$-alkyl, $C_2$-$C_6$-alkenyl, $C_2$-$C_6$-alkynyl and $C_1$-$C_6$-alkyl alkoxycarbonyl; $R^5$ is H and $R^6$ is unsubstituted and selected from the group consisting of $C_2$-$C_6$-alkenyl, $C_2$-$C_6$-alkynyl, $C_1$-$C_6$-alkyl alkoxy, $C_1$-$C_6$-alkyl carboxy, $C_1$-$C_6$-alkyl acylamino, $C_1$-$C_6$-alkyl amino, $C_1$-$C_6$-alkyl aminocarbonyl, $C_1$-$C_6$-alkyl alkoxycarbonyl, $C_1$-$C_6$-alkyl $C_3$-$C_8$-cycloalkyl and $C_1$-$C_6$-alkyl heterocycloalkyl; and X is S.

10. The thiazole according to claim 1; wherein $R^1$ is —$NR^5R^6$; $R^2$ is H; $R^3$ is methyl; $R^4$ is selected from the group consisting of $C_1$-$C_6$-alkyl, $C_2$-$C_6$-alkenyl, an $C_2$-$C_6$-alkynyl and —$NR^8R^9$ wherein $R^8$ and $R^9$ are independently selected from the group consisting of H, $C_1$-$C_6$-alkyl, $C_2$-$C_6$-alkenyl, $C_2$-$C_6$-alkynyl and $C_1$-$C_6$-alkyl alkoxycarbonyl; $R^5$ is H; and X is S.

11. The thiazole according to claim 1; wherein $R^1$ is —$NR^5R^6$; $R^2$ is H; $R^3$ is methyl; $R^4$ is an unsubstituted $C_1$-$C_6$-alkyl, and —$NR^8R^9$; wherein $R^8$ and $R^9$ are independently selected from the group consisting of H, $C_1$-$C_6$-alkyl, $C_2$-$C_6$-alkenyl, $C_2$-$C_6$-alkynyl and $C_1$-$C_6$-alkyl alkoxycarbonyl; $R^5$ is H; and X is S.

12. The thiazole according to claim 1; wherein $R^1$ is —$NR^5R^6$; $R^2$ is H; $R^3$ is methyl; $R^4$ is an unsubstituted $C_1$-$C_6$-alkyl, and —$NR^8R^9$ wherein $R^8$ and $R^9$ are independently selected from the group consisting of H, $C_1$-$C_6$-alkyl, $C_2$-$C_6$-alkenyl, $C_2$-$C_6$-alkynyl and $C_1$-$C_6$-alkyl alkoxycarbonyl; $R^5$ and $R^6$, together with the carbon atoms they are linked to, form an optionally substituted 5-8-membered saturated or aromatic ring containing optionally one or more heteroatoms selected from the group consisting of O, N and S; and X is S.

13. A thiazole selected from the group consisting of:
N-(4'-methyl-2-piperidin-1-yl-4,5'-bi-1,3-thiazol-2'-yl) acetamide;
N-[4'-methyl-2-(pyridin-3-ylamino)-4,5'-bi-1,3-thiazol-2'-yl]acetamide;
N-(4'-methyl-2-morpholin-4-yl-4,5'-bi-1,3-thiazol-2'-yl) acetamide;
N-[4'-methyl-2-(4-methylpiperazin-1-yl)-4,5'-bi-1,3-thiazol-2'-yl]acetamide;
methyl 1-[2-(acetylamino)-4'-methyl-4,5'-bi-1,3-thiazol-2'-yl]piperidine-3 carboxylate;
N-{2-[4-(2-hydroxyethyl)piperidin-1-yl]-4'-methyl-4,5'-bi-1,3-thiazol-2'-yl}acetamide;
N-(4'-methyl-2-pyrrolidin-1-yl-4,5'-bi-1,3-thiazol-2'-yl) acetamide;
N-[2-(3-hydroxypyrrolidin-1-yl)-4'methyl-4,5'-bi-1,3-thiazol-2'-yl]acetamide;
N-[2-(tert-butylamino)-4'-methyl-4,5'-bi-1,3-thiazol-2'-yl]acetamide;
N-{2-[(6-methoxypyridin-3-yl)amino]-4'-methyl-4,5'-bi-1,3-thiazol-2'-yl}acetamide;
N-{2-[(6-chloropyridin-3-yl)amino]-4'-methyl-4,5'-bi-1,3-thiazol-2'-yl}acetamide;
N-{4'-methyl-2-[(2-morpholin-4-ylethyl)amino]-4,5'-bi-1,3-thiazol-2'-yl}acetamide;
N-{4'-methyl-2-[(2-piperidin-1-ylethyl)amino]-4,5'-bi-1,3-thiazol-2'-yl}acetamide;
N-{2-[(2-methoxyethyl)amino]-4'-methyl-4,5'-bi-1,3-thiazol-2'-yl}acetamide;
N-[2-(cyclohexylamino)-4'-methyl-4,5'-bi-1,3-thiazol-2'-yl]acetamide;
N-{4'-methyl-2-[(3-morpholin-4-ylpropyl)amino]-4,5'-bi-1,3-thiazol-2'-yl}acetamide;
N-{4'-methyl-2-[(tetrahydrofuran-2-ylmethyl)amino]-4,5'-bi-1,3-thiazol-2'-yl}acetamide;
N-[2-(1-benzofuran-5-ylamino)-4'-methyl-4,5'-bi-1,3-thiazol-2'-yl]acetamide;
[4'-methyl-2-(pyridin-3-ylamino)-4,5'-bi-1,3-thiazol-2'-yl]formamide;
N-{2-[(2-fluoropyridin-3-yl)amino]-4'-methyl-4,5'-bi-1,3-thiazol-2'-yl}acetamide;
N-{2-[(2-cyanoethyl)amino]-4'-methyl-4, 5'-bi-1,3-thiazol-2'-yl}acetamide;
N-{2-[(3,3-diethoxypropyl)amino]-4'-methyl-4,5'-bi-1,3-thiazol-2'-yl}acetamide;
N-{2-[(2,2-diethoxyethyl)amino]-4'-methyl-4,5'-bi-1,3-thiazol-2'-yl}acetamide;
N-{4'-methyl-2-[(2-oxo-2-phenylethyl)amino]-4,5'-bi-1,3-thiazol-2'-yl}acetamide;
N-{2-[(2-chloropyridin-3-yl)amino]-4'-methyl-4,5'-bi-1,3-thiazol-2'-yl}acetamide;

N-[2'-(acetylamino)-4'-methyl-4,5'-bi-1,3-thiazol-2-yl]-beta-alanine;

4-{[2'-(acetylamino)-4'-methyl-4,5'-bi-1,3-thiazol-2-yl]amino}butanoic acid;

N-{2-[(2-chloropyridin-4-yDamino]-4'-methyl-4,5'-bi-1,3-thiazol-2'-yl}acetamide;

N-(5-{[2'-(acetylamino)-4'-methyl-4,5'-bi-1,3-thiazol-2-yl]amino}pyridin-2-yl) acetamide;

N-[2-(2,3-dihydro-1-benzofuran-5-ylamino)-4'-methyl-4,5'-bi-1,3-thiazol-2'-yl]acetamide;

N-(4'-methyl-2-{[2-(1-methylpyrrolidin-2-yl)ethyl]amino}-4,5'-bi-1,3-thiazol-2'-yl) acetamide;

N-{4'-methyl-2-[(2-pyrrolidin-1-ylethyl)amino]-4,5'-bi-1,3-thiazol-2'-yl}acetamide;

N-(4'-methyl-2-{[3-(2-oxopyrrolidin-1-yl)propyl]amino}-4,5'-bi-1,3-thiazol-2'-yl) acetamide;

N-(2-{[2-(acetylamino)ethyl]amino}-4'-methyl-4,5'-bi-1,3-thiazol-2'-yl) acetamide;

N-(2-{[2-(dimethylamino)ethyl]amino}-4'-methyl-4,5'-bi-1,3-thiazol-2'-yl) acetamide;

N-{2-[(2-hydroxyethyl)amino]-4'-methyl-4,5'-bi-1,3-thiazol-2'-yl}acetamide;

N-(2-{[3-(dimethylamino)propyl]amino}-4'-methyl-4,5'-bi-1,3-thiazol-2'-yl) acetamide;

N-{2-[(3-hydroxypropyl)amino]-4'-methyl-4,5'-bi-1,3-thiazol-2'-yl}acetamide;

N~3~-[2'-(acetylamino)-4'-methyl-4,5'-bi-1,3-thiazol-2-yl]-beta-alaninamide;

N-{2-[(6-cyanopyridin-3-yDamino]-4'-methyl-4,5'-bi-1,3-thiazol-2'-yl}acetamide;

N-[4'-methyl-2-(quinolin-3-ylamino)-4,5'-bi-1,3-thiazol-2'-yl]acetamide;

N-[4'-methyl-2-(quinolin-5-ylamino)-4,5'-bi-1,3-thiazol-2'-yl]acetamide;

N-[4'-methyl-2-(quinolin-6-ylamino)-4,5'-bi-1,3-thiazol-2'-yl]acetamide;

N-[2-(cyclopentylamino)-4'-methyl-4,5'-bi-1,3-thiazol-2'-yl]acetamide;

N-[2-(cyclopropylamino)-4'-methyl-4,5'-bi-1,3-thiazol-2'-yl]acetamide;

N-{2-[(4-hydroxybutyl)amino]-4'-methyl-4,5'-bi-1,3-thiazol-2'-yl}acetamide;

N-{4'-methyl-2-[(3-pyrrolidin-1-ylpropyl)amino]-4,5'-bi-1,3-thiazol-2'-yl}acetamide;

N-{2-[(1,1-dioxido-1-benzothien-6-yl)amino]-4'-methyl-4,5'-bi-1,3-thiazol-2'-yl}acetamide;

N-(2-{[(1-ethylpyrrolidin-2-yl)methyl]amino}-4'-methyl-4,5'-bi-1,3-thiazol-2'-yl) acetamide;

N-{2-[(cyanomethyl)amino]-4'-methyl-4,5'-bi-1,3-thiazol-2'-yl}acetamide;

N-[2-(isobutylamino)-4'-methyl-4,5'-bi-1,3-thiazol-2'-yl]acetamide;

N-{2-[(2,2-dimethylpropyl)amino]-4'-methyl-4,5'-bi-1,3-thiazol-2'-yl}acetamide;

N-(2-{[(cis)-2-(hydroxymethyl)cyclohexyl]amino}-4'-methyl-4,5'-bi-1,3-thiazol-2'-yl)acetamide;

N-(2-{[(trans)-2-(hydroxymethyl)cyclohexyl]amino}-4'-methyl-4,5'-bi-1,3-thiazol-2'-yl)acetamide;

N-[2-(sec-butylamino)-4'-methyl-4,5'-bi-1,3-thiazol-2'-yl]acetamide;

N-{2-[(cyclopropylmethyl)amino]-4'-methyl-4,5'-bi-1,3-thiazol-2'-yl}acetamide;

N-{2-[(cyclobutylamino)-4'-methyl-4,5'-bi-1,3-thiazol-2'-yl}acetamide;

N-[2-(2,3-dihydro-1H-inden-2-ylamino)-4'-methyl-4,5'-bi-1,3-thiazol-2'-yl]acetamide;

methyl 4-{[2'-(acetylamino)-4'-methyl-4,5'-bi-1,3-thiazol-2-yl]amino}butanoate;

N-[4'-methyl-2-(pyridin-3-ylamino)-4,5'-bi-1,3-thiazol-2'-yl]urea; and

N-(4'-methyl-2-piperidin-1-yl-4,5'-bi-1,3-thiazol-2'-yl) urea.

14. A pharmaceutical composition, comprising:
at least one thiazole derivative according to claim 1; and
a pharmaceutically acceptable carrier, diluent or excipient thereof.

15. A thiazole compound selected from the group consisting of:

3-{[2'-(acetylamino)-4'-methyl-4,5'-bi-1,3-thiazol-2'-yl]amino}benzoic acid;

4-{[2'-(acetylamino)-4'-methyl-4,5'-bi-1,3-thiazol-2'-yl]amino}benzoic acid;

N-[2-(benzylamino)-4'-methyl-4,5'-bi-1,3-thiazol-2'-yl]acetamide;

N-{4'-methyl-2-[(2-phenylethyl)amino]-4,5'-bi-1,3-thiazol-2'-yl}acetamide;

N-(4'-methyl-2-piperidin-1-yl-4,5'-bi-1,3-thiazol-2'-yl) acetamide;

N-[2-(allylamino)-4'-methyl-4,5'-bi-1,3-thiazol-2'-yl]acetamide;

N-[4'-methyl-2-(pyridin-3-ylamino)-4,5'-bi-1,3-thiazol-2'-yl]acetamide;

N-[4'-methyl-2-(pyridin-2-ylamino)-4,5'-bi-1,3-thiazol-2'-yl]acetamide;

N-{2-[(4-hydroxyphenyl)amino]-4'-methyl-4,5'-bi-1,3-thiazol-2'-yl}acetamide;

N-{4'-methyl-2-[(4-nitrophenyl)amino]-4,5'-bi-1,3-thiazol-2'-yl}acetamide;

4-{[2'-(acetylamino)-4-methyl-4,5'-bi-1,3-thiazol-2'-yl]amino}benzamide;

N-[2-({4-[(4-benzylpiperazin-1-yl)carbonyl]phenyl}amino)-4'-methyl-4,5'-bi-1,3-thiazol-2'-yl]acetamide;

N-(4'-methyl-2-morpholin-4-yl-4,5'-bi-1,3-thiazol-2'-yl) acetamide;

N-[4'-methyl-2-(4-methylpiperazin-1-yl)-4,5'-bi-1,3-thiazol-2'-yl]acetamide;

methyl 1-[2'-(acetylamino)-4'-methyl-4,5'-bi-1,3-thiazol-2'-yl]piperidine-3-carboxylate;

N-{2-[4-(2-hydroxyethyl)piperidin-1-yl]-4'-methyl-4,5'-bi-1,3-thiazol-2'-yl}acetamide;

N-(4'-methyl-2-pyrrolidin-1-yl-4,5'-bi-1,3-thiazol-2'-yl) acetamide;

N-[2-(3-hydroxypyrrolidin-1-yl)-4'-methyl-4,5'-bi-1,3-thiazol-2'-yl]acetamide;

N-[2-(tert-butylamino)-4'-methyl-4,5'-bi-1,3-thiazol-2'-yl]acetamide;

N-{2-[(6-methoxypyridin-3-yl)amino]-4'-methyl-4,5'-bi-1,3-thiazol-2'-yl}acetamide;

N-{2-[(6-chloropyridin-3-yDamino]-4'-methyl-4,5'-bi-1,3-thiazol-2'-yl}acetamide;

N-{2-[(4-cyanophenyl)amino]-4'-methyl-4,5'-bi-1,3-thiazol-2'-yl}acetamide;

N-{2-[(2-chlorophenyl)amino]-4'-methyl-4,5'-bi-1,3-thiazol-2'-yl}acetamide;

N-{2-[(3-chlorophenyl)amino]-4'-methyl-4,5'-bi-1,3-thiazol-2'-yl}acetamide;

N-{2-[(3-hydroxyphenyl)amino]-4'-methyl-4,5'-bi-1,3-thiazol-2'-yl}acetamide;

N-{4'-methyl-2-[(2-morpholin-4-ylethyl)amino]-4,5'-bi-1,3-thiazol-2'-yl}acetamide;

N-{4'-methyl-2-[(2-piperidin-1-ylethyl)amino]-4,5'-bi-1,3-thiazol-2'-yl}acetamide;

N-{2-[(2-methoxyethyl)amino]-4'-methyl-4,5'-bi-1,3-thiazol-2'-yl}acetamide;
N-[2-(cyclohexylamino)-4'-methyl-4,5'-bi-1,3-thiazol-2'-yl]acetamide;
N-{4'-methyl-2-[(3-morpholin-4-ylpropyl)amino]-4,5'-bi-1,3-thiazol-2'-yl}acetamide;
N-{4'-methyl-2-[(tetrahydrofuran-2-ylmethyl)amino]-4,5'-bi-1,3-thiazol-2'-yl}acetamide;
N-{2-[(2-hydroxy-2-phenylethyl)amino]-4'-methyl-4,5'-bi-1,3-thiazol-2'-yl}acetamide;
N-[2-(1-benzofuran-5-ylamino)-4'-methyl-4,5'-bi-1,3-thiazol-2'-yl]acetamide;
N-{2-[(3-cyanophenyl)amino]-4'-methyl-4,5'-bi-1,3-thiazol-2'-yl}acetamide;
[4'-methyl-2-(pyridin-3-ylamino)-4,5'-bi-1,3-thiazol-2'-yl]formamide;
ethyl N-({[2-(allylamino)-4'-methyl-4,5'-bi-1,3-thiazol-2'-yl]amino}carbonyl)-beta-alaninate;
N-{2-[(2-fluoropyridin-3-yl)amino]-4'-methyl-4,5'-bi-1,3-thiazol-2'-yl}acetamide;
N-{2-[(2-cyanoethyl)amino]-4'-methyl-4, 5 '-bi-1,3-thiazol-2'-yl}acetamide;
N-{2-[(3,3-diethoxypropyl)amino]-4'-methyl-4,5'-bi-1,3-thiazol-2'-yl}acetamide;
N-{2-[(2,2-diethoxyethyl)amino]-4'-methyl-4,5'-bi-1,3-thiazol-2'-yl}acetamide;
N-{4'-methyl-2-[(2-oxo-2-phenylethyl)amino]-4,5'-bi-1,3-thiazol-2'-yl}acetamide;
N-{2-[(2-chloropyridin-3-yl)amino]-4'-methyl-4,5'-bi-1,3-thiazol-2'-yl}acetamide;
N-(4'-methyl-2-{[3-(1,3-oxazol-5-yl)phenyl]amino}-4,5'-bi-1,3-thiazol-2'-yl) acetamide;
N-(4'-methyl-2-{[3-(1H-tetrazol-5-yl)phenyl]amino}-4,5'-bi-1,3-thiazol-2'-yl) acetamide;
N-(4'-methyl-2-[4-(1H-tetrazol-5-yl)phenyl]amino}-4,5'-bi-1,3-thiazol-2'-yl) acetamide;
N-{4'-Methyl-2-[2-(1H-tetrazol-5-yl)-ethylamino]-[4,5]bithiazolyl-2'-yl}-acetamide;
N-(2-{[3-(5-hydroxy-1,3,4-oxadiazol-2-yl)phenyl]amino}-4'-methyl-4,5'-bi-1,3-thiazol-2'-yl)acetamide;
N-(2-{[3-(5-amino-1,3,4-thiadiazol-2-yl)phenyl]amino}-4'-methyl-4,5'-bi-1,3-thiazol-2'-yl)acetamide;
N-[2'-(acetylamino)-4'-methyl-4,5'-bi-1,3-thiazol-2-yl]-beta-alanine;
5-(2-{[2'-(acetylamino)-4'-methyl-4,5'-bi-1,3-thiazol-2-yl]amino}ethyl)-1,3,4-oxadiazol-2-olate;
4-{[2'-(acetylamino)-4'-methyl-4,5'-bi-1,3-thiazol-2-yl]amino}butanoic acid;
N-(2-{[3-(5-hydroxy-1,3,4-oxadiazol-2-yl)propyl]amino}-4'-methyl-4,5'-bi-1,3-thiazol-2'-yl)acetamide;
3-{[2'-(acetylamino)-4'-methyl-4,5'-bi-1,3-thiazol-2-yl]amino}-N-hydroxy benzamide;
3-{[2'-(acetylamino)-4'-methyl-4,5'-bi-1,3-thiazol-2-yl]amino}-N-hydroxy benzene carboximidic acid;
N-(2-{[3-(5-hydroxy-1,2,4-oxadiazol-3-yl)phenyl]amino}-4'-methyl-4,5'-bi-1,3-thiazol-2'-yl)acetamide;
N-[2-({3-[(Z)-(2,4-dioxo-1,3-thiazolidin-5-ylidene)methyl]phenyl}amino)-4'-methyl-4,5'-bi-1,3-thiazol-2'-yl]acetamide;
N-[4'-methyl-2-({4-[(pyridin-2-ylamino)sulfonyl]phenyl}amino)-4,5'-bi-1,3-thiazol-2'-yl]acetamide;
N-(2-{[2-(2-hydroxyethyl)phenyl]amino}-4'-methyl-4,5'-bi-1,3-thiazol-2'-yl) acetamide;
N-(2-{[3-(hydroxymethyl)phenyl]amino}-4'-methyl-4,5'-bi-1,3-thiazol-2'-yl) acetamide;
N-(2-{[4-(2-hydroxyethyl)phenyl]amino}-4'-methyl-4,5'-bi-1,3-thiazol-2'-yl) acetamide;
N-[2-({3-[(2-hydroxyethyl)sulfonyl]phenyl}amino)-4'-methyl-4,5'-bi-1,3-thiazol-2'-yl]acetamide;
N-[2-({4-[(dimethylamino)sulfonyl]phenyl}amino)-4'-methyl-4,5'-bi-1,3-thiazol-2'-yl]acetamide;
N-(2-{[3-(aminosulfonyl)phenyl]amino}-4'-methyl-4,5'-bi-1,3-thiazol-2'-yl) acetamide;
N-{2-[(2-chloropyridin-4-yl)amino]-4'-methyl-4,5'-bi-1,3-thiazol-2'-yl}acetamide;
N-[4'-methyl-2-({4-[(methylamino)sulfonyl]phenyl}amino)-4,5'-bi-1,3-thiazol-2'-yl]acetamide;
N-(5-{[2'-(acetylamino)-4'-methyl-4,5'-bi-1,3-thiazol-2-yl]amino}pyridin-2-yl) acetamide;
N-[2-(2,3-dihydro-1-benzofuran-5-ylamino)-4'-methyl-4,5'-bi-1,3-thiazol-2'-yl]acetamide;
N-(4'-methyl-2-{[2-(1-methylpyrrolidin-2-yl)ethyl]amino}-4,5'-bi-1,3-thiazol-2'-yl) acetamide;
N-{4'-methyl-2-[(2-pyrrolidin-1-ylethyl)amino]-4,5'-bi-1,3-thiazol-2'-yl}acetamide;
N-(4'-methyl-2-{[3-(2-oxopyrrolidin-1-yl)propyl]amino}-4,5'-bi-1,3-thiazol-2'-yl) acetamide;
N-(2-{[2-(acetylamino)ethyl]amino}-4'-methyl-4,5'-bi-1,3-thiazol-2'-yl) acetamide;
N-(2-{[2-(dimethylamino)ethyl]amino}-4'-methyl-4,5'-bi-1,3-thiazol-2'-yl) acetamide;
N-{2-[(2-hydroxyethyl)amino]-4'-methyl-4,5'-bi-1,3-thiazol-2'-yl}acetamide;
N-(2-{[2-(4-hydroxyphenyl)ethyl]amino}-4'-methyl-4,5'-bi-1,3-thiazol-2'-yl) acetamide;
N-(2-{[3-(dimethylamino)propyl]amino}-4'-methyl-4,5'-bi-1,3-thiazol-2'-yl) acetamide;
N-{2-[(3-hydroxypropyl)amino]-4'-methyl-4,5'-bi-1,3-thiazol-2'-yl}acetamide;
N-(2-{[3-(1H-imidazol-1-yl)propyl]amino}-4'-methyl-4,5'-bi-1,3-thiazol-2'-yl) acetamide;
N~3~-[2'-(acetylamino)-4'-methyl-4,5'-bi-1,3-thiazol-2-yl]-beta-alaninamide;
N-{4'-methyl-2-[(2-methylprop-2-en-1-yl)amino]-4,5'-bi-1,3-thiazol-2'-yl}acetamide;
N-{2-[(2-hydroxyphenyl)amino]-4'-methyl-4,5'-bi-1,3-thiazol-2'-yl}acetamide;
N-{2-[(6-fluoropyridin-3-yl)amino]-4'-methyl-4,5'-bi-1,3-thiazol-2'-yl}acetamide;
N-{2-[(4-cyanophenyl)amino]-4'-methyl-4,5'-bi-1,3-thiazol-2'-yl}acetamide;
N-{2-[(6-cyanopyridin-3-yl)amino]-4'-methyl-4,5'-bi-1,3-thiazol-2'-yl}acetamide;
3-{[2'-(acetylamino)-4'-methyl-4,5'-bi-1,3-thiazol-2-yl]amino}benzamide;
N-{4'-methyl-2-[(2-nitrophenyl)amino]-4,5'-bi-1,3-thiazol-2'-yl}acetamide;
N-{4'-methyl-2-[(3-nitrophenyl)amino]-4,5'-bi-1,3-thiazol-2'-yl}acetamide;
N-[4'-methyl-2-(quinolin-3-ylamino)-4,5'-bi-1,3-thiazol-2'-yl]acetamide;
N-[4'-methyl-2-(quinolin-5-ylamino)-4,5'-bi-1,3-thiazol-2'-yl]acetamide;
N-[4'-methyl-2-(quinolin-6-ylamino)-4,5'-bi-1,3-thiazol-2'-yl]acetamide;
N-[2-(cyclopentylamino)-4'-methyl-4,5'-bi-1,3-thiazol-2'-yl]acetamide;
N-[2-(cyclopropylamino)-4'-methyl-4,5'-bi-1,3-thiazol-2'-yl]acetamide;
N-{4'-methyl-2-[(pyridin-3-ylmethyl)amino]-4,5'-bi-1,3-thiazol-2'-yl}acetamide;
N-{2-[(4-hydroxybutyl)amino]-4'-methyl-4,5'-bi-1,3-thiazol-2'-yl}acetamide;

N-(4'-methyl-2-{[3-(methylsulfonyl)phenyl]amino}-4,5'-bi-1,3-thiazol-2'-yl) acetamide;
N-{4'-methyl-2-[(3-pyrrolidin-1-ylpropyl)amino]-4,5'-bi-1,3-thiazol-2'-yl}acetamide;
N-{2-[(1,1-dioxido-1-benzothien-6-yl)amino]-4'-methyl-4,5'-bi-1,3-thiazol-2'-yl}acetamide;
N-(2-{[(1-ethylpyrrolidin-2-yl)methyl]amino}-4'-methyl-4,5'-bi-1,3-thiazol-2'-yl) acetamide;
N-{2-[(cyanomethyl)amino]-4'-methyl-4,5'-bi-1,3-thiazol-2'-yl}acetamide;
N-[2-(isobutylamino)-4'-methyl-4,5'-bi-1,3-thiazol-2'-yl]acetamide;
N-{2-[(2,2-dimethylpropyl)amino]-4'-methyl-4,5'-bi-1,3-thiazol-2'-yl}acetamide;
N-(2-{[(cis)-2-(hydroxymethyl)cyclohexyl]amino}-4'-methyl-4,5'-bi-1,3-thiazol-2'-yl)acetamide;
N-(2-{[(trans)-2-(hydroxymethyl)cyclohexyl]amino}-4'-methyl-4,5'-bi-1,3-thiazol-2'-yl)acetamide;
N-[2-(sec-butylamino)-4'-methyl-4,5'-bi-1,3-thiazol-2'-yl]acetamide;
N-{4'-methyl-2-[(pyridin-4-ylmethyl)amino]-4,5'-bi-1,3-thiazol-2'-yl}acetamide;
N-(4'-methyl-2-{[4-(morpholin-4-ylsulfonyl)phenyl]amino}-4,5'-bi-1,3-thiazol-2'-yl) acetamide;
N-[2-({3-[(butylamino)sulfonyl]phenyl}amino)-4'-methyl-4,5'-bi-1,3-thiazol-2'-yl]acetamide;
N-{2-[(cyclopropylmethyl)amino]-4'-methyl-4,5'-bi-1,3-thiazol-2'-yl}acetamide;
N-[2-(cyclobutylamino)-4'-methyl-4,5'-bi-1,3-thiazol-2'-yl]acetamide;
N-[2-(2,3-dihydro-1H-inden-2-ylamino)-4'-methyl-4,5'-bi-1,3-thiazol-2'-yl]acetamide;
N-(4'-methyl-2-{[2-(methylsulfonyl)phenyl]amino}-4,5'-bi-1,3-thiazol-2'-yl) acetamide;
N-(4'-methyl-2-{[2-(1H-1,2,4-triazol-1-yl)ethyl]amino}-4,5'-bi-1,3-thiazol-2'-yl) acetamide;
N-(2-{[3-(1-hydroxyethyl)phenyl]amino}-4'-methyl-4,5'-bi-1,3-thiazol-2'-yl) acetamide;
methyl (4-{[2'-(acetylamino)-4'-methyl-4,5'-bi-1,3-thiazol-2-yl]amino}phenyl)acetate;
methyl N-(4-{[2'-(acetylamino)-4'-methyl-4,5'-bi-1,3-thiazol-2-yl]amino}benzoyl)-beta-alaninate;
methyl N-(4-{[2'-(acetylamino)-4'-methyl-4,5'-bi-1,3-thiazol-2-yl]amino}benzoyl)glycinate;
methyl 3-(3-{[2'-(acetylamino)-4'-methyl-4,5'-bi-1,3-thiazol-2-yl]amino}phenyl) propanoate;
3-(4-{[2'-(acetylamino)-4'-methyl-4,5'-bi-1,3-thiazol-2-yl]amino}phenyl) propanoic acid;
methyl 4-{[2'-(acetylamino)-4'-methyl-4,5'-bi-1,3-thiazol-2-yl]amino}butanoate;
methyl (3-{[2'-(acetylamino)-4'-methyl-4,5'-bi-1,3-thiazol-2-yl]amino}phenyl)acetate;
N-[2-(allylamino)-4'-methyl-4,5'-bi-1,3-thiazol-2'-yl]urea;
N-[4'-methyl-2-(pyridin-3-ylamino)-4,5'-bi-1,3-thiazol-2'-yl]urea;
N-(4'-methyl-2-piperidin-1-yl-4,5'-bi-1,3-thiazol-2'-yl) urea;
N-(2-anilino-4'-methyl-4,5'-bi-1,3-thiazol-2'-yl)urea;
N-{2-[(4-hydroxyphenyl)amino]-4'-methyl-4,5'-bi-1,3-thiazol-2'-yl}urea;
N-[2-(pyridin-3-ylamino)-4,5'-bi-1,3-thiazol-2'-yl]acetamide;
(4-{[2'-(acetylamino)-4'-methyl-4,5'-bi-1,3-thiazol-2-yl]amino}phenyl)acetic acid;
N-(4-{[2'-(acetylamino)-4'-methyl-4,5'-bi-1,3-thiazol-2-yl]amino}benzoyl)-beta-alanine;
N-(4-{[2'-(acetylamino)-4'-methyl-4,5'-bi-1,3-thiazol-2-yl]amino}benzoyl)glycine;
3-(3-{[2'-(acetylamino)-4'-methyl-4,5'-bi-1,3-thiazol-2-yl]amino}phenyl) propanoic acid;
N-{2-[(4-ethoxyphenyl)amino]-4'-methyl-4,5'-bi-1,3-thiazol-2'-yl}acetamide;
N-{4'-methyl-2-[(4-methylphenyl)amino]-4,5'-bi-1,3-thiazol-2'-yl}acetamide;
N-{2-[(4-{[(4,6-dimethylpyrimidin-2-yl)amino]sulfonyl}phenyl)amino]-4,5'-bi-1,3-thiazol-2'-yl}acetamide;
N-{4'-methyl-2-[(4-{[(5-methylisoxazol-3-yl)amino]sulfonyl}phenyl)amino]-4,5'-bi-1,3-thiazol-2'-yl}acetamide;
N-[2-(allylamino)-4'-methyl-4,5'-bi-1,3-thiazol-2'-yl]propanamide;
N-{2-[(4-{[(2,6-dimethoxypyrimidin-4-yl)amino]sulfonyl}phenyl)amino]-4'-methyl-4,5'-bi-1,3-thiazol-2'-yl}acetamide;
N-{4'-methyl-2-[(4-{[(5-methylisoxazol-3-yl)amino]sulfonyl}phenyl)amino]-4,5'-bi-1,3-thiazol-2'-yl}propanamide;
N-{2-[(4-{[(4,6-dimethylpyrimidin-2-yl)amino]sulfonyl}phenyl)amino]-4'-methyl-4,5'-bi-1,3-thiazol-2'-yl}propanamide;
N-{2[(2-ethylphenyl)amino]-4'-methyl-4,5'-bi-1,3-thiazol-2'-yl}acetamide;
N-{4'-methyl-2[(2-methylphenyl)amino]-4,5'-bi-1,3-thiazol-2'-yl}acetamide;
N-{2-[(2,5-dimethoxyphenyl)amino]-4'-methyl-4,5'-bi-1,3-thiazol-2'-yl}acetamide; and
N-{2-[(3-acetylphenyl)amino]-4'-methyl-4,5'-bi-1,3-thiazol-2'-yl}acetamide.

* * * * *